United States Patent
Wong et al.

(10) Patent No.: US 10,358,478 B2
(45) Date of Patent: *Jul. 23, 2019

(54) MULTIMERIC IL-15 SOLUBLE FUSION MOLECULES AND METHODS OF MAKING AND USING SAME

(71) Applicant: Altor Bioscience Corporation, Miramar, FL (US)

(72) Inventors: Hing C. Wong, Weston, FL (US); Peter Rhode, Miami, FL (US); Bai Liu, Cooper City, FL (US); Xiaoyun Zhu, Miami, FL (US); Kai-ping Han, Miramar, FL (US)

(73) Assignee: Altor Bioscience Corporation, Miramar, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/213,991

(22) Filed: Jul. 19, 2016

(65) Prior Publication Data

US 2016/0355567 A1    Dec. 8, 2016

Related U.S. Application Data

(63) Continuation of application No. 13/946,313, filed on Jul. 19, 2013, now Pat. No. 9,428,573, which is a continuation of application No. 13/238,925, filed on Sep. 21, 2011, now Pat. No. 8,507,222.

(60) Provisional application No. 61/527,911, filed on Aug. 26, 2011, provisional application No. 61/384,817, filed on Sep. 21, 2010.

(51) Int. Cl.
| | |
|---|---|
| *C07K 14/715* | (2006.01) |
| *A61K 38/20* | (2006.01) |
| *C12N 15/62* | (2006.01) |
| *C12N 15/09* | (2006.01) |
| *C12P 21/00* | (2006.01) |
| *C07K 14/54* | (2006.01) |
| *C07K 16/18* | (2006.01) |
| *A61K 38/17* | (2006.01) |
| *A61K 45/06* | (2006.01) |
| *C07K 16/28* | (2006.01) |
| *A61K 39/395* | (2006.01) |
| *A61K 38/00* | (2006.01) |

(52) U.S. Cl.
CPC ...... *C07K 14/7155* (2013.01); *A61K 38/1793* (2013.01); *A61K 38/2086* (2013.01); *A61K 39/3955* (2013.01); *A61K 45/06* (2013.01); *C07K 14/5443* (2013.01); *C07K 16/18* (2013.01); *C07K 16/2887* (2013.01); *C12N 15/09* (2013.01); *C12N 15/62* (2013.01); *C12P 21/00* (2013.01); *A61K 38/00* (2013.01); *C07K 2317/622* (2013.01); *C07K 2317/732* (2013.01); *C07K 2319/00* (2013.01); *C07K 2319/21* (2013.01); *C07K 2319/22* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,116,964 A | 5/1992 | Capon et al. |
| 5,541,067 A | 7/1996 | Lo et al. |
| 5,620,939 A | 4/1997 | Halasa et al. |
| 6,344,192 B1 | 2/2002 | Grooten et al. |
| 8,124,084 B2 | 2/2012 | Lefrancois et al. |
| 8,507,222 B2 | 8/2013 | Wong et al. |
| 2003/0190888 A1 | 9/2003 | Fraser |
| 2004/0156826 A1 | 8/2004 | Dangond et al. |
| 2006/0263857 A1 | 11/2006 | Lefrancois et al. |
| 2009/0117618 A1 | 5/2009 | Herrmann et al. |
| 2009/0324538 A1 | 12/2009 | Wong et al. |

FOREIGN PATENT DOCUMENTS

| | | |
|---|---|---|
| EP | 0971728 A1 | 1/2000 |
| EP | 1777294 A1 | 4/2007 |
| EP | 1934353 A2 | 6/2008 |
| KR | 10-2007-0002052 A | 1/2007 |
| WO | WO-94/04689 A1 | 3/1994 |

(Continued)

OTHER PUBLICATIONS

Belmont H.J. et al. "Potent antitumor activity of a tumor-specific soluble TCR/IL-2 fusion protein." Clin Immunol. Oct. 2006;121(1):29-39.

Benton and David, "Screening λgt Recombinant Clones by Hybridization to Single Plaques in situ", Science, vol. 196:180-182. 1977.

Bessard et al., "High antitumor activity of RLI, an interleukin-15 (IL-15)-IL-15 receptor α fusion protein, in metastatic melanoma and colorectal cancer", Mol. Cancer Ther. vol. 8:2736-2745. Sep. 2009.

Bork, 2000, Genome Research 10:398-400.

(Continued)

*Primary Examiner* — Bridget E Bunner
*Assistant Examiner* — Fozia Hamud
(74) *Attorney, Agent, or Firm* — Mintz Levin Cohn Ferris Glovsky and Popeo, P.C.; Peter F. Corless

(57) ABSTRACT

The invention provides soluble fusion protein complexes having at least two soluble fusion proteins. The first fusion protein is a biologically active polypeptide covalently linked to an interleukin-15 (IL-15) polypeptide or a functional fragment thereof. The second fusion protein is a second biologically active polypeptide covalently linked to a soluble interleukin-15 receptor alpha (IL-15Rα) polypeptide or a functional fragment thereof. In the complexes of the invention, one or both of the first and second fusion proteins further includes an immunoglobulin Fc domain or a functional fragment thereof; and the first fusion protein binds to the soluble IL-15Rα domain of the second fusion protein to form a soluble fusion protein complex. The invention further provides methods for making and using the complexes of the invention.

18 Claims, 82 Drawing Sheets

Specification includes a Sequence Listing.

(56) References Cited

FOREIGN PATENT DOCUMENTS

| WO | WO-94/29350 A2 | 12/1994 |
|---|---|---|
| WO | WO-96/32478 A1 | 10/1996 |
| WO | WO-97/34631 A1 | 9/1997 |
| WO | WO-2005/046449 A2 | 5/2005 |
| WO | WO-2005085282 A1 | 9/2005 |
| WO | WO-2007001677 A2 | 1/2007 |
| WO | WO-2008/143794 A1 | 11/2008 |
| WO | WO-2009117117 A1 | 9/2009 |

OTHER PUBLICATIONS

Bouchard et al., "The Exon-3-Encoded Domain of IL-15Rα Contributes to IL-15 High-Affinity Binding and is Crucial for the IL-15 Antagonistic Effect of Soluble IL-15Rα", Journal of Molecular Biology, vol. 382:1-12. 2008.
Capon et al., "Desgining CD4 immunoadhesins for AIDS therapy", Nature, vol. 337:525-531. Feb. 1989.
Chamow and Ashenazi, "Immunoadhesins: principles and applications", Trends Biotechnology., vol. 14:52-60. Feb. 1996.
Cragg and Glennie, :Antibody specificity controls in vivo effector mechanisms of anti-CD20 reagents, Blood, vol. 103:2738-2743. Apr. 2004.
Davis, "Molecular Genetics of The T Cell-Receptor Beta Chain", Annual Review of Immunology, vol. 3:537-560. 1985.
Doerks et al., 1998, Trends in Genetics 14:248-250.
Dubois et al., "Preassociation of IL-15 with IL-15Rα-IgG1-Fc Enhances its Activity on Proliferation of NK and CD8+/CD44high T cells and Its Antitumor Action", Journal of Immunology, vol. 180:2099-2106. 2008.
Epardaud et al., "Interleukin-15/Interleukin-15Rα Complexes Promote Destruction of Established Tumors by Reviving Tumor-Resident CD8+ T Cells", Cancer Research, vol. 68:2972-2983. Apr. 2008.
Fleer, "Engineering yeast for high level expression" Current Opinion in Biotechnology, vol. 3:486-496. 1992.
Galfre and Milstein, "Preparation of Monoclonal Antibodies: Strategies and procedures", Methods in Enzymology, vol. 73:1-46. 1981.
Gillies et al., "An anti-CD20-IL-2 immunocytokine is highly efficacious in a CSID mouse model of establishedhuman B lymphoma", Blood, vol. 105:3972-3978. May 2005.
Graham et al., "Characteristics of a Human Cell Line Transformed by DNA from Human Adenovirus Tyoe 5", Journal of General Viology, vol. 36:59-72. 1977.
Grunstein and Hogness, "Colony hybridization: A method for the isolation of cloned DNAs that contain a specific gene", Proc. Nat. Acad. Sci. USA, vol. 72:3961-3965. Oct. 1975.
Han et al., "IL-15:IL-15 receptor alpha superagonist complex: High-level co-expression in recombinanty mammalian cells, purification and characterization", Cytokine, vol. 56:604-810. 2011.
Hessell et al., "Fc receptor but not complement binding is important in antibody protection against HIV", Nature, vol. 449:101-105. Sep. 2007.
Hezareh M et al. "Effector function activities of a panel of mutants of a broadly neutralizing antibody against human immunodeficiency virus type 1." J Virol. Dec. 2001;75(24):12161-8.
Hughes et al., "Transfer of a TCR Gene Derived from a Patient with a marked Antitumor Response Conveys Highly Active T-Cell Effector Functions", Human Gene Therapy, vol. 16:457-472. Apr. 2005.
Kimmel, "Identification and Characterization of Specific Clones: Strategy for Confirming the Validity of Presumptive Clones", Methods in Enzymology, vol. 152:507-511. 1967.
Lawrencia et al., "Transfection of urothelial cells using methyl-β-cyclodxtrin solubilized cholesterol and Dotap", Gene Therapy, vol. 8:760-768.2001.
Lazar E. et al. "Transforming growth factor alpha: mutation of aspartic acid 47 and leucine 48 results in different biological activities." Mol Cell Biol. Mar. 1988;8(3):1247-52.

Mortier et al., "Soluble Interleukin-15 Receptor α (IL-15Rα-sushi as a Selective and Potent Agonist of IL-15 Action through IL-15Rβ/γ", Journal of Biological Chemistrty, vol. 281:1612-1619. Jan. 2006.
Moskaug et al., "Translocation of Diptheria Toxin A-fragment to the Cytosol", Journal of Biological Chemistry, vol. 26:15709-15713. 1989.
Mosquera et al., "In Vitro and In Vivo Characterization of a Novel Antibody-Like Single-Chain TCR Human IgG1 Fusion Protein", Journal of Immunology,vol. 174:4381-4388. 2005.
Ng et al. "Liposomal Polyene Antobiotics", Methods in Enzymology, vol. 391:304-313. 2005.
Nogawa et al., "Intravesical administration of small interfering RNA targeting PLK-1 successfully prevents the growth of bladder cancer", Journal of CLinical Investigation, vol. 115:978-985. 2005.
Olsnes and Phil, "Chimeric Toxins", Pharmacology and Therapeutics, vol. 26:355-381. 1982.
Ortiz-Sánchez E, et al. "Antibody-cytokine fusion proteins: applications in cancer therapy." Expert Opin Biol Ther. May 2008;8(5):609-32.
Pastan et al., "Immunotoxins", Cell, vol. 47:641-648. Dec. 1986.
Pastan et al., "Recombinant Toxins as Novel Therapeutic Agents", Annual Review Biochemistry, vol. 61:331-354. 1992.
Pettit DK et al. "Structure-function studies of interleukin 15 using site-specific mutagenesis, polyethylene glycol conjugation, and homology modeling." J Biol Chem. Jan. 24, 1997;272(4):2312-8.
Rossi et al., "CD20-targeted tetrameric interferon-α, a novel and potent immunocytokine fir the therapy of B-cell lymphomas", Blood, vol. 114:3864-3870. Oct. 2009.
Rubenstein et al., "Converting IL-15 to a superagonist by binding to soluble IL-15Rα", Proc. Natl. Acad. Sci. USA, vol. 103:9166-9171. Jun. 2006.
Skolnick et al, 2000, Trends in Biotech. 18(1):34-39.
Sprent et al., "T-cell proliferation in vivo and the role of cytokines", Philos. Trans R. Soc. Lond. B. Biol. Sci., vol. 355:317-322. 2000.
Stoklasek et al., "Combined IL-15/IL-15Rα Immunotherapy Maximizes IL-15 Activity In Vivo", Journal of Immunology, vol. 177:6072-6080. 2006.
Tietze et al., "Delineation of antigen-specific and antigen-nonspecific CD8+ memory T-cell responses after cytokine-based cancer immunotherapy", Blood, vol. 119:3073-3082. Mar. 2012.
Tokuriki and Tawflik, Current Opinion in Structural Biology 2009, 19:596-604.
Tough et al., "An IFN-γ-Dependent Pathway Controls Stimulation of Memory Phenotype CD8+ T Cell Turnover In vivo by IL-12, IL-18, and IFN-γ", Journal of Immunology, vol. 166:6007-6011. 2001.
Trevisani et al., "Ethanol Causes Inflammation in the Airways by a Neurogenic and TRPV1-Dependent Mechanism", Journal of Pharmacology and Experimental Therapeutics, vol. 309:1167-1173. 2004.
Trevisani, "Ethanol elicits and potentiates nociceptor responses via the vanilloid receptor-1", Nature Neuroscience, vol. 5:546-551. 2001.
Tyagi et al., "Urodynamic and Immunohistochemical Evaluation of Intravesical Capsaicin Delivery Using Thermosensitive Hydrogel and Liposomes", Journal of Urology, vol. 171:483-489. Jan. 2004.
Urlaub and Chasin, "Isolation of Chinese hamster cell mutants deficient in dihydrofolate reductase activity", Proc. Natl. Acad. Sci. USA, vol. 77:4216-4220. Jul. 1980.
Villinger et al., "IL-15 is superior to IL-2 in the generation of long-lived antigen specific memory CD4 and CD8 T cells in rhesus macaques", Vaccine, vol. 22:3510-3521. 2004.
Wahl et al., "Molecular Hybridization of Immobilized Nucleic Acids: Theoretical Conepts and Practical Considerations", Methods in Enzymology, vol. 152:399-407. 1987.
Waldmann, "The biology of interleukin-2 and interleukin-15: implications for cancer therapy and vaccine design", Nature Reviews Immunology, vol. 6:595-601. Aug. 2006.
Waldmann T et al. 37 IL-15 Receptors, 2000, pp. 1521-1528.
Ward et al., "*E. coli* expression and purification of human and cynomolgus IL-15", Protein Expression and Purification, vol. 68:42-48. 2009.

(56) References Cited

OTHER PUBLICATIONS

Weidanz JA, "Display of functional alphabeta single-chain T-cell receptor molecules on the surface of bacteriophage." J Immunol Methods. Dec. 1, 1998;221(1-2):59-76.
Wells JA et al. "Additivity of mutational effects in proteins." Biochemistry. Sep. 18, 1990;29(37):8509-17.
Wen J. et al. "Targeting activity of a TCR/IL-2 fusion protein against established tumors." Cancer Immunol Immunother. Dec. 2008;57(12):1781-94.
Whitlow and Filpula, "Single-Chain Fv Proteins and Their Fusion Proteins", Methods: A Companioni to methods in Enzymology, vol. 2:97-105. Apr. 1991.
Wong et al., "Interleukin-15:Interieukin-15 receptor α scaffold for creation of multivalent targeted immune molecules", Protein Engineering, Design & Delection, vol. 24:373-383. Dec. 2010.
Xuan et al., "Targeted deluivery of interferon-alpha via fusion to anti-CD20 results in potent antitumor activity against B-cell lymphome", Blood, vol. 115:2864-2871. Apr. 2010.
Zhang et al., "Potent and Selective Stimulation of Memory-Phenotype CD8+ T Cells in Vivo by IL-15", Immunity, vol. 8:591-599. May 1998.
Zhu X et al. "Novel human interleukin-15 agonists." J Immunol. Sep. 15, 2009;183(6):3598-607.
Zhu X. et al. "Visualization of p53(264-272)/HLA-A*0201 complexes naturally presented on tumor cell surface by a multimeric soluble single-chain T cell receptor." J Immunol. Mar. 1, 2006;176(5):3223-32.
Bergamaschi, Cristina et al., "Intracellular Interaction of Interleukin-15 with Its Receptor alpha during Production leads to Mutual Stabilization and Increased Bioactivity," The Journal of Biological Chemistry, vol. 283.7 (2008):4189-4199.
Bevan, Michael J., "In Thymic Selection, Peptide Diversity Gives and Takes Away," Immunity, vol. 7 (1997):175-178.
Bjorkman, Pamela J., "MHC Restriction in Three Dimensions: A View of T Cell Receptor/Ligand Interactions," Cell, vol. 89 (1997):167-170.
Davis, Mark M. et al., "T-cell antigen receptor genes and T-cell recognition," Nature, vol. 334 (1986):395-402.
Davis, Mark M. et al., "Ligand Recognition by alphabeta Cell Receptors," Annual Reviews Immunology, vol. 16 (1998):523-544.
Gomes-Giacoia, Evan et al., "Intravesical ALT-803 adn BCG Treatment Reduces Tumor Burden in a Carcinogen Induced Bladder Cancer Rat Model; a Role for Cytokine Production adn NK Cell Expansion," PLoS One, vol. 9(6):e96705, 11 pages (2014).
Matsumoto, Kazuhiro et al., "Intravesical Interleukin-15 Gene Therapy in an Orthotopic Bladder Cancer Mode," Human Gene Therapy, vol. 22:1423-1432 (2011).
Rabinowitz, Joshua D. et al., "Kinetic discrimination in T-cell activation," Proc. Natl. Acad. Sci. USA, vol. 93 (1996):1401-1405.
Steel Jason C. et al., "Interleukin-15 and Its Receptor Augment Dendritic Cell Vaccination against the neu Oncogene through the Introduction of Antibodies Partially Independent of CD4 Help," Cancer Res., vol. 70(3):1072-1081 (2010).
Sukumar, Madhusudhanan et al., "Modulating immunometabolism of tumor specific CD8 T cells to enhance T cell based therapy for cancer," Journal for ImmunoTherapy of Cancer, vol. 2(Suppl. 3):O2, 2 pages (2014).
Tomalia, Donald A., "Starburst/Cascade Dendrimers: Fundamental Building Blocks for a New Nanoscopic Chemistry Set," Aldrichimica Acta, vol. 26.4 (1993):91-101.
Tonegawa, Susumu, "Somatic Generation of Immune Diversity," Bioscience Reports, vol. 8.1 (1988):3-26.
Valitutti, Salvatore et al., "Serial triggering of many T-cell receptors by a few peptide—MHC complexes," Nature, vol. 375 (1995):148-151.
Wu, Jennifer, "IL-15 Agonists: The Cancer Cure Cytokine," J. Mol. Genet. Med., vol. 7(4):1000085, 3 pages (2013).
Bernard et al., "Identification of an interleukin-15alpha receptor-binding site on human interleukin-15." J Biol. Chem. 279(23):24313-24322 (2004).
Beers and Berkow Editors, The Merck Manual (1999), 17*th* edition, pp. 986-995.
Stratagene Catalog, 1988, p. 39.

FIG. 3A atggacagacttacttcttcattcctgctcctgattgtccctgcgtacgtcttgtcccagtc
agtgacgcagcccgatgctcgcgtcactgtctctgaaggagcctctctgcagctgagatgca
agtattcctactctgggacaccttatctgttctggtatgtccagtacccgcggcaggggctg
cagctgctcctcaagtactattcaggagacccagtggttcaaggagtgaatggcttcgaggc
tgagttcagcaagagtaactcttccttccacctgcggaaagcctctgtgcactggagcgact
ctgctgtgtacttctgtgttttgagcgaggatagcaactatcagttgatctggggctctggg
accaagctaattataaagccagacactagtggtggcggtggcagcggcggtggtggttccgg
tggcggcggttctggcggtggcggttcctcgagcaattcaaaagtcattcagactccaagat
atctggtgaaagggcaaggacaaaaagcaaagatgaggtgtatccctgaaaagggacatcca
gttgtattctggtatcaacaaaataagaacaatgagtttaaattttgattaactttcagaa
tcaagaagttcttcagcaaatagacatgactgaaaaacgattctctgctgagtgtccttcaa
actcaccttgcagcctagaaattcagtcctctgaggcaggagactcagcactgtacctctgt
gccagcagtctgtcaggggcggcacagaagttttctttggtaaaggaaccaggctcacagt
tgtagaggacctgaacaaggtgttcccacccgaggtcgctgtgtttgagccatcagaagcag
agatctcccacacccaaaaggccacactggtgtgcctggccacaggcttcttccctgaccac
gtggagctgagctggtgggtgaatgggaaggaggtgcacagtggggtcagcacggacccgca
gcccctcaaggagcagcccgccctcaatgactccagatactgcctgagcagccgcctgaggg
tctcggccaccttctggcagaaccccgcaaccacttccgctgtcaagtccagttctacggg
ctctcggagaatgacgagtggacccaggatagggccaaacccgtcacccagatcgtcagcgc
cgaggcctggggtagagcagacgaattcatcacgtgccctcccccatgtccgtggaacacg
cagacatctgggtcaagagctacagcttgtactccagggagcggtacatttgtaactctggt
ttcaagcgtaaagccggcacgtccagcctgacggagtgcgtgttgaacaaggccacgaatgt
cgcccactggacaaccccagtctcaaatgcattagagaattcgcctccaccaagggcccat
cggtcttccccctggcaccctcctccaagagcacctctggggcacagcggccctgggctgc
ctggtcaaggactacttccccgaaccggtgacggtgtcgtggaactcaggcgccctgaccag
cggcgtgcacaccttcccggctgtcctacagtcctcaggactctactcctcagcagcgtgg
tgaccgtgccctccagcagcttgggcacccagacctacatctgcaacgtgaatcacaagccc
agcaacaccaaggtggacaagaaagttgagcccaaatcttgtgacaaaactcacacatgccc
accgtgcccagcacctgaactcctggggggaccgtcagtcttcctcttccccccaaaaccca
aggacaccctcatgatctcccggacccctgaggtcacatgcgtggtggtggacgtgag

FIG. 3B

```
ccacgaagaccctgaggtcaagttcaactggtacgtggacggcgtggaggtgcataatgcca
agacaaagccgcgggaggagcagtacaacagcacgtaccgtgtggtcagcgtcctcaccgtc
ctgcaccaggactggctgaatggcaaggagtacaagtgcaaggtctccaacaaagccctccc
agcccccatcgagaaaaccatctccaaagccaagggcagccccgagaaccacaggtgtaca
ccctgcccccatcccgggatgagctgaccaagaaccaggtcagcctgacctgcctggtcaaa
ggcttctatcccagcgacatcgccgtggagtgggagagcaatgggcagccggagaacaacta
caagaccacgcctcccgtgctggactccgacggctccttcttcctctacagcaagctcaccg
tggacaagagcaggtggcagcaggggaacgtcttctcatgctccgtgatgcatgaggctctg
cacaaccactacacgcagaagagcctctccctgtctccgggtaaa
```

FIG. 4A mdrltssflllivpayvlsqsvtqpdarvtvsegaslqlrckysysgtpylfwyvqypr
<        ><
  Ig leader         TCR-Vα qglqlllkyysgdpvvqgvngfeaefsksnssfhlrkasvhwsdsavyfcvlsedsnyq
  TCR-Vα liwgsgtkliikpdtsggggsggggsggggsggggsssnskviqtprylvkgggqkakm
        ><                    ><
  TCR-Vα          linker            TCR-Vβ rcipekghpvvfwyqqnknnefkflinfqnqevlqqidmtekrfsaecpsnspcsleiq
  TCR-Vβ sseaqdsalylcasslsgggtevffgkgtrltvvedlnkvfppevavfepseaeishtq
                        ><
  TCR-Vβ                      TCR-Cβ katlvclatgffpdhvelswwvngkevhsgvstdpqplkeqpalndsryclssrlrvsa
  TCR-Cβ

FIG. 4B tfwqnprnhfrcqvqfyglsendewtqdrakpvtqivsaeawgradef<u>itcpppmsveh</u>

>     <

TCR-Cβ                                          huIL-15RαSu

<u>adiwvksyslysreryicnsgfkrkagtssltecvlnkatnvahwttpslkcire</u>fast

>    < huIL-15RαSu                                            huIgG1

<u>kgpsvfplapsskstsggtaalgclvkdyfpepvtvswnsqaltsgvhtfpavlqssgl</u> huIgG1 constant region

<u>yslssvvtvpssslgtqtyicnvnhkpsntkvdkkvepkscdkthtcppcpapellggp</u> huIgG1 constant region

<u>svflfppkpkdtlmisrtpevtcvvvdvshedpevkfnwyvdgvevhnaktkpreeqyn</u> huIgG1 constant region

<u>styrvvsvltvlhqdwlngkeykckvsnkalpapiektiskakgqprepqvytlppsrd</u> huIgG1 constant region

<u>eltknqvsltclvkgfypsdiavewesngqpennykttppvldsdgsfflyskltvdks</u>

FIG. 4C huIgG1 constant region rwqqgnvfscsvmhealhnhytqkslslspgk

> huIgG1 constant region

FIG. 6A

```
ATGGAGACAGACACACTCCTGTTATGGGTACTGCTGCTCTGGGTTCCAGGTTCCACCGGTCA
GTCAGTGACGCAGCCCGATGCTCGCGTCACTGTCTCTGAAGGAGCCTCTCTGCAGCTGAGAT
GCAAGTATTCCTACTCTGGGACACCTTATCTGTTCTGGTATGTCCAGTACCCGCGGCAGGGG
CTGCAGCTGCTCCTCAAGTACTATTCAGGAGACCCAGTGGTTCAAGGAGTGAATGGCTTCGA
GGCTGAGTTCAGCAAGAGTAACTCTTCCTTCCACCTGCGGAAAGCCTCTGTGCACTGGAGCG
ACTCTGCTGTGTACTTCTGTGTTTTGAGCGAGGATAGCAACTATCAGTTGATCTGGGGCTCT
GGGACCAAGCTAATTATAAAGCCAGACACTAGTGGTGGCGGTGGCAGCGGCGGTGGTGGTTC
CGGTGGCGGCGGTTCTGGCGGTGGCGGTTCCTCGAGCAATTCAAAAGTCATTCAGACTCCAA
GATATCTGGTGAAAGGGCAAGGACAAAAAGCAAAGATGAGGTGTATCCCTGAAAAGGGACAT
CCAGTTGTATTCTGGTATCAACAAAATAAGAACAATGAGTTTAAATTTTTGATTAACTTTCA
GAATCAAGAAGTTCTTCAGCAAATAGACATGACTGAAAAACGATTCTCTGCTGAGTGTCCTT
CAAACTCACCTTGCAGCCTAGAAATTCAGTCCTCTGAGGCAGGAGACTCAGCACTGTACCTC
TGTGCCAGCAGTCTGTCAGGGGCGGCACAGAAGTTTTCTTTGGTAAAGGAACCAGGCTCAC
AGTTGTAGAGGACCTGAACAAGGTGTTCCCACCCGAGGTCGCTGTGTTTGAGCCATCAGAAG
CAGAGATCTCCCACACCCAAAAGGCCACACTGGTGTGCCTGGCCACAGGCTTCTTCCCTGAC
CACGTGGAGCTGAGCTGGTGGGTTAACGGGAAGGAGGTGCACAGTGGGGTCAGCACGGACCC
GCAGCCCCTCAAGGAGCAGCCCGCCCTCAATGACTCCAGATACTGCCTGAGCAGCCGCCTGA
GGGTCTCGGCCACCTTCTGGCAGAACCCCCGCAACCACTTCCGCTGTCAAGTCCAGTTCTAC
GGGCTCTCGGAGAATGACGAGTGGACCCAGGATAGGGCCAAACCCGTCACCCAGATCGTCAG
CGCCGAGGCCTGGGGTAGAGCAGACATCACGTGCCCTCCCCCATGTCCGTGGAACACGCAG
ACATCTGGGTCAAGAGCTACAGCTTGTACTCCAGGGAGCGGTACATTTGTAACTCTGGTTTC
AAGCGTAAAGCCGGCACGTCCAGCCTGACGGAGTGCGTGTTGAACAAGGCCACGAATGTCGC
CCACTGGACAACCCCCAGTCTCAAATGTATTAGAGCTAGCACCAAGGGCCCATCGGTCTTCC
CCCTGGCACCCTCCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGACCAGCGGCGTGCA
CACCTTCCCGGCTGTCCTACAGTCCTCAGGACTCTACTCCCTCAGCAGCGTGGTGACCGTGC
CCTCCAGCAGCTTGGGCACCCAGACCTACATCTGCAACGTGAATCACAAGCCCAGCAACACC
AAGGTGGACAAGAAAGTTGAGCCCAAATCTTGTGACAAAACTCACACATGCCCACCGTGCCC
AGCACCTGAACTCCTGGGGGGACCGTCAGTCTTCCTCTTCCCCCAAAACCCAAGGACACCC
TCATGATCTCCCGGACCCCTGAGGTCACATGCGTGGTGGTGGACGTGAGCCACGAAGA
```

FIG. 6B

```
CCCTGAGGTCAAGTTCAACTGGTACGTGGACGGCGTGGAGGTGCATAATGCCAAGACAAAGC
CGCGGGAGGAGCAGTACAACAGCACGTACCGTGTGGTCAGCGTCCTCACCGTCCTGCACCAG
GACTGGCTGAATGGCAAGGAGTACAAGTGCAAGGTCTCCAACAAAGCCCTCCCAGCCCCCAT
CGAGAAAACCATCTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTCAAAGGCTTCTAT
CCCAGCGACATCGCCGTGGAGTGGGAGAGCAATGGGCAGCCGGAGAACAACTACAAGACCAC
GCCTCCCGTGCTGGACTCCGACGGCTCCTTCTTCCTCTACAGCAAGCTCACCGTGGACAAGA
GCAGGTGGCAGCAGGGGAACGTCTTCTCATGCTCCGTGATGCATGAGGCTCTGCACAACCAC
TACACGCAGAAGAGCCTCTCCCTGTCTCCGGGTAAATAA
```

FIG. 7A metdtlllwvlllwvpgstggsvtqpdarvtvsegaslglrckysysgtpylfwyvqyp
<              ><
   Ig leader         TCR-Vα rqglqlllkyysgdpvvqgvngfeaefsksnssfhlrkasvhwsdsavyfcvlsedsny
   TCR-Vα qliwgsgtkliikpdtsggggsggggsggggsggggsssnskvigtprylvkgqgqkak
          ><                    ><
   TCR-Vα          linker            TCR-Vβ mrcipekghpvvfwyqqnknnefkflinfgnqevlqgidmtekrfsaecpsnspcslei
   TCR-Vβ gsseaqdsalylcasslsgggtevffgkgtrltvvedlnkvfppevavfepseaeisht
                              ><
   TCR-Vβ                         TCR-Cβ qkatlvclatgffpdhvelswwvngkevhsgvstdpqplkeqpalndsryclssrlrvs
   TCR-Cβ

FIG. 7B atfwqnprnhfrcqvqfyglsendewtqdrakpvtqivsaeawgraditcpppmsveha

><

TCR-Cβ                                                huIL-15RαSu diwvksyslysreryicnsqfkrkagtssltecvlnkatnvahwttpslkcirastkgp >< huIL-15RαSu                                                 huIgG1 svfplapsskstsggtaalgclvkdyfpepvtvswnsgaltsgvhtfpavlqssglysl huIgG1 constant region ssvvtvpssslgtqtyicnvnhkpsntkvdkkvepkscdkthtcppcpapellggpsvf huIgG1 constant region lfppkpkdtlmisrtpevtcvvvdvshedpevkfnwyvdgvevhnaktkpreeqynsty huIgG1 constant region rvvsvltvlhqdwlngkeykckvsnkalpapiektiskakgqprepqvytlppsrdelt huIgG1 constant region knqvsltclvkgfypsdiavewesngqpennykttppvldsdgsfflyskltvdksrwq

FIG. 7C huIgG1 constant region ggnvfscsvmhealhnhytqkslslspgk

> huIgG1 constant region

FIG. 9

```
ATGGACAGACTTACTTCTTCATTCCTGCTCCTGATTGTCCCTGCGTACGTCTTGGCCCAGAA
GGTAACACAGACTCAGACTTCAATTTCTGTGATGGAGAAGACAACGGTGACAATGGACTGTG
TGTATGAAACCCGGGACAGTTCTTACTTCTTATTCTGGTACAAGCAAACAGCAAGTGGGGAA
ATAGTTTTCCTTATTCGTCAGGACTCTTACAAAAGGAAAATGCAACAGAAGGTCATTATTC
TCTGAACTTTCAGAAGCCAAAAAGTTCCATCGGACTCATCATCACTGCCACACAGATTGAGG
ACTCAGCAGTATATTTCTGTGCTATGAGAGACACAAATGCTTACAAAGTCATCTTTGGAAAA
GGGACACATCTTCATGTTCTGCCTACTAGTGGTGGCGGTGGCAGCGGCGGTGGTGGTTCCCC
TGGTGGCGGCGGTTCTGGCGGTGGCGGTTCCTCGAGCGAGGCTGCAGTCACCCAAAGTCCAA
GAAGCAAGGTGGCAGTAACAGGAGGAAAGGTGACATTGAGCTGTCACCAGACTAATAACCAT
GACTATATGTACTGGTATCGGCAGGACACGGGGCATGGGCTGAGGCTGATCCATTACTCATA
TGTCGCTGACAGCACGGAGAAGGAGATATCCCTGATGGGTACAAGGCCTCCAGACCAAGCC
AAGAGAATTTCTCTCTCATTCTGGAGTTGGCTTCCCTTTCTCAGACAGCTGTATATTTCTGT
GCCAGCAGCCCCCACTCCTATGAACAGTACTTCGGTCCCGGCACCAGGCTCACGGTTTTAGA
GGACCTGAACAAGGTGTTCCCACCCGAGGTCGCTGTGTTTGAGCCATCAGAAGCAGAGATCT
CCCACACCCAAAAGGCCACACTGGTGTGCCTGGCCACAGGCTTCTTCCCTGACCACGTGGAG
CTGAGCTGGTGGGTTAACGGGAAGGAGGTGCACAGTGGGGTCAGCACGGACCCGCAGCCCCT
CAAGGAGCAGCCCGCCCTCAATGACTCCAGATACTGCCTGAGCAGCCGCCTGAGGGTCTCGG
CCACCTTCTGGCAGAACCCCCGCAACCACTTCCGCTGTCAAGTCCAGTTCTACGGGCTCTCG
GAGAATGACGAGTGGACCCAGGATAGGGCCAAACCTGTCACCCAGATCGTCAGCGCCGAGGC
CTGGGGTAGAGCAGACAACTGGGTGAATGTAATAAGTGATTTGAAAAAAATTGAAGATCTTA
TTCAATCTATGCATATTGATGCTACTTTATATACGGAAAGTGATGTTCACCCCAGTTGCAAA
GTAACAGCAATGAAGTGCTTTCTCTTGGAGTTACAAGTTATTTCACTTGAGTCCGGAGATGC
AAGTATTCATGATACAGTAGAAAATCTGATCATCCTAGCAAACGACAGTTTGTCTTCTAATG
GGAATGTAACAGAATCTGGATGCAAAGAATGTGAGGAACTGGAGGAAAAAATATTAAAGAA
TTTTTGCAGAGTTTTGTACATATTGTCCAAATGTTCATCAACACTTCTTAA
```

FIG. 10A mdrltssflllivpayvlagkvtgtgtsisvmekttvtmdcvyetrdssyflfwykqta
<           ><
  Ig leader         TCR-Vα sgeivflirqdsykkenateghyslnfqkpkssigliitatgiedsavyfcamrdtnay
  TCR-Vα kvifgkgthlhvlptsggggsggggspggggsggggssseaavtqsprskvavtggkvt
           ><                    ><
  TCR-Vα        linker              TCR-Vβ lschgtnnhdymywyrqdtghglrlihysyvadstekgdipdgykasrpsgenfslile
  TCR-Vβ laslsqtavyfcassphsyeqyfgpgtrltvledlnkvfppevavfepseaeishtqka
                               ><
  TCR-Vβ                          TCR-Cβ tlvclatgffpdhvelswwvngkevhsgvstdpqplkeqpalndsryclssrlrvsatf
  TCR-Cβ

FIG. 10B wqnprnhfrcqvqfyglsendewtqdrakpvtqivsaeawgradnwvnvisdlkkiedl

><

TCR-Cβ                                                huIL-15N72D iqsmhidatlytesdvhpsckvtamkcfllelqvislesgdasihdtvenliilandsl huIL-15N72D ssngnvtesgckeceeleeknikeflqsfvhivqmfints huIL-15N72D                           >

Reduced
1. T2 BF1 column pH4
2. T2 BF1 column pH3
3. T2 BF1 + R-protein A
4. c264scTCR/IgG1 BF1 + R-protein A
5. c264scTCR/IgG1ΔC$_H$1 BF1 + R-protein A Non-Reduced
6. T2 BF1 + R-protein A

| Proteins | Relative activity (%) |
|---|---|
| 264TCR-IL15N72D | 100 |
| T2M | 322 |

Binding of T2 or TCR-Ig to FcγRs on U937 cells

T2 Protein	c264scTCR/IgG1

FIG. 26A Mouse study
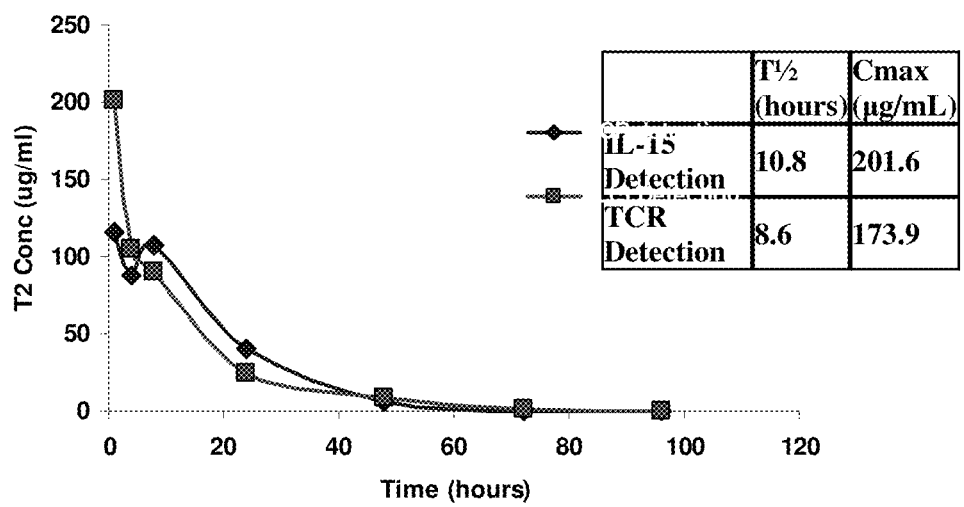
FIG. 26B Monkey study
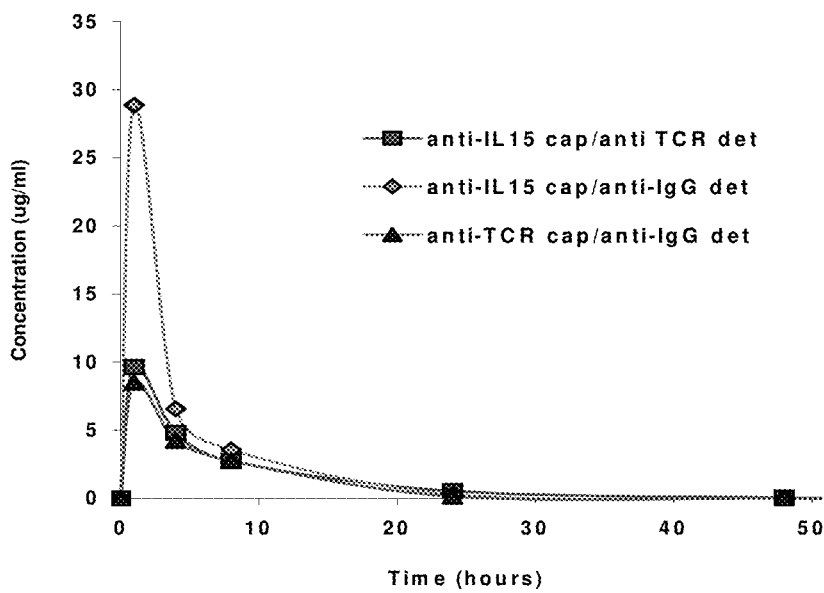

Fold increase=
% cells in media+T2 treated/
% cells in media alone

FIG. 37A
FIG. 37B
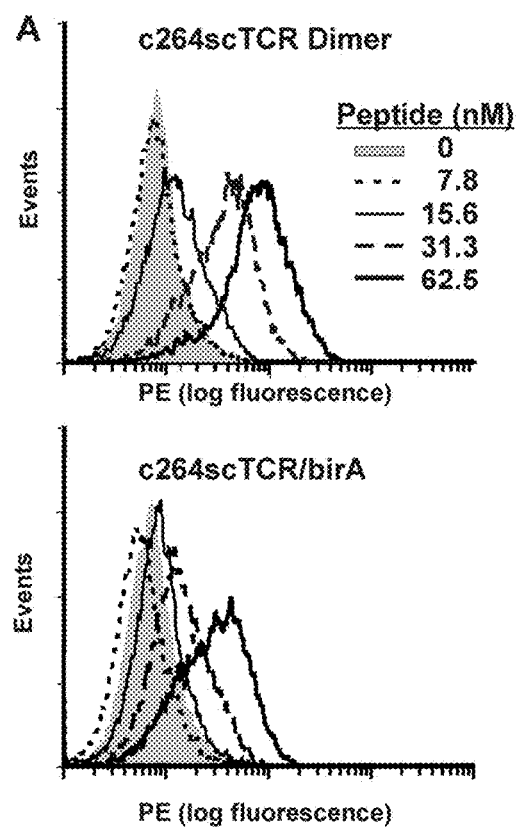
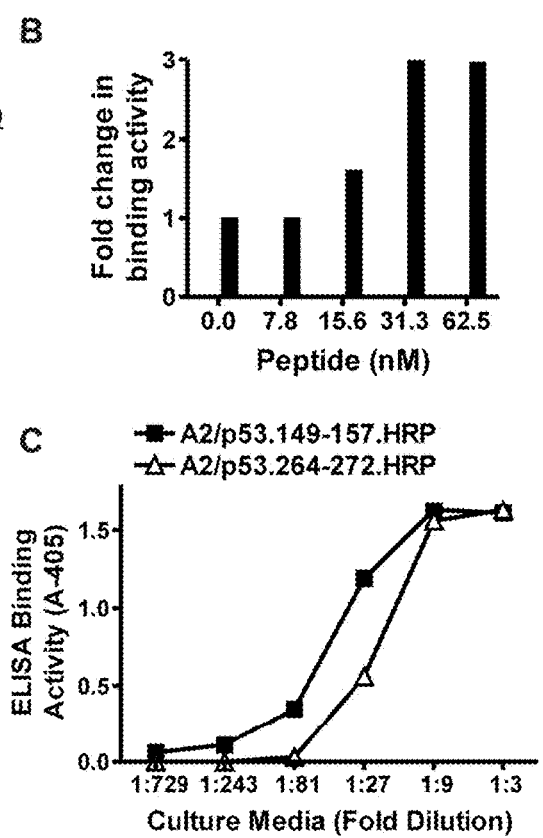
FIG. 37C

FIG. 39A
FIG. 39B
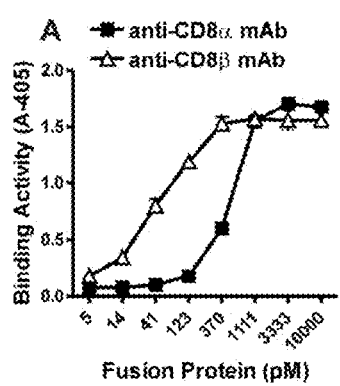
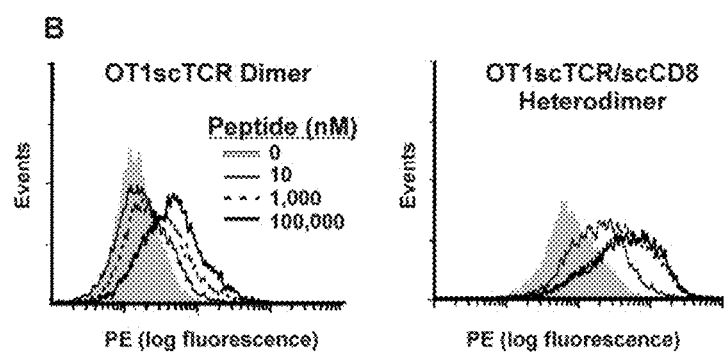

FIG. 40A
FIG. 40B
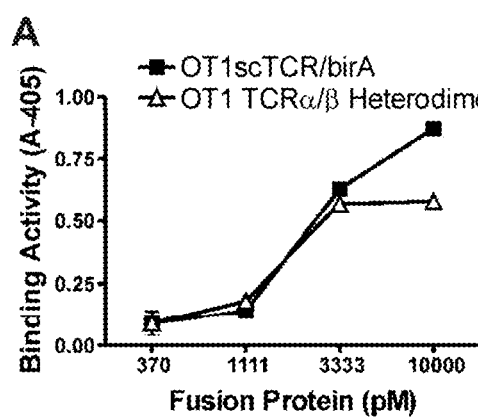
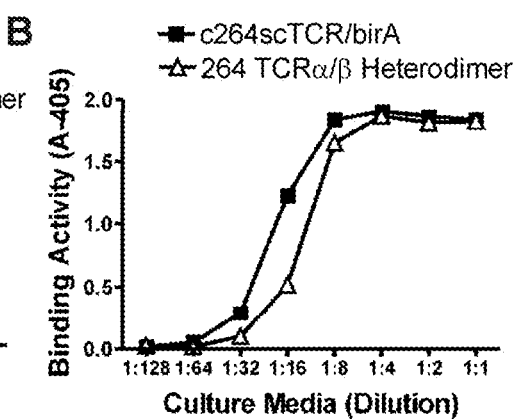

☰ 2° Ab alone
— scTCR/hIL-15:scTCR/hIL-15RαSu
— scTCR/hIL-15N72D:scTCR/hIL-15RαSu
--- scTCR/hIL-15D8N:scTCR/hIL-15RαSu ■ scTCR/hIL-15
◇ scTCR/hIL-15:scTCR/hIL-15RαSu
★ scTCR/hIL-15N72D
△ scTCR/hIL15N72D:scTCR/hIL-15RαSu
◆ scTCR/hIL-15D8N
▽ scTCR/hIL-15D8N:scTCR/hIL-15RαSu

FIG. 46 epkscdkthtcppcpapellggpsvflfppkpkdtlmisrtpevtcvvvdvshedpevkfnw
yvdgvevhnaktkpreeqynstyrvvsvltvlhqdwlngkeykckvsnkalpapiektiska
kgqprepqvytlppsrdeltknqvsltclvkgfypsdiavewesngqpennykttppvldsd
gsfflyskltvdksrwqqgnvfscsvmhealhnhytqkslslspgk

FIG. 51A

ATGGAGACAGACACACTCCTGTTATGGGTACTGCTGCTCTGGGTTCCAGG
<                 leader seq

TTCCACCGGTCAGTCAGTGACGCAGCCCGATGCTCGCGTCACTGTCTCTG
       ><         c264scTCR

AAGGAGCCTCTCTGCAGCTGAGATGCAAGTATTCCTACTCTGGGACACCT

TATCTGTTCTGGTATGTCCAGTACCCGCGGCAGGGGCTGCAGCTGCTCCT

CAAGTACTATTCAGGAGACCCAGTGGTTCAAGGAGTGAATGGCTTCGAGG

CTGAGTTCAGCAAGAGTAACTCTTCCTTCCACCTGCGGAAAGCCTCTGTG

CACTGGAGCGACTCTGCTGTGTACTTCTGTGTTTTGAGCGAGGATAGCAA

CTATCAGTTGATCTGGGGCTCTGGGACCAAGCTAATTATAAAGCCAGACA

CTAGTGGTGGCGGTGGCAGCGGCGGTGGTGGTTCCGGTGGCGGCGGTTCT

GGCGGTGGCGGTTCCTCGAGCAATTCAAAAGTCATTCAGACTCCAAGATA

TCTGGTGAAAGGGCAAGGACAAAAAGCAAAGATGAGGTGTATCCCTGAAA

AGGGACATCCAGTTGTATTCTGGTATCAACAAAATAAGAACAATGAGTTT

AAATTTTTGATTAACTTTCAGAATCAAGAAGTTCTTCAGCAAATAGACAT

GACTGAAAAACGATTCTCTGCTGAGTGTCCTTCAAACTCACCTTGCAGCC

TAGAAATTCAGTCCTCTGAGGCAGGAGACTCAGCACTGTACCTCTGTGCC

AGCAGTCTGTCAGGGGGCGGCACAGAAGTCTTCTTTGGTAAAGGAACCAG

GCTCACAGTTGTAGAGGACCTGAACAAGGTGTTCCCACCCGAGGTCGCTG

TGTTTGAGCCATCAGAAGCAGAGATCTCCCACACCCAAAAGGCCACACTG

GTGTGCCTGGCCACAGGCTTCTTCCCTGACCACGTGGAGCTGAGCTGGTG

GGTTAACGGGAAGGAGGTGCACAGTGGGGTCAGCACGGACCCGCAGCCCC

TCAAGGAGCAGCCCGCCCTCAATGACTCCAGATACTGCCTGAGCAGCCGC

CTGAGGGTCTCGGCCACCTTCTGGCAGAACCCCCGCAACCACTTCCGCTG

FIG. 51B

TCAAGTCCAGTTCTACGGGCTCTCGGAGAATGACGAGTGGACCCAGGATA

GGGCCAAACCCGTCACCCAGATCGTCAGCGCCGAGGCCTGGGGTAGAGCA

GACATCACGTGCCCTCCCCCATGTCCGTGGAACACGCAGACATCTGGGT
><      Human IL-15R • sushi domain

CAAGAGCTACAGCTTGTACTCCAGGGAGCGGTACATTTGTAACTCTGGTT

TCAAGCGTAAAGCCGGCACGTCCAGCCTGACGGAGTGCGTGTTGAACAAG

GCCACGAATGTCGCCCACTGGACAACCCCCAGTCTCAAATGCATTAGAGA
                                              ><

GCCGAAATCTTGTGACAAAACTCACACATGCCCACCGTGCCCAGCACCTG
           Human IgG1 CH2-CH3 (Fc) domain

AACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGT

GAGCCACGAAGACCCTGAGGTCAAGTTCAACTGGTACGTGGACGGCGTGG

AGGTGCATAATGCCAAGACAAAGCCGCGGGAGGAGCAGTACAACAGCACG

TACCGTGTGGTCAGCGTCCTCACCGTCCTGCACCAGGACTGGCTGAATGG

CAAGGAGTACAAGTGCAAGGTCTCCAACAAAGCCCTCCCAGCCCCCATCG

AGAAAACCATCTCCAAAGCCAAAGGGCAGCCCCGAGAACCACAGGTGTAC

ACCCTGCCCCCATCCCGGGATGAGCTGACCAAGAACCAGGTCAGCCTGAC

CTGCCTGGTCAAAGGCTTCTATCCCAGCGACATCGCCGTGGAGTGGGAGA

GCAATGGGCAGCCGGAGAACAACTACAAGACCACGCCTCCCGTGCTGGAC

TCCGACGGCTCCTTCTTCCTCTACAGCAAGCTCACCGTGGACAAGAGCAG

GTGGCAGCAGGGGAACGTCTTCTCATGCTCCGTGATGCATGAGGCTCTGC

ACAACCACTACACGCAGAAGAGCCTCTCCCTGTCTCCTGGTAAATAA
                                             >

FIG. 52 qsvtqpdarvtvsegaslqlrckysysgtpylfwyvqyprqglqlllkyysgdpvvqgvn
<                 c264scTCR gfeaefsksnssfhlrkasvhwsdsavyfcvlsedsnyqliwgsgtkliikpdtsggggs ggggsggggsggggsssnskviqtprylvkgqgqkakmrcipekghpvvfwyqqnknnef kflinfqnqevlqqidmtekrfsaecpsnspcsleiqsseagdsalylcasslsgggtev ffgkgtrltvvedlnkvfppevavfepseaeishtqkatlvclatgffpdhvelswwvng kevhsqvstdpqplkeqpalndsryclssrlrvsatfwqnprnhfrcqvqfyglsendew tqdrakpvtqivsaeawgraditcpppmsvehadiwvksyslysreryicnsgfkrkagt
               ><  Human IL-15R • sushi domain ssltecvlnkatnvahwttpslkcirepkscdkthtcppcpapellggpsvflfppkpkd
                    ><  Human IgG1 CH2-CH3 (Fc) domain tlmisrtpevtcvvvdvshedpevkfnwyvdgvevhnaktkpreeqynstyrvvsvltvl hqdwlngkeykckvsnkalpapiektiskakgqprepqvytlppsrdeltknqvsltclv kgfypsdiavewesngqpennykttppvldsdgsfflyskltvdksrwqqgnvfscsvmh ealhnhytqkslslspgk
              >

FIG. 53

ATGGATTTTCAGGTGCAGATTATCAGCTTCCTGCTAATCAGTGCTTCAGT
<      leader seq

CATAATGTCCAGAGGACAAATTGTTCTCTCCAGTCTCCAGCAATCCTGT
    ><

CTGCATCTCCAGGGGAGAAGGTCACAATGACTTGCAGGGCCAGCTCAAGT
   anti-CD20 light chain V domain

GTAAGTTACATCCACTGGTTCCAGCAGAAGCCAGGATCCTCCCCCAAACC

CTGGATTTATGCCACATCCAACCTGGCTTCTGGAGTCCCTGTTCGCTTCA

GTGGCAGTGGGTCTGGGACTTCTTACTCTCTCACAATCAGCAGAGTGGAG

GCTGAAGATGCTGCCACTTATTACTGCCAGCAGTGGACTAGTAACCCACC

CACGTTCGGAGGGGGGACCAAGCTGGAAATCAAAAGTGGAGGTGGCGGAT
           ><   linker

CAGGAGGCGGAGGTTCTGGCGGAGGTGGGAGTCAGGTACAACTGCAGCAG
        ><

CCTGGGGCTGAGCTGGTGAAGCCTGGGGCCTCAGTGAAGATGTCCTGCAA
   anti-CD20 heavy chain V domain

GGCTTCTGGCTACACATTTACCAGTTACAATATGCACTGGGTAAAACAGA

CACCTGGTCGGGGCCTGGAATGGATTGGAGCTATTTATCCCGGAAATGGT

GATACTTCCTACAATCAGAAGTTCAAAGGCAAGGCCACATTGACTGCAGA

CAAATCCTCCAGCACAGCCTACATGCAGCTCAGCAGCCTGACATCTGAGG

ACTCTGCGGTCTATTACTGTGCAAGATCGACTTACTACGGCGGTGACTGG

TACTTCAATGTCTGGGGCGCAGGGACCACGGTCACCGTCTCTGCAAACTG
              ><

GGTGAATGTAATAAGTGATTTGAAAAAAATTGAAGATCTTATTCAATCTA
     Human IL-15N72D

TGCATATTGATGCTACTTTATATACGGAAAGTGATGTTCACCCCAGTTGC

AAAGTAACAGCAATGAAGTGCTTTCTCTTGGAGTTACAAGTTATTTCACT

TGAGTCCGGAGATGCAAGTATTCATGATACAGTAGAAAATCTGATCATCC

TAGCAAACGACAGTTTGTCTTCTAATGGGAATGTAACAGAATCTGGATGC

AAAGAATGTGAGGAACTGGAGGAAAAAAATATTAAAGAATTTTTGCAGAG

TTTTGTACATATTGTCCAAATGTTCATCAACACTTCTTAA
               >

FIG. 54 qivlsqspailsaspgekvtmtcrasssvsyihwfqqkpgsspkpwiyatsnlasqvpvr
<            anti-CD20 light chain V domain fsgsgsgtsysltisrveaedaatyycqqwtsnpptfgggtkleiksggggsggggsggg
                                              ><    linker gsqvqlqqpgaelvkpgasvkmsckasgytftsynmhwvkqtpgrglewigaiypgngdt
 ><         anti-CD20 heavy chain V domain synqkfkgkatltadkssstaymqlssltsedsavyycarstyyggdwyfdvwgagttvt vsanwvnvisdlkkiedliqsmhidatlytesdvhpsckvtamkcfllelqvislesgda
   ><            Human IL-15N72D sihdtvenliilandslssngnvtesgckeceeleeknikeflqsfvhivqmfints
                                                        >

FIG. 55A

ATGGATTTTCAGGTGCAGATTATCAGCTTCCTGCTAATCAGTGCTTCAGT
<               leader seq

CATAATGTCCAGAGGACAAATTGTTCTCTCCCAGTCTCCAGCAATCCTGT
                 ><

CTGCATCTCCAGGGGAGAAGGTCACAATGACTTGCAGGGCCAGCTCAAGT
         anti-CD20 light chain V domain

GTAAGTTACATCCACTGGTTCCAGCAGAAGCCAGGATCCTCCCCCAAACC

CTGGATTTATGCCACATCCAACCTGGCTTCTGGAGTCCCTGTTCGCTTCA

GTGGCAGTGGGTCTGGGACTTCTTACTCTCTCACAATCAGCAGAGTGGAG

GCTGAAGATGCTGCCACTTATTACTGCCAGCAGTGGACTAGTAACCCACC

CACGTTCGGAGGGGGGACCAAGCTGGAAATCAAAAGTGGAGGTGGCGGAT
                                ><         linker

CCGGAGGTGGAGGTTCTGGTGGAGGTGGGAGTCAGGTACAACTGCAGCAG
                        ><

CCTGGGGCTGAGCTGGTGAAGCCTGGGGCCTCAGTGAAGATGTCCTGCAA
         anti-CD20 heavy chain V domain

GGCTTCTGGCTACACATTTACCAGTTACAATATGCACTGGGTAAAACAGA

CACCTGGTCGGGGCCTGGAATGGATTGGAGCTATTTATCCCGGAAATGGT

GATACTTCCTACAATCAGAAGTTCAAAGGCAAGGCCACATTGACTGCAGA

CAAATCCTCCAGCACAGCCTACATGCAGCTCAGCAGCCTGACATCTGAGG

ACTCTGCGGTCTATTACTGTGCAAGATCGACTTACTACGGCGGTGACTGG

TACTTCRATGTCTGGGGCGCAGGGACCACGGTCACMGTCTCTGCAATCAC
                                           ><

GTGCCCTCCCCCATGTCCGTGGAACACGCAGACATCTGGGTCAAGAGCT
           Human IL-15R · sushi domain

ACAGCTTGTACTCCAGGGAGCGGTACATTTGTAACTCTGGTTTCAAGCGT

AAAGCCGGCACGTCCAGCCTGACGGAGTGCGTGTTGAACAAGGCCACGAA

FIG. 55B

TGTCGCCCACTGGACAACCCCCAGTCTCAAATGCATTAGAGAGCCGAAAT
                                                  ><

CTTGTGACAAAACTCACACATGCCCACCGTGCCCAGCACCTGAACTCCTG
            Human IgG1 CH2-CH3 (Fc) domain
GGGGGACCGTCAGTCTTCCTCTTCCCCCCAAAACCCAAGGACACCCTCAT

GATCTCCCGGACCCCTGAGGTCACATGCGTGGTGGTGGACGTGAGCCACG

AAGACCCTGAGGTCAAGTTCAACTGGTACGTGGACGGCGTGGAGGTGCAT

AATGCCAAGACAAAGCCGCGGGAGGAGCAGTACAACAGCACGTACCGTGT

GGTCAGCGTCCTCACCGTCCTGCACCAGGACTGGCTGAATGGCAAGGAGT

ACAAGTGCAAGGTCTCCAACAAAGCCCTCCCAGCCCCCATCGAGAAAACC

ATCTCCAAAGCCAAAGGGCAGCCCCGAGAACCACAGGTGTACACCCTGCC

CCCATCCCGGGATGAGCTGACCAAGAACCAGGTCAGCCTGACCTGCCTGG

TCAAAGGCTTCTATCCCAGCGACATCGCCGTGGAGTGGGAGAGCAATGGG

CAGCCGGAGAACAACTACAAGACCACGCCTCCCGTGCTGGACTCCGACGG

CTCCTTCTTCCTCTACAGCAAGCTCACCGTGGACAAGAGCAGGTGGCAGC

AGGGGAACGTCTTCTCATGCTCCGTGATGCATGAGGCTCTGCACAACCAC

TACACGCAGAAGAGCCTCTCCCTGTCTCCTGGTAAATAA
                                      >

FIG. 56 qivlsqspailsaspgekvtmtcrasssvsyihwfqqkpgsspkpwiyatsnlasgvpvr
<            anti-CD20 light chain V domain fsgsgsgtsysltisrveaedaatyycqqwtsnpptfgggtkleiksggggsggggsggg
                                                ><   linker gsqvqlqqpgaelvkpgasvkmsckasgytftsynmhwvkqtpgrglewigaiypgngdt
 ><          anti-CD20 heavy chain V domain synqkfkgkatltadkssstaymqlssltsedsavyycarstyyggdwyfnvwgagttvt vsaitcpppmsvehadiwvksyslysreryicnsgfkrkagtssltecvlnkatnvahwt
 ><           Human IL-15R · sushi domain tpslkcirepkscdkthtcppcpapellggpsvflfppkpkdtlmisrtpevtcvvvdvs
        ><   Human IgG1 CH2-CH3 (Fc) domain hedpevkfnwyvdgvevhnaktkpreeqynstyrvvsvltvlhqdwlngkeykckvsnka lpapiektiskakgqprepqvytlppsrdeltknqvsltclvkgfypsdiavewesngqp ennykttppvldsdgsfflyskltvdksrwqqgnvfscsvmhealhnhytqkslslspgk
                                                            >

FIG. 60

```
ATGGATTTTCAGGTGCAGATTATCAGCTTCCTGCTAATCAGTGCTTCAGT
<                    leader seq

CATAATGTCCAGAGGACAAATTGTTCTCTCCAGTCTCCAGCAATCCTGT
              ><

CTGCATCTCCAGGGGAGAAGGTCACAATGACTTGCAGGGCCAGCTCAAGT
  anti-CD20 light chain V / human kappa C domains

GTAAGTTACATCCACTGGTTCCAGCAGAAGCCAGGATCCTCCCCCAAACC

CTGGATTTATGCCACATCCAACCTGGCTTCTGGAGTCCCTGTTCGCTTCA

GTGGCAGTGGGTCTGGGACTTCTTACTCTCTCACAATCAGCAGAGTGGAG

GCTGAAGATGCTGCCACTTATTACTGCCAGCAGTGGACTAGTAACCCACC

CACGTTCGGAGGGGGGACCAAGCTGGAAATCAAACGTACGGTTGCTGCAC

CATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGT

ACAGTGGAAGGTGGATAACGCCCTCCAATCGGGTAACTCCCAGGAGAGTG

TCACAGAGCAGGACAGCAAGGACAGCACCTACAGCCTCAGCAGCACCCTG

ACGCTGAGCAAAGCAGACTACGAGAAACACAAAGTCTACGCCTGCGAAGT

CACCCATCAGGGCCTGAGCTCGCCCGTCACAAAGAGCTTCAACAGGGGAG

AGTGTAACTGGGTGAATGTAATAAGTGATTTGAAAAAATTGAAGATCTT
    ><            Human IL-15N72D

ATTCAATCTATGCATATTGATGCTACTTTATATACGGAAAGTGATGTTCA

CCCCAGTTGCAAAGTAACAGCAATGAAGTGCTTTCTCTTGGAGTTACAAG

TTATTTCACTTGAGTCCGGAGATGCAAGTATTCATGATACAGTAGAAAAT

CTGATCATCCTAGCAAACGACAGTTTGTCTTCTAATGGGAATGTAACAGA

ATCTGGATGCAAAGAATGTGAGGAACTGGAGGAAAAAAATATTAAAGAAT

TTTTGCAGAGTTTTGTACATATTGTCCAAATGTTCATCAACACTTCTTAA
                                                 >
```

FIG. 61 qivlsqspailsaspgekvtmtcrasssvsyihwfqqkpgsspkpwiyatsnlasgvpvr
<            anti-CD20 light chain V domain fsgsgsgtsysltisrveaedaatyycqqwtsnpptfgggtkleikrtvaapsvfifpps
                                                          >< deqlksgtasvvcllnnfypreakvqwkvdnalqsgnsqesvteqdskdstyslsstltl
            human kappa C domain skadyekhkvyacevthqglsspvtksfnrgecnwvnvisdlkkiedliqsmhidatlyt
                              ><       Human IL-15N72D esdvhpsckvtamkcfllelqvislesgdasihdtvenliilandslssngnvtesgcke ceeleekn ikeflqsfvhivqmfints
                            >

FIG. 62A

ATGGGTTGGAGTCTCATCTTGCTCTTCCTTGTCGCTGTTGCTACACGTGT
<                leader seq

CCTGTCCCAGGTACAACTGCAGCAGCCTGGGGCTGAGCTGGTGAAGCCTG
       ><

GGGCCTCAGTGAAGATGTCCTGCAAGGCTTCTGGCTACACATTTACCAGT
  anti-CD20 heavy chain V / human HC CH1 domains

TACAATATGCACTGGGTAAAACAGACACCTGGTCGGGGCCTGGAATGGAT

TGGAGCTATTTATCCCGGAAATGGTGATACTTCCTACAATCAGAAGTTCA

AAGGCAAGGCCACATTGACTGCAGACAAATCCTCCAGCACAGCCTACATG

CAGCTCAGCAGCCTGACATCTGAGGACTCTGCGGTCTATTACTGTGCAAG

ATCGACTTACTACGGCGGTGACTGGTACTTCGATGTCTGGGGCGCAGGGA

CCACGGTCACCGTCTCTGCAGCTAGCACCAAGGGCCCATCGGTCTTCCCC

CTGGCACCCTCCTCCAAGAGCACCTCTGGGGGCACAGCGGCCCTGGGCTG

CCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGG

CACCCAGACCTACATCTGCAACGTGAATCACAAGCCCAGCAACACCAAGG

TGGACAAGAAAGTTATCACGTGCCCTCCCCCCATGTCCGTGGAACACGCA
            ><      Human IL-15R · sushi domain

GACATCTGGGTCAAGAGCTACAGCTTGTACTCCAGGGAGCGGTACATTTG

TAACTCTGGTTTCAAGCGTAAAGCCGGCACGTCCAGCCTGACGGAGTGCG

TGTTGAACAAGGCCACGAATGTCGCCCACTGGACAACCCCCAGTCTCAAA

TGCATTAGAGAGCCCAAATCTTGTGACAAAACTCACACATGCCCACCGTG
       ><      Human IgG1 CH2-CH3 (Fc) domain

CCCAGCACCTGAACTCCTGGGGGGACCGTCAGTCTTCCTCTTCCCCCCAA

FIG. 62B

AACCCAAGGACACCCTCATGATCTCCCGGACCCCTGAGGTCACATGCGTG
GTGGTGGACGTGAGCCACGAAGACCCTGAGGTCAAGTTCAACTGGTACGT
GGACGGCGTGGAGGTGCATAATGCCAAGACAAAGCCGCGGGAGGAGCAGT
ACAACAGCACGTACCGTGTGGTCAGCGTCCTCACCGTCCTGCACCAGGAC
TGGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAAC
CACAGGTGTACACCCTGCCCCCATCCCGGGATGAGCTGACCAAGAACCAG
GTCAGCCTGACCTGCCTGGTCAAAGGCTTCTATCCCAGCGACATCGCCGT
GGAGTGGGAGAGCAATGGGCAGCCGGAGAACAACTACAAGACCACGCCTC
CCGTGCTGGACTCCGACGGCTCCTTCTTCCTCTACAGCAAGCTCACCGTG
GACAAGAGCAGGTGGCAGCAGGGGAACGTCTTCTCATGCTCCGTGATGCA
TGAGGCTCTGCACAACCACTACACGCAGAAGAGCCTCTCCCTGTCTCCTG
GTAAATAA
         >

FIG. 63 qvqlqqpgaelvkpgasvkmsckasgytftsynmhwvkqtpgrglewigaiypgngdtsy
<            anti-CD20 heavy chain V domain nqkfkgkatltadkssstaymqlssltsedsavyycarstyyggdwyfdvwgagttvts aastkgpsvfplapsskstsggtaalgclvkdyfpepvtvswnsgaltsgvhtfpavlqs
><            Human IgG1 HC CH1 domains sglyslssvvtvpssslgtqtyicnvnhkpsntkvdkkvitcpppmsvehadiwvksysl
                                  >< ysreryicnsgfkrkagtssltecvlnkatnvahwttpslkcirepkscdkthtcppcpa
         Human IL-15R • sushi domain        >< pellggpsvflfppkpkdtlmisrtpevtcvvvdvshedpevkfnwyvdgvevhnaktkp
           Human IgG1 CH2-CH3 (Fc) domain reeqynstyrvvsvltvlhqdwlngkeykckvsnkalpapiektiskakgqprepqvytl ppsrdeltknqvsltclvkgfypsdiavewesngqpennykttppvldsdgsfflysklt vdksrwqqgnvfscsvmhealhnhytqkslslspgk
                                    >

MULTIMERIC IL-15 SOLUBLE FUSION MOLECULES AND METHODS OF MAKING AND USING SAME

RELATED APPLICATIONS

This application is a continuation application of U.S. Ser. No. 13/946,313, filed on Jul. 19, 2013, now U.S. Pat. No. 9,428,573, which is a continuation application of U.S. Ser. No. 13/238,925, filed on Sep. 21, 2011 (now U.S. Pat. No. 8,507,222), which claims the benefit of U.S. Provisional Application Ser. No. 61/384,817, filed Sep. 21, 2010 and U.S. Provisional Application Ser. No. 61/527,911, filed Aug. 26, 2011, the entire contents of each of which are hereby incorporated herein by reference.

GOVERNMENT SUPPORT

Research supporting this application was carried out by the United States of America as represented by the Secretary, Department of Health and Human Services.

SEQUENCE LISTING

The instant application contains a Sequence Listing which has been submitted in ASCII format via EFS-Web and is hereby incorporated by reference in its entirety. Said ASCII copy, created on Oct. 21, 2011, is named 84648340.txt and is 69,187 bytes in size.

BACKGROUND

Previous studies have demonstrated the utility of creating multimeric targeting proteins for the purposes of either augmenting effective affinity through the formation of multivalent molecules or broadening the spectrum of recognition through the formation of multiple specific molecules. A variety of protein interaction domains have been employed to generate recombinant proteins with dimeric and multimeric binding sites. Initially, fusions of the targeting domains to leucine zipper domains were commonly used for dimerization. In this approach, hydrophobic interaction of leucine zipper domains is mediated by regularly spaced leucines in parallel α-helices, while the dimerization partner is determined by other amino acids immediately outside of the hydrophobic core, mainly charged residues, forming salt bridges (1-3). This interaction is exemplified by the Fos and Jun family of proteins, which preferentially form heterodimers without significant interference of the target domain specificity. This approach provides a versatile scaffold to create multimeric complexes (4,5). However, there are limitations that significantly affect the usefulness of this approach for therapeutic protein development. Most prominently, Fos and Jun are intracellular proteins that accumulate almost exclusively within the nucleus. Thus, soluble and secreted Fos and Jun fusions are usually produced using the baculovirus-infected or stably transformed insect cell system, a relatively low yielding and not easily scalable manufacturing process (6,7). In an attempt to create bispecific molecules, antibody domains linked to Fos-Jun were produced in bacterial or mammalian cells, but the main limitation was subunit homodimerization (8,9) which complicated the purification process and reduced the overall yield (8,9). Furthermore, the difference in patterns of glycosylation of proteins produced by insect or bacterial cells raises concerns of potential immunogenicity of the products when used in therapeutic applications.

In addition to leucine zipper motifs, immunoglobulin (IgG) constant domains, helix-turn-helix self dimerizing peptides, tri- and tetrameric subdomains of collagen and p53 have been used as scaffolds by which to create multivalent molecules (8,10-13). Aside from the IgG fragments, these interaction domains primarily serve as molecular scaffolds and lack other functional activities per se. Moreover, fusion proteins containing these domains often require further optimization to promote stable multimer formation and specialized production cell lines and purification methods that are tedious or impose regulatory hurdles for therapeutic development (10,12). Many of these scaffolds are derivatives of either nonhuman protein domains or non-native components of plasma that may exhibit poor pharmacokinetic properties and pose the risk of immunogenic responses that could limit their therapeutic potential.

SUMMARY OF THE INVENTION

The invention provides soluble fusion protein complexes having at least two soluble fusion proteins. In certain embodiments, the first fusion protein includes a first biologically active polypeptide covalently linked to interleukin-15 (IL-15) polypeptide or a functional fragment thereof. The second fusion protein includes a second biologically active polypeptide covalently linked to soluble interleukin-15 receptor alpha (IL-15Rα) polypeptide or a functional fragment thereof. In the complexes, either one or both of the first and second fusion proteins further include an immunoglobulin Fc domain or a functional fragment thereof. In the complex, the IL-15 domain of the first fusion protein binds to the soluble IL-15Rα domain of the second fusion protein to form a soluble fusion protein complex.

In certain embodiments, in the soluble fusion protein complexes, one of the first and second biologically active polypeptides includes a first soluble T-cell receptor (TCR) or functional fragment thereof. In certain embodiments, the soluble fusion protein complex including a first soluble TCR includes a second soluble TCR as the biologically active polypeptide, thereby creating a multivalent TCR fusion protein complex with increased binding activity. In certain embodiments, the TCRs in the complex includes at least two different TCRs. In certain embodiments, all of the TCRs are the same. In certain embodiments when at least two different TCRs are present, the TCRs bind to separate target molecules. In certain embodiments when at least two different TCRs are present, the TCRs bind to distinct epitopes on the same target molecule. In certain embodiments, the TCRs are specific for recognition of a particular antigen.

In the soluble fusion complex of the invention, in certain embodiments, the TCRs are independently selected from a heterodimer comprising α and β chain TCR and a single chain TCR polypeptide. In certain embodiments, the single chain TCR includes a TCR V-α chain covalently linked to a TCR V-β chain by a peptide linker sequence. In certain embodiments, the single chain TCR further includes a soluble TCR Cβ chain fragment covalently linked to a TCR V-β chain. In certain embodiments, the single chain TCR further includes a soluble TCR Cα chain fragment covalently linked to a TCR V-α chain. In certain embodiments of the soluble fusion protein complex, the first biologically active polypeptide includes a TCR α polypeptide or functional fragment thereof and the second biologically active polypeptide includes a TCR β polypeptide or functional fragment thereof.

In certain embodiments, in soluble fusion protein complex one or both of the first and second biologically active polypeptide includes an antibody or functional fragment thereof. In certain embodiments, the antibodies in the complex includes at least two different antibodies. In certain embodiments, all of the antibodies are the same. In certain embodiments when at least two different antibodies are present, the antibodies bind to separate target molecules. In certain embodiments when at least two different antibodies are present, the antibodies bind to distinct epitopes on the same target molecule. In certain embodiments, the antibodies are specific for recognition of a particular antigen.

In certain embodiments of the soluble fusion protein complex, the antibody is a single-chain antibody or single-chain Fv. In certain embodiments, the single-chain antibody comprises an immunoglobulin light chain variable domain covalently linked to immunoglobulin heavy chain variable domain by polypeptide linker sequence. In certain embodiments, the first biologically active polypeptide comprises an antibody heavy chain polypeptide or functional fragment thereof and the second biologically active polypeptide comprises an antibody light chain polypeptide or functional fragment thereof.

In certain embodiments of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt) and the like and variants thereof are referred to using the native amino acid, its position in the mature sequence and the variant amino acid. For example, huIL15N72D refers to human IL-15 comprising a substitution of N to D at position 72. In certain embodiments, the IL-15 variant functions as an IL-15 agonist as demonstrated, e.g., by increased binding activity for the IL-15RβγC receptors compared to the native IL-15 polypeptide. In certain embodiments, the IL-15 variant functions as an IL-15 antagonist as demonstrated by e.g., decreased binding activity for the IL-15RβγC receptors compared to the native IL-15 polypeptide. In certain embodiments, the IL-15 variant has increased binding affinity or a decreased binding activity for the IL-15RβγC receptors compared to the native IL-15 polypeptide. In certain embodiments, the sequence of the IL-15 variant has at least one (i.e., 1, 2, 3, 4, 5, 6, 7, 8, 9, 10, or more) amino acid change compared to the native IL-15 sequence. The amino acid change can include one or more of an amino acid substitution or deletion in the domain of IL-15 that interacts with IL-15Rβ and/or IL-15RγC. In certain embodiments, the amino acid change is one or more amino acid substitutions or deletions at position 8, 61, 65, 72, 92, 101, 108, or 111 of the mature human IL-15 sequence (SEQ ID NO:1). For example, the amino acid change is the substitution of D to N or A at position 8, D to A at position 61, N to A at position 65, N to R at position 72 or Q to A at position 108 of the mature human IL-15 sequence, or any combination of these substitutions. In certain embodiments, the amino acid change is the substitution of N to D at position 72 of the mature human IL-15 sequence.

In certain embodiments of the invention, in the soluble fusion protein complex, the Fc domain or functional fragment thereof includes an Fc domain selected from the group consisting of IgG Fc domain, human IgG1 Fc domain, human IgG2 Fc domain, human IgG3 Fc domain, human IgG4 Fc domain, IgA Fc domain, IgD Fc domain, IgE Fc domain, and IgM Fc domain; or any combination thereof. In certain embodiments, the Fc domain includes an amino acid change that results in an Fc domain with altered complement or Fc receptor binding properties Amino acid changes to produce an Fc domain with altered complement or Fc receptor binding properties are known in the art. For example, a substitution of leucine residues at positions 234 and 235 of the IgG1 CH2 (numbering based on antibody consensus sequence) (i.e. . . . P E L L G G . . . (SEQ ID NO: 1)) with alanine residues (i.e. . . . P E A A G G . . . (SEQ ID NO: 2)) results in a loss of Fc gamma receptor binding whereas the substitution of the lysine residue at position 322 of the IgG1 CH2 (numbering based on antibody consensus sequence) (i.e. . . . K C K S L . . . (SEQ ID NO: 3)) with an alanine residue (i.e. . . . K C A S L . . . (SEQ ID NO: 4)) results in a loss of complement activation. In certain embodiments, such mutations can be combined.

In certain embodiments of the soluble fusion protein complex, the first biologically active polypeptide is covalently linked to IL-15 polypeptide (or functional fragment thereof) by a polypeptide linker sequence. In certain embodiments of the soluble fusion protein complex, the second biologically active polypeptide is covalently linked to IL-15Rα polypeptide (or functional fragment thereof) by polypeptide linker sequence. In certain embodiments of the soluble fusion protein complex, the IL-15Rα polypeptide (or functional fragment thereof) is covalently linked to the Fc domain (or functional fragment thereof) by polypeptide linker sequence. Each polypeptide linker sequence can be selected independently. In certain embodiments the polypeptide linker sequences are the same. In certain embodiments, they are different.

In certain embodiments, the antigen for the TCR domain includes a peptide antigen presented in an MHC or HLA molecule. In certain embodiments, the peptide antigen is derived from (i.e., includes at least a partial sequence of) a tumor associated polypeptide or virus encoded polypeptide. In certain embodiments, the antigen for the antibody domain comprises a cell surface receptor or ligand.

In certain embodiments, the antigen for the antibody domain is one or more of a CD antigen, cytokine or chemokine receptor or ligand, growth factor receptor or ligand, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

In certain embodiments of the soluble fusion protein complex, the IL-15Rα polypeptide includes the extracellular domain of the IL-15 receptor alpha capable for binding IL-15 polypeptide. The soluble human IL-15Rα polypeptide is referred to herein as hIL-15Rα, huIL-15Rα, hIL-15Rα, huIL-15Rα, and the like. In certain embodiments, the IL-15Rα polypeptide includes either the IL-15Rα sushi (Su) domain or the IL-15RαΔE3 domain.

In certain embodiments, the soluble fusion protein complexes of the invention are mutimerized, e.g., dimerized, trimerized, or otherwise multimerized (e.g., 4 complexes, 5 complexes, etc.) In certain embodiments, the multimers are homomultimers. In certain embodiments, the multimers are heteromultimers. In certain embodiments, the soluble fusion protein complexes are joined by covalent bonds, e.g., disulfide bonds, chemical cross-linking agents. In certain embodiments, the disulfide bond covalently links the Fc domain of the second polypeptide of the first soluble fusion protein complex to the Fc domain of the second polypeptide of the second soluble fusion protein complex.

In certain embodiments, the soluble fusion protein complexes of the invention include an IL-15 polypeptide, IL-15 variant or a functional fragment thereof and a soluble IL-15Rα polypeptide or a functional fragment thereof, wherein one or both of the IL-15 and IL-15Rα polypeptides further include an immunoglobulin Fc domain or a functional fragment thereof.

In certain embodiments, the soluble fusion protein complexes of the invention include at least one of the soluble fusion proteins comprise a detectable label. Detectable labels include, but are not limited to, biotin, streptavidin, an enzyme or catalytically active fragment thereof, a radionuclide, a nanoparticle, a paramagnetic metal ion, or a fluorescent, phosphorescent, or chemiluminescent molecule; or any combination thereof.

The invention provides nucleic acid sequences encoding any of the fusion proteins of the invention. In certain embodiments, the nucleic acid sequence further includes one or more translational and/or transcriptional control sequences, e.g., a promoter, translation initiation signal, and leader sequence; operably linked to the sequence encoding the fusion protein. In certain embodiments, the nucleic acid sequence is in a vector for replication, expression, or both.

The invention provides method for making the soluble fusion protein complexes of the invention. The method includes the steps of:
 a) introducing into a first host cell a DNA vector with appropriate control sequences encoding the first fusion protein,
 b) culturing the first host cell in media under conditions sufficient to express the first fusion protein in the cell or the media;
 c) purifying the first fusion protein from the host cells or media,
 d) introducing into a second host cell a DNA vector with appropriate control sequences encoding the second fusion protein,
 e) culturing the second host cell in media under conditions sufficient to express the second fusion protein in the cell or the media; and
 f) purifying the second fusion protein from the host cells or media, and
 g) mixing the first and second fusion proteins under conditions sufficient to allow binding between IL-15 domain of a first fusion protein and the soluble IL-15Rα domain of a second fusion protein to form the soluble fusion protein complex.

In certain embodiments, the method further includes mixing the first and second fusion protein under conditions sufficient to allow formation of a disulfide bond between the polypeptides expressed from the expression vectors.

The invention provides methods for making soluble fusion protein complexes of the invention, the methods including the steps of:
 a) introducing into a host cell a DNA vector with appropriate control sequences encoding the first fusion protein and a DNA vector with appropriate control sequences encoding the second fusion protein,
 b) culturing the host cell in media under conditions sufficient to express the fusion proteins in the cell or the media and allow association between IL-15 domain of a first fusion protein and the soluble IL-15Rα domain of a second fusion protein to form the soluble fusion protein complex;
 c) purifying the soluble fusion protein complex from the host cells or media.

In certain embodiments, the method further includes mixing the first and second fusion protein under conditions sufficient to allow formation of a disulfide bond between the polypeptides expressed from the expression vectors.

The invention provides methods for making soluble fusion protein complexes of the invention, the methods including the steps of:
 a) introducing into a host cell a DNA vector with appropriate control sequences encoding the first and second fusion proteins,
 b) culturing the host cell in media under conditions sufficient to express the fusion proteins in the cell or the media and allow association between IL-15 domain of a first fusion protein and the soluble IL-15Rα domain of a second fusion protein to form the soluble fusion protein complex, and to allow formation of a disulfide bond between the polypeptides encoded by a nucleic acid of the invention;
 c) purifying the soluble fusion protein complex from the host cells or media.

In certain embodiments, the method further includes mixing the first and second fusion protein under conditions sufficient to allow formation of a disulfide bond between the polypeptides expressed from the expression vectors.

The invention provides methods for killing a target cell, the method including the steps of:
 a) contacting a plurality of cells with a soluble fusion protein complex of the invention, wherein the plurality of cells further include immune cells bearing the IL-15R chains recognized by the IL-15 domain, or immune cells bearing Fc receptor chains recognized by the Fc domain, and the target cells bearing an antigen recognized by at least one of the biologically active polypeptides,
 b) forming a specific binding complex (bridge) between the antigen on the target cells and the IL-15R or Fc receptor chains on the immune cells sufficient to bind and activate the immune cells; and
 c) killing the target cells by the bound activated immune cells.

In certain embodiments of the killing methods, the target cells are tumor cells or virally infected cells.

In certain embodiments of the killing methods, the biologically active polypeptide includes a TCR.

In certain embodiments of the killing methods, the antigen on the target cells includes a tumor or virally encoded peptide antigen presented in an MHC or HLA molecule and recognized by the TCR. The immune cells are, for example, T-cells, LAK cells, NK cells, macrophages, monocytes or granulocytes.

The invention provides methods for preventing or treating disease in a patient in which the diseased cells express a disease associated antigen, the method including the steps of:
 a) administering to the patient a soluble fusion protein complex of the invention having a biologically active polypeptide recognizing a disease-associated antigen;
 b) forming a specific binding complex (bridge) between antigen-expressing diseased cells and IL-15R or Fc receptor expressing immune cells sufficient to localize the immune cells; and
 c) damaging or killing the disease cells sufficient to prevent or treat the disease in the patient.

The invention provides method for preventing or treating disease in a patient in which the diseased cells express a disease associated antigen, the method including the steps of:
 a) mixing immune cells bearing IL-15R chains or Fc receptor chains with a soluble fusion protein complex of the invention including a biologically active polypeptide recognizing a disease-associated antigen,
 b) administering to the patient the immune cell-fusion protein complex mixture;

c) forming a specific binding complex (bridge) between antigen-expressing diseased cells and IL-15R or Fc receptor expressing immune cells sufficient to localize the immune cells; and d) damaging or killing the disease cells sufficient to prevent or treat the disease in the patient.

In certain embodiments of the method for preventing or treating disease in a patient in which the diseased cells express a disease associated antigen, the disease is cancer or viral infection. In certain embodiments, the disease associated antigen is a peptide/MHC complex.

The invention provides methods of stimulating immune responses in a mammal by administering to the mammal an effective amount of the soluble fusion protein complex of the invention.

The invention provides methods of suppressing immune responses in a mammal by administering to the mammal an effective amount of the soluble fusion protein complex of any one of the invention.

The invention provides methods for detecting cells or tissue having an antigen presented on the cells or tissue, the method including the steps of:

a) contacting the cells or tissue with at least one soluble fusion protein complex of the invention including a detectable label under conditions that form a specific binding complex between the antigen and the biologically active polypeptide of the soluble fusion protein complex, b) washing the cells or tissue under conditions appropriate to remove any soluble fusion protein complex not bound to the antigen; and c) detecting the specific binding complex as being indicative of cells or tissue comprising the antigen.

In certain embodiments of the detection methods, the biologically active polypeptide comprises a TCR and the antigen comprises a peptide antigen presented in an MHC or HLA molecule that is recognized by the TCR. The detection methods provided herein are highly sensitive. For example, in the methods, the number of copies of the antigen present is 1000 or fewer copies per cell. The detection methods provided herein can be practiced in vivo, in vitro, or ex vivo.

The invention provides methods of increasing the per-molecule binding activity of a soluble fusion protein complex of the invention by forming a dimer of a first soluble fusion protein complex and a second soluble fusion protein complex in which the binding site of the first biologically active polypeptide and the second biologically active peptide of each fusion protein complex are the same or are different. In certain embodiments, the binding is increased synergistically. For example, the per-molecule binding activity is increased by 10% or more, 20% or more, 30% or more, 40% or more, 50% or more, 60% or more, or 70% or more.

The invention also provides method of increasing the per-molecule IL-15 activity of a soluble fusion protein complex of the invention by forming a dimer of a first soluble fusion protein complex and a second soluble fusion protein complex.

In one aspect, the invention provides a method for making an interleukin-15 (IL-15):interleukin-15 receptor alpha (IL-15Rα) fusion protein complex, the method involving introducing into a host cell (e.g., a mammalian cell) a first DNA vector encoding IL-15 (or IL-15 variant) and a second DNA vector encoding an IL-15Rα fusion protein; culturing the host cell in media under conditions sufficient to express the IL-15 (or IL-15 variant) and the IL-15Rα fusion protein; and purifying the IL-15:IL-15Rα fusion protein complex from the host cell or media.

In another aspect, the invention provides a method of making an IL-15:IL-15Rα complex containing an IL-15Rα/Fc fusion protein, the method involving introducing into a host cell a first DNA encoding IL-15 (or IL-15 variant) and a second DNA encoding an IL-15Rα/Fc fusion protein; culturing the host cell in media under conditions sufficient to express the IL-15 (or IL-15 variant) and the IL-15Rα/Fc fusion protein; and purifying the IL-15:IL-15Rα/Fc complex from the host cell or media.

In another aspect, the invention provides a method of making an IL-15:IL-15Rα fusion protein complex containing an IL-15Rα/Fc fusion protein, the method involving co-expressing IL-15 (or IL-15 variant) and an IL-15Rα/Fc fusion protein in a host cell; culturing the host cell in media under conditions sufficient to express the IL-15 (or IL-15 variant) and the IL-15Rα/Fc fusion protein; and purifying the IL-15:IL-15Rα/Fc fusion protein complex from the host cell or media.

In another aspect, the invention provides a method of making an IL-15N72D:IL-15RαSu/Fc fusion protein complex involving co-expressing IL-15N72D and an IL-15RαSu/Fc fusion protein in a host cell; culturing the host cell in media under conditions sufficient to express the IL-15N72D and the IL-15RαSu/Fc fusion protein; and purifying the IL-15N72D:IL-15RαSu/Fc fusion protein complex from the host cell or media where both IL-15 binding sites of the IL-15N72D:IL-15RαSu/Fc complex are fully occupied.

In another aspect, the invention provides a cell containing a first polynucleotide encoding IL-15 or an IL-15 variant and a second polynucleotide encoding an IL-15 receptor fusion protein. In one embodiment, the cell comprises a first expression vector encoding IL-15N72D and a second expression vector encoding an IL-15RαSu/Fc fusion protein.

In another aspect, the invention provides an isolated fully occupied IL-15N72D:IL-15RαSu/Fc complex containing a dimeric IL-15RαSu/Fc and two IL-15N72D molecules. In one embodiment, the complex is at least 90-95% or more purified fully occupied; has an isoelectric point between 5.6 to 6.5; has a molecular weight of about 114 kDa; and/or is glycosylated on either or both the IL-15N72D and IL-15RαSu/Fc polypeptides.

In another aspect, the invention provides an isolated fully occupied IL-15N72D:IL-15RαSu/Fc complex produced according to any method of expression and purification delineated herein.

In another aspect, the invention provides a method of modulating (e.g., increasing or decreasing) an immune response in a subject, the method involving administering to the subject a fully occupied IL-15N72D:IL-15RαSu/Fc complex.

In another aspect, the invention provides a method of enhancing an immune response in a subject having neoplasia, the method involving administering to the subject the fully occupied IL-15N72D:IL-15RαSu/Fc complex.

In various embodiments of the above aspects or any other aspect of the invention delineated herein, the IL-15Rα fusion protein comprises soluble IL-15Rα covalently linked to a biologically active polypeptide (e.g., the heavy chain constant domain of IgG, an Fc domain of the heavy chain constant domain of IgG). In other embodiments of the invention of the above aspects, IL-15 comprises IL-15 covalently linked to a second biologically active polypeptide. In other embodiments, purifying the IL-15:IL-15Rα complex from the host cell or media involves capturing the IL-15:IL-15Rα complex on an affinity reagent that specifically binds the IL-15:IL-15Rα fusion protein complex. In other embodiments, the IL-15Rα fusion protein contains an IL-15Rα/Fc fusion protein and the affinity reagent specifically binds the Fc domain. In other embodiments, the affinity reagent is Protein A or Protein G. In other embodiments, the affinity reagent is an antibody. In other embodiments, purifying the IL-15:IL-15Rα complex from the host cell or media comprises ion exchange chromatography. In other embodiments, purifying the IL-15:IL-15Rα complex from the host cell or media comprises size exclusion chromatography. In other embodiments, the IL-15Rα comprises IL-15RαSushi (IL-15RαSu). In other embodiments, the IL-15 is a variant IL-15 (e.g., IL-15N72D). In other embodiments, the IL-15 binding sites of the IL-15:IL-15Rα complex are fully occupied. In other embodiments, both IL-15 binding sites of the IL-15:IL-15RαSu/Fc complex are fully occupied. In other embodiments, the IL-15:IL-15Rα complex is purified based on the complex charge or size properties. In other embodiments, the fully occupied IL-15N72D:IL-15RαSu/Fc fusion protein complex is purified by anion exchange chromatography based on the complex charge properties. In other embodiments, the fully occupied IL-15N72D:IL-15RαSu/Fc fusion protein complex is purified using a quaternary amine-based resin with binding conditions employing low ionic strength neutral pH buffers and elution conditions employing buffers of increasing ionic strength.

The invention also includes kits including one or more of the soluble fusion protein complexes of the invention, one or more specific reagents (e.g., a nucleotide encoding one or more soluble fusion protein complexes of the invention) for making the soluble fusion protein complexes of the invention, and/or specific materials for using one or more soluble fusion protein complexes of the invention. Materials in kits are provided in appropriate packaging, typically with instructions for use.

Other embodiments will be clear from the disclosure infra.

BRIEF DESCRIPTION OF THE DRAWINGS

FIGS. 3A-3B show the sequence of the c264scTCR/huIL15RαSushi/huIgG1 nucleic acid sequence (SEQ ID NO: 34).

FIGS. 4A-4C show the protein sequence of the c264scTCR/huIL15RαSushi/huIgG1 peptide (SEQ ID NO: 35).

FIGS. 6A-6B show the sequence of the c264scTCR/huIL15RαSushi/huIgG1 nucleic acid sequence (SEQ ID NO: 36).

FIGS. 7A-7C show the protein sequence of the c264scTCR/huIL15RαSushi/huIgG1 peptide (SEQ ID NO: 37).

FIG. 9 shows the sequence of the c149scTCR/huIL15N72D nucleic acid sequence (SEQ ID NO: 38).

FIGS. 10A-10B show the protein sequence of the c149scTCR/huIL15N72D peptide (SEQ ID NO: 39).

FIG. 19A is a flow cytometry analysis showing results from an assay in which Fc-gamma receptor bearing U937 cells were incubated with 33 nM of T2 protein (composed of c264scTCR/huIL15N72D and c264scTCR/huIL15RαSushi/huIgG1 chains), c264scTCR/huIgG1 or A2AL9scTCR/IgG1 (negative control) for 20 min. Cells were washed once and incubated with PE-conjugated p53 (aa 264-272) peptide/HLA-A2 tetramer for 20 min. The binding to Fc gamma receptors on U937 cell surface was analyzed with flow cytometry. FIG. 19B is a flow cytometry analysis showing results from a similar U937 binding studies using a range of protein concentrations as indicated was carried out and the mean fluorescent intensity for the stained cells was plotted.

FIGS. 26A-26B show the results from pharmacokinetic assay in which A. mice or B. monkeys were injected with purified T2 protein composed of c264scTCR/huIL15N72D and c264scTCR/huIL15RαSushi/huIgG1 chains. Samples were collected at the indicated times. FIG. 26A shows ELISA format assays in which goat anti-human IgG Ab was used to coat the wells, and anti-human TCR Ab (W4F-BN) was used for detection; or goat anti-human IgG Ab was used to coat the plates, and anti-human IL-15 Ab was used for detection as indicated to quantify the amount of the T2 protein in the blood at the times indicated. In FIG. 26B, anti-human TCR Ab (βF-1) was used to coat the wells, and HRP conjugated goat anti-human IgG Ab was used for detection; or anti-human IL-15 Ab was used to coat the plates, and HRP conjugated goat anti-human IgG Ab was used for detection; or anti-human IL-15 Ab was used to coat the plates and anti-human TCR Ab (W4F-BN) was used for detection.

FIG. 32A shows flow cytometry histograms and FIG. 32B shows signal to noise ratio of peptide-specific to non-specific cell staining.

FIG. 36B shows SEC analysis of c264scTCR fusion proteins. Panels show size analysis of c264scTCR/hIL-15 (top), c264scTCR/hIL-5RαSu/birA (middle) and c264scTCR/hIL-15:c264scTCR/hIL-15RαSu/birA complex (c264scTCR dimer) (bottom) with dashed lines indicating relative protein peaks.

FIGS. 37A-37C show characterization of the binding activity of the c264scTCR dimer comprising the c264scTCR/hIL-15:c264scTCR/hIL-15RαSu/birA complex and c264scTCR/c149scTCR heterodimer comprising the c149scTCR/hIL-15:c264scTCR/hIL-15RαSu/birA complex. In FIG. 37A, T2 cells were pulsed with 0-62.5 nM of p53 (aa264-272) peptide. The cells were stained with equivalent amounts (80 nM) of PE-conjugated multimers of the c264scTCR dimer or c264scTCR/birA. In FIG. 37B, the relative increase in cell staining comparing c264scTCR dimer with c264scTCR/birA reagents was determined at different peptide concentrations. Fold increase=(Geo mean of T2 cells stained by c264scTCR dimer)/(Geo Mean of T2 cells stained by c264scTCR/birA). In FIG. 37C, the p53 peptide/HLA-A*0201 binding activity of c264scTCR/c149scTCR heterodimer was determined by ELISA. Anti-hIL-15 monoclonal antibody (R&D System) was used as a capturing antibody. A2/p53.264-272.HRP or A2/p53.149-157.HRP tetramers were used as the probes. The data represent the means±SD of triplicate determinations.

FIGS. 39A-39B show OTscTCR/scCD8 heterodimer comprising the OT1scTCR/hIL-15:scCD8/hIL-15RαSu/birA complex exhibits enhanced pMHCI binding activity. In FIG. 39A, murine CD8 expression of OT1scTCR/scCD8 heterodimer was determined by ELISA. Anti-mTCR H57-597 mAb was used as capturing antibody. The biotinylated anti-murine CD8α or CD8β mAb was used as a probe followed by SA-HRP. The data represent the means±SD of triplicate determinations. In FIG. 39B, EL4 cells were loaded with OVA (aa257-264) peptide at the indicated concentration and stained with OT1scTCR dimer-SA-PE (top) and OT1scTCR/scCD8 heterodimer-SA-PE (bottom) at 200 nM.

FIGS. 40A-40B depict fusion proteins containing TCR α/β heterodimers comprising the TCRα/hIL-15:TCRβ/hIL-15RαSu/birA complex retain pMHCI binding activity. In FIG. 40A, binding activity of OT1scTCR/birA and OT1 TCRα/β heterodimer to OVA (aa257-264)/H-2Kb complex was determined by ELISA. Anti-mTCR H57-597 mAb was used as capturing antibody. Kb/OVA.257-264.HRP tetramer was used as a probe. In FIG. 40B, binding activity of 264scTCR/birA and 264 TCRα/β heterodimer to p53 (aa264-272)/HLA-A*0201 complex was determined by ELISA. Anti-TCR mAb was used as capturing antibody. A2/p53.264-272.HRP tetramer was used as a probe. The data represent the means±SD of triplicate determinations.

In FIG. 41A, 32Dβ cells were incubated with 320 nM of the c264scTCR dimers comprising IL-15 wild type or IL-15N72D or IL-15D8N mutein domains. The binding of the fusion proteins was in turn detected with anti-human TCR Cβ Ab. In FIG. 41B, the ability of the c264scTCR dimers comprising IL-15 wild type or mutein domains to support proliferation of 32Dβ cells was determined as described in the Examples. The data represent the means±range of duplicate determinations.

FIG. 46 shows the protein sequence (SEQ ID NO: 40) of the human IgG1 CH2-CH3 domain or Fc domain covalently and/or genetically fused with other protein domains to generate the fusion protein complexes.

In FIG. 49A, C57BL/6 mice were treated i.v. with equivalent molar IL-15 doses of hIL-15 (1 mg/kg), IL15N72D:IL15Rα-Fc (4 mg/kg), T2M2 (various doses) or an equivalent volume of PBS on study day 1. On study day 4, the percentage of PBMC CD8+ and NKp46+ cells were assessed by flow cytometry. In FIG. 49B, nude mice were treated i.v. with IL15N72D/IL15Rα-Fc (0.2 mg/kg) or T2M2 (2 mg/kg) of study day 1. On day 4 and 7 post treatment, the percentage of PBMC NKp46+ cells was assessed by flow cytometry.

In FIG. 50A, A375 human melanoma tumor cells (1×10⁶) were injected s.c. into nude mice (5-6/group). Tumors were allowed to establish and mice were treated i.v. with equivalent molar doses of IL-15 (0.35 mg/kg), scTCR-IL15 fusions (1.6 mg/kg), scTCR-IL15/scTCR-IL15Rα complex (3.2 mg/kg), or PBS. The mice were treated three times a week for three weeks starting on study day 11. In FIG. 50B, A375-tumor bearing nude mice were also treated i.v. with 4 mg/kg T2M as in A. In FIG. 50C, A375 tumor bearing nude mice were i.v. with equivalent molar doses of IL-15 (0.2 mg/kg), T2M2 (2 mg/kg) or PBS. Tumors were measured every other day and tumor volumes (mean±SEM) were plotted.

FIGS. 51A-51B show the nucleic acid sequence of c264scTCR/huIL15RαSushi/huIgG1 CH2-CH3 (Fc) construct (also referred to as T2MΔTCRΔCH1 and T2M2) (SEQ ID NO: 41).

FIG. 52 shows the protein sequence of the mature c264scTCR/huIL15RαSushi/huIgG1 CH2-CH3 (Fc) fusion protein (also referred to as T2MΔTCRΔCH1 and T2M2) (SEQ ID NO: 42).

FIG. 53 shows the nucleic acid sequence of anti-CD20 scAb/hIL-15N72D construct (SEQ ID NO: 43).

FIG. 54 shows the protein sequence of the mature anti-CD20 scAb/hIL-15N72D fusion protein (SEQ ID NO: 44).

FIGS. 55A-55B show the nucleic acid sequence of anti-CD20 scAb/huIL-15RαSu/huIgG1 Fc construct (SEQ ID NO: 45).

FIG. 56 shows the protein sequence of the mature anti-CD20 scAb/huIL-15RαSu/huIgG1 Fc fusion protein (SEQ ID NO: 46).

FIG. 60 shows the nucleic acid sequence of anti-CD20 light chain V domain/human kappa constant domain/hIL-15N72D construct (SEQ ID NO: 47).

FIG. 61 shows the protein sequence of the mature anti-CD20 light chain V domain/human kappa constant domain/hIL-15N72D fusion protein (SEQ ID NO: 48).

FIGS. 62A-62B show the nucleic acid sequence of anti-CD20 heavy chain V domain/human IgG1 CH1 domain/huIL-15RαSu/huIgG1 Fc construct (SEQ ID NO: 49).

FIG. 63 shows the protein sequence of the mature anti-CD20 heavy chain V domain/human IgG1 CH1 domain/huIL-15RαSu/huIgG1 Fc fusion protein (SEQ ID NO: 50).

(FIG. 65A) IEF pH 3-10 gel analysis. Lane 1, IEF Marker. Lane 2, IL-15N72D:IL-15RαSu/Fc complex purified by rProtein A column Lane 3, IL-15RαSu/Fc. Lane 4, IL-15 wt. (FIG. 65B) IEF pH3-10 gel analysis. Lane 1, IEF Marker. Lane 2, IL-15N72D:IL-15RαSu/Fc complex purified by Q step 1 elution. Lane 3, Q1c by Q step 2 elution. Lane 4, Q2c by Q step 2 elution. (FIG. 65C) SDS-PAGE (reduced) analysis. Lane 1, MW maker. Lane 2, IL-15N72D:IL-15RαSu/Fc complex purified by rProtein A column. Lane 3, IL-15N72D:IL-15RαSu/Fc complex purified by Q (Q2c) by Q step 2 elution. Lane 4, IL-15RαSu/Fc (from Q flow through). (FIG. 65D) SDS-PAGE (reduced) analysis showing protein deglycosylation. Lane 1, MW markers. Lanes 2 and 3 show N-Glycosidase F digested and undigested IL-15N72D:IL-15RαSu/Fc protein, respectively. Lane 4, IL-15 wt.

DETAILED DESCRIPTION AND PREFERRED EMBODIMENTS

Definitions

Figure 1:
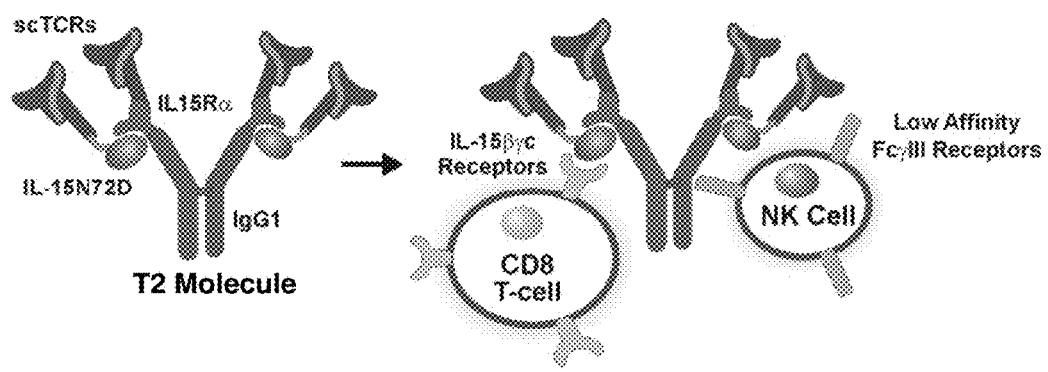
FIG. 1 shows fusion protein referred to as the T2 molecule (T2M) consists of a multichain polypeptide.

The following definitions are provided for specific terms that are used in the following written description.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the term "IL-15:IL-15Rα fusion protein complex" is a complex having IL-15 non-covalently bound to the IL-15Rα domain of a soluble IL-15Rα covalently linked to a biologically active polypeptide. The IL-15 can be either IL-15 or IL-15 covalently linked to a second biologically active polypeptide.

As used herein, the term "co-expressed" is intended to mean that two distinct polypeptides are expressed simultaneously in a host cell such that the two polypeptides can interact or bind either in the host cell or in the host cell culture medium and form a complex.

As used herein, the term "affinity reagent" is intended to mean any composition that specifically binds to another molecule. Examples of affinity regents include polyclonal antibodies, monoclonal antibodies, Protein A, and Protein G.

An "antibody" is any immunoglobulin, including antibodies and fragments thereof, that binds a specific epitope. The term encompasses polyclonal, monoclonal, chimeric, Fabs, Fvs, single-chain antibodies and single or multiple immunoglobulin variable chain or CDR domain designs as well as bispecific and multispecific antibodies.

The term "antigen" as used herein is meant any substance that causes the immune system to produce antibodies or specific cell-mediated immune responses against it. A disease associated antigen is any substance that is associated with any disease that causes the immune system to produce antibodies or a specific-cell mediated response against it.

The term "biologically active polypeptide" as used herein is meant to refer to an amino acid sequence such as a protein, polypeptide or peptide; a sugar or polysaccharide; a lipid or a glycolipid, glycoprotein, or lipoprotein that can produce the desired effects as discussed herein, including a TCR or antibody with antigen binding activity, a CD molecule including CD8 or an antibody domain including an Fc domain.

The term "cell" as used herein is meant to include any prokaryotic, eukaryotic, primary cell or immortalized cell line, any group of such cells as in, a tissue or an organ. Preferably the cells are of mammalian and particularly of human origin, and can be infected by one or more pathogens. A "host cell" in accord with the invention can be a transfected, transformed, transduced or infected cell of any origin, including prokaryotic, eukaryotic, mammalian, avian, insect, plant or bacteria cells, or it can be a cells of any origin that can be used to propagate a nucleic acid described herein.

The term "conjugate molecule" as it is used herein is meant to refer to a TCR or antibody molecule and an effector molecule usually a chemical or synthesized molecule covalently linked (i.e. fused) by chemical or other suitable method. If desired, the conjugate molecule can be fused at one or several sites through a peptide linker sequence or a carrier molecule. Alternatively, the peptide linker or carrier may be used to assist in construction of the conjugate molecule. Specifically preferred conjugate molecules are conjugate toxins or detectable labels.

The term "effector molecule" as used herein is meant to refer to an amino acid sequence such as a protein, polypeptide or peptide; a sugar or polysaccharide; a lipid or a glycolipid, glycoprotein, lipoprotein or chemical agent that can produce the desired effects as discussed herein, including an IL-15 domain, IL-15 variant or IL-15 receptor such as IL-15R-alpha, IL-15RαSu, IL-15Rα exon 3 deletion, IL-2R-beta or gamma-C, or functional fragments thereof and such polypeptides further comprising an immunoglobulin Fc domain or a functional fragment thereof.

The terms "fusion molecule" and "fusion protein" are used interchangeably and are meant to refer to a biologically active polypeptide usually a TCR or antibody and an effector molecule usually a protein or peptide sequence covalently linked (i.e. fused) by recombinant, chemical or other suitable method. If desired, the fusion molecule can be fused at one or several sites through a peptide linker sequence. Alternatively, the peptide linker may be used to assist in construction of the fusion molecule. Specifically preferred fusion molecules are fusion proteins. Generally fusion molecule also can be comprised of conjugate molecules.

The term "host cell" is meant to refer to any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

The term "immune response" as used herein is meant to refer to the process whereby immune cells are stimulated and/or recruited from the blood to lymphoid as well as non-lymphoid tissues via a multifactorial process that involves distinct adhesive and/or activation steps. Activation conditions cause the release of cytokines, growth factors, chemokines and other factors, upregulate expression of adhesion and other activation molecules on the immune cells, promote adhesion, morphological changes, and/or extravasation concurrent with chemotaxis through the tissues, increase cell proliferation and cytotoxic activity, stimulate antigen presentation and provide other phenotypic changes including generation of memory cell types Immune response is also meant to refer to the activity of immune cells to suppress or regulate inflammatory or cytotoxic activity of other immune cells Immune response refers to the activity of immune cells in vivo or in vitro.

As used herein, the terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkers).

The term "polypeptide" is meant to refer to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted. Peptides useful in accordance with the present invention in general will be generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis.

The terms "prevent", "preventing", "prevention", "prophylactic treatment" and the like are meant to refer to reducing the probability of developing a disorder or condition in a subject, who does not have, but is at risk of or susceptible to developing a disorder or condition. Prevention and the like do not mean preventing a subject from ever getting the specific disease or disorder. Prevention may require the administration of multiple doses. Prevention can include the prevention of a recurrence of a disease in a subject for whom all disease symptoms were eliminated, or prevention of recurrence in a relapsing-remitting disease.

The term "single chain antibody" is meant to refer to an antibody based on a single chain format. Single chain antibodies can consist of the minimal binding subunit of antibodies. Single-chain antibodies can combine only those antigen-binding regions (e.g., all or some of the complement determining regions, CDRs present in the heavy chain variable region and/or the light chain variable region) of antibodies on a single stably-folded polypeptide chain. As such, single-chain antibodies are of considerably smaller size than classical immunoglobulins but retain the antigen-specific binding properties of antibodies. Single chain antibodies may be linked to a wide range of ligands, for example effector molecules or drug conjugates.

The term "soluble" as used herein is meant that the fusion molecule and particularly a fusion protein that is not readily sedimented under low G-force centrifugation (e.g. less than about 30,000 revolutions per minute in a standard centrifuge) from an aqueous buffer, e.g., cell media. Further, the fusion molecule is soluble if it remains in aqueous solution at a temperature greater than about 5-37° C. and at or near neutral pH in the presence of low or no concentration of an anionic or non-ionic detergent. Under these conditions, a soluble protein will often have a low sedimentation value e.g., less than about 10 to 50 svedberg units.

Aqueous solutions referenced herein typically have a buffering compound to establish pH, typically within a pH range of about 5-9, and an ionic strength range between about 2 mM and 500 mM. Sometimes a protease inhibitor or mild non-ionic detergent is added. Additionally, a carrier protein may be added if desired such as bovine serum albumin (BSA) to a few mg/ml. Exemplary aqueous buffers include standard phosphate buffered saline, tris-buffered saline, or other well-known buffers and cell media formulations.

The term "stimulate" or "stimulating" is meant to refer to increase, to amplify, to augment, to boost a physiological activity, e.g., an immune response. Stimulation can be a positive alteration. An exemplary increase can be e.g., by 5%, 10%, 25%, 50%, 75%, or even 90-100%. Other exemplary increases include 2-fold, 5-fold, 10-fold, 20-fold, 40-fold, or even 100-fold.

The term "suppress" or "suppressing" is meant to refer to decrease, to attenuate, to diminish, to arrest, or to stabilize a physiological activity, e.g., an immune response. Suppression may be a negative alteration. An exemplary decrease can be e.g., by 5%, 10%, 25%, 50%, 75%, or even 90-100%. Exemplary decreases include 2-fold, 5-fold, 10-fold, 20-fold, 40-fold, or even 100-fold.

The term "T-cell Receptor" (TCR) is meant to refer to polypeptides of or derived from a complex of integral membrane proteins that participates in the activation of T cells in response to the presentation of antigen. In some cases, T cells recognize a peptide bound to the MHC product through the $\alpha\beta$ or $\gamma\delta$-heterodimeric T cell receptor (TCR). The TCR repertoire has extensive diversity created by the same gene rearrangement mechanisms used in antibody heavy and light chain genes [Tonegawa, S. (1988) *Biosci. Rep.* 8:3-26]. Most of the diversity is generated at the junctions of variable (V) and joining (J) (or diversity, D) regions that encode the complementarity determining region 3 (CDR3) of the $\alpha$ and $\beta$ chains [Davis and Bjorkman (1988) *Nature* 334:395-402]. However, TCRs do not undergo somatic point mutations as do antibodies and, perhaps not coincidentally. TCRs also do not undergo the same extent of affinity maturation as antibodies. TCRs as they occur in nature appear to have affinities that range from $10^5$ to $10^7$ $M^{-1}$, whereas antibodies typically have affinities that range from $10^5$ to $10^9$ $M^{-1}$ [Davis et al. (1998) *Annu. Rev. Immunol.* 16:523-544; Eisen et al. (1996) *Adv. Protein Chem.* 49:1-56]. While the absence of somatic mutation in TCRs may be associated with lower affinities, it has also been argued that there is not a selective advantage for a TCR to have higher affinity. In fact, the serial-triggering [Valitutti et al. (1995) *Nature* 375:148-151] and kinetic proofreading [Rabinowitz et al. (1996) *Proc. Natl. Acad. Sci. USA* 93:1401-1405] models of T cell activation both suggest that longer off-rates (associated with higher affinity) would be detrimental to the signaling process. It is also possible that higher affinity TCRs might not maintain the peptide specificity required for T cell responses. For example, peptides bound within the MHC groove display limited accessible surface [Bjorkman, P. J. (1997) *Cell* 89:167-170], which may in turn limit the amount of energy that can be generated in the interaction. On the other hand, raising the affinity of a TCR by directing the energy toward the MHC helices would presumably lead to thymic deletion during negative selection [Bevan, M. J. (1997) *Immunity* 7:175-178]. The term "TCR" encompasses polyclonal, monoclonal, chimeric, humanized, heterodimeric and single-chain T-cell receptors or functional fragment thereof, including molecule comprising the TCR Vα and Vβ domains. The term "TCR" also encompasses T-cell receptors disclosed in for example, US Provisional application Entitled "T CELL RECEPTOR FUSIONS AND CONJUGATES AND METHODS OF USE THEREOF", filed Mar. 19, 2008 and US Patent Publication US 20030144474.

The term "vector" is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

The terms "Fc domain" or "Fc region" is meant to refer to the immunoglobulin heavy chain "fragment crystallizable" region. Generally, an Fc domain is capable of interacting with a second Fc domain to form a dimeric complex. The Fc domain may be capable of binding cell surface receptors called Fc receptors and/or proteins of the complement system or may be modified to reduce or augment these binding activities. The Fc domain may be derived from IgG, IgA, IgD, IgM or IgE antibody isotypes and effect immune activity including opsonization, cell lysis, degranulation of mast cells, basophils, and eosinophils, and other Fc receptor-dependent processes; activation of the complement pathway; and protein stability in vivo.

The abbreviations used are: IgG, immunoglobulin; h, human; IL, interleukin; R, receptor; Su, sushi domain; TCR, T cell receptor; sc, single-chain; sTNFR, soluble tumor necrosis factor-α (TNF-α) receptor; NK, natural killer; KD, equilibrium dissociation constant; CTLs, cytotoxic T lymphocytes; aa, amino acid(s); OVA, ovalbumin; VSV, vesicular stomatitis virus; IMDM, Iscove's modified Dulbecco's medium; CHO, Chinese hamster ovary; mAb, monoclonal antibody; β2m, β2 microglobulin; SA, streptavidin; HRP, horse radish peroxidase; PE, phycoerythrin; ABTS, 2,2'-azinobis [3-ethylbenzothiazoline-6-sulfonic acid]-diammonium salt; PLE, peptide loading enhancer; c264scTCR, soluble single-chain TCR specific to human p53 (aa264-272) peptide/HLA-A*0201 complex; c149scTCR, soluble single-chain TCR specific to human p53 (aa149-157) peptide/HLA-A*0201 complex; OT1scTCR, soluble single-chain TCR specific to OVA (aa257-264) peptide/H-2Kb complex; SEC, size-exclusion chromatography; pMHCI, peptide/MHC class I; SPR, surface plasmon resonance; MW, molecular weight; m, murine; A, absorbance; RU, response units.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

"More than one" is understood as 2, 3, 4, 5, 6, 7, 8, 9, 10, 11, 12, 13, 14, 15, 16, 17, 18, 19, 20, 25, 30, 40, 50, 100, etc., or any value therebetween. "At least" a specific value, is understood to be that value and all values greater than that value.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Fc Domain

Immunoglobulins of IgG class are among the most abundant proteins in human blood. Their circulation half-lives can reach as long as 21 days. Fusion proteins have been reported to combine the Fc regions of IgG with the domains of another protein, such as various cytokines and soluble receptors (see, for example, Capon et al., Nature, 337:525-531, 1989; Chamow et al., Trends Biotechnol., 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and $C_H1$ domains and light chains. The dimer nature of fusion proteins comprising the Fc domain may be advantageous in providing higher order interactions (i.e. bivalent or bispecific binding) with other molecules. Due to the structural homology, Fc fusion proteins exhibit in vivo pharmacokinetic profile comparable to that of human IgG with a similar isotype. To extend the circulating half-life of IL-15 or IL-15 fusion protein and/or to increase its biological activity, it is desirable to make fusion protein complexes containing the IL-15 domain non-covalently bound to IL-15Rα covalently linked to the Fc portion of the human heavy chain IgG protein as disclosed or described in this invention.

The term "Fc" refers to molecule or sequence comprising the sequence of a non-antigen-binding fragment of whole antibody, whether in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. Fc domains containing binding sites for Protein A, Protein G, various Fc receptors and complement proteins In some embodiments, the term "Fc variant" refers to a molecule or sequence that is modified from a native Fc but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, in certain embodiments, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means.

T-Cell Receptors (TCR)

T-cells are a subgroup of cells which together with other immune cell types (polymorphonuclear, eosinophils, basophils, mast cells, B-cells, NK cells), constitute the cellular component of the immune system. Under physiological conditions T-cells function in immune surveillance and in the elimination of foreign antigen. However, under pathological conditions there is compelling evidence that T-cells play a major role in the causation and propagation of disease. In these disorders, breakdown of T-cell immunological tolerance, either central or peripheral is a fundamental process in the causation of autoimmune disease.

The TCR complex is composed of at least seven transmembrane proteins. The disulfide-linked ($\alpha\beta$ or $\gamma\delta$) heterodimer forms the monotypic antigen recognition unit, while the invariant chains of CD3, consisting of $\epsilon$, $\gamma$, $\delta$, $\zeta$, and $\eta$ chains, are responsible for coupling the ligand binding to signaling pathways that result in T-cell activation and the elaboration of the cellular immune responses. Despite the gene diversity of the TCR chains, two structural features are common to all known subunits. Firstly, they are transmembrane proteins with a single transmembrane spanning domain—presumably alpha-helical. Secondly, all the TCR chains have the unusual feature of possessing a charged amino acid within the predicted transmembrane domain.

The invariant chains have a single negative charge, conserved between the mouse and human, and the variant chains possess one (TCR-$\beta$) or two (TCR-$\alpha$) positive charges. The transmembrane sequence of TCR-$\alpha$ is highly conserved in a number of species and thus phylogenetically may serve an important functional role. The octapeptide sequence containing the hydrophilic amino acids arginine and lysine is identical between the species.

A T-cell response is modulated by antigen binding to a TCR. One type of TCR is a membrane bound heterodimer consisting of an $\alpha$ and $\beta$ chain resembling an immunoglobulin variable (V) and constant (C) region. The TCR $\alpha$ chain includes a covalently linked V-$\alpha$ and C-$\alpha$ chain, whereas the $\beta$ chain includes a V-$\beta$ chain covalently linked to a C-$\beta$ chain. The V-$\alpha$ and V-$\beta$ chains form a pocket or cleft that can bind a superantigen or antigen in the context of a major histocompatibility complex (MHC) (known in humans as an HLA complex). See generally Davis *Ann. Rev. of Immunology* 3: 537 (1985); *Fundamental Immunology* 3rd Ed., W. Paul Ed. Rsen Press LTD. New York (1993).

The extracellular domains of the TCR chains ($\alpha\beta$ or $\gamma\delta$) can also engineered as fusions to heterologous transmembrane domains for expression on the cell surface. Such TCRs may include fusions to CD3, CD28, CD8, 4-1BB and/or chimeric activation receptor (CAR) transmembrane or activation domains. TCRs can also be the soluble proteins comprising one or more of the antigen binding domains of $\alpha\beta$ or $\gamma\delta$ chains. Such TCRs may include the TCR variable domains or function fragments thereof with or without the TCR constant domains. Soluble TCRs may be heterodimeric or single-chain molecules.

Fusions Protein Complexes

The soluble fusion protein and conjugate molecule complexes of the invention comprise at least two soluble fusion proteins. In certain embodiments, the first fusion protein comprises a first biologically active polypeptide covalently linked to interleukin-15 (IL-15) or functional fragment thereof; and the second fusion protein comprises a second biologically active polypeptide covalently linked to soluble interleukin-15 receptor alpha (IL-15R$\alpha$) polypeptide or functional fragment thereof, and wherein IL-15 domain of a first fusion protein binds to the soluble IL-15R$\alpha$ domain of the second fusion protein to form a soluble fusion protein complex. Fusion protein complexes of the invention also comprise immunoglobulin Fc domain or a functional fragment thereof linked to one or both of the first and second fusion proteins. Preferably the Fc domains linked to the first and second fusion proteins interact to from a fusion protein complex. Such a complex may be stabilized by disulfide bond formation between the immunoglobulin Fc domains. In certain embodiments, the soluble fusion protein complexes of the invention include an IL-15 polypeptide, IL-15 variant or a functional fragment thereof and a soluble IL-15R$\alpha$ polypeptide or a functional fragment thereof, wherein one or both of the IL-15 and IL-15R$\alpha$ polypeptides further include an immunoglobulin Fc domain or a functional fragment thereof.

In certain examples, one of the biologically active polypeptides comprises a first soluble TCR or fragment thereof. The other or second biologically active polypeptide comprises the first soluble TCR or functional fragment thereof and thus creates a multivalent TCR fusion protein complex with increased binding activity for cognate ligands compared to the monovalent TCR. Further, the other biologically active polypeptide comprises a second soluble TCR or functional fragment thereof, different than the first soluble TCR. In certain examples, TCRs are produced that have higher affinity, or increased binding affinity for cognate ligands as compared, for example, to the native TCR. If the soluble TCR of the invention as described herein has a higher avidity or affinity for its ligand, then it is useful as a specific probe for cell-surface bound antigen. In certain preferred examples of the invention, the TCR is specific for recognition of a particular antigen.

In exemplary embodiments, TCR is a heterodimer comprising an α chain (herein referred to as α, alpha, or a chain) and a β chain (herein referred to as β, beta, or b chain). In other exemplary embodiments, the TCR comprises a single chain TCR polypeptide. The single chain TCR may comprise a TCR V-α chain covalently linked to a TCR V-β chain by a peptide linker sequence. The single chain TCR may further comprise a soluble TCR Cβ chain fragment covalently linked to a TCR V-β chain. The single chain TCR may further comprise a soluble TCR Cα chain fragment covalently linked to a TCR V-α chain.

In a further embodiment, one or both of the first and second biologically active polypeptides comprises an antibody or functional fragment thereof.

In another embodiment, the antigen for the TCR domain comprises peptide antigen presented in an MHC or HLA molecule. In a further embodiment, the peptide antigen is derived from a tumor associated polypeptide or virus encoded polypeptide.

In another embodiment, the antigen for the antibody domain comprises a cell surface receptor or ligand.

In a further embodiment, the antigen comprises a CD antigen, cytokine or chemokine receptor or ligand, growth factor receptor or ligand, tissue factor, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

As used herein, the term "biologically active polypeptide" or "effector molecule" is meant an amino acid sequence such as a protein, polypeptide or peptide; a sugar or polysaccharide; a lipid or a glycolipid, glycoprotein, or lipoprotein that can produce the desired effects as discussed herein. Effector molecules also include chemical agents. Also contemplated are effector molecule nucleic acids encoding a biologically active or effector protein, polypeptide, or peptide. Thus, suitable molecules include regulatory factors, enzymes, antibodies, or drugs as well as DNA, RNA, and oligonucleotides. The biologically active polypeptides or effector molecule can be naturally-occurring or it can be synthesized from known components, e.g., by recombinant or chemical synthesis and can include heterologous components. A biologically active polypeptides or effector molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis. Desired effects of the invention include, but are not limited to, for example, forming a fusion protein complex of the invention with increased binding activity, killing a target cell, e.g. either to induce cell proliferation or cell death, initiate an immune response, in preventing or treating a disease, or to act as a detection molecule for diagnostic purposes. For such detection, an assay could be used, for example an assay that includes sequential steps of culturing cells to proliferate same, and contacting the cells with a TCR fusion complex of the invention and then evaluating whether the TCR fusion complex inhibits further development of the cells.

Covalently linking the effector molecule to the fusion protein complexes of the invention in accordance with the invention provides a number of significant advantages. Fusion protein complexes of the invention can be produced that contain a single effector molecule, including such a peptide of known structure. Additionally, a wide variety of effector molecules can be produced in similar DNA vectors. That is, a library of different effector molecules can be linked to the fusion protein complexes for recognition of infected or diseased cells. Further, for therapeutic applications, rather than administration of a the fusion protein complex of the invention to a subject, a DNA expression vector coding for the fusion protein complex can be administered for in vivo expression of the fusion protein complex. Such an approach avoids costly purification steps typically associated with preparation of recombinant proteins and avoids the complexities of antigen uptake and processing associated with conventional approaches.

As noted, components of the fusion proteins disclosed herein, e.g., effector molecule such as cytokines, chemokines, growth factors, protein toxins, immunoglobulin domains or other bioactive molecules and any peptide linkers, can be organized in nearly any fashion provided that the fusion protein has the function for which it was intended. In particular, each component of the fusion protein can be spaced from another component by at least one suitable peptide linker sequence if desired. Additionally, the fusion proteins may include tags, e.g., to facilitate modification, identification and/or purification of the fusion protein. More specific fusion proteins are in the Examples described below.

Linkers

The fusion complexes of the invention preferably also include a flexible linker sequence interposed between the IL-15 or IL-15Rα domains and the biologically active polypeptide. The linker sequence should allow effective positioning of the biologically active polypeptide with respect to the IL-15 or IL-15Rα domains to allow functional activity of both domains. In embodiments where the biologically active polypeptide is a TCR, the linker sequence positions the TCR molecule binding groove so that the T cell receptor can recognize presenting MHC-peptide complexes and can deliver the effector molecule to a desired site. Successful presentation of the effector molecule can modulate the activity of a cell either to induce or to inhibit T-cell proliferation, or to initiate or inhibit an immune response to a particular site, as determined by the assays disclosed below, including the in vitro assays that includes sequential steps of culturing T cells to proliferate same, and contacting the T cells with a TCR fusion complex of the invention and then evaluating whether the TCR fusion complex inhibits further development of the cells.

In certain embodiments, the soluble fusion protein complex has a linker wherein the first biologically active polypeptide is covalently linked to IL-15 (or functional fragment thereof) by polypeptide linker sequence.

In other certain embodiments, the soluble fusion protein complex as described herein has a linker wherein the second biologically active polypeptide is covalently linked to IL-15Rα polypeptide (or functional fragment thereof) by polypeptide linker sequence.

The linker sequence is preferably encoded by a nucleotide sequence resulting in a peptide that can effectively position the binding groove of a TCR molecule for recognition of a presenting antigen or the binding domain of an antibody molecule for recognition of an antigen. As used herein, the phrase "effective positioning of the biologically active polypeptide with respect to the IL-15 or IL-15Rα domains", or other similar phrase, is intended to mean the biologically active polypeptide linked to the IL-15 or IL-15Rα domains is positioned so that the IL-15 or IL-15Rα domains are capable of interacting with each other to form a protein complex. In certain embodiments, the IL-15 or IL-15Rα domains are effectively positioned to allow interactions with immune cells to initiate or inhibit an immune reaction, or to inhibit or stimulate cell development.

The fusion complexes of the invention preferably also include a flexible linker sequence interposed between the IL-15 or IL-15Rα domains and the immunoglobulin Fc domain. The linker sequence should allow effective positioning of the Fc domain, biologically active polypeptide and IL-15 or IL-15Rα domains to allow functional activity of each domain. In certain embodiments, the Fc domains are effectively positioned to allow proper fusion protein complex formation and/or interactions with Fc receptors on immune cells or proteins of the complement system to stimulate Fc-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences can also be used to link two or more polypeptides of the biologically active polypeptide to generated a single-chain molecule with the desired functional activity.

Preferably the linker sequence comprises from about 7 to 20 amino acids, more preferably from about 8 to 16 amino acids. The linker sequence is preferably flexible so as not hold the biologically active polypeptide or effector molecule in a single undesired conformation. The linker sequence can be used, e.g., to space the recognition site from the fused molecule. Specifically, the peptide linker sequence can be positioned between the biologically active polypeptide and the effector molecule, e.g., to chemically cross-link same and to provide molecular flexibility. The linker preferably predominantly comprises amino acids with small side chains, such as glycine, alanine and serine, to provide for flexibility. Preferably about 80 or 90 percent or greater of the linker sequence comprises glycine, alanine or serine residues, particularly glycine and serine residues. For a fusion protein complex that comprise a heterodimer TCR, the linker sequence is suitably linked to the β chain of the TCR molecule, although the linker sequence also could be attached to the α chain of the TCR molecule. Alternatively, linker sequence may be linked to both α and β chains of the TCR molecule. When such a β peptide chain is expressed along with the α chain, the linked TCR polypeptide should fold resulting in a functional TCR molecule as generally depicted in FIG. 1. One suitable linker sequence is ASGGGGSGGG (i.e., Ala Ser Gly Gly Gly Gly Ser Gly Gly Gly) (SEQ ID NO: 5), preferably linked to the first amino acid of the β domain of the TCR. Different linker sequences could be used including any of a number of flexible linker designs that have been used successfully to join antibody variable regions together, see Whitlow, M. et al., (1991) *Methods: A Companion to Methods in Enzymology* 2:97-105. In some examples, for covalently linking an effector molecule to a TCR β chain molecule, the amino sequence of the linker should be capable of spanning suitable distance from the C-terminal residue of the TCR β chain to the N-terminal residue of the effector molecule. Suitable linker sequences can be readily identified empirically. Additionally, suitable size and sequences of linker sequences also can be determined by conventional computer modeling techniques based on the predicted size and shape of the TCR molecule.

In general, preparation of the fusion protein complexes of the invention can be accomplished by procedures disclosed herein and by recognized recombinant DNA techniques involving, e.g., polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, transformation or transfection of a host, culturing of the host. Additionally, the fusion molecules can be isolated and purified using chaotropic agents and well known electrophoretic, centrifugation and chromatographic methods. See generally, Sambrook et al., *Molecular Cloning: A Laboratory Manual* (2nd ed. (1989); and Ausubel et al., *Current Protocols in Molecular Biology*, John Wiley & Sons, New York (1989) for disclosure relating to these methods.

As used herein, biologically active polypeptides or effector molecules of the invention may include factors such as cytokines, chemokines, growth factors, protein toxins, immunoglobulin domains or other bioactive proteins such as enzymes. Also biologically active polypeptides may include conjugates to other compounds such as non-protein toxins, cytotoxic agents, chemotherapeutic agents, detectable labels, radioactive materials and such.

Cytokines of the invention are defined by any factor produced by cells that affect other cells and are responsible for any of a number of multiple effects of cellular immunity. Examples of cytokines include but are not limited to the IL-2 family, interferon (IFN), IL-10, IL-1, IL-17, TGF and TNF cytokine families, and to IL-1 through IL-35, IFN-α, IFN-β, IFNγ, TGF-β, TNF-α, and TNFβ.

In an aspect of the invention, the first fusion protein comprises a first biologically active polypeptide covalently linked to interleukin-15 (IL-15) domain or a functional fragment thereof. IL-15 is a cytokine that affects T-cell activation and proliferation. IL-15 activity in affecting immune cell activation and proliferation is similar in some respects to IL2, although fundamental differences have been well characterized (Waldmann, T A, 2006, *Nature Rev. Immunol.* 6:595-601).

In another aspect of the invention, the first fusion protein comprises an interleukin-15 (IL-15) domain that is an IL-15 variant (also referred to herein as IL-15 mutant). The IL-15 variant preferably comprises a different amino acid sequence that the native (or wild type) IL-15 protein. The IL-15 variant preferably binds the IL-15Rα polypeptide and functions as an IL-15 agonist or antagonist. Preferably IL-15 variants with agonist activity have super agonist activity. In some embodiments, the IL-15 variant can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In some examples, the IL-15 variant binds with increased or decreased activity to the IL-15RβγC receptors. In some embodiments, the sequence of the IL-15 variant has at least one amino acid change, e.g. substitution or deletion, compared to the native IL-2 sequence, such changes resulting in IL-15 agonist or antagonist activity. Preferably the amino acid substitutions/deletions are in the domains of IL-15 that interact with IL-15Rβ and/or γC. More preferably, the amino acid substitutions/deletions do not affect binding to the IL-15Rα polypeptide or the ability to produce the IL-15 variant. Suitable amino acid substitutions/deletions to generate IL-15 variants can be identified based on putative or known IL-15 structures, comparisons of IL-15 with homologous molecules such as IL-2 with known structure, through rational or random mutagenesis and functional assays, as provided herein, or other empirical methods. Additionally suitable amino acid substitutions can be conservative or non-conservative changes and insertions of additional amino acids. Preferably IL-15 variants of the invention contain one or more than one amino acid substitutions/deletions at position 6, 8, 10, 61, 65, 72, 92, 101, 104, 105, 108, 109, 111, or 112 of the mature human IL-15 sequence; particularly, D8N ("D8" refers to the amino acid and residue position in the native mature human IL-15 sequence and "N" refers to the substituted amino acid residue at that position in the IL-15 variant), I6S, D8A, D61A, N65A, N72R, V104P or Q108A substitutions result in IL-15 variants with antagonist activity and N72D substitutions result in IL-15 variants with agonist activity.

Chemokines, similar to cytokines, are defined as any chemical factor or molecule which when exposed to other cells are responsible for any of a number of multiple effects of cellular immunity. Suitable chemokines may include but are not limited to the CXC, CC, C, and $CX_3C$ chemokine families and to CCL-1 through CCL-28, CXC-1 through CXC-17, XCL-1, XCL-2, CX3CL1, MIP-1b, IL-8, MCP-1, and Rantes.

Growth factors include any molecules which when exposed to a particular cell induce proliferation and/or differentiation of the affected cell. Growth factors include proteins and chemical molecules, some of which include: GM-CSF, G-CSF, human growth factor and stem cell growth factor. Additional growth factors may also be suitable for uses described herein.

Toxins or cytotoxic agents include any substance that has a lethal effect or an inhibitory effect on growth when exposed to cells. More specifically, the effector molecule can be a cell toxin of, e.g., plant or bacterial origin such as, e.g., diphtheria toxin (DT), shiga toxin, abrin, cholera toxin, ricin, saporin, *pseudomonas* exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C).

Further, the effector molecule can be a chemotherapeutic drug such as, e.g., vindesine, vincristine, vinblastin, methotrexate, adriamycin, bleomycin, or cisplatin.

Additionally, the effector molecule can be a detectably-labeled molecule suitable for diagnostic or imaging studies. Such labels include biotin or streptavidin/avidin, a detectable nanoparticles or crystal, an enzyme or catalytically active fragment thereof, a fluorescent label such as green fluorescent protein, FITC, phycoerythrin, cychome, texas red or quantum dots; a radionuclide e.g., iodine-131, yttrium-90, rhenium-188 or bismuth-212; a phosphorescent or chemiluminescent molecules or a label detectable by PET, ultrasound or MRI such as Gd—or paramagnetic metal ion-based contrast agents. See e.g., Moskaug, et al. *J. Biol. Chem.* 264, 15709 (1989); Pastan, I. et al. *Cell* 47, 641, 1986; Pastan et al., Recombinant Toxins as Novel Therapeutic Agents, *Ann. Rev. Biochem.* 61, 331, (1992); "Chimeric Toxins" Olsnes and Phil, *Pharmac. Ther.*, 25, 355 (1982); published PCT application no. WO 94/29350; published PCT application no. WO 94/04689; published PCT application no. WO2005046449 and U.S. Pat. No. 5,620,939 for disclosure relating to making and using proteins comprising effectors or tags.

A protein fusion or conjugate complex that includes a covalently linked IL-15 and IL-15Rα domains has several important uses. For example, the protein fusion or conjugate complex comprising a TCR can be employed to deliver the IL-15:IL-15Rα complex to certain cells capable of specifically binding the TCR. Accordingly, the protein fusion or conjugate complex provide means of selectively damaging or killing cells comprising the ligand. Examples of cells or tissue capable of being damaged or killed by the protein fusion or conjugate complexes comprising a TCR include tumors and virally or bacterially infected cells expressing one or more ligands capable of being specifically bound by the TCR. Cells or tissue susceptible to being damaged or killed can be readily assayed by the methods disclosed herein.

The IL-15 and IL-15Rα polypeptides of the invention suitably correspond in amino acid sequence to naturally occurring IL-15 and IL-15Rα molecules, e.g. IL-15 and IL-15Rα molecules of a human, mouse or other rodent, or other mammal. Sequences of these polypeptides and encoding nucleic acids are known in the literature, including human interleukin 15 (IL15) mRNA—GenBank: U14407.1, *Mus musculus* interleukin 15 (IL15) mRNA—GenBank: U14332.1, human interleukin-15 receptor alpha chain precursor (IL15RA) mRNA—GenBank: U31628.1, *Mus musculus* interleukin 15 receptor, alpha chain-GenBank: BC095982.1.

In some settings it can be useful to make the protein fusion or conjugate complexes of the present invention polyvalent, e.g., to increase the valency of the sc-TCR or sc-antibody. In particular, interactions between the IL-15 and IL-15Rα domains of the fusion protein complex provide a means of generating polyvalent complexes. In addition, the polyvalent fusion protein can made by covalently or non-covalently linking together between one and four proteins (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding tag sequences that can be modified such as the biotinylation BirA tag or amino acid residues with chemically reactive side chains such as Cys or His. Such amino acid tags or chemically reactive amino acids may be positioned in a variety of positions in the fusion protein, preferably distal to the active site of the biologically active polypeptide or effector molecule. For example, the C-terminus of a soluble fusion protein can be covalently linked to a tag or other fused protein which includes such a reactive amino acid(s). Suitable side chains can be included to chemically link two or more fusion proteins to a suitable dendrimer or other nanoparticle to give a multivalent molecule. Dendrimers are synthetic chemical polymers that can have any one of a number of different functional groups of their surface (D. Tomalia, Aldrichimica Acta, 26:91:101 (1993)). Exemplary dendrimers for use in accordance with the present invention include e.g. E9 starburst polyamine dendrimer and E9 combust polyamine dendrimer, which can link cystine residues. Exemplary nanoparticles include liposomes, core-shell particles or PLGA-based particles.

In another embodiment of the invention, one or both of the polypeptides of the fusion protein complex comprises an immunoglobulin domain. Alternatively, the protein binding domain-IL-15 fusion protein can be further linked to an immunoglobulin domain. The preferred immunoglobulin domains comprise regions that allow interaction with other immunoglobulin domains to form multichain proteins as provided above. For example, the immunoglobulin heavy chain regions, such as the IgG1 $C_H2$-$C_H3$, are capable of stably interacting to create the Fc region. Preferred immunoglobulin domains including Fc domains also comprise regions with effector functions, including Fc receptor or complement protein binding activity, and/or with glycosylation sites. In some embodiments, the immunoglobulin domains of the fusion protein complex contain mutations that reduce or augment Fc receptor or complement binding activity or glycosylation, thereby affecting the biological activity of the resulting protein. For example, immunoglobulin domains containing mutations that reduce binding to Fc receptors could be used to generate fusion protein complex of the invention with lower binding activity to Fc receptor-bearing cells, which may be advantageous for reagents designed to recognize or detect specific antigens.

Nucleic Acids and Vectors

The invention further provides nucleic acid sequences and particularly DNA sequences that encode the present fusion proteins. Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate preparative methods described herein and to obtain significant quantities of the fusion protein. The DNA sequence can be inserted into an appropriate expression vector, i.e., a vector that contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See generally Sambrook et al., supra and Ausubel et al. supra.

Included in the invention are methods for making a soluble fusion protein complex, the method comprising introducing into a host cell a DNA vector as described herein encoding the first and second fusion proteins, culturing the host cell in media under conditions sufficient to express the fusion proteins in the cell or the media and allow association between IL-15 domain of a first fusion protein and the soluble IL-15Rα domain of a second fusion protein to form the soluble fusion protein complex, purifying the soluble fusion protein complex from the host cells or media.

In general, a preferred DNA vector according to the invention comprises a nucleotide sequence linked by phosphodiester bonds comprising, in a 5' to 3' direction a first cloning site for introduction of a first nucleotide sequence encoding a biologically active polypeptide, operatively linked to a sequence encoding an effector molecule.

The fusion protein components encoded by the DNA vector can be provided in a cassette format. By the term "cassette" is meant that each component can be readily substituted for another component by standard recombinant methods. In particular, a DNA vector configured in a cassette format is particularly desirable when the encoded fusion complex is to be used against pathogens that may have or have capacity to develop serotypes.

To make the vector coding for a fusion protein complex, the sequence coding for the biologically active polypeptide is linked to a sequence coding for the effector peptide by use of suitable ligases. DNA coding for the presenting peptide can be obtained by isolating DNA from natural sources such as from a suitable cell line or by known synthetic methods, e.g. the phosphate triester method. See, e.g., Oligonucleotide Synthesis, IRL Press (M. J. Gait, ed., 1984). Synthetic oligonucleotides also may be prepared using commercially available automated oligonucleotide synthesizers. Once isolated, the gene coding for the biologically active polypeptide can be amplified by the polymerase chain reaction (PCR) or other means known in the art. Suitable PCR primers to amplify the biologically active polypeptide gene may add restriction sites to the PCR product. The PCR product preferably includes splice sites for the effector peptide and leader sequences necessary for proper expression and secretion of the biologically active polypeptide-effector fusion complex. The PCR product also preferably includes a sequence coding for the linker sequence, or a restriction enzyme site for ligation of such a sequence.

The fusion proteins described herein are preferably produced by standard recombinant DNA techniques. For example, once a DNA molecule encoding the biologically active polypeptide is isolated, sequence can be ligated to another DNA molecule encoding the effector polypeptide. The nucleotide sequence coding for a biologically active polypeptide may be directly joined to a DNA sequence coding for the effector peptide or, more typically, a DNA sequence coding for the linker sequence as discussed herein may be interposed between the sequence coding for the biologically active polypeptide and the sequence coding for the effector peptide and joined using suitable ligases. The resultant hybrid DNA molecule can be expressed in a suitable host cell to produce the fusion protein complex. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein.

Other nucleotide sequences also can be included in the gene construct. For example, a promoter sequence, which controls expression of the sequence coding for the biologically active polypeptide fused to the effector peptide, or a leader sequence, which directs the fusion protein to the cell surface or the culture medium, can be included in the construct or present in the expression vector into which the construct is inserted. An immunoglobulin or CMV promoter is particularly preferred.

In obtaining variant biologically active polypeptide, IL-15, IL-15Rα or Fc domain coding sequences, those of ordinary skill in the art will recognize that the polypeptides may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein. In other instance, modifications to amino acid positions can be made to reduce or enhance the biological activity of the protein. Such changes can be introduced randomly or via site-specific mutations based on known or presumed structural or functional properties of targeted residue(s). Following expression of the variant protein, the changes in the biological activity due to the modification can be readily assessed using binding or functional assays.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50 C, 6×SSC (sodium chloride/sodium citrate buffer) and 0.1% SDS (sodium dodecyl sulfate) indicate about 60-70% homology, hybridization and wash conditions of 50-65 C, 1×SSC and 0.1% SDS indicate about 82-97% homology, and hybridization and wash conditions of 52 C, 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the world wide web at ncbi.nlm.nih.gov and a version of ClustalW is available at 2.ebi.ac.uk.

The components of the fusion protein can be organized in nearly any order provided each is capable of performing its intended function. For example, in one embodiment, the biologically active polypeptide is situated at the C or N terminal end of the effector molecule.

Preferred effector molecules of the invention will have sizes conducive to the function for which those domains are intended. The effector molecules of the invention can be made and fused to the biologically active polypeptide by a variety of methods including well-known chemical cross-linking methods. See e.g., Means, G. E. and Feeney, R. E. (1974) in *Chemical Modification of Proteins*, Holden-Day. See also, S. S. Wong (1991) in *Chemistry of Protein Conjugation and Cross-Linking*, CRC Press. However it is generally preferred to use recombinant manipulations to make the in-frame fusion protein.

As noted, a fusion molecule or a conjugate molecule in accord with the invention can be organized in several ways. In an exemplary configuration, the C-terminus of the biologically active polypeptide is operatively linked to the N-terminus of the effector molecule. That linkage can be achieved by recombinant methods if desired. However, in another configuration, the N-terminus of the biologically active polypeptide is linked to the C-terminus of the effector molecule.

Alternatively, or in addition, one or more additional effector molecules can be inserted into the biologically active polypeptide or conjugate complexes as needed.

Vectors and Expression

A number of strategies can be employed to express protein fusion complexes of the invention. For example, the fusion protein construct described above can be incorporated into a suitable vector by known means such as by use of restriction enzymes to make cuts in the vector for insertion of the construct followed by ligation. The vector containing the gene construct is then introduced into a suitable host for expression of the fusion protein. See, generally, Sambrook et al., supra. Selection of suitable vectors can be made empirically based on factors relating to the cloning protocol. For example, the vector should be compatible with, and have the proper replicon for the host that is being employed. Further the vector must be able to accommodate the DNA sequence coding for the fusion protein complex that is to be expressed. Suitable host cells include eukaryotic and prokaryotic cells, preferably those cells that can be easily transformed and exhibit rapid growth in culture medium. Specifically preferred hosts cells include prokaryotes such as *E. coli*, *Bacillus subtillus*, etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See Sambrook, supra. Stable transformed or transfected cell lines can then be selected. Cells expressing a fusion protein complex of the invention can be determined by known procedures. For example, expression of a fusion protein complex linked to an immunoglobulin can be determined by an ELISA specific for the linked immunoglobulin and/or by immuno-blotting. Other methods for detecting expression of fusion proteins comprising biologically active polypeptides linked to IL-15 or IL-15Rα domains are disclosed in the Examples.

As mentioned generally above, a host cell can be used for preparative purposes to propagate nucleic acid encoding a desired fusion protein. Thus a host cell can include a prokaryotic or eukaryotic cell in which production of the fusion protein is specifically intended. Thus host cells specifically include yeast, fly, worm, plant, frog, mammalian cells and organs that are capable of propagating nucleic acid encoding the fusion. Non-limiting examples of mammalian cell lines which can be used include CHO dhfr-cells (Urlaub and Chasm, *Proc. Natl. Acad. Sci. USA*, 77:4216 (1980)), 293 cells (Graham et al., *J Gen. Virol.*, 36:59 (1977)) or myeloma cells like SP2 or NSO (Galfre and Milstein, *Meth. Enzymol.*, 73(B):3 (1981)).

Host cells capable of propagating nucleic acid encoding a desired fusion protein comples encompass non-mammalian eukaryotic cells as well, including insect (e.g., Sp. *frugiperda*), yeast (e.g., *S. cerevisiae*, *S. pombe*, *P. pastoris.*, *K. lactis*, *H. polymorpha*; as generally reviewed by Fleer, R., *Current Opinion in Biotechnology*, 3(5):486496 (1992)), fungal and plant cells. Also contemplated are certain prokaryotes such as *E. coli* and *Bacillus*.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the biologically active polypeptide coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His *S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 μg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art (λZAP and pBLUESCRIPT SK-1, Stratagene, La Jolla, Calif., pET, Novagen Inc., Madison, Wis., cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into *S. cerevisiae* cells by protoplast transformation or electroporation. Electroporation of *S. cerevisiae* is readily accomplished, and yields transformation efficiencies comparable to spheroplast transformation.

The present invention further provides a production process for isolating a fusion protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium to stimulate transcription of the nucleotides sequence encoding the fusion protein of interest. Subsequently, the fusion protein of interest is isolated from harvested host cells or from the culture medium. Standard protein purification techniques can be used to isolate the protein of interest from the medium or from the harvested cells. In particular, the purification techniques can be used to express and purify a desired fusion protein on a large-scale (i.e. in at least milligram quantities) from a variety of implementations including roller bottles, spinner flasks, tissue culture plates, bioreactor, or a fermentor.

An expressed protein fusion complex can be isolated and purified by known methods. Typically the culture medium is centrifuged or filtered and then the supernatant is purified by affinity or immunoaffinity chromatography, e.g. Protein-A or Protein-G affinity chromatography or an immunoaffinity protocol comprising use of monoclonal antibodies that bind the expressed fusion complex such as a linked TCR or immunoglobulin region thereof. The fusion proteins of the present invention can be separated and purified by appropriate combination of known techniques. These methods include, for example, methods utilizing solubility such as salt precipitation and solvent precipitation, methods utilizing the difference in molecular weight such as dialysis, ultrafiltration, gel-filtration, and SDS-polyacrylamide gel electrophoresis, methods utilizing a difference in electrical charge such as ion-exchange column chromatography, methods utilizing specific affinity such as affinity chromatography, methods utilizing a difference in hydrophobicity such as reverse-phase high performance liquid chromatography and methods utilizing a difference in isoelectric point, such as isoelectric focusing electrophoresis, metal affinity columns such as Ni-NTA. See generally Sambrook et al. and Ausubel et al. supra for disclosure relating to these methods.

It is preferred that the fusion proteins of the present invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

Soluble TCR fusion complexes of the invention contain TCR domains that is sufficiently truncated so the TCR fusion complex can be secreted into culture medium after expression. Thus, a truncated TCR fusion complex will not include regions rich in hydrophobic residues, typically the transmembrane and cytoplasmic domains of the TCR molecule. Thus, for example, for a preferred truncated TCR molecule of the invention, preferably from about the final cysteine to the C-terminal residue of the β chain and from about the final cysteine to the C-terminal residue of the α chain of the TCR molecule are not included in the truncated TCR fusion complex.

The present fusion protein complexes are suitable for in vitro or in vivo use with a variety of cells that are cancerous or are infected or that may become infected by one or more diseases.

DETAILED DESCRIPTION

Human interleukin-15 (hIL-15) is trans-presented to immune effector cells by the human IL-15 receptor α chain (hIL-15Rα) expressed on antigen presenting cells. IL-15Rα binds hIL-15 with high affinity (38 pM) mainly through the extracellular sushi domain (hIL-15RαSu). Here we demonstrate that the hIL-15 and hIL-15RαSu domains can be used as a scaffold to construct multi-domain fusion complexes. Both bivalent and bispecific T cell receptor (TCR) fusion complexes were formed using this scaffold through the combination of various single-chain (sc) TCR domains fused to the N-termini of the hIL-15 and hIL-15RαSu chains. In these fusions, the scTCR domains retain the antigen binding activity and the hIL-15 domain exhibits receptor binding and biological activity. Bivalent scTCR fusions exhibited improved antigen binding capacity due to increased molecular binding avidity whereas fusions comprising two different scTCR domains were capable of binding two cognate peptide/MHC complexes. Bispecific molecules containing scTCR and scCD8αβ domains also exhibit significantly better binding to cognate peptide/MHC complex than either the bivalent or monovalent scTCR molecules, demonstrating that the IL-15:IL-15Rα scaffold exhibits flexibility necessary to support multi-domain interactions with given target. Surprisingly, functional TCRs could also be formed by co-expressing the TCR α and β chains separately as fusions to the hIL-15 and hIL-15RαSu domains. Finally we show that the fused hIL-15 domain can be manipulated through site-specific mutations to provide superagonist or antagonist cytokine activity. Together, these properties indicate that the hIL-15 and hIL-15RαSu domains can be used as versatile, functional scaffold for generating novel targeted immune molecules.

IgG domains, particularly the Fc fragment, have been used successfully as dimeric scaffolds for a number of therapeutic molecules including approved biologic drugs. For example, etanercept is a dimer of soluble human p75 tumor necrosis factor-α (TNF-α) receptor (sTNFR) linked to the Fc domain of human IgG1. This dimerization allows etanercept to be up to 1,000 times more potent at inhibiting TNF-α activity than the monomeric sTNFR and provides the fusion with a five-fold longer serum half-life than the monomeric form. As a result, etanercept is effective at neutralization of the pro-inflammatory activity of TNF-α in vivo and improving patient outcomes for a number of different autoimmune indications.

In addition to its dimerization activity, the Fc fragment also provides cytotoxic effector functions through the complement activation and interaction with Fcγ receptors displayed on natural killer (NK) cells, neutrophils, phagocytes and dendritic cells. In the context of anti-cancer therapeutic antibodies and other antibody domain-Fc fusion proteins, these activities likely play an important role in efficacy observed in animal tumor models and in cancer patients. However these cytotoxic effector responses may not be sufficient in a number of therapeutic applications. Thus, there has been considerable interest in improving and expanding on the effector activity of the Fc domain and developing other means of recruiting cytolytic immune responses, including T cell activity, to the disease site via targeted therapeutic molecules. IgG domains have been used as a scaffold to form bispecific antibodies to improve the quality and quantity of products generated by the traditional hybridoma fusion technology. Although these methods bypass the shortcomings of other scaffolds, it has been difficult to produce bispecific antibodies in mammalian cells at levels sufficient to support clinical development and use.

In an effort to develop a new, human-derived immunostimulatory multimeric scaffold, we focused on the use of human IL-15 (hIL-15) and IL-15 receptor domains hIL-15 is a member of the small four α-helix bundle family of cytokines that associates with the hIL-15 receptor α-chain (hIL-15Rα) with a high binding affinity (Equilibrium dissociation constant (KD)~$10^{-11}$ M). The resulting complex is then trans-presented to the human IL-2/15 receptor β/common γ chain (hIL-15RβγC) complexes displayed on the surface of T cells and NK cells. This cytokine/receptor interaction results in expansion and activation of effector T cells and NK cells, which play an important role in eradicating virally infected and malignant cells. Normally, hIL-15 and hIL-15Rα are co-produced in dendritic cells to form complexes intracellularly that are subsequently secreted and displayed as heterodimeric molecules on cell surfaces. Thus, the characteristics of hIL-15 and hIL-15Rα interactions suggest that these inter chain binding domains could serve as a novel, human-derived immunostimulatory scaffold to make soluble dimeric molecules capable of target-specific binding. Herein, we describe the generation and characterization of a number of fusion proteins comprising T cell receptor (TCR) and CD8 binding domains to demonstrate the feasibility of using hIL-15-hIL-15Rα scaffold to create both soluble homodimers with increased functional binding affinity toward target antigens and heterodimers for multiple-site-specific protein complexes. We also show that these fusion proteins retain potent hIL-15 activity capable of stimulating immune effector cell responses.

Herein, we demonstrate the potential uses of a hIL-15-hIL-15RαSu-based scaffold to create novel, dimeric molecules. The dimeric fusion protein complexes retained immunostimulatory and target-specific biological activity of their hIL-15 domains and binding domains, indicating that the addition of hIL-15 and hIL-15Rα did not significantly alter the spatial arrangement of the fusion domains and provided an adequate degree of conformational flexibility without impacting cytokine activity. Thus, this scaffold could be used to form multivalent fusion complexes, such as the c264scTCR dimer, to increase the overall binding affinity of molecules, or bispecific molecules, such as the c264scTCR/c149scTCR heterodimer. In all cases, the soluble fusion proteins were produced at relatively high levels in recombinant CHO cell culture (mgs per liter in cell culture supernatant without extensive cell line screening or optimization) and could be readily purified from the cell culture supernatants. We also demonstrated that the utility of the hIL-15-hIL-15RαSu-based scaffold could be expanded to create soluble, biologically active, two-chain molecules, such as α/β TCRs, by fusing the extracellular domains of the two polypeptide chains to the N-termini of hIL-15 and hIL-15RαSu. This format resulted in a moderate decrease in hIL-15 activity, possibly due to steric hindrance between the interfolded TCR α/β chains fused to the distal N-termini of the hIL-15-hIL-15RαSu complex and the hIL-15RβγC binding site located in the middle of the complex. Other formats are possible and can be generated using routine methods.

The hIL-15-hIL-15RαSu-based scaffold was also used to generate an OT1scTCR/scCD8 heterodimer in which the CD8 α/β and TCR domains are capable of binding the same pMHCI complex but at a spatially distinct sites. Previous studies using soluble pMHCI reagents have determined that CD8 stabilizes and enhances TCR:pMHCI interactions at the cell surface through effects on both the off-rate and the on-rate. This effect is important in determining the dependency of the T cells on CD8 co-receptor activity, such that the requirement for CD8 for pMHCI-specific T cell activation is inversely correlated with TCR:pMHCI affinity. However, several binding studies using soluble purified CD8 α/β, TCR and pMHCI proteins have shown that TCR:pMHCI interactions are not affected by the presence or absence of CD8, suggesting no cooperative binding effects.

The results of our cell-based and SPR binding studies with the OT1scTCR/scCD8 heterodimer are in contrast with these earlier reports in showing that TCR and CD8 domains displayed on the same soluble molecule exhibited much better peptide/MHC binding activity than was observed with molecules carrying monovalent or divalent TCR domains. This effect is reflected in both a slower off-rate and faster on-rate of the pMHCI:OT1scTCR/scCD8 heterodimer complex, consistent with the observations for pMHCI binding to CD8 and TCR molecules on T cells. Thus, the OT1scTCR/scCD8 heterodimer mimics binding of the OT1 TCR on T cells, which exhibits a strong dependence of CD8 coreceptor activity for pMHC interactions. These results indicate that the scTCR/scCD8 heterodimer and variants of this molecule could serve as very useful tools for further dissecting molecular interactions between the tertiary TCR:pMHCI:CD8 complex in a cell-free system. In addition, scTCR/scCD8 heterodimer-based reagents with enhanced pMHCI binding activity could have utility in detecting antigen presentation on diseased cells, without the need of mutating the TCR domain for increased binding affinity.

The results of our SPR experiments on the OT1scTCR fusions differ from those reported by Alam et al. where the binding affinity of monovalent OT1 TCRα/β heterodimer to immobilized OVA peptide/H-2Kb complex was shown to be approximately 6 μM. In our studies, we were unable to detect OVA peptide/H-2Kb-binding of the OT1scTCR/birA monomer and the OT1scTCR/birA dimer exhibited an apparent KD of 30 μM. It is possible that the OT1 TCR lost binding activity when formatted as a single-chain Vα-linker-Vβ-Cβ molecule. However, we observed equivalent activity when comparing OT1scTCR/birA and a two-chain construct. Moreover, previous studies have shown that OVA peptide/H-2Kb tetramers with Kb mutations that abrogate CD8 binding exhibit little or no specific binding activity to OT1 TCR-bearing cells even when high concentrations of tetramers were used, suggesting very low affinity interactions between OT1 TCR and its cognate pMHCI. In contrast, OVA peptide/H-2Kb tetramers without the CD8 binding mutations were able to brightly stain OT1 TCR-bearing cells, consistent with the ability of CD8 to enhance OT1 TCR binding activity observed in this study.

The hIL-15-hIL-15RαSu-based scaffold can be exploited much like the Fc domain of the IgG scaffold to generate multivalent or multispecific targeted therapeutics. With its potent activity for stimulating proliferation and activation of effector NK and CD8$^+$ memory T cells, the hIL-15 domain expands the scope of potential immunotherapeutic mechanisms beyond antibody-dependent cellular cytotoxicity and complement activation associated with IgG-based approaches. Using approaches similar to those used to manipulate the activity of the Fc domain of IgG molecules, we demonstrate that the IL-15 domain can be mutated to increase or decrease its functional activity. We show that hIL-15-hIL-15RαSu fusion molecule containing an N72D mutation in the IL-15 domain exhibit a 3-4 fold increase in biological activity, whereas IL-15 D8N mutation exhibit little or no activity. While IL-15 superagonist-based fusion proteins could serve as targeted immunotherapeutics for cancer and infectious diseases, an IL-15 antagonist capable of inhibiting IL-15 responsive cells at the disease site may have therapeutic potential in treating allograft rejection and inflammatory autoimmune diseases, particularly if memory CD8 T cells play a role in disease pathology. A non-targeted IL-15 mutant/Fcγ2a antagonist protein has already been shown to be effective at inhibiting islet and cardiac allograft rejection and preventing development and progression of arthritis in experimental animal models. Similar approaches with IL-15 antagonist domains in the context of the hIL-15:hIL-15RαSu fusion proteins are possible. In addition, under certain circumstances, it may be desirable to have a functionally inert scaffold for generation of multimeric molecules. For example, we have found that scTCR/hIL-15:scTCR/hIL-15RαSu fusions containing an IL-15 D8N mutation, which eliminates interactions with IL-15Rβγ, provide better TCR antigen-specific staining of cells displaying IL-15 receptor complex.

Although we have focused on TCRs and CD8 molecules as targeting domains for demonstration purposes herein, it is understood that the hIL-15-hIL-15RαSu scaffold could be used to construct other novel molecules with protein domains derived from antibodies, adhesion molecules, or other receptors. It is also possible to create protein domain fusions to the C-termini of the hIL-15 and hIL-15RαSu which, based on the crystal structure, are accessible for modification. The resulting molecules can contain up to four different target-recognition capabilities. With the appropriate fusion partners, these types of molecules can promote the conjugation of immune effectors cells and target cells and achieve effective killing of target cells. In addition, the IL-15 domain of the complex can further augment these processes by providing immunostimulatory activity to support effector cell proliferation and cytotoxicity. A variety of multi-functional molecules based on this concept for use as anti-cancer and anti-viral immunotherapeutic agents.

Previously, the poor expression level in standard mammalian cell system limited the development of recombinant hIL-15 as a therapeutic. As demonstrated herein, expression of scTCR/hIL-15:scTCR/hIL-15RαSu complexes at levels capable of supporting clinical development and potentially product commercialization can be achieved. In addition, it has been shown that the IL-15Rα chain enhances the in vivo activity of hIL-15, without being bound by mechanism, possibly by improving the pharmacokinetics of the cytokine. These two characteristics of hIL-15:hIL-15RαSu complexes, in combination with its multivalent nature and/or multispecific targeting design, provides an opportunity to capture the full potential of hIL-15 as an immunotherapeutic agent against cancer and viral infections.

As provided in the Examples, hIL-15-hIL-15RαSu fusion protein complexes comprising immunoglobulin Fc domains were found to have additional advantages. Association of the Fc domains allows generation of multichain molecules capable of multivalent and multispecific interactions. In fact, the fusion protein complexes of the invention comprising the multiple domains of the same scTCR exhibited enhanced antigen binding activity than that expected based on the activity of the dimeric scTCR fusion. In some cases, the fusion complex of the invention is capable of binding and activating both IL-15RβγC-bearing immune cells and Fc receptor-bearing immune cells, allowing for potent immune stimulatory activity. The protein fusion complex of the invention comprising two IL-15 domains was found to exhibited better IL-15 activity than that expected when compared to other IL-15 fusion proteins. Additionally, the protein fusion complex of the invention was more effective at mediating antibody Fc depended cellular cytotoxicity against peptide/MHC presenting target cells than the TCR-IgG1 fusion protein. The improved activity may have been the result of enhanced binding of the protein fusion complexes to the peptide/MHC complex and/or increase reactivity to the effector cells displaying Fc receptors or IL-15 receptors. Moreover, through mutagenesis analysis it was found that of each of the TCR, IL-15 and IgG Fc domains of the fusion protein complexes could be readily and independently manipulated to alter its binding and functional activity to provide a multispecific complex with the desired biological effects.

The fusion protein complexes of the invention were demonstrated to have a significantly better pharmacokinetic profile in mammals than free IL-15. In addition, based on the similar PK profile observed with different methods of analysis, the fusion protein complexes remains intact in vivo as a multichain molecule with no evidence of polypeptide chain cleavage or dissociation. Additionally, the fusion protein complexes of the invention are shown to be capable of mediating antitumor activity against both target bearing and non-target bearing tumors in animals and exhibited more potent antitumor efficacy than rhIL-15 administered at an equivalent molar dose. Moreover, treatment with effective doses of the fusion proteins was well tolerated in these animal models.

EXAMPLE 1

Construction of Expression Vectors Containing c264scTCR/huIL15RαSushi-huIgG1 and c149scTCR/huIL15N72D Gene Fusions The fusion protein referred to as the T2 molecule (T2M) consists of a multichain polypeptide (FIG. 1). In one embodiment of the invention, one of these polypeptides comprises a fusion between a protein-binding domain and IL-15 (or IL-15 variants) as disclosed in WO2008143794 (incorporated herein by reference). A second polypeptide of T2 comprises a fusion between a protein binding domain, an IL-15Rα domain and an immunoglobulin domain. Alternatively, the protein binding domain-IL-15 fusion protein can be further linked to an immunoglobulin domain. The preferred immunoglobulin domains comprise regions that allow interaction with other immunoglobulin domains to form multichain proteins. For example, the immunoglobulin heavy chain regions, such as the IgG1 $C_H2$-$C_H3$, are capable of interacting to create the Fc region. Preferred immunoglobulin domains also comprise regions with effector functions, including Fc receptor or complement protein binding activity, and/or with glycosylation sites. In some embodiments, the immunoglobulin domains of the T2 molecule contain mutations that reduce or augment Fc receptor or complement binding activity or glycosylation, thereby affecting the biological activity of the resulting protein. For example, immunoglobulin domains containing mutations that reduce binding to Fc receptors could be used to generate T2 molecules with lower binding activity to Fc receptor-bearing cells, which may be advantageous for reagents designed to recognize or detect TCR-specific antigens.

Figure 2:
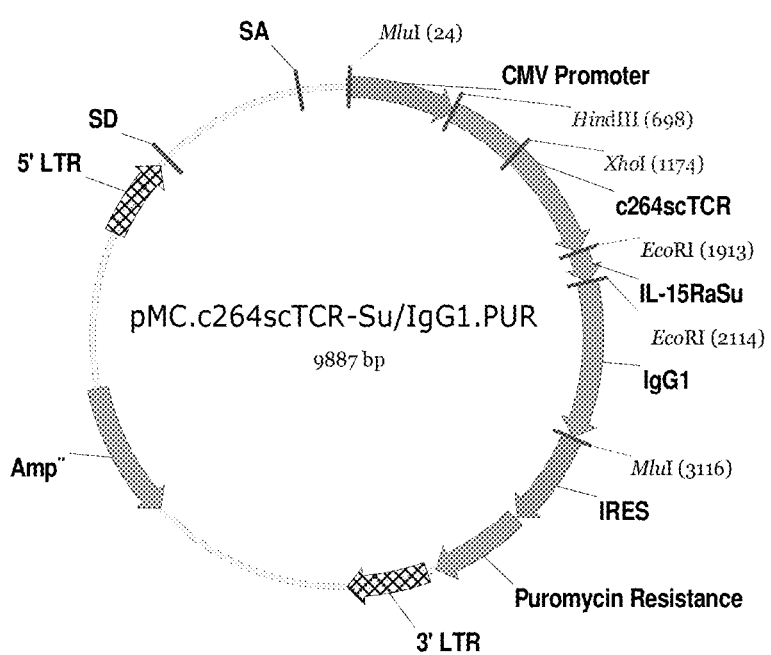
FIG. 2 shows the vector (pMC.c264scTCR-Su/IgG1.PUR) containing the correct human IL15RαSushi gene insert.

Construction of an expression vector containing the p53 (aa 264-272) single-chain TCR (referred to a c264scTCR) fused to human IL-15Rα sushi domain (huIL15RαSushi) and human IgG1 constant regions (huIgG1 $C_H1$-$C_H2$-$C_H3$) was carried out as follows. The c264scTCR/huIgG1 gene fragment was removed from the previous constructed the pNEF38-c264scTCR/huIgG1 vector by restricted digestion with PacI and MluI. The gene fragment was gel-purified and ligated to pMSGV vector digested with the same restriction enzymes, resulted in the construct called as pMSGV-c264scTCR/huIgG1. A DNA fragment containing the CMV promoter was purified from pcDNA3.1 following digestion with NruI and HindIII. This fragment was ligated into pMSGV-c264scTCR/huIgG1 which had been digested with PacI and filled in with DNA polymerase to create blunt ends and then digested with HindIII. The resulting construct was named as pMC-c264scTCR/huIgG1. A huIL15RαSushi gene fragment from a previous constructed, pNEF38-c264scTCR/huIL15RαSushi (see WO2008143794), was amplified with front primer:

(SEQ ID NO: 6)
5'-TGTTGGGAATTCATCACGTGCCCTC-3' and back primer:

(SEQ ID NO: 7)
5'-TGGTGTGAATTCTCTAATGCATTTGAGACTGG-3' by KOD Hot Start DNA Polymerase (EMD) under following PCR conditions: 95 C, 2 min, 1 cycle; 95 C, 20 sec, 65 C, 20 sec; 70 C, 20 sec, 35 cycles; 72 C, 10 min, 1 cycle. The PCR product of human IL15RαSushi gene was gel-purified and digested with EcoRI. The gene was ligated into pMC-c264scTCR/huIgG1 which had been digested with EcoRI. Cloning of the DNA fragment encoding the human IL15RαSushi domain into the pMC-c264scTCR/huIgG1 resulted in a c264scTCR/huIL15RαSushi-huIgG1 fusion gene comprising the following sequence: 3'-immunoglobulin heavy chain leader-264 TCR V-α-peptide linker-264 TCR V-β-human TCR C-β-human IL15RαSushi-human IgG1 heavy chain. The resulting vector (pMC.c264scTCR-Su/IgG1.PUR), shown in FIG. 2, containing the correct human IL15RαSushi gene insert was identified based on the diagnostic PCR and reconfirmed by DNA sequencing. The sequences of the c264scTCR/huIL15RαSushi/huIgG1 gene and protein are shown at FIG. 3A and FIG. 3B and FIG. 4A, FIG. 4B, and FIG. 4C, respectively.

A different expression vector containing c264scTCR/huIL15RαSushi-huIgG1 gene fusion was constructed that lacked the internal EcoRI sites (and corresponding coding sequences). For this vector, a portion of the c264scTCR gene fragment was amplified from the c264scTCR/huIgG1 vector with front primer:

(SEQ ID NO: 8)
5'GTACGACTTAATTAACTCGAGCCACCATGGAGACAGACACACTCCTGT
TATGG3' and back primer:

(SEQ ID NO: 9)
5'CTTCCCGTTAACCCACCAGCTCAGCTCCACGTG3'.

The remainder of the TCR (3 constant region of the c264scTCR gene fragment was amplified from c264scTCR/huIgG1 vector with front primer:

(SEQ ID NO: 10)
5'CTGGTGGGTTAACGGGAAGGAGGTGCACAGTGGGGTC3' and back primer:

(SEQ ID NO: 11)
5'GAGGGCACGTGATGTCTGCTCTACCCCAGGCCTC3'

The huIL15RαSushi gene fragment was amplified from the c264scTCR/huIL15RαSushi vector with front primer:

(SEQ ID NO: 12)
5'GTAGAGCAGACATCACGTGCCCTCCCCCCATG3' and the back primer:

(SEQ ID NO: 13)
5'CCTTGGTGCTAGCTCTAATACATTTGAGACTGGGGGTTGTCC3'.

The huIgG1 heavy chain constant region gene fragment was amplified from the c264scTCR/huIgG1 vector with front primer:

(SEQ ID NO: 14)
5'CCAGTCTCAAATGTATTAGAGCTAGCACCAAGGGCCCATCGGTC3' and back primer:

(SEQ ID NO: 15)
5'GTAATATTCTAGACGCGTTCATTATTTACCAGGAGACAGGGAGAGGCT
CTTC3'.

The resulting products containing the TCR β constant region sequence and huIL15RαSushi gene were used as templates to generate a gene fragment by PCR using with front primer:

(SEQ ID NO: 10)
5'CTGGTGGGTTAACGGGAAGGAGGTGCACAGTGGGGTC3' and back primer:

(SEQ ID NO: 13)
5'CCTTGGTGCTAGCTCTAATACATTTGAGACTGGGGGTTGTCC3'

The resulting PCR product and the huIgG1 gene fragment served as templates to generate a TCRβc/huIL15RαSushi/huIgG1 fusion gene by PCR with front primer:

(SEQ ID NO: 10)
5'CTGGTGGGTTAACGGGAAGGAGGTGCACAGTGGGGTC3' and back primer:

(SEQ ID NO: 15)
5'GTAATATTCTAGACGCGTTCATTATTTACCAGGAGACAGGGAGAGGCT
CTTC3'

To generate the c149scTCR/IL15N72D gene fusion, a c149scTCR gene fragment (TCR-α, linker, TCR-β and TCR-β constant fragment) was amplified from c149scTCR/huIgG1 expression vector with the front primer:

(SEQ ID NO: 16)
5'GACTTCAAGCTTAATTAAGCCACCATGGACAGACTTACTTCTTC3' and the back primer:

(SEQ ID NO: 9)
5'-CTTCCCGTTAACCCACCAGCTCAGCTCCACGTG-3'

The remainder of the TCR β constant region of the c149scTCR/huIgG1 vector was amplified with front primer:

(SEQ ID NO: 10)
5'CTGGTGGGTTAACGGGAAGGAGGTGCACAGTGGGGTC3' and the back primer:

(SEQ ID NO: 17)
5'CACCCAGTTGTCTGCTCTACCCCAGGCCTC3'

The huIL15N72D gene was amplified from c264scTCR/huIL15N72D expression vector with the front primer:

(SEQ ID NO: 18)
5'CTGGGGTAGAGCAGACAACTGGGTGAATGTAATAAGTGATTTG3' and the back primer:

(SEQ ID NO: 19)
5'CCTCATGCATTCGAATCCGGATCATTAAGAAGTGTTGATGAACAT
TTGG3'

The resulting products containing the TCR β constant region sequence and huIL15N72D gene were used as templates to generate a gene fragment by PCR using with front primer:

```
                                              (SEQ ID NO: 10)
5'CTGGTGGGTTAACGGGAAGGAGGTGCACAGTGGGGTC3'
``` and the back primer:

```
                                              (SEQ ID NO: 19)
5'CCTCATGCATTCGAATCCGGATCATTAAGAAGTGTTGATGAACAT
TTGG3'
```

Figure 5:
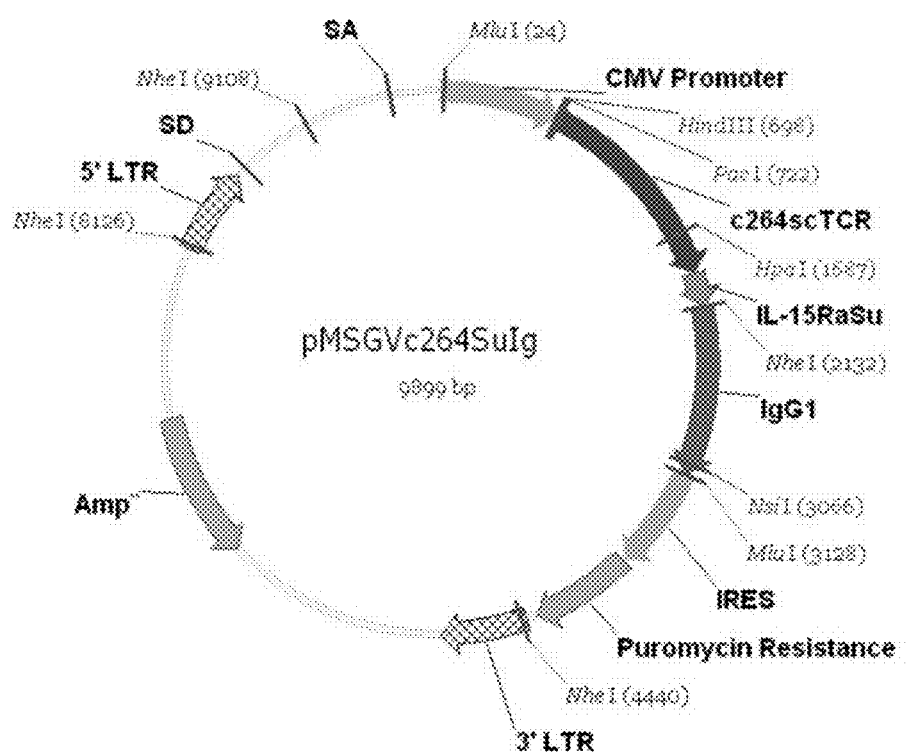
FIG. 5 shows the vector designated as c264scTCR/Sushi/hIgG1-pMSGVc or pMSGVc264SuIg.

The c264scTCR PCR product was digested with PacI and HpaI and the TCRβc/huIL15RαSushi/huIgG1 fusion gene was digested with HpaI and NsiI. The digested gene fragments were ligated into a CMV promoter-containing pMSGV retrovirus vector. The resulting vector was designated as c264scTCR/Sushi/hIgG1-pMSGVc or pMSGVc264SuIg (FIG. 5). The sequences of the c264scTCR/huIL15RαSushi/huIgG1 gene and protein are shown at FIG. 6A and FIG. 6B and FIG. 7A, FIG. 7B, and FIG. 7C, respectively.

Generation of expression vectors producing a fusion between single-chain TCR binding domain (i.e. c264scTCR) and IL-15 (or IL-15 variants) has been disclosed in WO2008143794. Particularly useful IL-15 variants are those that reduce or eliminate IL-15 biological activity or that increase IL-15 biological activity. For example, human IL-15 variants with substitutions at position 72 (i.e. N72D substitution) can increase the IL-15 biological activity 5 to 10 fold. IL-15 variants are provided in the table below:

| Mutants | Position | 8 | 61 | 65 | 72 | 108 | IL15Rβγc receptor binding | IL15Rα binding | Proliferation Activity |
|---|---|---|---|---|---|---|---|---|---|
|  | WT aa | D | D | N | N | Q | + | + | + |
| 1 | 8 | N |  |  |  |  | − | + | − |
| 2 | 8 | A |  |  |  |  | − | + | − |
| 3 | 61 |  | A |  |  |  | − | + | − |
| 4 | 65 |  |  | D |  |  | − | + | − |
| 5 | 65 |  |  | A |  |  | − | + | − |
| 6 | 72 |  |  |  | D |  | 3+ | + | 3+ |
| 8 | 72 |  |  |  | R |  | − | + | − |
| 9 | 108 |  |  |  |  | A | − | + | − |
| 10 | 8 + 65 | N |  | A |  |  | − | + | − |
| 11 | 8 + 108 | A |  |  |  | A | − | + | − |
| 12 | 8 + 65 | S |  | R |  |  | − | + | − |

The fusion protein complexes comprising IL-15 variants as described in the table immediately above were characterized for their ability to bind the TCR-specific antigen, p53 (aa264-272)/HLA-A2.1. To generate cells presenting p53 (aa264-272)/HLA-A2.1, HLA-A2.1-positive T2 cells (2×10⁶/mL) were loaded with 20 μM p53 (aa264-272) peptide at 37° C. in the presence of 1×PLE (Altos Bioscience) for 2-3 hrs. T2 cells that were not incubated with peptide and 32Dβ cells expressing IL-2/15Rβγ$_C$ serve as controls. The p53 peptide-loaded T2 cells, control T2 cells, or 32Dβ cells (2×10⁵/100 μL) were then incubated for 30 min at 4 C with 320 nM of following dimeric fusion protein complexes: 1) c264scTCR/huIL15+c264scTCR/huIL15Rα Sushi, 2) c264scTCR/huIL15D8A+c264scTCR/huIL15Rα Sushi, and 3) c264scTCR/huIL15D8N+c264scTCR/huIL15Rα Sushi. These complexes were generated by incubating 160 nM of purified c264scTCRhuIL15 fusion protein and 160 nM of purified c264scTCRhuIL15Rα Sushi fusion protein at 4 C for 3 hours. Following staining, cells were washed once with washing buffer (PBS containing 0.5% BSA and 0.05% sodium azide) and stained with 0.5 μg of biotinylated mouse monoclonal anti-human TCR Cβ antibody (BF1) in 100 μL of washing buffer for 30 min at 4 C. Cells were washed once and stained with 0.5μ·g of R-Phycoerythrin conjugated streptavidin in 100 μL of washing buffer for 30 min at 4 C. Cells were washed and resuspended for analysis by flow cytometry.

The c264scTCR/huIL15D8A+c264scTCR/huIL15RαSushi complex and c264scTCR/huIL15D8N+c264scTCR/huIL15RαSushi complex exhibited equivalent activity as the c264scTCR/huIL15+c264scTCR/huIL15RαSushi complex for specifically staining p53 peptide-loaded T2 cells. These results indicate that the multivalent scTCR domains are fully functional in each of these fusion complexes. Fusion protein complexes comprising IL-15 variants (D8A and D8N) do not show binding activity to the IL-15Rβγ$_c$ receptors present on the 32Dβ cells. Similar studies of IL-15Rβγ$_c$ receptor binding were carried out with other fusion proteins comprising IL-15 variants and are summarized in Table 1. The results indicate that fusion proteins and fusion protein complexes of the invention comprising IL-15 variants retain activity to recognize peptide/MHC complexes and exhibit decreased or increased binding activity for IL-15Rβγ$_c$ receptors.

For certain T2 molecules, it is useful to have multiple different binding domains fused to the IL-15 and IL-15Rα components. In one example to illustrate the activity of such molecules, a single-chain TCR domain (called c149scTCR), specific to the p53 (aa 149-157) peptide presented in the context of HLA-A2, was linked to the IL-15N72D domain and the resulting fusion protein co-expressed with the c264scTCR/huIL15RαSushi/huIgG1 fusion protein to produce a multichain T2 protein with c264scTCR and c149scTCR binding domains.

To generate the c149scTCR/IL15N72D gene fusion, a c149scTCR gene fragment (TCR-α, linker, TCR-β and TCR-β constant fragment) was amplified from c149scTCR/huIgG1 expression vector with the front primer:

```
                                              (SEQ ID NO: 16)
5'GACTTCAAGCTTAATTAAGCCACCATGGACAGACTTACTTCTTC3'
``` and the back primer:

```
                                              (SEQ ID NO: 9)
5'-CTTCCCGTTAACCCACCAGCTCAGCTCCACGTG-3'
```

The remainder of the TCR β constant region of the c149scTCR/huIgG1 vector was amplified with front primer:

```
                                              (SEQ ID NO: 10)
5'CTGGTGGGTTAACGGGAAGGAGGTGCACAGTGGGGTC3'
``` and the back primer:

```
                                              (SEQ ID NO: 17)
5'CACCCAGTTGTCTGCTCTACCCCAGGCCTC3'
```

The huIL15N72D gene was amplified from c264scTCR/huIL15N72D expression vector with the front primer:

```
                                              (SEQ ID NO: 18)
5'CTGGGGTAGAGCAGACAACTGGGTGAATGTAATAAGTGATTTG3'
``` and the back primer:

(SEQ ID NO: 19)
5'CCTCATGCATTCGAATCCGGATCATTAAGAAGTGTTGATGAACAT
TTGG3'

The resulting products containing the TCR β constant region sequence and huIL15N72D gene were used as templates to generate a gene fragment by PCR using with front primer:

(SEQ ID NO: 10)
5'CTGGTGGGTTAACGGGAAGGAGGTGCACAGTGGGGTC3' and the back primer:

(SEQ ID NO: 19)
5'CCTCATGCATTCGAATCCGGATCATTAAGAAGTGTTGATGAACAT
TTGG3'

Figure 8:
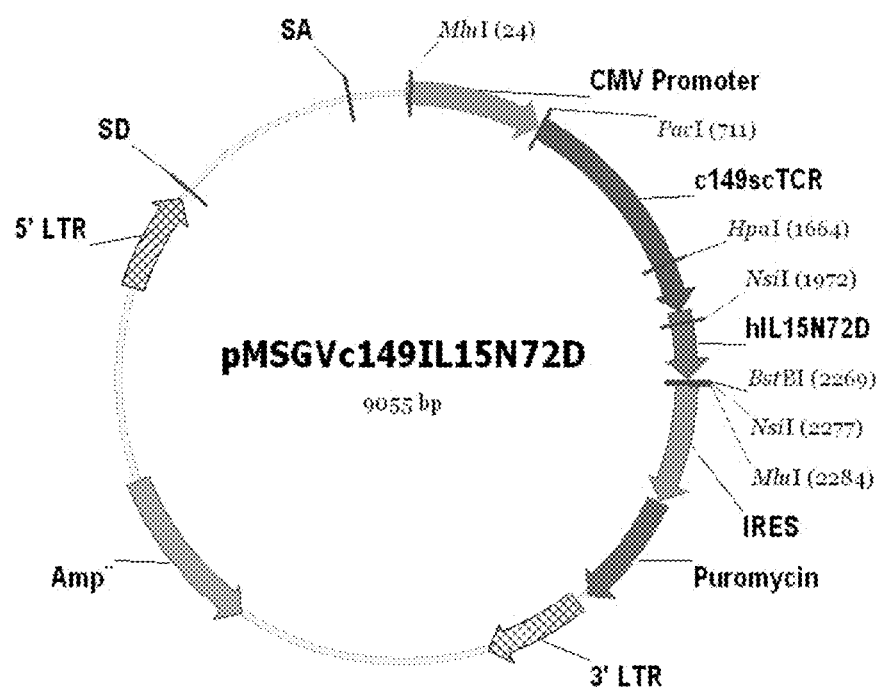
FIG. 8 shows the vector designated as c149scTCR/IL15N72D-pMSGVn or pMSGV-c149IL15N72D.

The c149scTCR PCR product was digested with Pac I and Hpa I and the TCRβc/huIL15N72D PCR product was digested with Hpa I and BstB I. The digested gene fragments were ligated into a CMV promoter-containing pMSGV retrovirus vector. The resulting vector was designated as c149scTCR/IL15N72D-pMSGVN or pMSGV-c149IL15N72D (FIG. 8). The sequences of the c149scTCR/huIL15N72D gene and protein are shown at FIG. 9 and FIG. 10A and FIG. 10B, respectively.

EXAMPLE 2

Generation of Transfected Host Cell Lines Producing Fusion Proteins

The expression vectors can be introduced into a variety of host cell lines by several different transformation, transfection or transduction methods. In one such method, CHO-K1 cells ($5 \times 10^5$) were seeded in a 6-well plate and cultured overnight in a $CO_2$ incubator. The cells were transfected with 5 μg of expression vector containing the c264scTCR/huIL15N72D fusion genes using 10 μL of Mirus TransIT-LT1 reagent (Mirus) according to the manufacturer's protocol. The cells were selected with 4 mg/mL of G418 (Invitrogen) one day after the transfection. The G418 resistant cells were expanded and TCR/IL15 fusion protein expressing cells were subcloned three times by the limiting dilution and production cell lines were screened based on the level of soluble fusion protein secreted into the culture media by TCR and huIL15-specific ELISA with a capture antibody, anti-human TCR Cβ antibody (BF1), and a detection antibody, biotinylated anti-human IL-15 antibody (BAM 247, R&D Systems) described previously (see WO2008143794). The c264scTCR/IL15N72D producing cell line was then transducted with the pseudotyped retroviral vector containing c264scTCR/huIL15RαSushi/huIgG1 fusion gene as follows.

To produce the pseudotyped retroviral vector, $2 \times 10^6$ of the 293GP packaging cells in a poly-lysine coated 10 cm dish (BD Bioscience) were cultured for 2 days at 37° C. in a $CO_2$ incubator. The cells were then co-transfected using Lipofectamine 2000 (Invitrogen) with 9 μg of the plasmid pMC-c264scTCR/huIL15RαSushi/huIgG1 and 4 μg of the plasmid pMD-G encoding VSV-G envelope protein. The supernatant containing virus was collected 48 hrs post-transfection and cell debris was removed by passing through a 0.45 μM polyvinylidene fluoride filter. Virus was applied to the c264scTCR/IL15N72D producing cells ($1 \times 10^5$ cells/well in a 6-well plate) in the presence of 10 μg/ml of polybrene (Sigma-Aldrich). Cells were selected with 10 μg/ml of puromycin and 2 mg/ml of G418 2 days post-transduction. The puromycin and G418 resistant cells were expanded and the T2 fusion protein complex expressing cells were subcloned three times by the limiting dilution and production cell lines were screened based on the level of soluble fusion protein secreted into the culture media using a huIgG1/huIL15-specific ELISA with a capture antibody, anti-human IgG antibody (Jackson ImmunoResearch), and a detection antibody, biotinylated anti-human IL-15 antibody (BAM 247, R&D Systems).

EXAMPLE 3

Generation and Purification of T2 Fusion Proteins

Cell lines expressing c264scTCR/huIL15N72D and c264scTCR/huIL15RαSushi/huIgG1 were cultured under growth conditions (i.e. 25-37° C. for 5 to 28 days in small scale culture flasks, spinner or shaker flasks or in large scale hollow-fiber, wave bag or stir tank bioreactors or equivalent culture vessels and reactors) to produce the T2 molecule as a soluble protein in the culture media. To purify the T2 molecule the culture media was pH-adjusted and loaded on to an immunoaffinity column containing an anti-TCR antibody (BF1) covalently coupled to Sepharose. The column was washed and T2 molecules eluted with 0.5 M Na-citrate pH 4.0. The eluted protein was concentrated and buffer exchanged into phosphate buffered saline (PBS) and then loaded on rProtein A-Sepharose column Following wash steps, the protein was eluted with 0.5 M Na-citrate pH 4.0 and then buffer exchanged into PBS. The resulting protein was characterized by Coomassie-stained SDS-PAGE and size exclusion chromatography.

Figure 11:
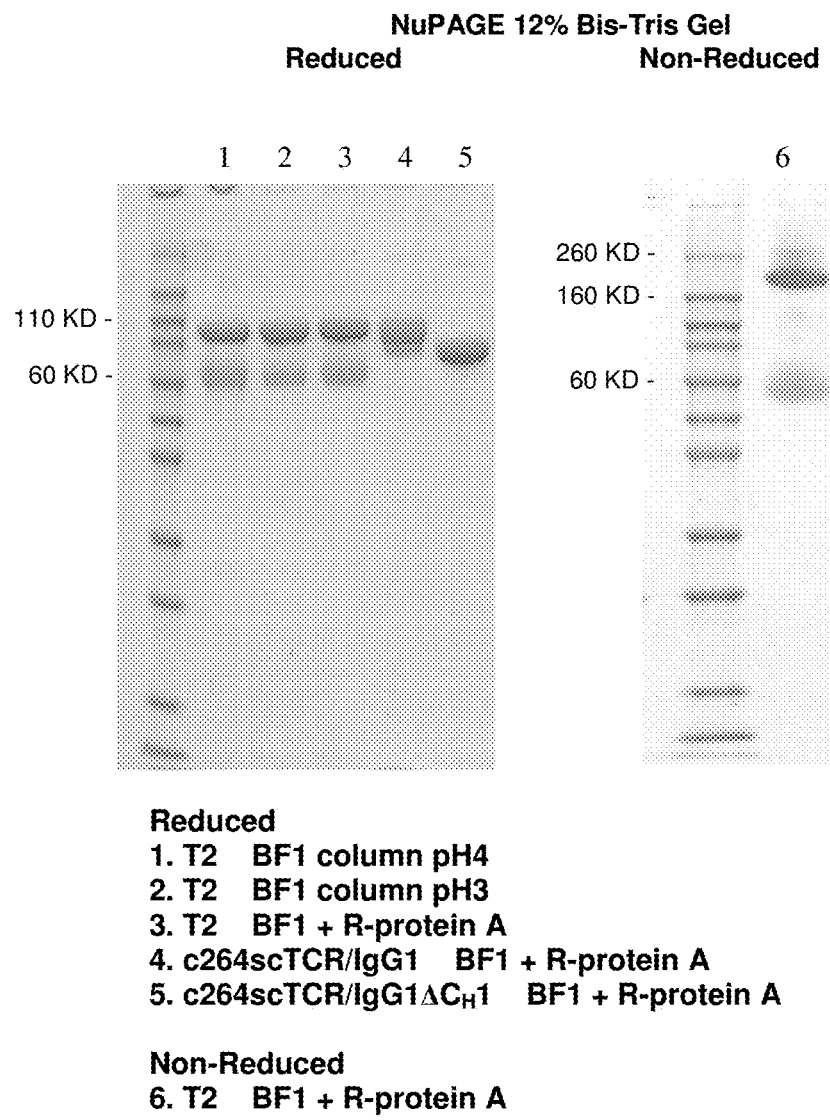
FIG. 11 shows an SDS-PAGE analysis of purification fractions of the T2, c264scTCR/huIgG1 and c264scTCR/huIgG1ΔCH1 fusion proteins under reducing and non-reducing conditions. Under reducing conditions, the T2 molecule bands migrate at molecular weights consisted with the c264scTCR/huIL15 and c264scTCR/huIL15RαSushi/huIgG1 polypeptides. Under non-reducing denaturing conditions, the c264scTCR/huIL15RαSushi/huIgG1 band migrates at a molecular weight consistent with a dimeric disulfide-linked c264scTCR/huIL15RαSushi/huIgG1 complex and a c264scTCR/huIL15N72D polypeptide.
Figure 12:
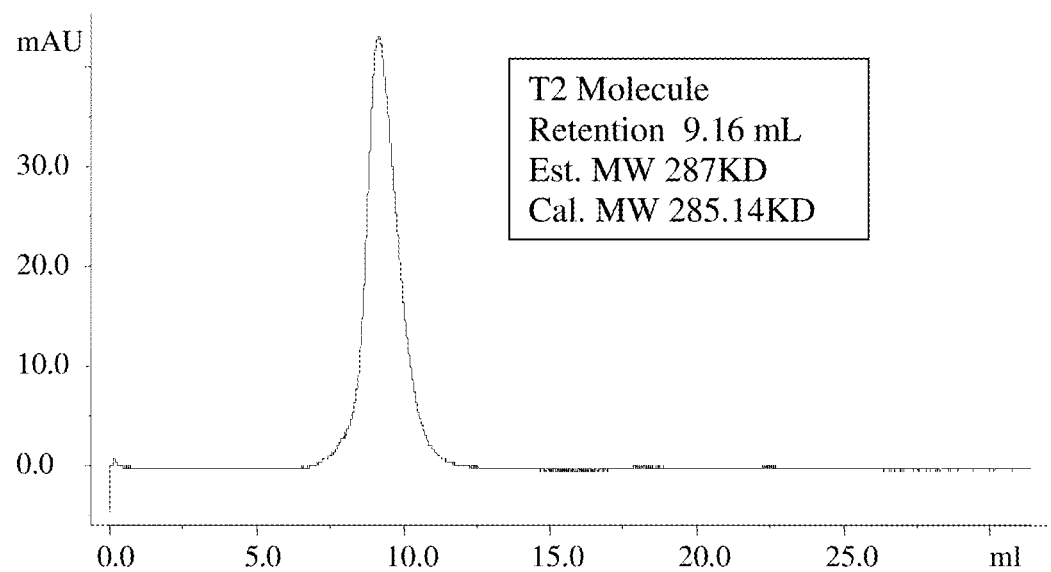
FIG. 12 shows results from size exclusion gel filtration chromatography demonstrating that the native T2 protein eluted at the expected molecular weight of a four-chain (2×c264scTCR/IL15N72D, 2×c264scTCR/huIL15RαSushi/huIgG1) molecule.

Under reducing SDS-PAGE conditions, the purified T2 protein migrated as two polypeptide bands corresponding to the molecular weights expected of the c264scTCR/huIL15N72D and c264scTCR/huIL15RαSushi/huIgG1 components compared to purified c264scTCR/huIgG1 and c264scTCR/huIgG1ΔCH1 fusion proteins which migrate a single bands expected of homodimeric molecules (FIG. 11). Under non-reducing denaturing conditions, the c264scTCR/huIL15RαSushi/huIgG1 band migrates at a molecular weight consistent with a dimeric polypeptide whereas the c264scTCR/huIL15N72D band is consistent with its monomeric form (FIG. 11). By size exclusion gel filtration chromatography, the native T2 protein eluted at the expected molecular weight of a four-chain (2×c264scTCR/IL15N72D, 2×c264scTCR/huIL15RαSushi/huIgG1) molecule (FIG. 12). These results confirm that the T2 molecule exhibits a multichain conformation consistent with the interactions between the huIL15N72D and huIL15RαSushi domains and covalent interactions between the huIgG1 as shown in FIG. 1.

Similar mammalian cell expression and affinity chromatography purification methods were used to generate other T2 protein complexes described herein.

EXAMPLE 4

In Vitro Characterization of the Binding Activities of the T2 Molecule

In vitro assays were carried out to characterize the binding activities of the domains of the T2 molecule and to compare these activities with those of other fusion molecules. To characterize the IgG1 domain, microtiter wells were coated with anti-human IgG1 antibody and equivalent molar amounts of purified T2 protein, composed of c264scTCR/huIL15N72D and c264scTCR/huIL15RαSushi/huIgG1 chains, or purified c264scTCR/huIgG1 fusion protein were applied to the wells. Following binding and washing steps, the bound proteins were detected with anti-human IgG1 antibody under standard ELISA conditions.

Figure 13:
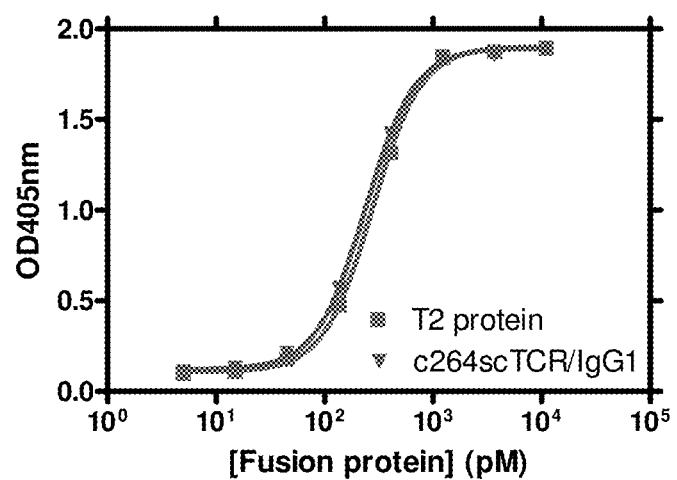
FIG. 13 shows results from an in vitro binding assay in which equimolar amounts of purified T2 protein, composed of c264scTCR/huIL15N72D and c264scTCR/huIL15RαSushi/huIgG1 chains, or purified c264scTCR/huIgG1 fusion protein were captured on wells coated with anti-human IgG1 antibody. Following binding, proteins were detected using anti-human IgG1 antibody under standard ELISA conditions.

The results of the assay shown in FIG. 13 demonstrate that the IgG1 domain of the T2 molecule shows equivalent antibody binding activity as the comparable domain of the TCR/IgG1 fusion, indicating that the T2 IgG1 domain retains a native conformation. The TCR domain of the T2 molecule was assessed in a similar assay. Equivalent molar amounts of T2 or c264scTCR/huIgG1 proteins were captured on anti-human IgG1 Ab coated wells and detected with an anti-human TCR Cβ antibody (W4F).

Figure 14:
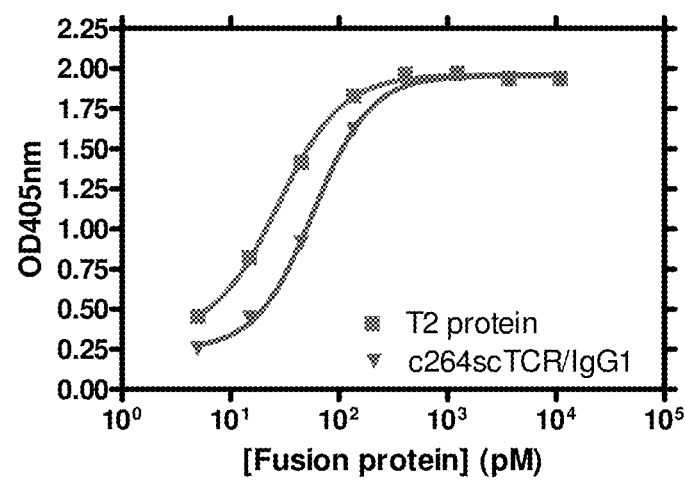
FIG. 14 shows results from an in vitro binding assay in which equimolar amounts of T2 or c264scTCR/huIgG1 proteins were captured on anti-human IgG1 Ab coated wells and detected with an anti-human TCR Cβ antibody (W4F).
Figure 15:
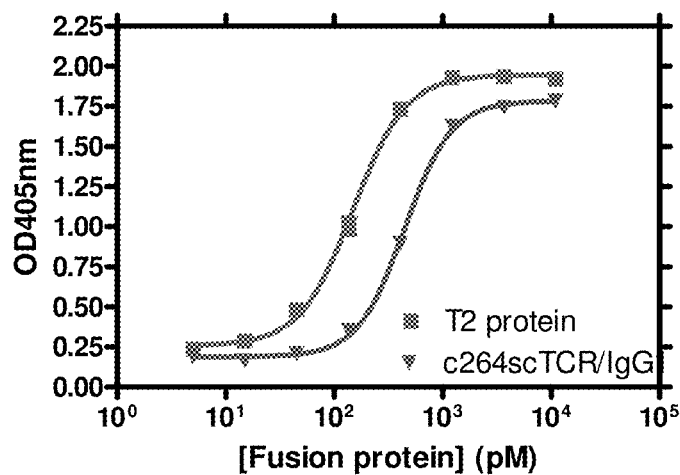
FIG. 15 shows results from an in vitro binding assay in which the peptide/MHC binding activity of the TCR domains of the T2 molecule was assessed. Equimolar amounts of T2 (composed of c264scTCR/huIL15N72D and c264scTCR/huIL15RαSushi/huIgG1 chains) or c264scTCR/huIgG1 proteins were captured on anti-human IgG1 Ab coated wells and detected with p53 (aa 264-272) peptide/HLA-A2 streptavidin-HRP tetramers.

As shown in FIG. 14, the T2 protein exhibited 2-fold higher reactivity than the c264scTCR/huIgG1 protein to the anti-TCR antibody. This is expected given the four-chain TCR fusion protein composition of the T2 molecule compared with the homodimeric composition of the c264scTCR/huIgG1 fusion. The peptide/MHC binding activity of the TCR domains of the T2 molecule was assessed. Equivalent molar amounts of T2 (composed of c264scTCR/huIL15N72D and c264scTCR/huIL15RαSushi/huIgG1 chains) or c264scTCR/huIgG1 proteins were captured on anti-human IgG1 Ab coated wells and detected with p53 (aa 264-272) peptide/HLA-A2 streptavidin-HRP tetramers. As shown in FIG. 15, the T2 protein exhibited 3-fold higher binding activity than the c264scTCR/huIgG1 protein to the peptide/MHC reagent. This was unexpected since based on its structure and anti-TCR Ab reactivity (see FIG. 14) the T2 protein was anticipated to only exhibit 2-fold higher TCR binding activity than c264scTCR/huIgG1. Thus the T2 molecular structure provides a better antigen-specific binding activity than expected based on the individual components. This enhanced binding activity may be the result of less steric interference, better avidity effects, cooperative interactions and/or a better conformational fit between the TCR domain and peptide/MHC antigen.

EXAMPLE 5

Characterization of the Biological Activity of the T2 IL-15 Domain

The activity of the IL-15 domain of the T2 molecule was also assessed. Microtiter wells were coated with anti-human IL-15 antibody and equivalent molar amounts of purified T2 protein, composed of c264scTCR/huIL15N72D and c264scTCR/huIL15RαSushi/huIgG1 chains, or purified c264scTCR/huIL15N72D fusion protein were applied to the wells. Following binding and washing steps, the bound proteins were detected with anti-human IL-15 antibody under standard ELISA conditions.

Figure 16:
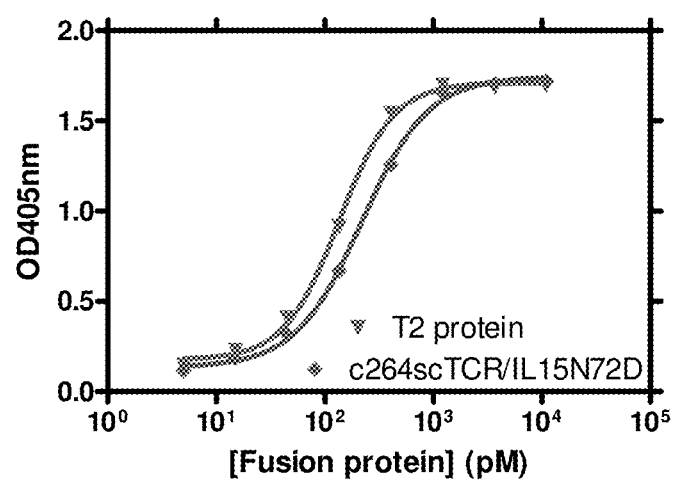
FIG. 16 shows results from an in vitro assay to demonstrate the activity of the IL-15 domain of the T2 molecule. Microtiter wells were coated with anti-human IL-15 antibody and equivalent molar amounts of purified T2 protein, composed of c264scTCR/huIL15N72D and c264scTCR/huIL15RαSushi/huIgG1 chains, or purified c264scTCR/huIL15N72D fusion protein were applied to the wells. Following binding and washing steps, the bound proteins were detected with anti-human IL-15 antibody under standard ELISA conditions.

As shown in FIG. 16, the T2 protein exhibited increased reactivity (1.6-fold higher) compared to c264scTCR/huIL15N72D fusion for the anti-IL15 Ab, as expected based on hypothesis that each T2 molecule contains two IL-15 domains. The biological activity of the IL-15 domain of the T2 molecules was further characterized in proliferation assays using the cytokine-dependent 32Dβ cell line. To measure cell proliferation, 32Dβcells ($2 \times 10^4$ cells/well) were incubated with increasing concentrations of T2 protein (composed of c264scTCR/huIL15N72D and c264scTCR/huIL15RαSushi/huIgG1 chains) or c264scTCR/huIL15N72D fusion protein for 48 h at 37° C. Cell proliferation reagent WST-1 (Roche Applied Science) was added during the last 4 h of cell growth according to the manufacturer's procedures. Conversion of WST-1 to the colored formazan dye by metabolically active cells was determined through absorbance measurements at 440 nm.

Figure 17:
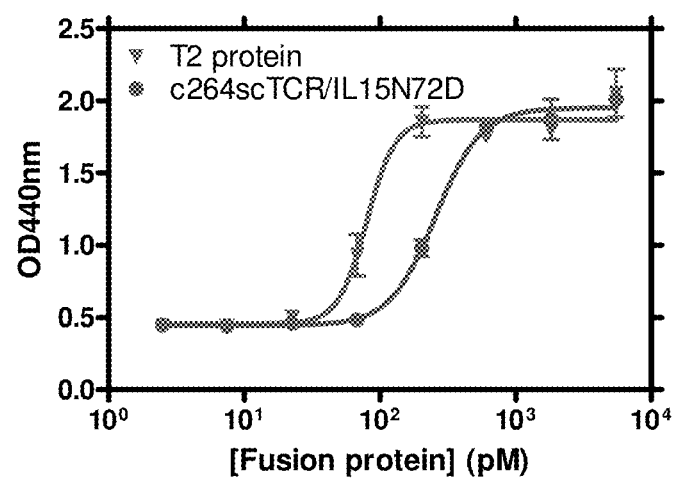
FIG. 17 shows the results from a proliferation assay to further characterize the functional activity of the IL-15 domain of the T2 molecules using the cytokine-dependent 32Dβ cell line. To measure cell proliferation, 32Dβcells ($2 \times 10^4$ cells/well) were incubated with increasing concentrations of T2 protein (composed of c264scTCR/huIL15N72D and c264scTCR/huIL15RαSushi/huIgG1 chains) or c264scTCR/huIL15N72D fusion protein for 48 h at 37° C. Cell proliferation reagent WST-1 (Roche® Applied Science) was added during the last 4 h of cell growth according to the manufacturer's procedures. Conversion of WST-1 to the colored formazan dye by metabolically active cells was determined through absorbance measurements at 440 nm.

As shown in FIG. 17, the T2 protein exhibits 3-fold better biological activity than the c264scTCR/huIL15N72D fusion protein. This was unexpected since based on its structure and anti-IL-15 Ab reactivity (see FIG. 16), the T2 protein was anticipated to only exhibit 2-fold higher IL-15 activity than c264scTCR/huIL15N72D. Together these results illustrate a number of advantages to the T2 molecular format in providing increased TCR binding activity and IL-15 biological activity than was not observed with these components alone or in the context of other fusion protein formats.

Figure 18A:
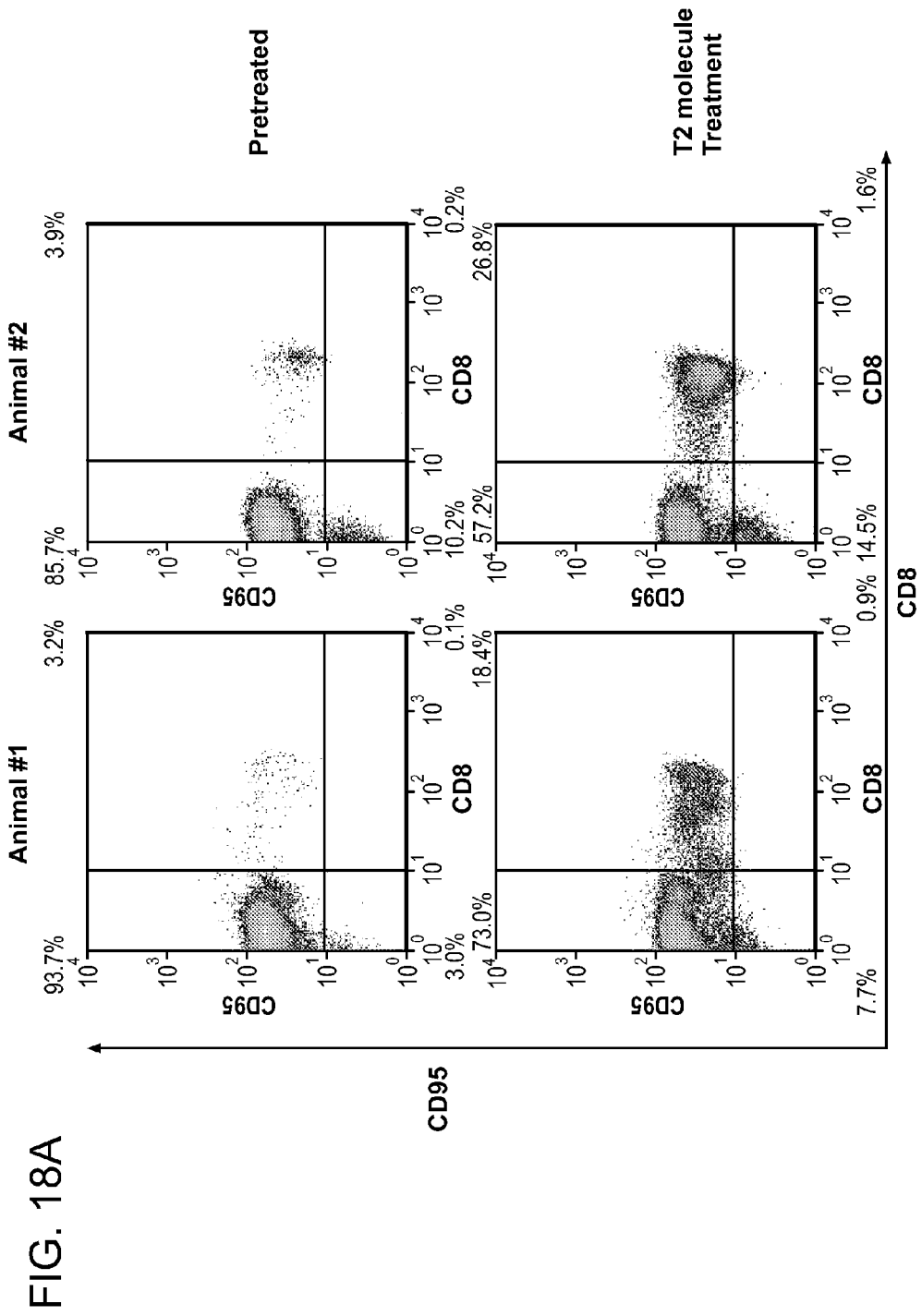
FIGS. 18A-18B show the results from an in vivo primate model to determine the ability of the T2 protein to promote proliferation of IL-15 responsive immune cells. Blood was collected five days after injection with T2 protein and was stained for CD8 memory T cells markers (CD8 and CD95) (FIG. 18A) and NK cell markers (CD56 and CD16) (FIG. 18B) and compared to blood taken prior to treatment.
Figure 18B:
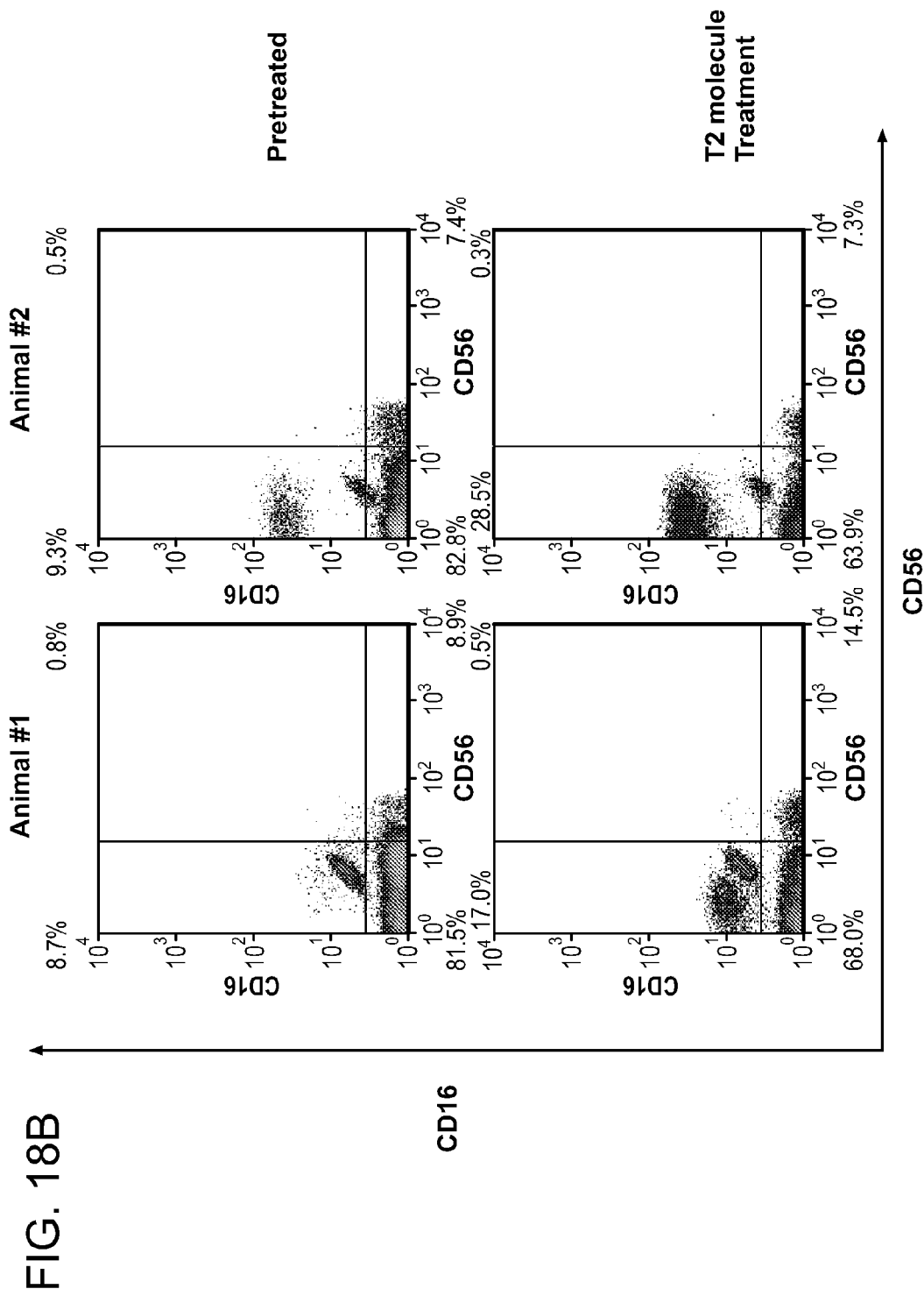

The ability of the T2 protein to promote proliferation of IL-15-responsive immune cells was examined in a primate model. Cynomolgus monkeys (n=2, 1m, 1f) were injected intravenously with purified T2 protein (composed of c264scTCR/huIL15N72D and c264scTCR/huIL15RαSushi/huIgG1 chains) at 0.5 mg/kg. Blood collected 5 days later was stained for CD8 memory T cells markers (CD8 and CD95) and NK cell markers (CD56 and CD16) and compared to blood taken prior to treatment. As shown in FIGS. 18A-18B, T2 treatment resulted in an expansion of $CD8^+$ $CD95^+$ memory T cells (FIG. 18A) and $CD56^{dim}$ $CD16^+$ effector NK cells (FIG. 18B). These results are consistent with the T2 molecule displaying potent IL-15 activity in vivo.

EXAMPLE 6

Characterization of the Binding and Biological Activity of the T2 Fc Domain

Figure 19A:
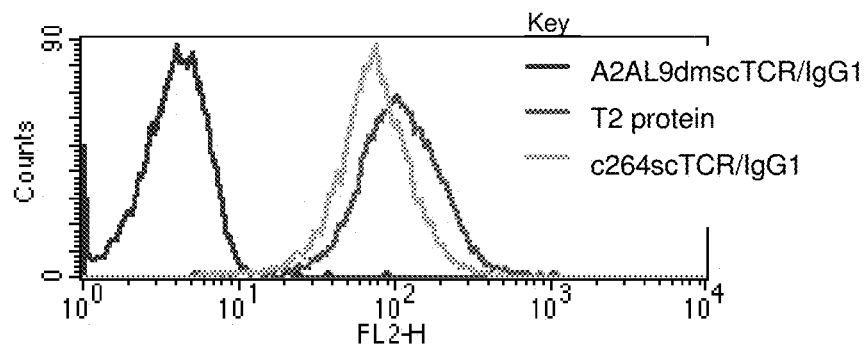
FIGS. 19A-19B show cell binding assays characterizing the binding activity of the IgG1 Fc domain of the T2 molecule.
Figure 19B:
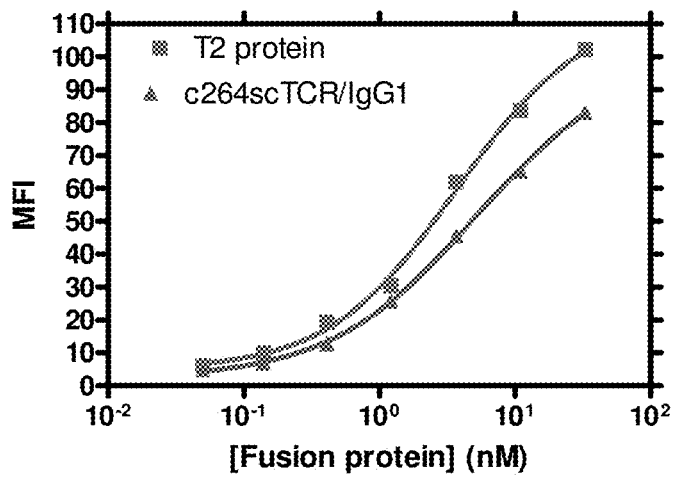

The binding activity of the IgG1 Fc domain of the T2 molecule was characterized in cell binding assays. Fc-gamma receptor bearing U937 cells were incubated with 33 nM of T2 protein (composed of c264scTCR/huIL15N72D and c264scTCR/huIL15RαSushi/huIgG1 chains), c264scTCR/huIgG1 or A2AL9scTCR/IgG1 (negative control) for 20 min. Cells were washed once and incubated with PE-conjugated p53 (aa 264-272) peptide/HLA-A2 tetramer for 20 min. The binding to Fc gamma receptors on U937 cell surface was analyzed with flow cytometry as shown in FIG. 19A. Similar U937 binding studies using a range of protein concentrations was also carried out and the mean fluorescent intensity for the stained cells was plotted in FIG. 19B.

The results of these studies indicate that the U937 cells are stained more effectively with the T2 molecules than the corresponding c264scTCR/huIgG1 fusion proteins, verifying the Fc receptor binding activity of the T2 molecules. To assess the biological activity of the Fc domains, the ability of the T2 molecule to mediate antibody dependent cellular cytotoxicity (ADCC) activity was assessed. In this study, T2 protein, c264scTCR/huIgG1 or A2AL9scTCR/IgG1 (negative control) were added to a 96-well plate at 0.137 to 100 nM. HLA-A2-positive T2 target cells were pulsed with 10 μM of p53 aa264-272 peptide and labeled with 50 ug/ml of Calcein-AM. The fusion proteins were mixed with $1 \times 10^4$ of the target cell per well and $1 \times 10^6$/well of fresh human PBMC were added. The plate was incubated at 37° C. in a $CO_2$ incubator for 2 hrs and 100 μl of the conditional medium were collected and analyzed for Calcein released from lysed cells. Calcein was quantitated with a fluorescence reader at Ex-485 nm, Em-538 nm, and Cutoff-530 nm. The specific cell lysis is calculated with the following formula: Specific Lysis=[exp−(background−auto release)]/ [Complete release−(background-auto release)]×100%. Exp=fusion protein+T2 cells+PBMC; Background=medium only; Auto release=T2 cells only; Complete release=T2 cells+0.5% Triton X-100.

Figure 20:
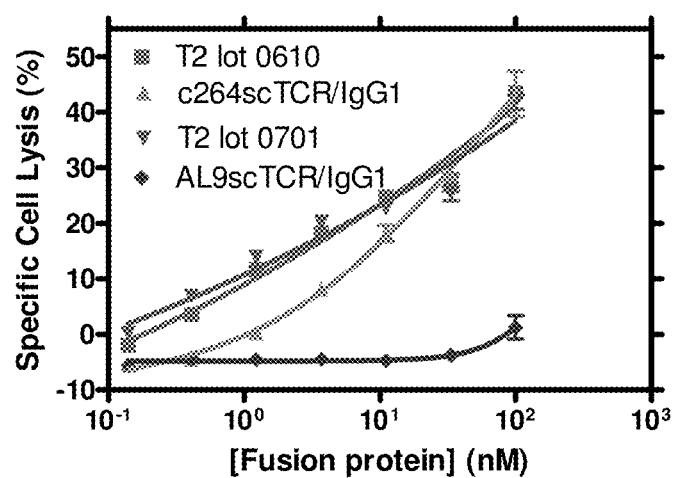
FIG. 20 shows results from an assay to assess the biological activity of the Fc domains of the T2 molecules to mediate antibody dependent cellular cytotoxicity activity. T2 protein, c264scTCR/huIgG1 or A2AL9scTCR/IgG1 (negative control) were added to a 96-well plate at a concentration of 0.137 nM to 100 nM. HLA-A2-positive T2 target cells were pulsed with 10 μM of p53 aa264-272 peptide and labeled with 50 μg/ml of Calcein-AM. The fusion proteins were mixed with 1×10$^4$ of the target cell per well and 1×10$^6$/well of fresh human PBMC were added. The plate was incubated at 37° C. in a CO$_2$ incubator for 2 hrs and 100 μl of the conditional medium were collected and analyzed quantitatively for Calcein released from lysed cells.

The results of triplicate determinations per data point are shown in FIG. 20 where two different lots of the T2 proteins were characterized. The results indicate that the T2 protein was more effective at mediating ADCC-like activity against peptide/MHC presenting target cells than the TCR-IgG1 fusion protein. The improved activity may have been the result of enhanced binding of the T2 molecules to the peptide/MHC complex and/or increase reactivity to the effector cells displaying Fc receptors or IL-15 receptors.

EXAMPLE 7

Figure 21A:
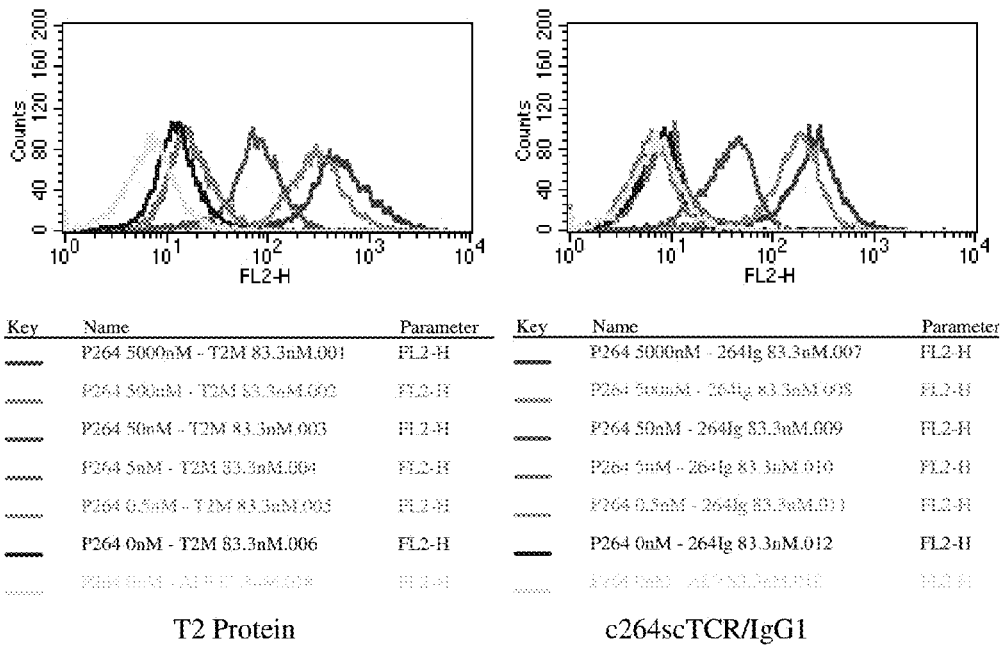
FIGS. 21A-21B show results from an assay in which HLA-A2-positive T2 cells were pulsed with various amounts of p53 aa264-272 peptide to assess the binding activity of T2 protein to peptide/MHC targets on cell surface. The peptide-loaded cells were incubated with T2 protein (composed of c264scTCR/huIL15N72D and c264scTCR/huIL15RαSushi/huIgG1 chains), c264scTCR/huIgG1 or A2AL9scTCR/IgG1 (negative control), each at 83 nM. The cells were incubated with biotinylated anti-TCR Ab (BF1) and streptavidin-PE. The cells were then analyzed for antibody staining by flow cytometry for FIG. 21A and the mean fluorescence staining intensity of the cells loaded different concentrations of peptide are plotted for FIG. 21B.
Figure 21B:
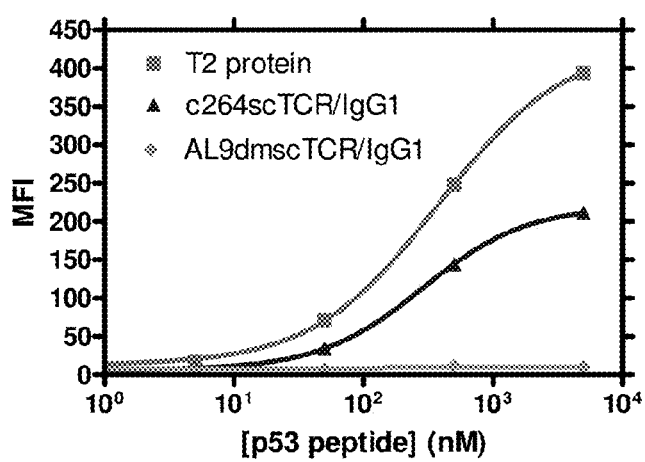

Characterization of T2 Molecule Binding to Peptide/MHC Complexes Displayed on Cells To assess the binding activity of T2 protein to peptide/MHC targets on cells, HLA-A2-positive T2 cells were pulsed with various amounts of p53 aa264-272 peptide. The cells were then incubated with T2 protein (composed of c264scTCR/huIL15N72D and c264scTCR/huIL15RαSushi/huIgG1 chains), c264scTCR/huIgG1 or A2AL9scTCR/IgG1 (negative control), each at 83 nM. The cells were incubated with biotinylated anti-TCR Ab (BF1) and streptavidin-PE. The cell were then analyzed by flow cytometry as shown in FIG. 21A. The mean fluorescent intensity for the stained cells was plotted in FIG. 21B.

The results show that the T2 molecules exhibit enhanced ability to detect p53 peptide/HLA-A2 complexes on cells compared to the c264scTCR/huIgG1 fusion protein. These results indicate that the T2 protein is capable of binding more effectively than c264scTCR/huIgG1 fusions to tumor-associated peptide antigens on target cells.

Similar results are expected using T2 molecules comprising TCR domains specific to other peptide/MHC targets. For example, various peptides derived from the human tumor associated proteins; p53, gp100, MART1, MAGE-A3, PSMA, PSA, Her2/neu, hTERT, tyrosinase, survivin, WT1, PR1, NY-ESO1, EGFR, BRAF and others, are known to bind HLA molecules and be targets for human T cell responses via TCR interactions. Additionally, TCRs specific to HLA complexes displaying viral peptide antigens from HIV, HCV, HBC, CMV, HTLV, HPV, EBV and other virus have been identified. These TCR could be fused to the IL-15 or huIL15RαSushi proteins and characterized for peptide/MHC reactivity on the appropriate peptide loaded antigen presenting cells as described above.

EXAMPLE 8

Characterization of T2 Molecules Bearing Two Different TCR Domains

As indicated above, it is useful to have multiple different TCR domains fused to the IL-15, IL-15Rα and IgG components of the T2 molecule. This allows more than one antigen targeting activity to be present in a single multichain protein. To demonstrate the feasibility of this approach, c264scTCR-Sushi-hIgG1-pMSGVc and c149scTCR-hIL15N72D-pMSGVn expression vectors were co-transfected into CHO cells cultured in IMDM-10 medium. The culture supernatant was harvested after 6 days culture of the transfectants at room temperature. The T2 molecules of c149scTCR/huIL15N72D and c264scTCR/huIL15RαSushi/huIgG1 were characterized with ELISAs. The purified T2-molecules of c264scTCR/huIL15RαSushi/huIgG1 and c264 scTCR/huIL15N72D were used as a control. In one assay to assess the TCR domains, wells were coated with anti-human TCR Ab (BF1), the fusion protein was added and the bound protein was detected with biotinylated anti-human TCR Ab (W4F-BN).

Figure 22:
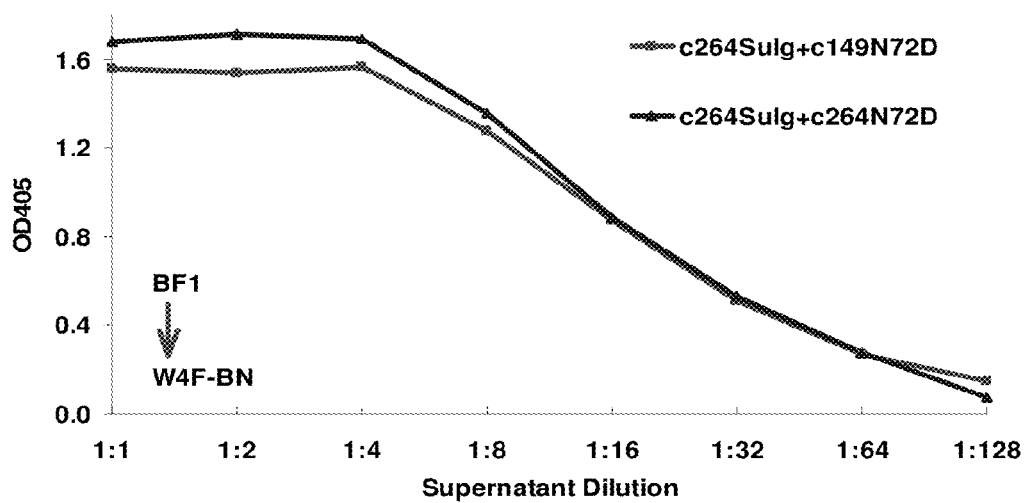
FIG. 22 shows the results from an ELISA in which T2 molecules of c149scTCR/huIL15N72D and c264scTCR/huIL15RαSushi/huIgG1 or c264scTCR/huIL15N72D and c264scTCR/huIL15RαSushi/huIgG1 (in cell culture supernatant) were captured on microtiter plates coated with the anti-human TCR antibody BF1, and the bound T2 molecules were detected using the anti-human TCR antibody W4F-BN.

The results shown in FIG. 22 indicate that the TCR domains of T2 molecules composed of c149scTCR/huIL15N72D and c264scTCR/huIL15RαSushi/huIgG1 were detectable by anti-TCR antibodies. To assess the IgG1 and IL-15 domains of the T2 proteins, an ELISA comprised of a goat anti-human IgG Ab capture and anti-human IL-15 Ab detection described above as used.

Figure 23:
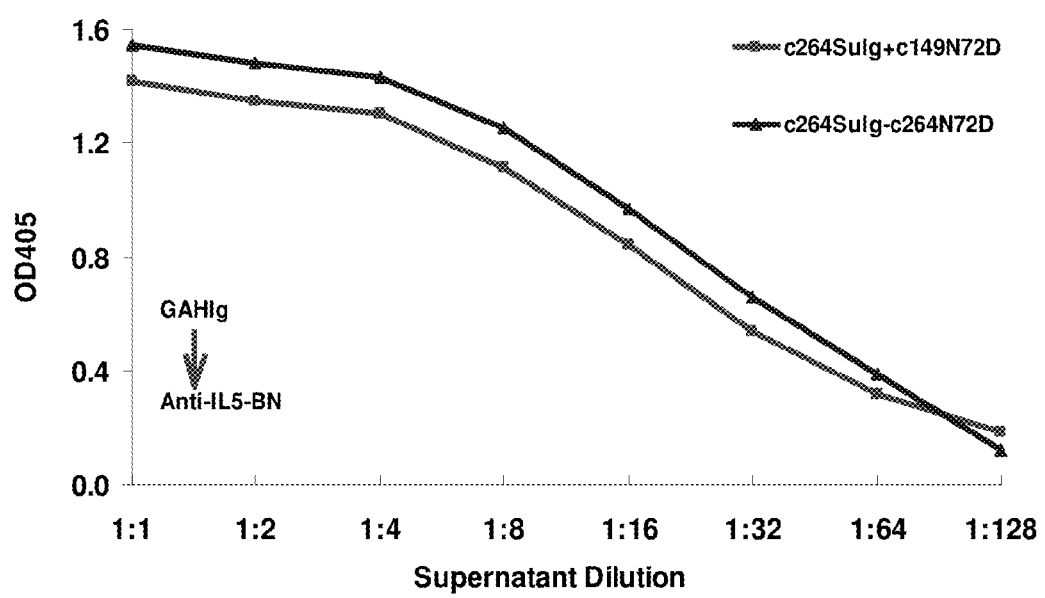
FIG. 23 shows the results from an ELISA in which T2 molecules of c149scTCR/huIL15N72D and c264scTCR/huIL15RαSushi/huIgG1 or c264scTCR/huIL15N72D and c264scTCR/huIL15RαSushi/huIgG1 (in cell culture supernatant) were captured on microtiter plates coated with the goat anti-human IgG antibody, and bound T2 molecules were detected using the anti-human IL-15 antibody.

As shown in FIG. 23, the T2 molecule composed of c149scTCR/huIL15N72D and c264scTCR/huIL15RαSushi/huIgG1 was detectable in this format indicating interaction between the protein chains containing the IgG and IL-15N72D domains. The activity of the c149scTCR domain was also examined in an ELISA using anti-human IgG Ab capture and detection with p53 (aa 149-157) peptide/HLA-A2 streptavidin-HRP tetramers.

Figure 24:
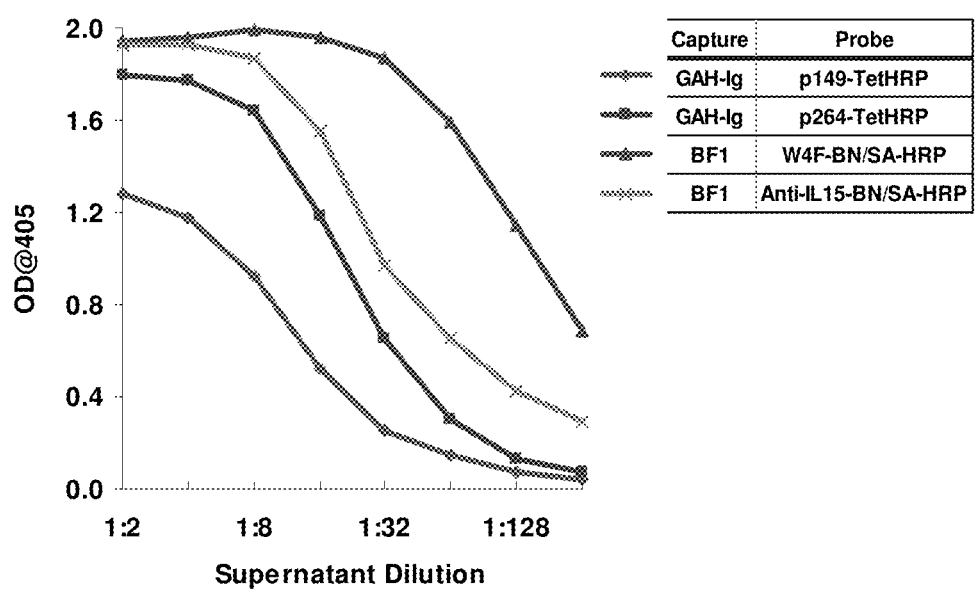
FIG. 24 shows the results from an ELISA in which T2 molecules of c149scTCR/huIL15N72D and c264scTCR/huIL15RαSushi/huIgG1 (in cell culture supernatant) were captured on microtiter plates were coated with either goat anti-human IgG antibody or anti-human TCR antibody BF1. The BF1-captured T2 molecules were detected with either anti-human TCR antibody W4F-BN or anti-human IL-15 antibody. The goat anti-human IgG Ab-captured T2 molecules were detected with either the p53 (aa 149-157) peptide/HLA-A2 streptavidin-HRP tetramers or the p53 (aa 264-272) peptide/HLA-A2 streptavidin-HRP tetramers.

Shown in FIG. 24, the T2 molecule composed of c149scTCR/huIL15N72D and c264scTCR/huIL15RαSushi/huIgG1 was detectable in this format indicating molecules with a IgG1 domain also have binding activity to the p53 (aa 149-157) peptide/HLA-A2 complex via interactions between the c149scTCR/huIL15N72D and c264scTCR/huIL15RαSushi/huIgG1 chains. Additional assays consisting of anti-human IgG Ab capture and detection with either p53 (aa 149-157) peptide/HLA-A2 or p53 (aa 264-272) peptide/HLA-A2 tetramers or anti-TCR Ab (BF1) capture and anti-TCR Ab or anti IL15 Ab detection verified that each of the domains was functionally linked in the T2 protein composed of the c264scTCR/huIL15RαSushi/huIgG1 and c149scTCR/huIL15N72D chains (FIG. 24).

T2 molecules in which these two TCR domains were expressed on the other protein chains, i.e. c264scTCR/huIL15N72D and c149scTCR/huIL15RαSushi/huIgG1 chains, were also generated. The Fc and TCR activity of these molecules were assessed following binding to U937 cells and detection with p53 (aa 264-272) peptide/HLA-A2 tetramers followed by flow cytometry.

Figure 25:
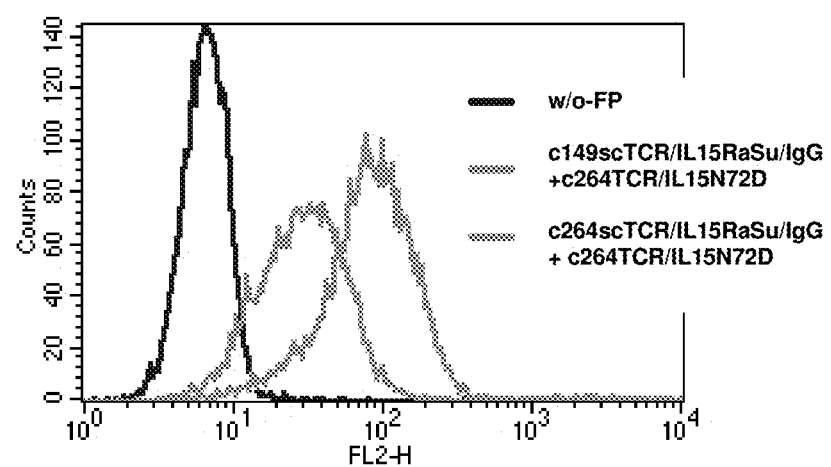
FIG. 25 shows results from a flow cytometry assay in which T2 molecules comprising two different TCR domains, i.e. c264scTCR/huIL15N72D and c149scTCR/huIL15RαSushi/huIgG1 chains, were characterized. The Fc and TCR activity of these molecules were assessed following binding to Fc-gamma receptor bearing U937 cells and detection with p53 (aa 264-272) peptide/HLA-A2 tetramers followed by flow cytometry.

As shown in FIG. 25, T2 molecules composed of c264scTCR/huIL15N72D and c149scTCR/huIL15RαSushi/huIgG1 chains were capable of binding Fc gamma receptors on U937 cells via the Fc domain and recognizing p53 (aa 264-272) peptide/HLA-A2 complex via the c264scTCR domain. These studies verify the T2 molecules with multiple functional TCR domains and IL-15 and IL15Rα and IgG1 domains are capable of forming structures as shown in FIG. 1.

EXAMPLE 9

Characterization of T2 Protein Pharmacokinetics in Mice and Cynomolgus Monkeys

A major limitation with potential therapies with IL-15 is the very short biological half-life of the cytokine in vivo. To assess the biological pharmacokinetic properties of the T2 molecules in an animal model, HLA-A2/Kb-transgenic mice (5 mice/timepoint) were injected intravenously with purified T2 protein (composed of c264scTCR/huIL15N72D and c264scTCR/huIL15RαSushi/huIgG1 chains) at 135 µg/mouse. The HLA-A2/Kb-transgenic mouse model was selected since presence of HLA-A2.1 domain, for which this c264scTCR is restricted, may influence the pharmacokinetics of the protein and should give a more relevant "humanized" view of pharmacokinetics than other non-human models. In this study, blood was collected at 0, 1, 4, 8, 24, 48, and 72, 96 hours post injection and the levels of T2 protein in the serum was measured by ELISA. Two different ELISA formats were used: 1) goat anti-human IgG Ab capture and anti-human TCR Ab (W4F-BN) detection or 2) goat anti-human IgG Ab capture and anti-human IL-15 Ab detection. These assays allow assessment of the stability of the intact protein and multichain protein complex.

As shown in FIG. 26A, the T2 molecule had a biological half-life of about 9-11 hours following intravenous injection. This is considerably longer than the reported ~1 hour half-life of human IL-15 observed in mice after IP injection (Stoklasek T A et al. 2006. J. Immunol. 177: 6072). Additionally the T2 molecule reached serum concentrations consistent with the dose delivered, whereas very little of the administered dose of IL-15 was recovered in the serum in the study reported previously (Stoklasek T A et al. 2006. J. Immunol. 177: 6072). Thus, the T2 molecule has a significantly better pharmacokinetic profile than free human IL-15. In addition, based on the similar PK profile observed with the two ELISAs, the T2 protein remained intact as a multichain molecule with no evidence of cleavage.

To assess the biological pharmacokinetic properties of the T2 molecules in a primate model, cynomolgus monkeys (n=2, 1m, 1f) were injected intravenously with purified T2 protein (composed of c264scTCR/huIL15N72D and c264scTCR/huIL15RαSushi/huIgG1 chains) at 0.5 mg/kg. In this study, blood was collected at 0, 1, 4, 8, 24, 48, 72, 96 and 120 hours post injection and the levels of T2 protein in the serum was measured by ELISA. Three different ELISA formats were used: 1) anti-human TCR Ab (βF-1) capture and HRP conjugated goat anti-human IgG Ab detection or 2) anti-human IL-15 Ab capture and HRP conjugated goat anti-human IgG Ab detection or 3) anti-human IL-15 Ab capture and anti-human TCR Ab (W4F-BN) detection. These assays allow assessment of the stability of the intact protein and the multichain protein complex.

As shown in FIG. 26B, the T2 molecule had a biological half-life of about 4-6 hours following intravenous injection. This is considerably longer than the reported ~1 hour half-life of IL-15 observed in monkeys following subcutaneous injection (Villinger, F. et al. 2004. Vaccine 22: 3510). Thus, the T2 molecule appears to have a significantly better pharmacokinetic profile than free IL-15. In addition, based on the similar PK profile observed with the three ELISAs, these data supports the murine PK data that suggests the T2 protein remains intact as a multichain molecule with no evidence of cleavage.

EXAMPLE 10

Figure 27:
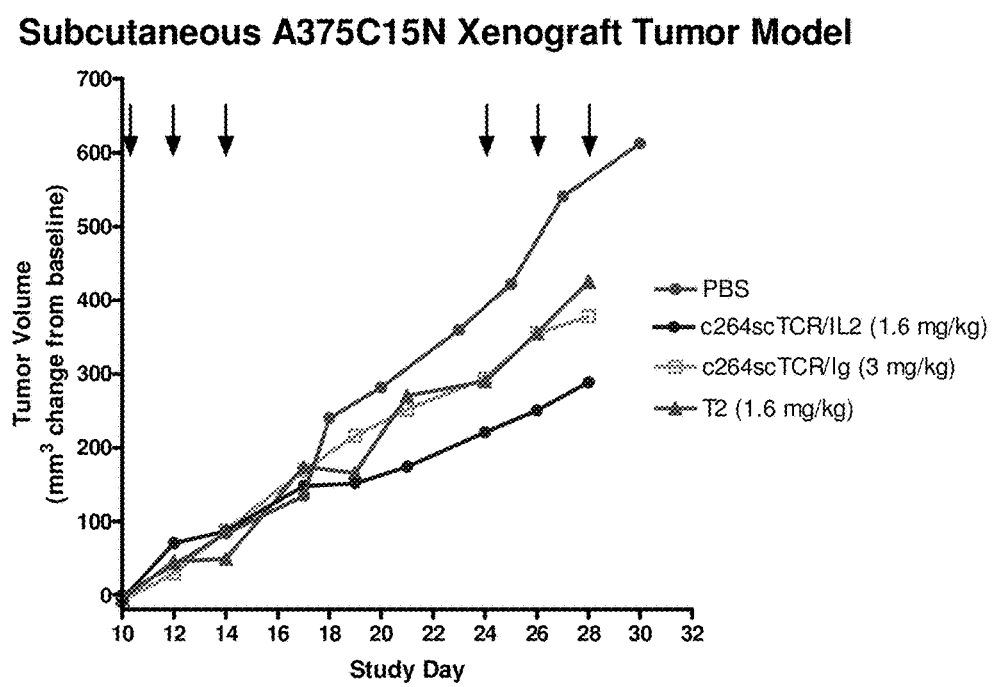
FIG. 27 shows results from a primary tumor growth model using a human p53+ HLA-A2+ A375 melanoma cell line in nude mice. Tumor-bearing mice were injected intravenously with 32 μg/dose (1.6 mg/kg) T2 protein composed of c264scTCR/huIL15N72D and c264scTCR/huIL15RαSushi/huIgG1 chains, 32 μg/dose (1.6 mg/kg) c264scTCR/huIL2, or 60 μg/dose (3 mg/kg) 264scTCR/huIgG1. Tumor growth was measured and data are shown in the figure.

Anti-Tumor Activity of T2 Molecules Against Solid Human Tumors in Xenograft Tumor Mouse Model To determine the therapeutic effects of the T2 protein, we examined antitumor activity in a primary tumor growth model with the human p53+ HLA-A2+ A375 melanoma cell line in nude mice. Tumor cells were injected subcutaneously into nude mice and tumors were allowed to grow to 100 mm³ before treatment began. Tumor-bearing mice were injected intravenously with 32 µg/dose (1.6 mg/kg) T2 protein composed of c264scTCR/huIL15N72D and c264scTCR/huIL15RαSushi/huIgG1 chains, 32 µg/dose (1.6 mg/kg) c264scTCR/huIL2, or 60 µg/dose (3 mg/kg) 264scTCR/huIgG1. The mice were treated every other day for one week (3 injections) followed by a 9 day rest period and then every other day for an additional week (3 injections). During the study, tumor growth was measured and the tumor volumes were plotted (FIG. 27). The results were compared to A375 tumor growth in mice treated with only PBS.

As shown in FIG. 27, A375 tumor growth was inhibited in nude mice treated with either T2 molecule or TCR-IL2 or TCR-IgG fusion proteins. Previous studies showed that the antitumor effects of the p53 specific TCR-IL2 or TCR-IgG fusion proteins in this model were the results of targeting the effector domain activity to the tumor site via the TCR domain (Belmont et al. 2006 Clin. Immunol. 121:29, Mosquera et al. 2005 J. Immunol. 174:4781). To assess this possibility, T2 proteins with non-targeted TCR domains will be tested in the A375 tumor xenograft mouse model. A decrease in efficacy of the non-targeted T2 molecules compared with the p53-specific T2 proteins against the A375 tumor will provide evidence that tumor antigen targeting play a role in the antitumor activity of the T2 molecules.

EXAMPLE 11

Characterization of T2 Molecules with Mutations in the IL-15 and Fc Domains

Figure 28:
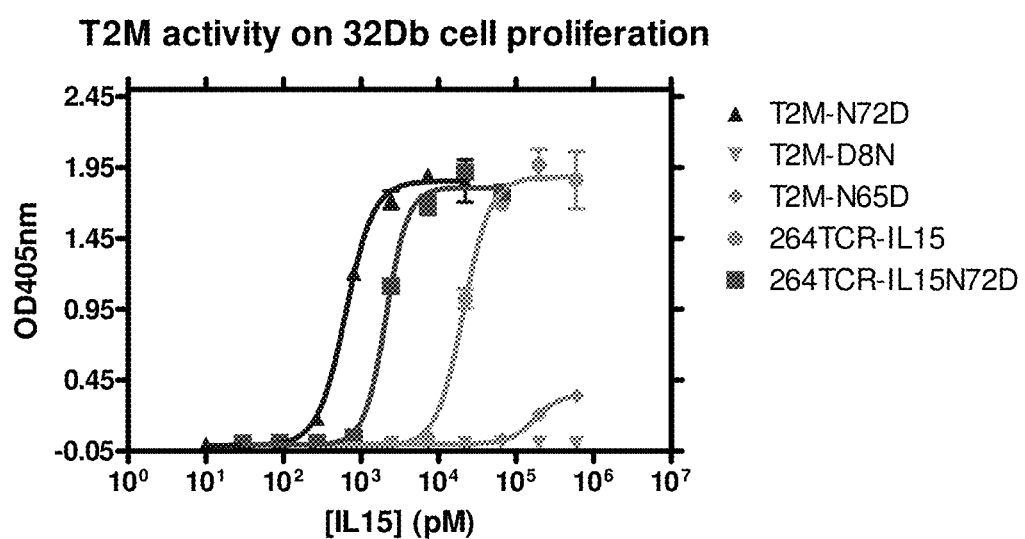
FIG. 28 shows the results from IL-15 activity assays of T2 molecules with various point mutations in the IL-15 domain as measured by proliferation of 32Dβ cells.

As disclosed in WO2008143794, mutations can be introduced into the IL-15 domain that increase or decrease its ability to interact with the IL-15Rβγ chains and affect its biological activities. For example, as indicated above, the N72D substitution can increase the IL-15 biological activity 5 to 10 fold. In other instances, it is useful to decrease IL-15 activity to provide antagonist function. To examine the effects of such mutations in the context of the T2 molecular format, c264scTCR/huIL15 constructs containing substitutions at positions 8 (i.e., D8N) and 65 (i.e., N65D) of the IL-15 domain were generated and co-expressed with the c264scTCR/huIL15RαSushi/huIgG1 protein. The resulting complexes of c264scTCR/huIL15 variant and c264scTCR/huIL15RαSushi/huIgG1 chains were tested for IL-15 biological activity using the 32Dβ cells as described in Example 5. As shown in FIG. 28, the T2 molecules comprising IL-15 D8N and N65D variants exhibited a significant decrease in their ability to support 32Dβ cell proliferation compared to the T2 molecules comprising IL-15 N72D domain or the c264scTCR/huIL15 fusions. Consistent with the results of Example 5, the T2 molecules comprising IL-15 N72D domain exhibited more IL-15 activity than either the c264scTCR/huIL15N72D or c264scTCR/huIL15 fusions.

Mutations were also introduced into the IgG1 Fc domain that were previously shown to decrease its ability to interact with Fc gamma receptor or complement (Hessell, A. J., et al. 2007. Nature 449: 101-1040, incorporated herein by reference). For example, the substitution of leucine residues at positions 234 and 235 of the IgG1 $C_H2$ (numbering based on antibody consensus sequence) (i.e. . . . P E L L G G (SEQ ID NO: 1)) with alanine residues (i.e. . . . P E A A G G . . . (SEQ ID NO: 2)) results in a loss of Fc gamma receptor binding whereas the substitution of the lysine residue at position 322 of the IgG1 $C_H2$ (numbering based on antibody consensus sequence) (i.e. . . . K C K S L . . . (SEQ ID NO: 3)) with an alanine residue (i.e. . . . K C A S L . . . (SEQ ID NO: 4)) results in a loss of complement activation (Hessell, A. J., et al. 2007. Nature 449: 101-1040, incorporated herein by reference). These substitutions were introduced into the c264scTCR/huIL15RαSushi/huIgG1 construct and the resulting protein was co-expressed with c264scTCR/huIL15N72D or the other TCR-IL-15 variants described above. The ability of these complexes to mediate ADCC activity of human PBMCs against p53 aa264-272 peptide-loaded HLA-A2-positive T2 target cells was assessed as described in Example 6. Other mutations known to alter Fc function are provided, for example, in Lazar et al., PNAS, 103:4005-4010, 2006 (incorporated herein by reference).

Figure 29:
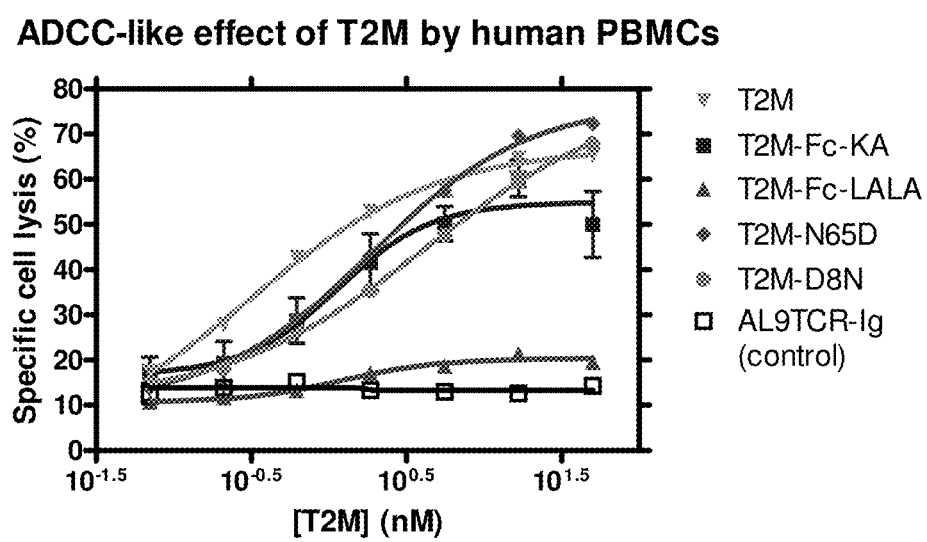
FIG. 29 shows results from an antibody dependent cellular cytotoxicity assay using T2 molecules with various point mutations in the IL-15 and IgG Fc domains as measured by PBMC-dependent lysis of peptide-loaded T2 target cells.

As show in FIG. 29, the T2 complex comprising the c264scTCR/huIL15RαSushi/huIgG1-LALA and c264scTCR/huIL15N72D chains was not capable of mediating high levels of ADCC activity consistent with the loss of Fc gamma receptor binding exhibited by the Fc-LALA variant. In contrast, complexes comprising c264scTCR/huIL15RαSushi/huIgG1-KA and c264scTCR/huIL15N72D chains or the IL-15 variants (N65D or D8N) described above exhibited the same level of ADCC activity as the c264scTCR/huIL15RαSushi/huIgG1-c264scTCR/huIL15N72D complex. Without being bound by mechanism, these data are also expected based on the likelihood that the IL-15 domain and the Fc complement-binding domain are not involved in mediating ADCC activity.

The effects of the IL-15 and Fc mutations on the ability of the T2 molecules to stimulate human NK and T cell responses were also examined Human PBMCs at 1.8 to 5×10$^5$ cells/mL were incubated for 4 days at 37° C. in media containing 1 nM T2 molecules comprising the mutations described above or with 10 ng/mL recombinant human IL-2 or IL-15 as a control.

NK cell cytotoxicity was then assessed using NK-sensitive K-562 cells as target cells following labeling with 50 ug/ml of Calcein-AM. Various ratios of PBMCs and K-562 cells were mixed and incubated at 37° C. in a CO$_2$ incubator for 2 hrs and 100 µl of the conditional medium were collected and analyzed for Calcein released from lysed cells. Calcein was quantitated with a fluorescence reader at Ex-485 nm, Em-538 nm, and Cutoff-530 nm. The specific cell lysis is calculated with the following formula: Specific Lysis=[exp−(background−auto release)]/[Complete release−(background−auto release)]×100%. Exp=K-562 cells+PBMC; Background=medium only; Auto release=K-562 cells only; Complete release=K-562 cells+0.5% Triton X-100.

Figure 30:
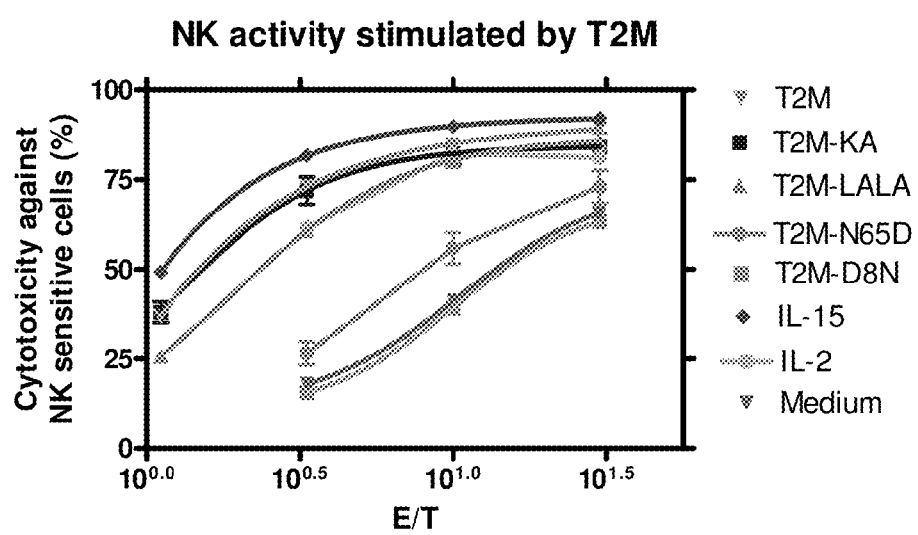
FIG. 30 shows results from an assay to detect the effects of the IL-15 and Fc mutations on the ability of the T2 molecules to stimulate human NK and T cell responses. Human PBMCs at 1.8 to 5×10$^5$ cells/mL were incubated for 4 days at 37° C. in media containing 1 nM T2 molecules comprising the mutations indicated or with 10 ng/mL recombinant human IL-2 or IL-15 as a control. NK cell cytotoxicity was then assessed using NK-sensitive K-562 cells as target cells following labeling with 50 ug/ml of Calcein-AM.
Figure 31:
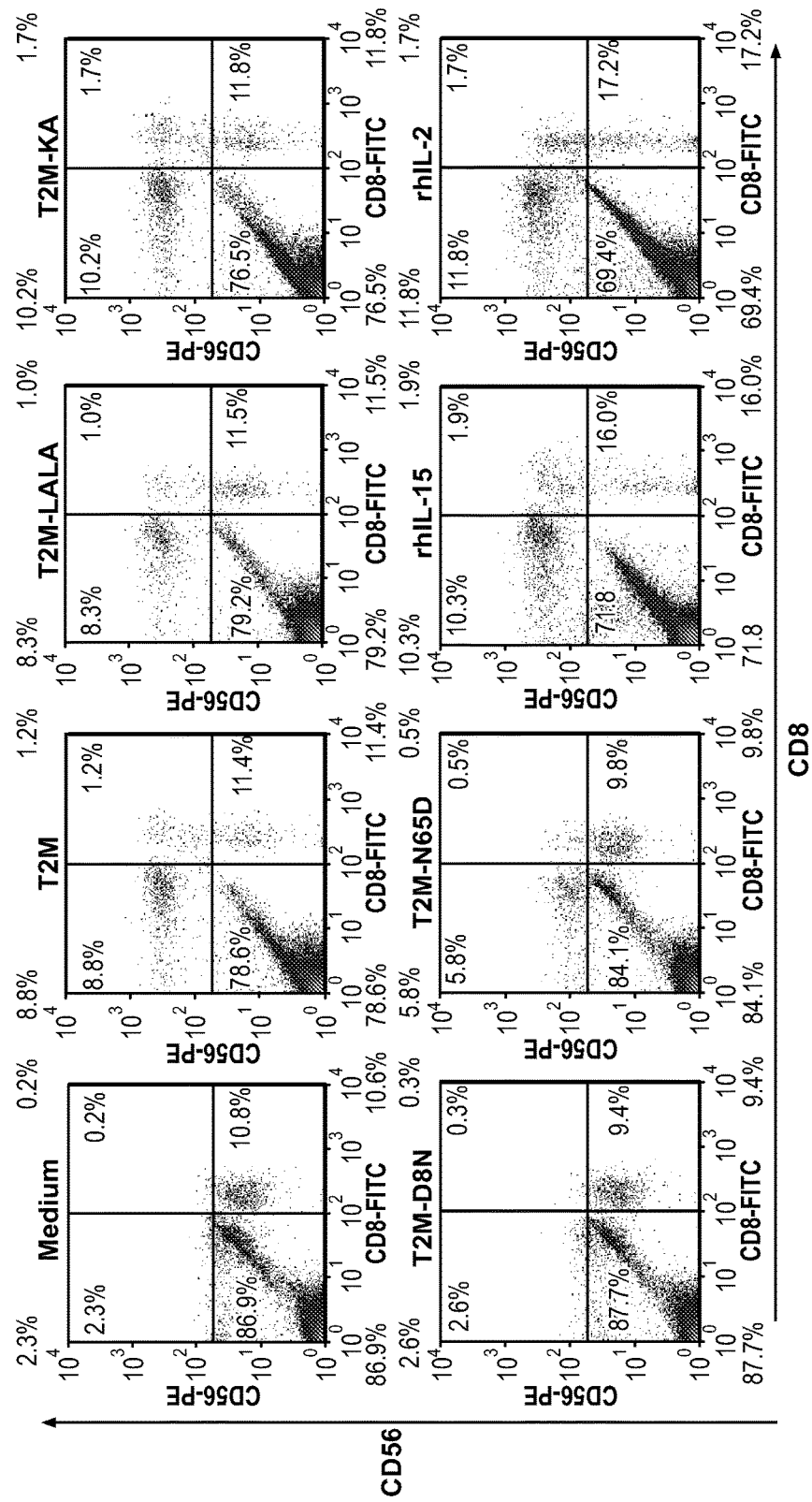
FIG. 31 shows results from NK cell proliferation assay in which human PBMCs were incubated with T2 molecules comprising various point mutations in the IL-15 and IgG Fc domains or with recombinant human IL-2 or IL-15 as a control. T2 molecules comprising the c264scTCR/huIL15RαSushi/huIgG1 and c264scTCR/huIL15N72D chains or those with the Fc domain LALA and KA variants resulted in an increase in proliferation of CD56+NK cells whereas T2 molecules comprising IL-15 N65D or D8N substitutions did not provide as much NK cell proliferative activity.

As shown in FIG. 30, incubation with the T2 molecule comprising the c264scTCR/huIL15RαSushi/huIgG1 and c264scTCR/huIL15N72D chains was capable of stimulating NK cell cytolytic activity of human PBMCs compared to that observed following incubation with media alone. In addition the T2 molecules comprising the Fc domain LALA and KA variants were also capable of stimulating NK cell activity whereas those comprising N65D or D8N substitutions in the IL-15 domain should little or no ability to stimulate NK cell cytotoxicity. Consistent with these results, incubation of human PBMCs with T2 molecules comprising the c264scTCR/huIL15RαSushi/huIgG1 and c264scTCR/huIL15N72D chains or those with the Fc domain LALA and KA variants resulted in an increase in proliferation of CD56+NK cells whereas T2 molecules comprising IL-15 N65D or D8N substitutions did not provide as much NK cell proliferative activity (FIG. 31). These results are expected based on the functionality of each of the IL-15 domain.

Figure 32A:
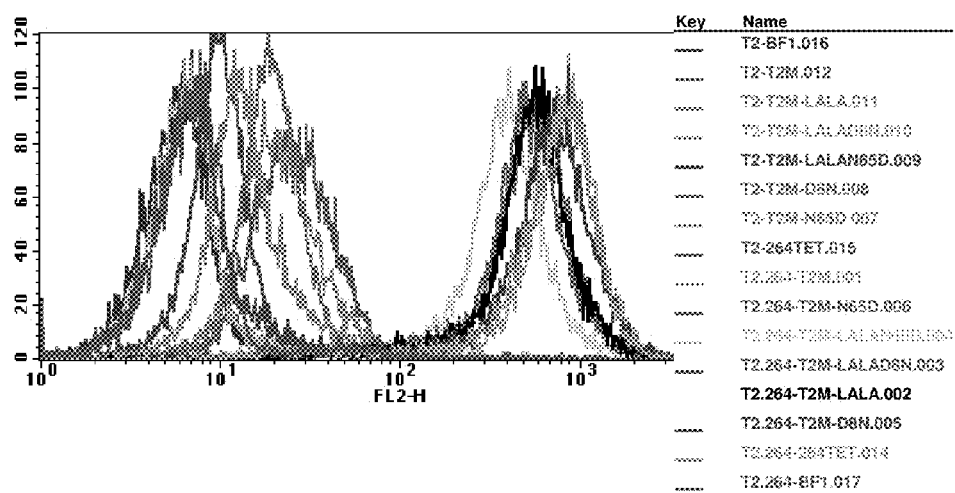
FIGS. 32A-32B show results from flow cytometry assays to test the antigen specific binding of T2 molecules including IL-15 and Fc mutations to T2 cells with (T2.265) and without loaded p53 peptide (T2).
Figure 32B:
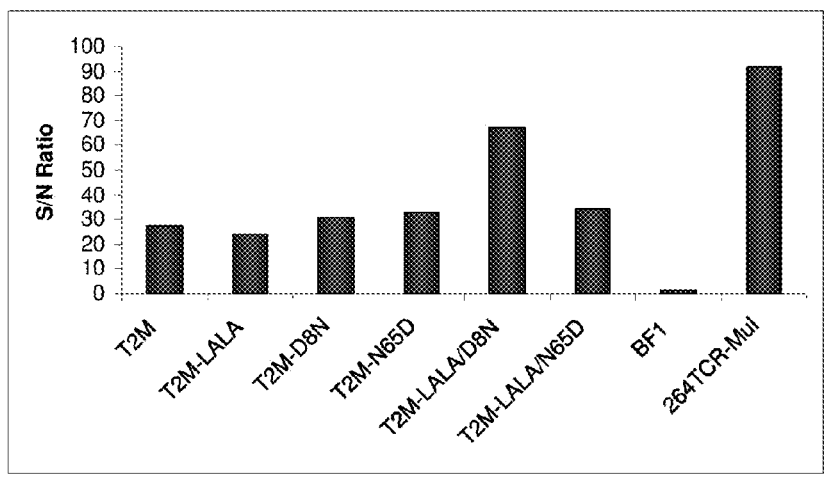

For some applications, decreased interactions between the T2 molecules and the IL-15 or Fc receptors may be desirable to reduce non-specific binding to cells bearing these receptors. To assess this, T2 molecules containing IL-15 and Fc mutations were evaluated for TCR-specific target cell recognition using T2 cells loaded with peptide. Cell staining with the T2 molecules or c264scTCR-streptavidin tetramer positive control was performed on T2 cells with (T2.265) and without loaded p53 peptide (T2) using the method described in Example 7 (FIG. 32A). Based on the staining of unloaded cells, it is clear that the T2 molecule comprising the c264scTCR/huIL15RαSushi/huIgG1 and c264scTCR/huIL15N72D chains shows significant cell binding compared to the c264scTCR-streptavidin tetramer or BF1 antibody controls. Introduction of the Fc LALA or IL-15 N65D or D8N mutations reduced this cell binding indicating that interactions with both Fc and IL-15 receptors play a role in T2 complex binding. Combination of the Fc LALA and IL-15 N65D or D8N mutations further reduced T2 complex binding such that the molecule comprising c264scTCR/huIL15RαSushi/huIgG1-LALA and c264scTCR/huIL15 D8N did not show binding to unloaded T2 cells above the BF1 antibody negative control. Staining of p53 peptide loaded cells was also effected by introduction of the Fc or IL-15 mutations. However, when the mean fluorescence intensity of T2 molecule staining for peptide loaded verses non-loaded cells was compared (specific to nonspecific ratio), it is clear that the T2 molecule comprising c264scTCR/huIL15RαSushi/huIgG1-LALA and c264scTCR/huIL15 D8N chains provided the highest staining specificity for the p53 peptide antigen (FIG. 32B). These results indicate that the binding activities of each of the TCR, IL-15 and IgG Fc domains of the T2 molecule can be readily and independently manipulated to provide a multi-specific complex with the desired biological activity.

In other cases, it is useful to modify the activity of the IL-15 domain and the IgG Fc domains to optimize the therapeutic index and minimize toxicity of the T2 complex. For example, targeted complexes relying in part on ADCC activity for their therapeutic effect may require dosing at high levels (i.e. 1-20 mg/kg) that exceed the tolerable dose level of the IL-15 component. In such a case, complexes containing a mutation in the IL-15 domain that reduces its activity are expected to provide better therapeutic activity and lower toxicity. T2 molecules containing N65D or D8N substitutions in the IL-15 domain described above or other substitutions including I6S, D8A, D61A, N65A, N72R, V104P or Q108A, which has been found to reduce IL-15 activity, are of particular interest.

EXAMPLE 12

Characterization of Non-Targeted T2 Molecules

Figure 33A:
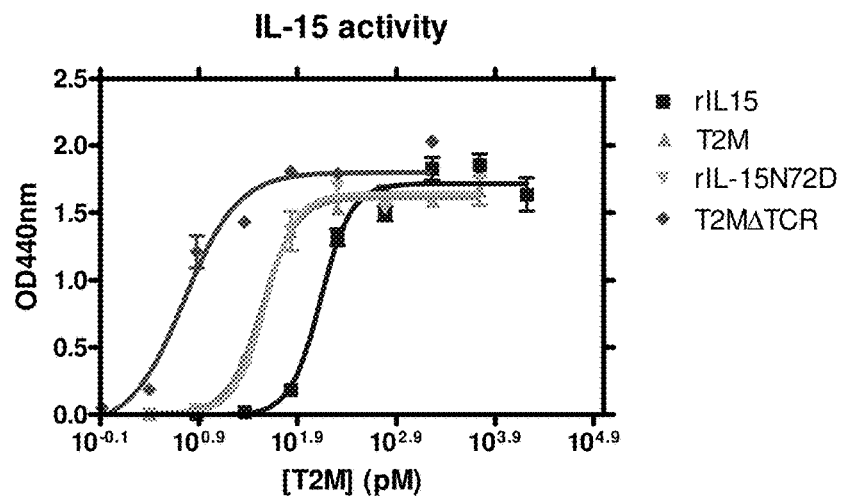
FIGS. 33A-33C show results from assays to detect the activity of various T2 molecules and IL-15 molecules to support 32Dβ cell growth (FIG. 33A), to stimulate expansion of various T cell populations (FIG. 33B), and to stimulate NK cell activity (FIG. 33C).

In some applications, it is not necessary to target specific antigens with the T2 complex. In such molecules the antigen-specific domains such as the TCR binding domains can be inactivated by mutations or completely deleted. Using the methods described herein, the activity of such a molecule comprising huIL15RαSushi/huIgG1 and huIL15 D8N chains referred to as T2MΔTCR was compared to the T2 molecule comprising c264scTCR/huIL15RαSushi/huIgG1 and c264scTCR/huIL15N72D chains (referred to as T2M) and a T2 molecule lacking the huIgG1 chain (c264scTCR/huIL15RαSushi and c264scTCR/huIL15N72D, referred to as T2MΔIg or c264scTCR dimer). When tested for ability to support 32Dβ cell growth as described in Example 5, the T2MΔTCR exhibited very potent IL-15 activity (FIG. 33A) that was >24 fold that observed with recombinant human IL-15.

Figure 33B:
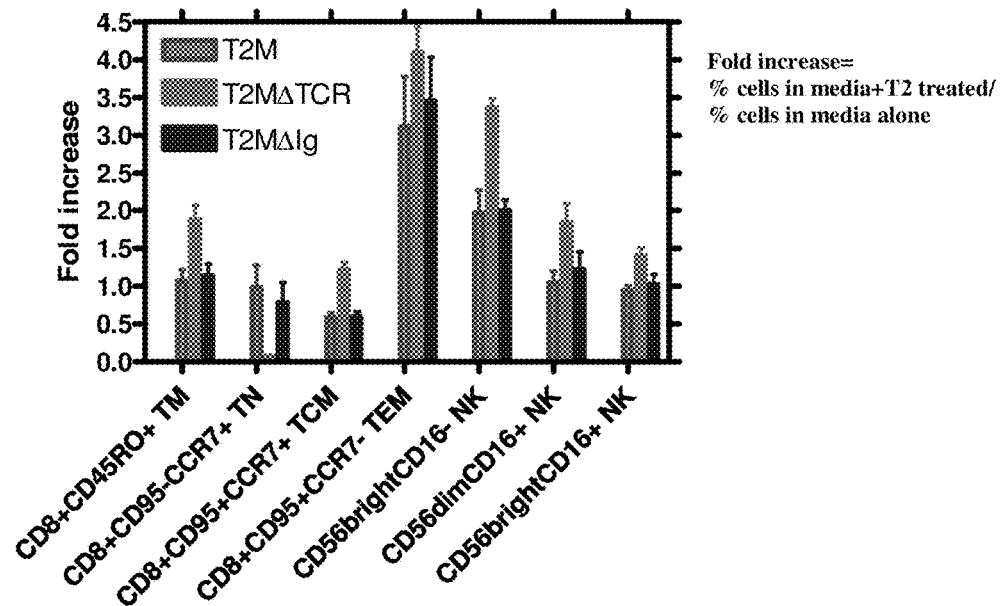
Figure 33C:
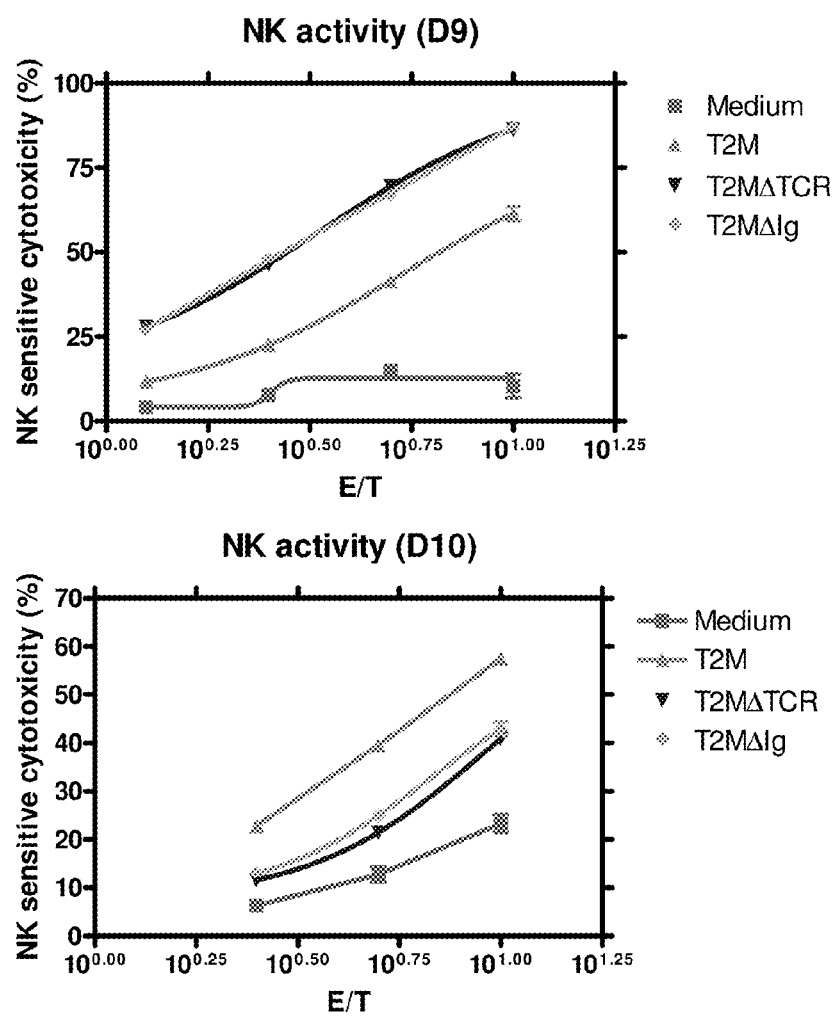

The ability of the T2MΔTCR to support human immune cell growth was also assessed. Human PBMC at 1×10$^6$ cells/ml were incubated with media in the presence or absence of T2M (0.5 nM), T2MΔTCR (0.5 nM), or T2MΔIg (1 nM) for 7 days. Cells were stained with anti-CD45RO and anti-CD8, or anti-CD8, anti-CD95, and anti-CCR7, or anti-CD56 and anti-CD16, and analyzed with FACScan. The averaged results from 8 different donors shown in FIG. 33B indicate that the T2MΔTCR and other T2 molecules could effectively stimulate expansion of various CD8+ memory T cell and NK cell subsets including effector memory T cells. The NK cell activity of these cells was examined using the methods described in Example 11. Representative results from 2 donor PBMC preparations shown in FIG. 33C indicate that the T2MΔTCR and other T2 molecules could effectively stimulate NK cell cytolytic activity. Overall these results indicate that the T2MΔTCR protein is a potent immunostimulatory molecule.

EXAMPLE 13

In Vivo Activity of T2 Molecules

To further characterize the immunostimulatory activity of the T2 molecules, T2M, T2MΔTCR, T2MΔTCR lacking the IgG1 CH1 domain (T2MΔTCRΔCH1), T2M with the Fc-LALA mutation (T2MLALA) and T2 with the IL-15 D8N mutation (T2MD8N) were tested for their ability to induce expansion of NK and CD8 T-cells in C57BL/6 mice. In addition, c264scTCR/huIL15N72D, c264scTCR/huIL15RαSushi and c264scTCR/huIL15N72D+ c264scTCR/huIL15RαSushi complexes were evaluated.

Figure 34A:
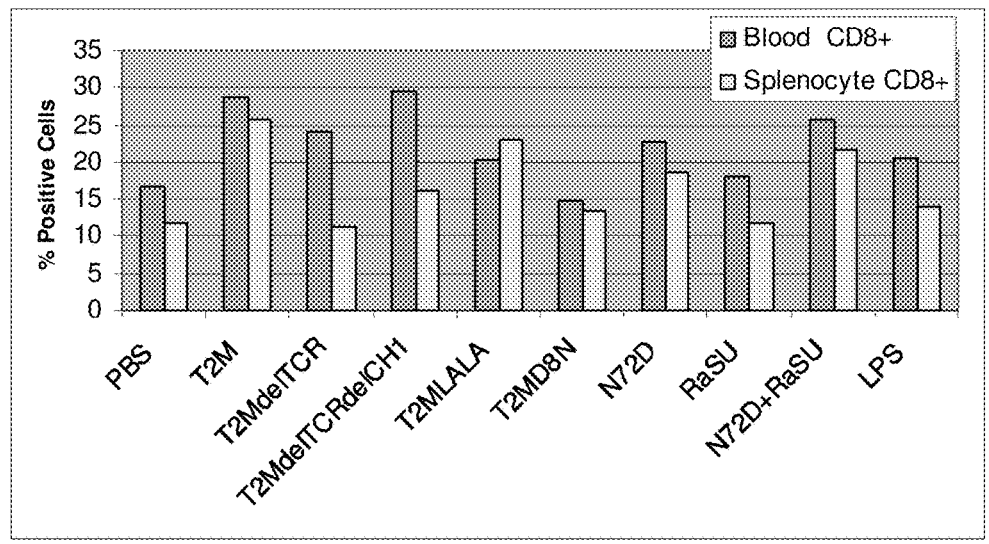
FIGS. 34A-34B show results from an in vivo assay to determine the immunostimulatory activity of various T2 molecules in mice as indicated by changes in the percentage of CD8+ T-cells and NK cells, respectively, in blood and spleen cells as detected using flow cytometry.
Figure 34B:
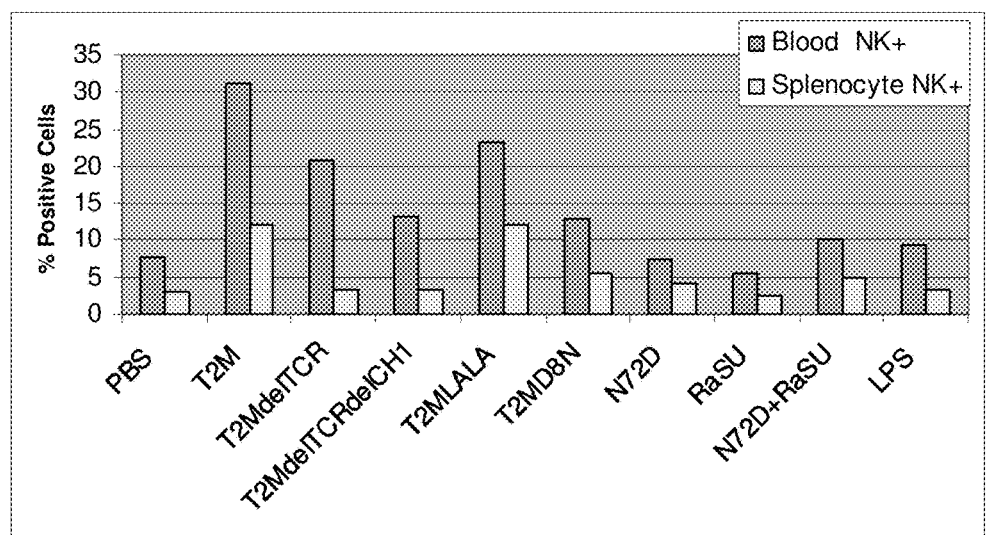

Mice were i.v. injected on day 1 and 4 with the fusion proteins at an amount equivalent to a 2.5 μg dose of IL-15. On day 8, blood cells and splenocytes were collected, stained for CD8 T-cells and NK cells, and analyzed by flow cytometry. The results shown in FIGS. 34A-34B indicate that T2 molecules are effective at expanding both blood and splenic NK cells and CD8 T cells in vivo. T2MLALA showed similar activity as T2M, suggesting FcR binding and signaling may not play a significant role in NK and CD8 T cell expansion. T2MD8N treatment resulted in decreased activity when compared with T2M, confirming the finding that D8N mutation diminished the molecule's immunostimulatory activity in vitro using human PBMC. Deletion of TCR (T2MΔTCR) and deletions of TCR and CH1 (T2MΔTCRΔCH1) showed decreased activity. These effects may have been due to the shorter half-lives of these smaller molecules. The c264scTCR/huIL15N72D, c264scTCR/huIL15RαSushi and c264scTCR/huIL15N72D+ c264scTCR/huIL15RαSushi complexes also showed reduced in vivo activity relative to the T2M, verifying the in vitro results indicating that the T2 molecule is a more potent immunostimulatory compound.

EXAMPLE 14

Multispecific T2 Molecules

To further characterize the ability of the IL-15 and IL-15Rα/IgG Fc fusion domains to act as a scaffold for multiple binding domains, a fusion protein complex (OT1-CD8-T2M) was created comprising a single-chain TCR domain (OT1scTCR) specific for H-2Kb-restricted OVA aa257-264 peptide (SIINFEKL (SEQ ID NO: 20)) linked to huIL15N72D and a single chain CD8α/β domain linked to the huIL15RαSushi/huIgG1 fusion. The single chain CD8α/β domain comprises the extracellular domain of murine CD8α linked via a (G4S)4 peptide linker (SEQ ID NO: 21) to the extracellular domain of murine CD8β. It is well characterized that CD8 binds to a site in the MHC molecule distal to the TCR-specific peptide/MHC interface. Thus both the OTscTCR and scCD8α/β domains of the OT1-CD8-T2M complex are expected to interact at different sites on the OVA aa257-264/H-2Kb-molecule.

To test this, binding activity of OT1-CD8-T2M was compared to that of the OT1scTCR/huIL15N72D fusion by ELISA. Equal molar amounts of each protein was captured on a well coated with anti-TCR cβ mAb (H57) and probed with OVA aa257-264/H-2K$^b$ tetramers or mAbs to IL15, CD8α, CD8β or TCR Vα2. Assays were also preformed with wells coated with anti-human Ig and probed with anti-TCR Vα2.

Figure 35A:
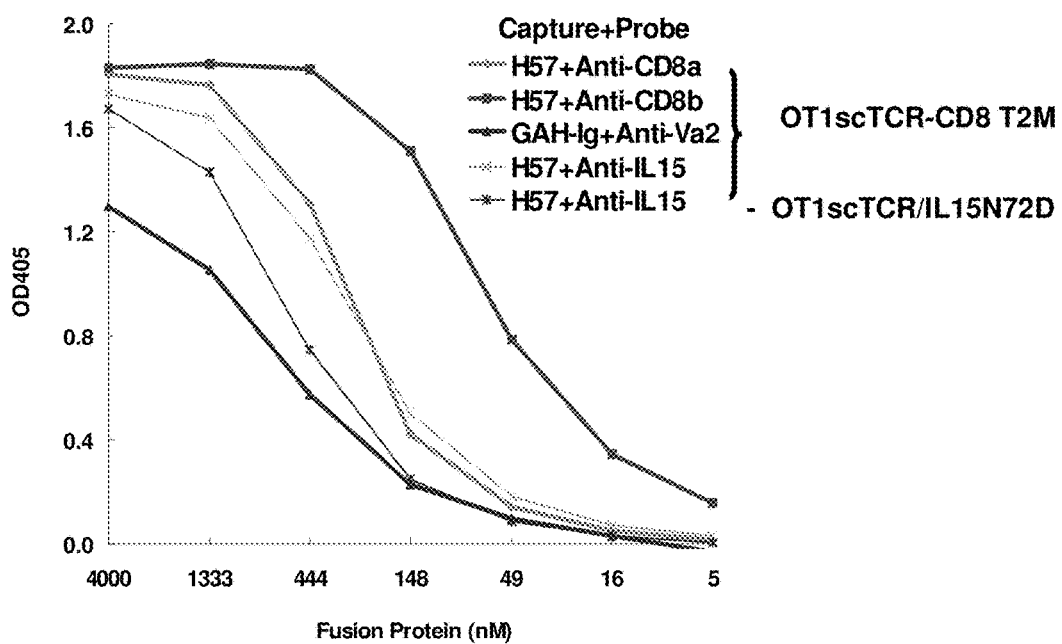
FIGS. 35A-35B show results from an ELISA using a multispecific T2 molecule comprising 1) the huIL15N72D domain fused to a scTCR specific to the peptide from amino acids 257-264 of ovalbumin and 2) a single chain CD8α/β domain linked to the huIL15RαSushi/huIgG1 fusion. Binding activity of OT1-CD8-T2M was compared to that of the OT1scTCR/huIL15N72D fusion by ELISA. Equal molar amounts of each protein was captured on a well coated with anti-TCR mAb (H57) and probed with OVA aa257-264/H-2Kb tetramers or mAbs to IL15, CD8α, CD8β or TCR Vα2. Assays were also preformed with wells coated with anti-human Ig and probed with anti-TCR Vα2.
Figure 35B:
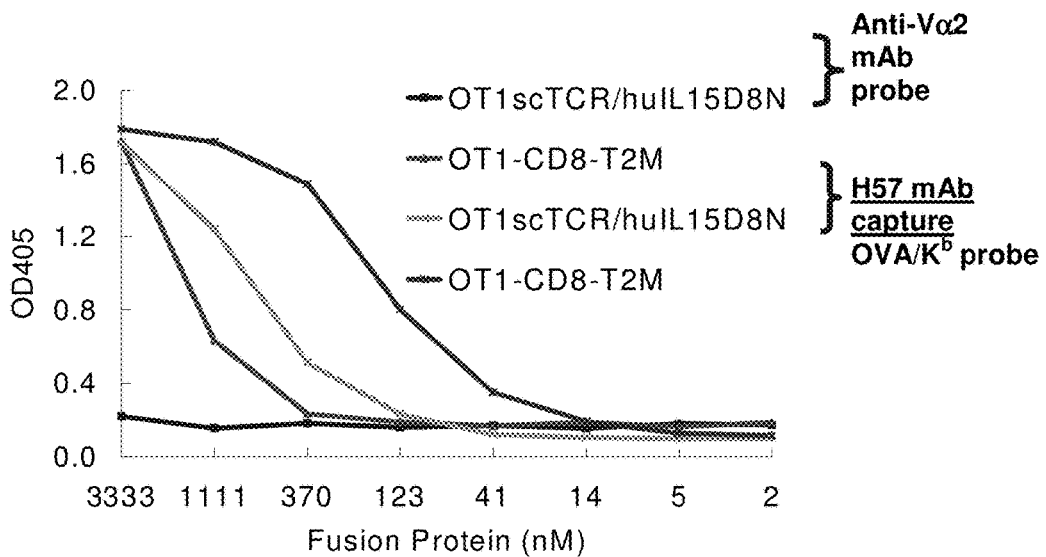

As shown in FIG. 35A, the OT1-CD8-T2M protein exhibited reactivity to anti-IL15, CD8α, CD8β, TCR Vα2 and human Ig antibodies. There was about a 3-fold higher reactivity to anti-TCR Vα2 mAb than OT1scTCR/huIL15N72D, as expected based on the multivalent format of the T2M fusion complex. However, the OT1scTCR/huIL15N72D fusion showed little or no binding to OVA aa257-264/H-2K$^b$ tetramers whereas binding was clearly apparent with the OT1-CD8-T2M protein (FIG. 35B). These results indicate that both the OTscTCR and scCD8α/β domains of the OT1-CD8-T2M complex bind to the OVA aa257-264/H-2K$^b$ molecule to provide high affinity stable interactions.

EXAMPLE 15

IL-15:IL-15Rα Domains as a Functional Scaffold

Preparation of Peptide/MHC Class I (pMHCI) Tetramers—The murine H-2Kb gene was cloned from total RNA extracted from C57BL/6 mouse lymphocytes as described above. The extracellular region was ligated into the HLA-A*0201 heavy chain expression vector (31) replacing the HLA-A*0201 coding sequence (31). The β2m, HLA-A*0201 and H-2Kb expression vectors were individually transformed into E. coli and expression of the recombinant proteins were induced as described (31), and were expressed as insoluble inclusion bodies. The active and soluble proteins in complex with the peptides were obtained by the re-folding method (Altman JD, Davis MM. "MHC-Peptide Tetramers to Visualize Antigen-Specific T Cells." Curr Protoc Immunol. 2003 May; Chapter 17:Unit 17.3; Altman JD, Davis MM. "MHC-Peptide Tetramers to Visualize Antigen-Specific T Cells." Curr Protoc Immunol. 2016 Nov 1;115:17.3.1-17.3.44). The p53 (aa264-272) and (aa149-157) peptide/HLA-A*0201 reagents are referred to as A2/p53.264-272 and A2/p53.149-157, respectively, and the OVA (aa257-264) peptide/H-2Kb is referred to as Kb/OVA.257-264.

ELISA—Immunoplates (Maxisorb, Nunc, Rochester, N.Y.) were coated with (BF1) 8A3.31 mAb for capturing c264scTCR fusion proteins or with H57-597 mAb for capturing OT1scTCR fusion proteins. After washing, the proteins were detected using various probes as detailed in the Results section. ABTS (2,2'-azinobis [3-ethylbenzothiazoline-6-sulfonic acid]-diammonium salt) substrate was then added and absorbance was measured at 405 nm using a 96-well plate reader (Versamax, Sunnyvale, Calif.).

Flow Cytometry—For characterization of the c264scTCR fusion protein complexes, T2 cells were pulsed with p53 (aa264-272) peptide at 37° C. for 2 h in the presence of peptide loading enhancer (PLE, Altor BioScience Corp., Miramar, Fla.). For the OT1scTCR fusion protein complexes, murine lymphoma EL4 cells were pulsed with OVA peptide at 100 µg/ml and PLE at 37° C. for 6 h. The various birA fusion proteins (complexed with SA-PE) were added and incubated at 4° C. for 1 h. The samples were washed two times and analyzed on a FACScan flow cytometer using CellQuest software (BD Biosciences, San Jose, Calif.).

To assess IL-15 domain binding activity, 32Dβ cells were incubated with 320 nM of the c264scTCR fusion protein complexes for 30 min at 4° C. The binding of the proteins was in turn detected with biotinylated (BF1) 8A3.31 mAb for 15 min and SA-PE (5 µg/ml each) for 15 min. The stained cells were analyzed by flow cytometry as described above.

Cell Proliferation Assays—Cell proliferation was measured as previously described (25). Briefly, 32Dβ cells ($1 \times 10^5$ cells/well) were incubated with increasing concentrations of scTCR/hIL-15 or scTCR/hIL-15 muteins in the presence or absence of an equal molar concentration of scTCR/hIL-15RαSu for 48 h at 37° C. Cell proliferation reagent WST-1 (Roche Applied Science, Indianapolis, Ind.) was added during the last 4 h of cell growth according to the manufacturer's procedures. Conversion of WST-1 to the colored formazan dye by metabolically active cells was determined through absorbance measurements at 440 nm. The $EC_{50}$ was determined with the dose-response curve generated from the experimental data by nonlinear regression variable slope curve-fitting with Prizm4 software (GraphPad Software, La Jolla, Calif.).

Surface Plasmon Resonance—The affinity constants of the OT1scTCR fusion proteins to their cognate pMHCI were determined using surface plasmon resonance (SPR) methodology on a BIAcore 2000 instrument (GE Healthcare, Piscataway, N.J.). Biotinylated pMHCI complexes were immobilized onto the streptavidin-coated surface of a SA5 sensor chip (GE Healthcare, Piscataway, N.J.) by injecting protein at 2 µg/ml in HBS buffer (10 mM HEPES, 150 mM NaCl, 3.4 mM EDTA, 0.005% P20 surfactant, pH 7.4) at a flow rate of 10 µl/min. This resulted in 1000-1200 RU of immobilized pMHCI complexes.

The purified OT1scTCR fusion proteins were diluted to 1 µM, 0.5 µM and 0.25 µM in HBS. Each concentration was injected once (50 µl) at a flow rate of 10 µl/min over a freshly immobilized pMHCI surface as well as over a control streptavidin surface blocked with biotin (baseline) and the binding curves were registered. The dissociation constant ($K_D$) and association ($k_{on}$) and dissociation ($k_{off}$) rates were calculated from the corrected binding curves (baseline subtracted) using the BIAevaluation 4.1.1 software (GE Healthcare Sciences, Piscataway, N.J.).

Figure 36A:
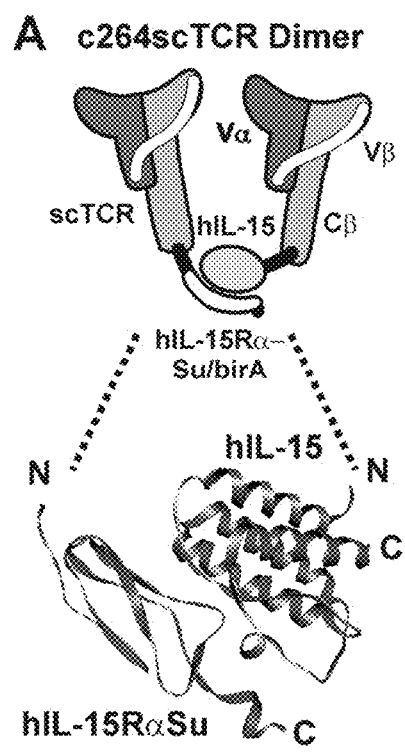
FIGS. 36A-36B show a schematic diagram of the c264scTCR/hIL-15:c264scTCR/hIL-15RαSu/birA complex (c264scTCR dimer). The model of the dimeric hIL-15-hIL-15RαSu domains is based on the published crystal structure of the human IL-15:IL-15Rα complex (33) (PDB 2Z3Q)

Creation of scTCR Dimers Using the hIL-15:hIL-15Rα Scaffold—We have previously shown that a biologically active, bifunctional fusion protein, designated as c264scTCR/hIL-15, could be created by fusing the N-terminus of hIL-15 to a three-domain, HLA-A*0201-restricted chimeric TCR specific for the p53 (aa264-272) peptide antigen (c264scTCR) (25) (FIG. 36A). We constructed a similar fusion protein with c264scTCR and the sushi-binding domain (aa 1-66) of human IL-15Rα (hIL-15RαSu), which has been shown to contain the structural elements responsible for hIL-15 binding. This fusion protein was genetically linked to a birA peptide tag to allow for biotinylation and subsequent multimerization in the presence of streptavidin (32). This fusion protein is designated c264scTCR/hIL-15RαSu/birA and its expression and purification from CHO cells were similar to that of c264scTCR/hIL-15 (25). These fusion proteins are readily produced at a level of mgs per liter of cell-culture supernatants (data not shown).

Based on the high specific binding activity between the hIL-15 and hIL-15RαSu domains, we anticipated that the fusion proteins could form a heterodimeric complex. In addition, examination of the crystal structure of the human IL-15:IL15Rα complex indicated that the N-termini of the two proteins are at opposite ends of the complex approximately 50 Å apart (33). Hence, fusion of the scTCR domains to these regions is not expected to block complex formation.

Initial evidence of binding between the c264scTCR/hIL-15 and c264scTCR/hIL-15RαSu/birA fusion proteins was observed in ELISAs using the plate-bound c264scTCR/hIL-15RαSu/birA to capture hIL-15 and c264scTCR/hIL-15 proteins (25). To further characterize the dimeric c264scTCR fusion protein complexes (referred to as c264scTCR dimer), equal molar amounts of purified c264scTCR/hIL-15 and c264scTCR/hIL-15RαSu/BirA fusion proteins were mixed and allowed to associate at room temperature for more than 10 min. The complexes and the individual protein fusions were evaluated by size exclusion chromatography.

Figure 36B:
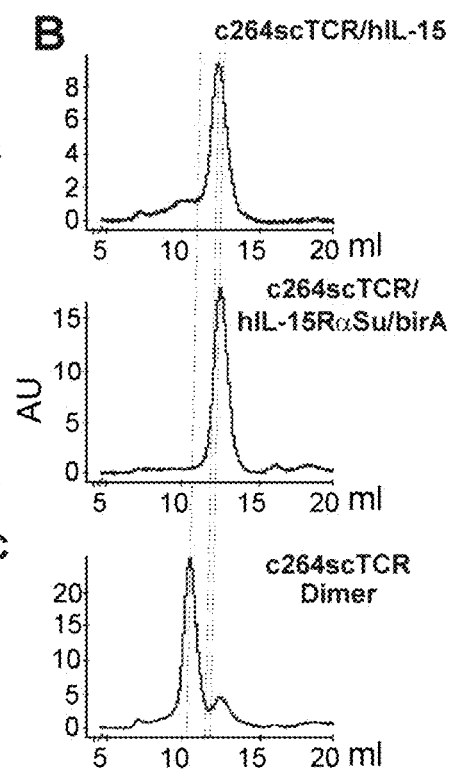

As shown in FIG. 36B, the major species in the purified c264scTCR/hIL-15 and c264scTCR/hIL-15RαSu/BirA fusion protein preparations displayed an SEC profile consistent with monomeric proteins (molecular weight (MW)=115 and 113 kDa, respectively) whereas the mixture of the two proteins resulted in a major peak with a molecular weight corresponding to a dimeric complex (MW>192 kDa). Thus, the appearance of the larger molecular weight species in the c264scTCR dimer preparations is evidence that the heterodimeric complex has been generated.

The c264scTCR dimer was compared with monomeric c264scTCR/BirA protein for their ability to bind the TCR-specific antigen, p53 (aa264-272)/HLA-A*0201. In each case, the proteins were biotinylated with biotin ligase followed by complexing with SA-PE (32) to generate multimeric flow cytometry staining reagents as previously described (32). When used to stain HLA-A*0201-positive T2 cells pulsed with varying concentrations of p53 (aa264-272) peptide, both reagents exhibited antigen-specific binding that increased in a peptide-concentration dependent manner (FIG. 37A). However, the staining reagents comprising the c264scTCR dimer stained up to three times better than the monomer-derived c264scTCR/birA counterparts (FIG. 37B). Without being bound by mechanism, these data suggest that dimerization through IL-15:IL-15Rα interaction preserves the functional activity of the scTCRs and increases the effective affinity of scTCR fusion complex to its cognate HLA/peptide through increased avidity. Similar results were observed when biotinylation via the birA tag was directed to the C-terminus of the scTCR/hIL-15 of the complex (data not shown). This demonstrates that the C termini of the complex are accessible to conjugation to molecular probes of significant size (MW of streptavidin is approximately 60 kDa) without interfering with either the dimerization or antigen binding domains of the fusion protein complex.

These studies were extended to examine the possibility of generating bispecific molecules. A second scTCR (c149scTCR) was created which recognizes an HLA-A*0201 restricted epitope of the human p53 protein spanning the amino acid residues of 149 to 157 (24). This scTCR was fused to hIL-15 and the resulting protein, designated c149scTCR/hIL-15, was co-expressed in CHO cells with the c264scTCR/hIL-15αSu/birA fusion. The fusion complex observed in the supernatant of the recombinant CHO cell culture was immobilized using an anti-IL-15 antibody and probed either by HRP-labeled p53 (aa264-272) or p53 (aa149-157) peptide/HLA-A*0201 tetramers. As shown in FIG. 37C, the anti-IL-15 antibody captured fusion protein complex was able to bind both of the peptide-loaded HLA tetramers. The result demonstrates that the individual scTCR molecules retain functional activity when fused to the hIL-15-hIL-15RαSu scaffold and the spatial arrangement of hIL-15-hIL-15RαSu complex does not significantly interfere with the packing of the scTCR domains which have an individual molecular weight of approximately 40 kDa.

Figure 42:
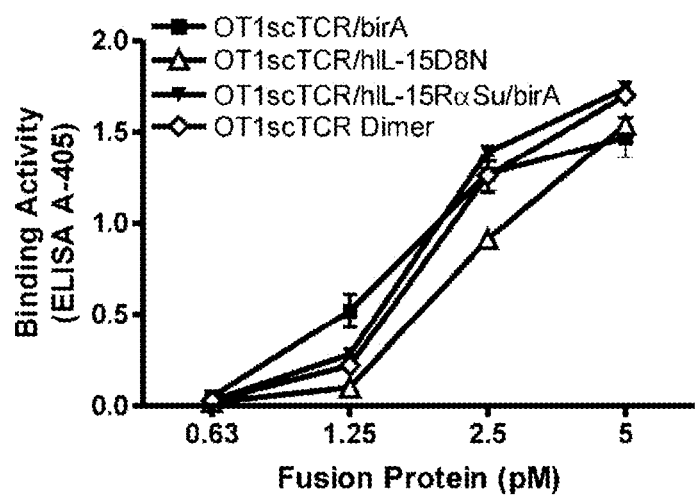
FIG. 42 shows OVA (aa257-264)/H-2K$^b$ binding activity of OT1scTCR/hIL-15D8N, OT1scTCR/hIL-15RαSu/birA and OT1scTCR dimer were determined by ELISA. Anti-mTCR H57-597 mAb was used as capturing antibody. Kb/OVA.257-264.HRP tetramer was used as a probe. The data represent the means±SD of triplicate determinations.

To demonstrate the broad utility of the hIL-15-hIL-15RαSu scaffold for protein dimerization, we created a second dimeric scTCR fusion complex by pairing two single-chain OT1 TCRs, one fused to the N-terminus of hIL-15 and another to the N-terminus of hIL-15RαSu/birA protein. OT1 is a well-characterized TCR recognizing an epitope of OVA protein spanning the amino acid residues 257 to 264 in the context of murine H-2Kb (34). OT1 single-chain TCR (OT1scTCR) gene was generated and fused to the hIL-15 and OT1scTCR/hIL-15RαSu/birA constructs for recombinant CHO cell expression. The affinity purified OT1scTCR fusion proteins were found to have pMHCI binding activity in ELISA using anti-mouse TCR Cβ H57 antibody as a capture reagent and HRP-labeled, OVA (aa257-264) peptide-loaded H-2Kb tetramer (FIG. 42). To distinguish the difference in binding activity between the OT1scTCR dimer and OT1scTCR/birA monomer, we conducted flow cytometry analysis similar to those described above for the c264scTCR dimers but with H-2Kb-positive EL4 cells loaded with OVA (aa257-264) peptide.

Figure 38:
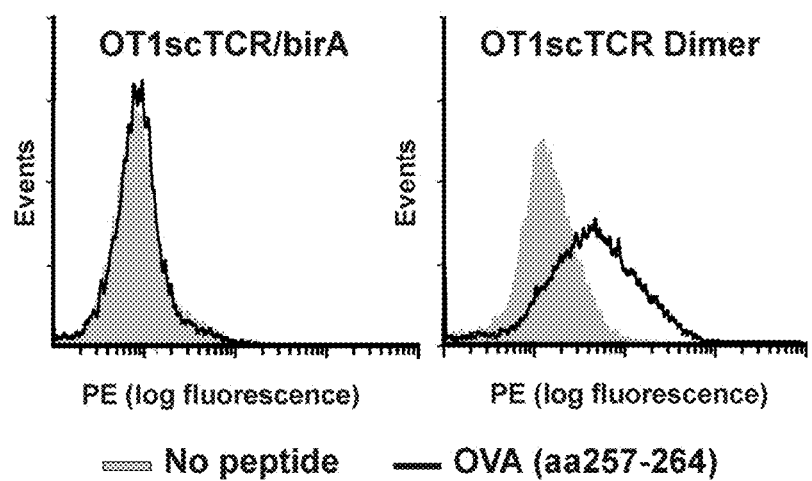
FIG. 38 shows the characterization of the binding activity of the OT1scTCR dimer comprising the OT1scTCR/hIL-15:OT1scTCR/hIL-15RαSu/birA complex. EL4 cells were loaded with OVA (aa257-264) peptide and stained with OT1scTCR/birA-SA-PE (top) and OT1scTCR dimer-SA-PE (bottom) at 200 nM.

As shown in FIG. 38, SA-PE tetramers comprising the OT1scTCR dimer indeed stained significantly better than those comprising monomeric OT1scTCR/birA fusions. We also performed surface plasmon resonance assays to assess the binding affinity of the OT1scTCR monomer and dimer against the biotinylated OVA (aa257-264) peptide-loaded H2-Kb/birA complexes immobilized on a streptavidin sensor chip. The apparent binding affinity (KD) of the OT1scTCR dimer to OVA peptide/H-2Kb complexes was estimated to be about 30 μM, whereas no binding was observed for the monomeric OT1scTCR/birA fusion protein (Table 1). These data confirm that dimerization through hIL-15-hIL-15Rα interaction preserves the biological activity of the scTCRs and increases the effective affinity of the scTCR molecule to its cognate pMHCI complexes through increased avidity.

Creation of an OT1scTCR/scCD8 Heterodimer—Since the CD8 molecule has been previously demonstrated to play a pivotal role in the interaction between OT1 TCR and its cognate OVA peptide/H2-Kb complex (35-37), the hIL-15-hIL-15RαSu scaffold provides an opportunity to assess whether CD8 molecule enhances OT1 TCR binding affinity to OVA peptide/H-2Kb expressed on the cell surface and under cell-free and adhesion molecule-free conditions. To achieve this, we first created a murine CD8 molecule in single-chain format (scCD8) by fusing the extracellular domains of the α and β chains of the murine CD8 using a flexible linker. This fusion gene was fused to the hIL-15RαSu/birA construct in a retroviral expression vector. Recombinant retrovirus was then used to infect a CHO cell line expressing the OT1scTCR/hIL-15 fusion protein. The heterodimeric fusion protein complex was purified from the supernatant of the cultured recombinant CHO cells using the anti-TCR antibody-based affinity chromatography as described above. This purified protein was subjected to ELISA using anti-TCR antibody as the capture reagent and either the biotinylated anti-mCD8α or anti-mCD8β mAbs as probes.

As shown in FIG. 39A, the anti-TCR Ab-immobilized fusion complex contains both the CD8α and CD8β and, thus, indicates formation of an OT1scTCR/scCD8 heterodimer. We used flow cytometry analysis to compare the binding activity of the OT1scTCR/scCD8 heterodimer with the OT1scTCR dimer to varying amounts of OVA peptide/H-2Kb complexes displayed on the cell surface. As shown in FIG. 39B, SA-PE staining reagents comprising the OT1scTCR/scCD8 heterodimer could readily detect OVA peptide/H-2Kb complexes on EL4 cells loaded with as little as 10 ng/ml OVA peptide, whereas little or no staining was observed at this peptide concentration when comparable reagents comprising the OT1scTCR dimer were used. Higher background OT1scTCR/scCD8 heterodimer staining was observed on EL4 cells that were not pulsed with peptide, suggesting peptide-independent interactions were occurring between the CD8 domain and MHC molecules on the cell surface. Similar effects have been reported for pMHCI tetramers binding to CD8 molecules expressed on T cells (38).

Figure 43:
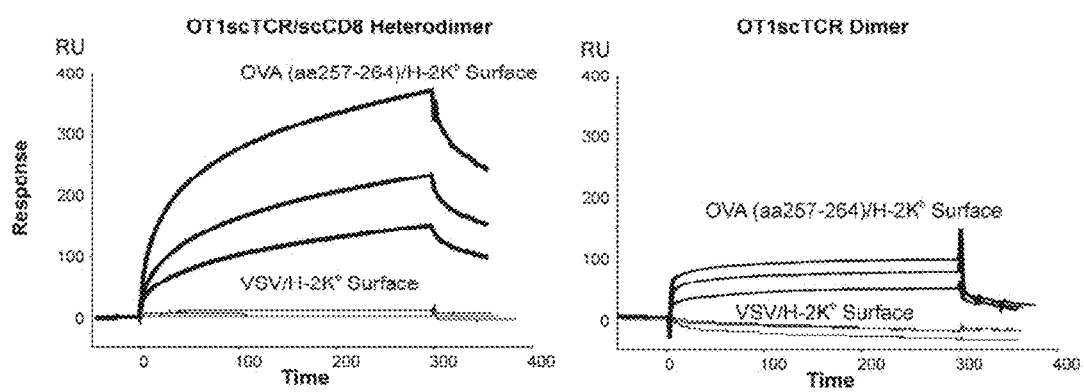
FIG. 43 shows OT1scTCR fusion protein binding curves to OVA (aa257-264)/H-2K$^b$ and control VSV/H-2K$^b$ complexes determined by SPR.

The results for peptide-specific interactions of the OT1scTCR/scCD8 heterodimer were further confirmed by surface plasmon resonance analysis. The binding affinity (KD) of the OT1scTCR/scCD8 heterodimer to OVA peptide/H-2Kb complexes was estimated to be 2.6 μM, which is significantly higher than the ~30 μM observed for the OT1scTCR dimer (Table 1, FIG. 43). Neither fusion protein showed any binding to control VSV peptide/H-2Kb complexes.

The difference in specific pMHCI binding activity is surprising given that the bivalent nature of the OT1scTCR dimer is expected to provide increased functional affinity in this assay format. Additionally, similar SPR binding studies conducted with soluble TCR, CD8 α/β and pMHCI proteins as independent components showed only weak interactions (KD 30-100 μM) between CD8 protein and peptide/H-2Kb complexes and no apparent cooperative effects of CD8 on TCR:peptide/H-2Kb interactions (39-41). Taken together, these data indicate that the addition of the CD8 α/β domain to the OT1scTCR fusion has a greater impact on pMHCI binding than creation of the bivalent OT1scTCR molecule. Our results further demonstrate that the hIL-15-hIL-15RαSu scaffold could be used to create functional bi-specific molecules with the flexibility to accommodate complex protein-protein interactions. In addition, we show for the first time that a functional CD8 molecule can be constructed as a soluble single-chain molecule and demonstrate that the scCD8 domain when complexed with OT1scTCR in a heterodimeric molecule enhances TCR:pMHCI interactions in cell-free conditions without the presence of other adhesion molecules.

Creation of Functional TCR α/β Heterodimers—As indicated above, the N-termini of the hIL-15 and hIL-15Rα domains are at distal ends of the complex raising questions as to whether this scaffold is suitable for fusions to polypeptides of a multi-chain protein. To determine whether a soluble, biologically active, heterodimeric TCR α/β could be constructed using the hIL-15 and hIL-15RαSu scaffold, the C-terminal ends of the extracellular OT1 TCR Vα-Cα and Vβ-Cβ domains were linked to the N-termini of hIL-15 and hIL-15RαSu/birA chains, respectively. Based on the published α/β TCR crystal structures, the TCR Cα and Cβ C-terminal amino acids of the properly folded OT1 TCR α/β molecule are expected to be ~18 Å apart (42). The OT1 TCRα/hIL-15 and OT1 TCRβ/hIL-15RαSu/birA fusion genes were cloned into two separate expression vectors and co-transfected into CHO cells. The secreted fusion protein complex was purified using anti-TCR Cβ mAb affinity chromatography as described above. When analyzed by Coomassie-stained SDS-PAGE under reducing condition, the purified protein bands migrated at 50 kDa, consistent with the calculated monomeric MW (40 kDa) of each of the two fusion molecules (data not shown).

The purified protein was further characterized in the functional ELISA (anti-TCR Cβ mAb capture: OVA peptide/H2-Kb tetramer probe). As shown in FIG. 40A, the purified protein was found to have equivalent pMHCI binding activity as OT1 TCR in the single-chain format. Similar results were observed for hIL-15-hIL-15RαSu/birA fusions to the Vα-Cα and Vβ-Cβ chains of the p53-specific 264 TCR (FIG. 40B). Previous attempts to produce soluble α/β TCR heterodimers in mammalian cells have been largely unsuccessful (43,44). Thus, our results suggest that the TCR α and β chains were appropriately folded through the association of the hIL-15 and hIL-15RαSu/birA domains within the transfected cells. Intriguingly, the fusion to N-termini of the hIL-15-hIL-15RαSu scaffold is able to provide the spatial arrangement sufficient for functionally independent binding domains as observed with the c264scTCR/c149scTCR heterodimeric complex while retaining flexibility to permit folding of closely paired chains such as the α and β chains of OT1 TCR and 264 TCR.

Figure 41A:
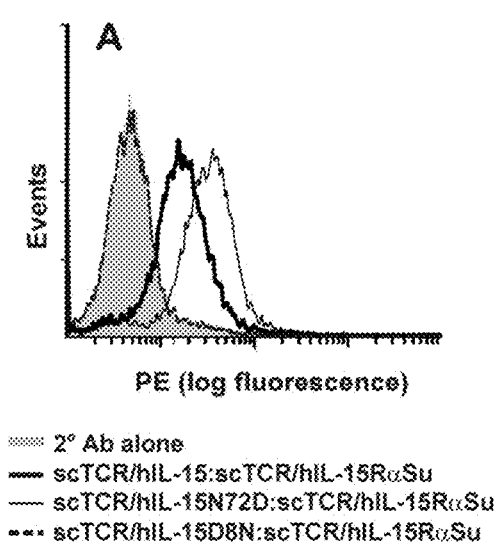
FIGS. 41A-41B show IL-15 binding and functional activity of fusion proteins.
Figure 41B:
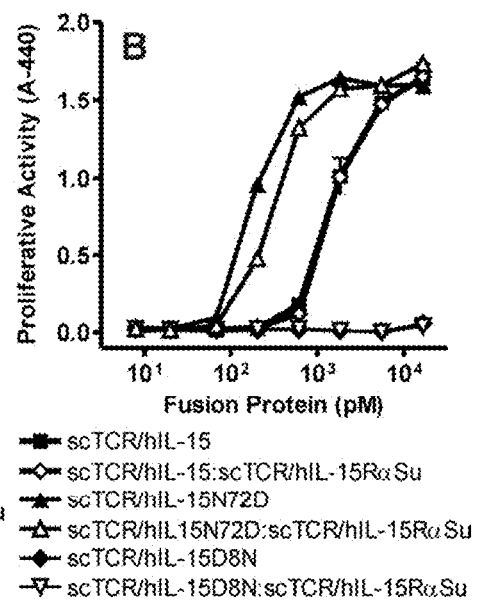

Biological Activity of the hIL-15 Domain for the hIL-15: hIL-15RαSu Fusion Complexes—The IL-15 receptor (IL-15RβγC) binding capability of the hIL-15-hIL-15Rα domain of the c264scTCR dimer was evaluated by flow cytometry analysis using 32Dβ cells which carries the hIL-15Rβ and the murine γC (mγC) chains. These studies were carried out using c264scTCR dimers containing the wild-type hIL-15 domain, as well as dimers with hIL-15 mutein domains previously shown to enhance (N72D) or reduce (D8N) binding to the hIL-15Rβ chain (25). Additionally we have demonstrated that these mutations do not affect formation of the hIL-15:hIL-15RαSu complex (25). Following incubation with the c264scTCR dimers, the 32Dβ cells were stained with anti-TCR mAb to detect cell-bound fusion protein dimers. As shown in FIGS. 41A-41B, the 32Dβ cells were stained positively by the c264scTCR dimers containing hIL-15 wild-type or hIL-15N72D domains but not with those containing the hIL-15D8N domain, indicating that the IL-15-hIL-15RαSu portion of the complex retains the expected IL-15RβγC binding activity.

The hIL-15 biological activity of the fusion protein dimers were also examined in cell proliferation assays using 32Dβ cells. As shown in FIG. 42, the hIL-15 wild-type domain in the monomeric (scTCR/hIL-15 fusions) or dimeric (scTCR/hIL-15:scTCR/hIL-15RαSu) fusion formats were able to support the growth of 32Dβ cells in a concentration-dependent manner, exhibiting half-maximal stimulation ($EC_{50}$) at ~300 pM. The hIL-15N72D or D8N domains either increased or eliminated the biological activity of the fusion proteins, respectively, regardless whether they were present in the monomeric or dimeric fusions. These results are consistent with the functional activity observed for non-fusion IL-15 cytokine carrying the N72D or D8N mutations (25). Thus, formation of the fusion protein complex containing two independent TCR domains does not significantly change the biological activity of the IL-15 domain. In contrast, there was at least a 3 fold loss of IL-15 activity for the OT1 TCRα/β heterodimer complex (data not shown), suggesting formation of the heterodimeric TCR structure inhibits, to some extent, the ability of the hIL-15 domain to interact with hIL-15RβmγC. Additionally, these results indicate that the hIL-15 domain can be readily manipulated to allow enhanced or reduced receptor binding and functional activity, thus providing additional flexibility for the use of the hIL-15-hIL-15RαSu scaffold in different applications.

EXAMPLE 16

Toxicity Profile and Anti-Tumor Activity of T2 Molecules in Immunocompetent Mice To determine the further in vivo effects of the of the T2 molecules, T2M lacking the IgG1 CH1 domain (T2MΔCH1) and the non-targeted T2MΔTCRΔCH1 protein complexes, we examined toxicity and antitumor activity in tumor-bearing immunocompetent C57BL mice. B16 ($5\times10^5$/mouse) or EG7 ($1\times10^6$/mouse) murine tumor cells were injected subcutaneously into C57BL/6NHsd mice on study day 0. Tumor-bearing mice were injected intravenously on study days 1, 4, 8 and 11 with 51 or 25.5 µg/dose T2 protein (composed of c264scTCR/huIL15N72D and c264scTCR/huIL15RαSushi/huIgG1 chains), 47.7 µg/dose T2MΔCH1 (composed of c264scTCR/huIL15N72D and c264scTCR/huIL15RαSushi/huIgG1 CH2-CH3 chains) (molar equivalent to 51 µg/dose T2 protein), 16.6 or 8.3 µg/dose T2MΔTCRΔCH1 (composed of huIL15N72D and huIL15RαSushi/huIgG1 CH2-CH3 chains) (molar equivalent to 51 and 25.5 µg/dose T2 protein, respectively), or 1.2 µg/dose rhIL-15 (molar equivalent to 25.5 µg/dose T2 protein). During the study, animal weights and tumor volumes were measured and the results were plotted (FIGS. 44A-44B and FIGS. 45A-45B).

Figure 44A:
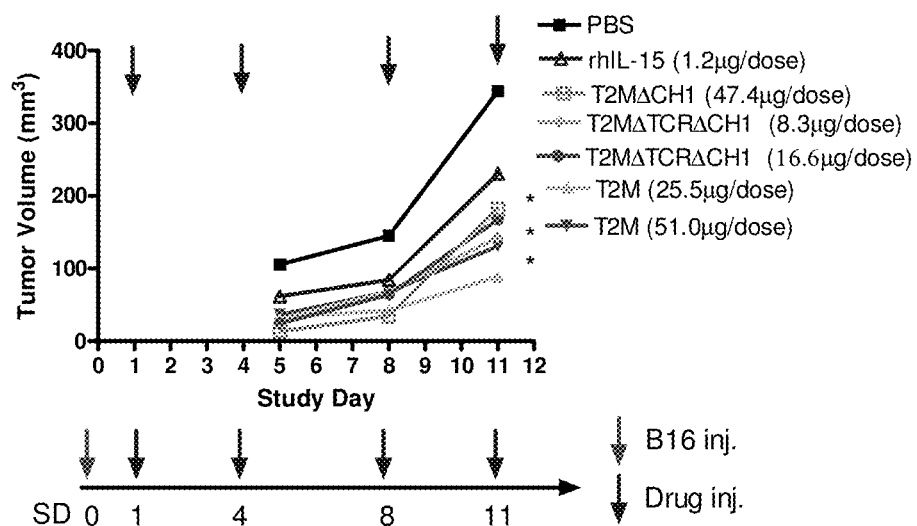
FIGS. 44A-44B show results from a primary tumor growth model using murine B16 tumor cell line in immunocompetent mice. Tumor-bearing mice were injected intravenously with rhIL-15, T2M, T2MΔCH1 and T2MΔTCRΔCH1 proteins or PBS (control). Tumor growth was measured and data are shown in FIG. 44A. Post treatment changes in animal body weight are shown in FIG. 44B.
Figure 44B:
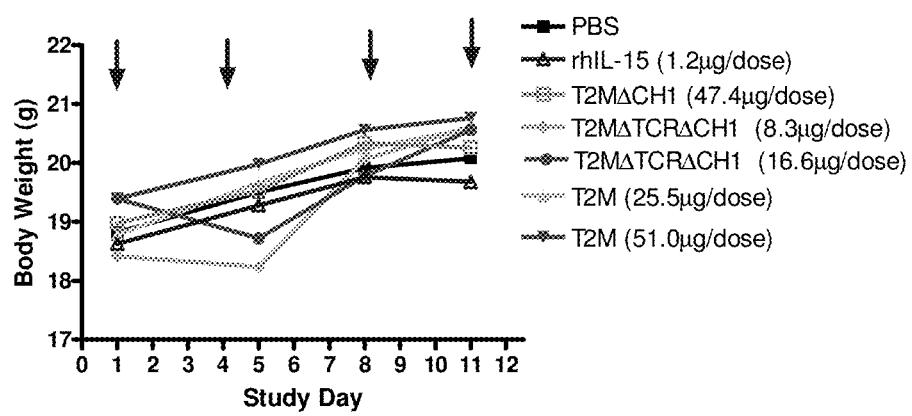
Figure 45A:
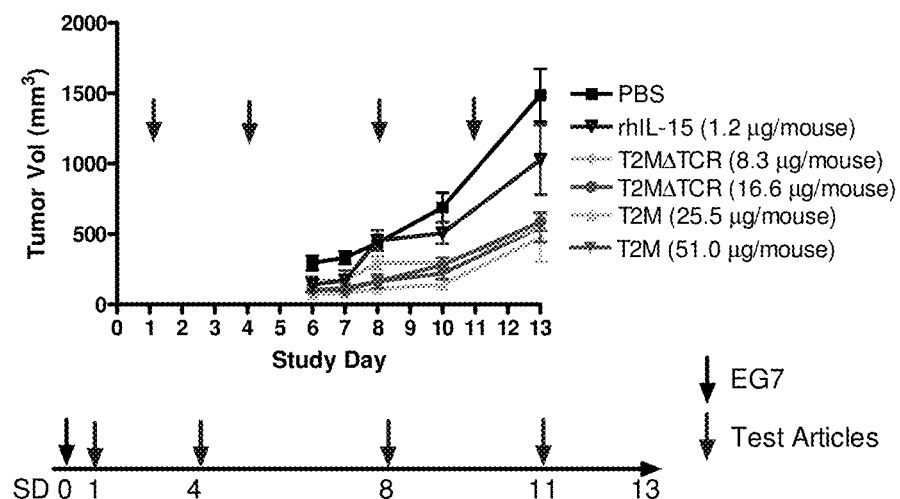
FIGS. 45A-45B show results from a primary tumor growth model using murine EG7 tumor cell line in immunocompetent mice. Tumor-bearing mice were injected intravenously with rhIL-15, T2M and T2MΔTCRΔCH1 proteins or PBS (control). Tumor growth was measured and data are shown in FIG. 45A. Post treatment changes in animal body weight are shown in FIG. 45B.
Figure 45B:
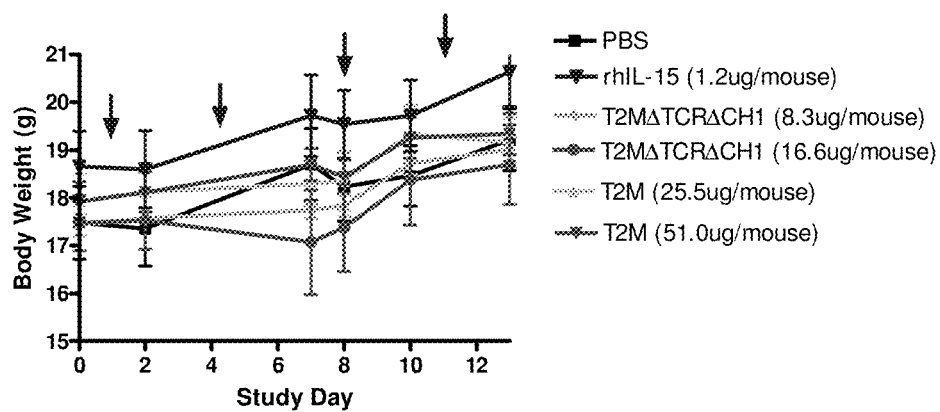

Treatment with the T2M, T2MΔCH1 and T2MΔTCRΔCH1 proteins significantly inhibited B16 (FIG. 44A) and EG7 (FIG. 45A) tumor growth compared to that observed following PBS treatment and each of the fusion protein complexes was more efficacious than rhIL-15 administered at an equivalent molar level. Additionally, there was little of no toxicological effect of T2M, T2MΔCH1 and T2MΔTCRΔCH1 treatment as measured by changes in body weight of the tumor-bearing mice (FIG. 44B and FIG. 45B). Without being bound by mechanism, these data are consistent with the in vivo immunostimulatory activity of these molecules in immunocompetent animals (Example 13).

EXAMPLE 17

Further Characterization of the Immunostimulatory and Anti-Tumor Activity of T2M and Derivatives Thereof To further characterize similar targeted IL-15:IL-15Rα-Fc complexes, recombinant CHO cell lines were generated that co-express the c264scTCR/huIL-15 and c264scTCR/huIL15Rα/IgG1 Fc fusion proteins. In one case the human IgG1 domain contained the entire heavy chain constant (CH1-CH2-CH3) and in a second case the CH2-CH3 domain (i.e. ΔCH1) or Fc domain was used, as indicated above. The protein sequence of the human IgG1 CH2-CH3 domain or Fc domain is shown in FIG. 46. For simplicity, in this example, the resulting c264scTCR/huIL15N72D superagonist:c264scTCR/huIL15Rα/IgG1 CH1-CH2-CH3 complex is referred to as T2 molecules (T2M) and the c264scTCR/huIL15N72D superagonist:c264scTCR/huIL15Rα/IgG1 CH2-CH3 complex as T2M2 (also above as T2MΔCH1). The advantage of these complexes is that dimerization through the Fc domains and interactions between IL-15 and IL-15Rα domains yield tetrameric targeting molecules capable of binding to IL-15Rβγ-positive cells and Fc receptor (FcR)-positive cells. Additionally the activity of each of these domains can be analyzed by mutants that reduce interactions with the cognate receptors. Following soluble expression by recombinant CHO cells, these complexes were purified to homogeneity by affinity chromatography using anti-TCR Cβ mAb-Sepharose and Protein A Sepharose. Size exclusion chromatography indicated that the molecules migrated at the size expected for intact complexes.

Figure 47:
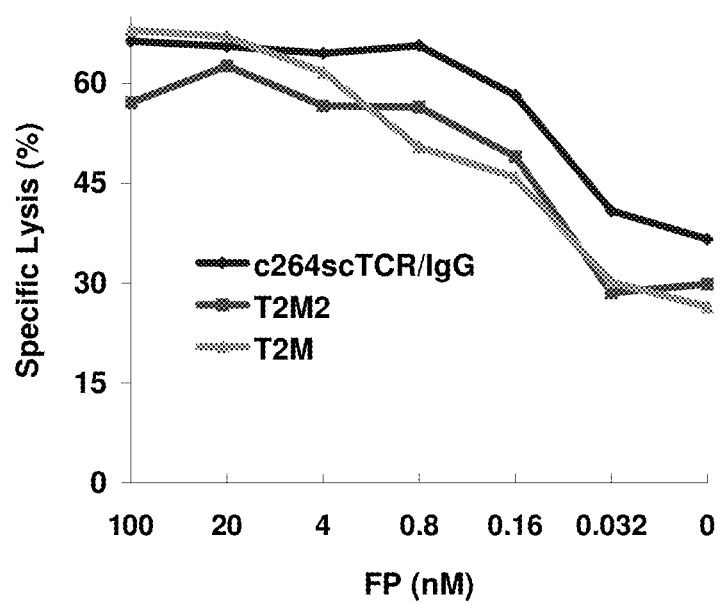
FIG. 47 shows results of an assay to determine the antibody dependent cellular cytotoxicity activity mediated by T2M and scTCR-huIgG1 proteins against cells expressing peptide MHC targets. Various amounts of fusion protein (T2M, T2M2 or c264scTCR-Ig) were mixed with fresh human PBMCs and p53 peptide-pulsed HLA-A2-positive T2 cells (Calcein labeled) (E:T ratio, 40:1). After 2 hr incubation, the culture medium was collected and analyzed quantitatively for Calcein released from lysed cells.
Figure 48A:
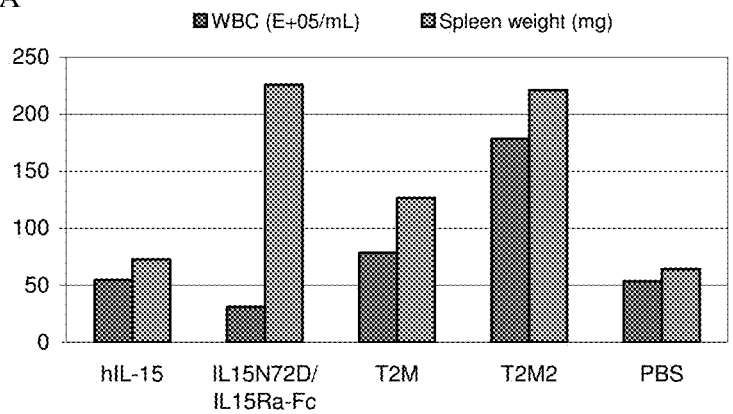
FIGS. 48A-48C show results from in vivo assays to determine the immunostimulatory activity of various T2 molecules in mice. C57BL/6 mice were treated i.v. with equivalent molar IL-15 doses of hIL-15 (1 mg/kg), IL15N72D:IL15Rα-Fc (3.6 mg/kg), T2M (11 mg/kg), T2M2 (10 mg/kg) or an equivalent volume of PBS on study day 1. On study day 4, the mice were sacrificed and blood WBC counts and spleen weights were determined as shown in FIG. 48A. Changes in the percentage of peripheral blood mononuclear cells (PBMC) CD8+ and NKp46+ cells were assessed flow cytometry as shown in FIG. 48B. PBMCs were also used to assess NK cell activity based on lysis of NK-sensitive Yac-1 target cells in a calcein release assay as shown in FIG. 48C.
Figure 48B:
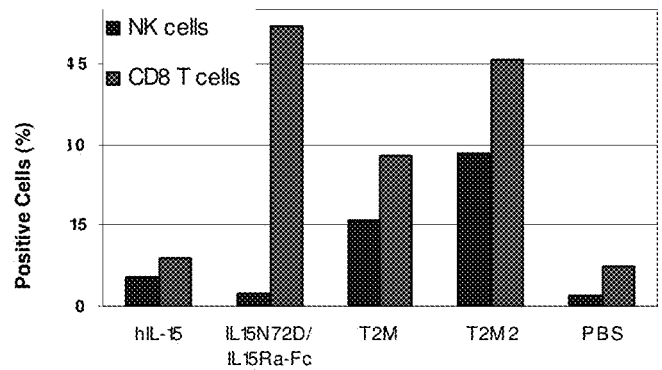
Figure 48C:
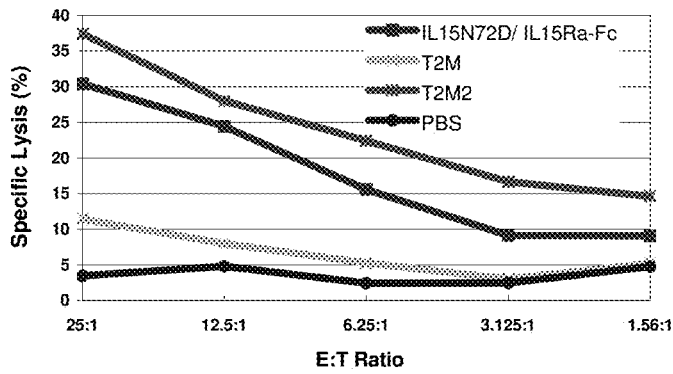
Figure 49A:
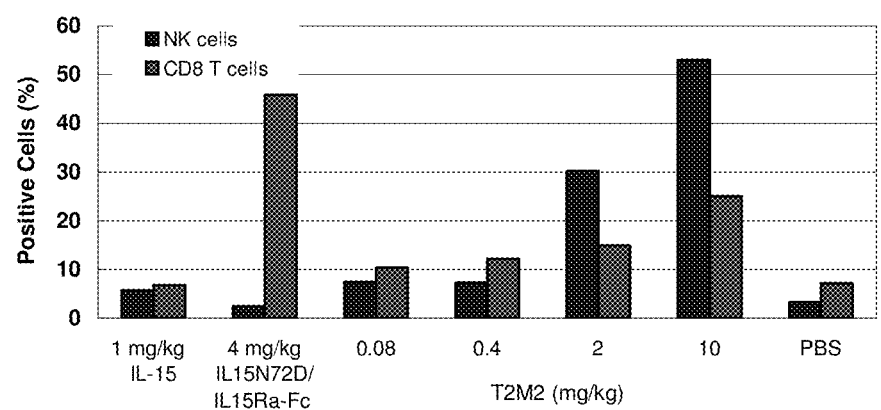
FIGS. 49A-49B show results from in vivo assays to determine the dose and temporal responses of various T2 molecules on immune activity in mice.
Figure 49B:
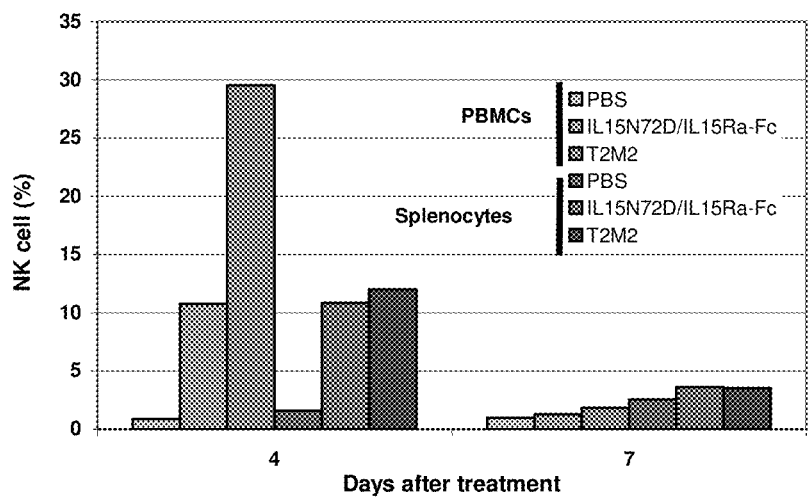

Similar to analysis described above, the ELISA-based methods have confirmed that the scTCR and IL-15 domains of T2M and T2M2 retain their respective binding activities. Additionally, the IgG1 domain of T2M and T2M2 retains the ability to bind Fc receptor (FcR) bearing cells, allowing specific detection with peptide/HLA tetramers with comparable activity to that of scTCR-IgG1 fusions. T2M and T2M2 were capable of mediating ADCC activity of human lymphocytes against target cells displaying the p53 (aa264-272)/HLA-A2 complex (FIG. 47). These results verify that T2M and T2M2 retain the antibody-like effector functions previously described for the scTCR-IgG fusions. Studies with complexes containing Fc mutations (LALA) that reduce FcR binding activity demonstrated that a functional Fc domain was required for ADCC activity. T2M and T2M2 also supported growth of the IL-15 dependent 32Dβ cell line, though T2M2 showed about ~3 fold less in vitro IL-15 activity than T2M. The ability of these molecules to stimulate immune responses in mice was also assessed. Treatment of C57BL/6 mice with IL-15 (1 mg/kg) had little or no effect on white blood cell (WBC) counts, spleen weight or the NK and CD8+ T cell populations in the blood whereas treatment with the IL-15N72D:IL-15Rα-IgG CH2-CH3 complex (at a molar equivalent IL-15 dose) resulted in splenomegaly and elevated blood CD8+ T cell levels (FIGS. 48A-48B), consistent with the results observed previously for similar IL-15:IL-15Rα-Fc complexes. Both the T2M and T2M2 complexes stimulated an increase in WBC levels, spleen weight and blood NK and CD8+ T cell populations, with the T2M2 complex showing the more potent immunostimulatory effect at an equivalent molar dose (despite exhibiting lower IL-15 activity on 32Dβ cells). Similar treatment dependent effects on NK and CD8+ T cell populations were observed in the spleen. Splenocytes isolated from T2M2 and IL-15N72D/IL-15Rα-IgG complex treated mice showed cytolytic activity against NK-sensitive YAC cells (FIG. 48C). Dose response studies indicate that these effects are observed with a single dose level as low as 0.4 mg/kg (FIG. 49A). Treatment of nude mice with T2M2 and IL-15N72D/IL-15Rα-IgG show an increase in the percentage of NK cells in the blood and spleen 4 days post treatment that decreases to near baseline levels 7 days post treatment (FIG. 49B). Taken together, these results indicate that the T2M2 complex was capable stimulating CD8+ T cell and NK cell responses in mice with significantly higher activity than that of IL-15 and for NK cells than that of the IL-15N72D/IL-15Rα-IgG complex.

Figure 50A:
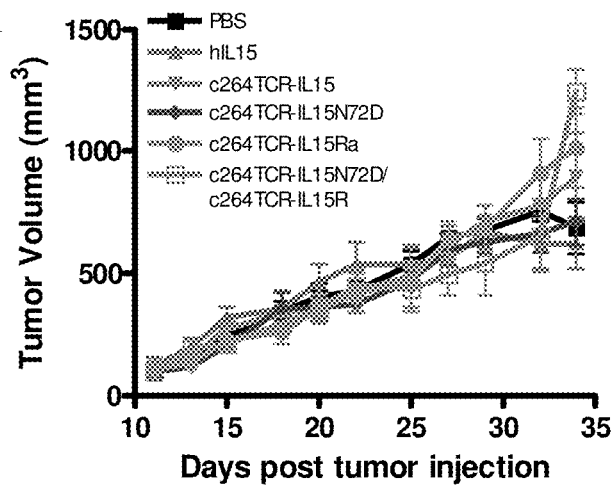
FIGS. 50A-50C show results from a primary tumor growth model using a human p53+ HLA-A2+ A375 melanoma cell line in nude mice.
Figure 50B:
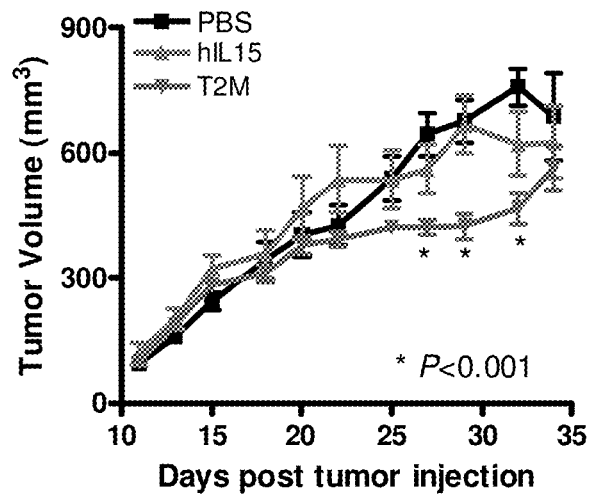
Figure 50C:
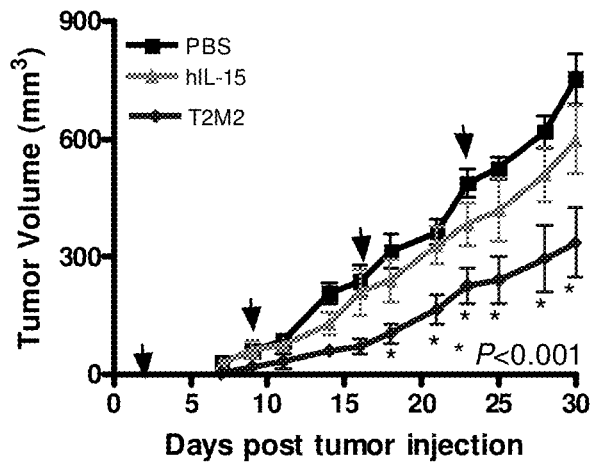

The antitumor activity of these complexes was further examined in the subcutaneous A375 xenograft model in nude mice. In initial studies, administration of recombinant human IL-15, the c264scTCR-IL15 and c264scTCR-IL15N72D fusion proteins or the c264scTCR-IL15N72D/c264scTCR-IL15Rα complex showed no effect on s.c. A375 tumor xenografts compared to PBS or c264scTCR-IL15Rα fusion protein treatment (FIG. 50A). The lack of an effect of the TCR-IL15 fusions in this model is likely due the inability of these proteins to stimulate NK cell responses in contrast to the reported results with the c264scTCR-IL2 fusion. As show above, when T2M complexes were tested in this model, they exhibited modest but statistically significant anti-tumor activity consistent with their ability to stimulate NK cell proliferation (FIG. 50B). However, in contrast to treatment with equivalent molar amounts of c264scTCR-IL15 fusion, the T2M dosing schedule (4 mg/kg every other day for 3 weeks) resulted in significant weight loss and two of 6 mice died after the last dose. Clinical observations included mouse inactivity, hunched posture, and ruddy skin. Concurrent studies of IL-15 protein complexes in other models confirmed that repeated every other day dosing was not well tolerated and that weekly dosing provided immune stimulation without excessive toxicity. A change of the dosing regimen from every other day to weekly schedule, T2M2 complex, at a dose level shown to be effective at inducing NK cell proliferation, exhibited significant more potent anti-tumor activity compared to IL-15 or PBS treatment (FIG. 50C). More importantly, this weekly dosing regimen was also well tolerated by the tumor-bearing nude mice and immunocompetent mice.

The toxicity profiles of the scTCR-IL15 fusions and T2M complexes were assessed concurrently with the in vivo activity studies described above. As indicated above, 3 weeks of every other day treatment with scTCR-IL15 fusions was well-tolerated by tumor bearing nude mice but T2M (4 mg/kg) treatment resulted in mortality in >30% of the animals. This was further evaluated in HLA-A*0201/Kb-transgenic mice administered 9, 18, or 36 mg/kg T2M or molar equivalent amounts of T2M2 complexes every other day for 1 week. At 1 week following initiation of treatment, dose and time dependent effects on body weight and clinical observations were seen. Mice receiving 36 mg/kg T2M exhibited a 20% loss in body weight compared to a 12% decrease observed in mice treated with equivalent amounts of T2M2. No change in body weight was observed in mice treated with ~9 mg/kg T2M or T2M2 over the 1 week period. Interestingly the higher toxicity observed with T2M did not correlate with increased immune cell activation as the mice treated with T2M2 showed higher levels of WBC counts and NK cell levels than T2M-treated mice. Minimal effects on mouse body weight, spleen weight and immune cells was observed following single dose i.v. administration of 0.4 mg/kg T2M2. Additionally preliminary studies in cynomolgus monkeys indicated that a single 0.5 mg/kg i.v. dose of T2M did not cause any observed toxicological effect but was capable of inducing CD8+ memory T cell and effector NK cell expansion. The results of these studies indicate that targeted IL-15 fusion complexes can be generated that have potent immunostimulatory and anticancer activity and favorable toxicity and pharmacokinetic profiles. Through these studies an optimized TCR-targeted T2M2 (also referred to as T2M☐CH1 composed of c264scTCR/huIL15N72D and c264scTCR/huIL15RαSushi/huIgG1 CH2-CH3 chains) was defined and characterized. The nucleic acid and protein sequences of the c264scTCR/ huIL15RαSushi/huIgG1 CH2-CH3 construct are shown in FIG. 51A and FIG. 51B and FIG. 52, respectively.

EXAMPLE 18

Characterization of T2 Molecules Comprising Antibody Targeting Domains

To demonstrate the utility of the huIL-15:huIL-15RαSu scaffold to create additional disease targeted molecules, constructs were made linking the C-terminal end of an anti-human CD20 single chain antibody to the N-termini of huIL-15N72D and huIL-15RαSu/huIgG1 CH2-CH3 (Fc) chains. The anti-human CD20 single chain antibody (anti-CD20 scAb) sequence comprises the coding regions of the heavy and light chain V domains of the rituximab antibody linked via a flexible linker sequence. The nucleic acid and protein sequences of the anti-CD20 scAb/hIL-15N72D construct are shown in FIG. 53 and FIG. 54, respectively. The nucleic acid and protein sequences of the anti-CD20 scAb/huIL-15RαSu/huIgG1 Fc construct are shown in FIG. 55A and FIG. 55B and FIG. 56, respectively. These sequences were cloned into expression vectors as described above and the expression vectors transfected into CHO cells. Co-expression of the two constructs allowed formation and secretion of a soluble anti-CD20 scAb/huIL-15N72D:anti-CD20 scAb/huIL-15RαSu/huIgG1 Fc complex (referred to as anti-CD20 scAb T2M) which was purified from the CHO cell culture supernatant using Protein A affinity chromatography.

Figure 57:
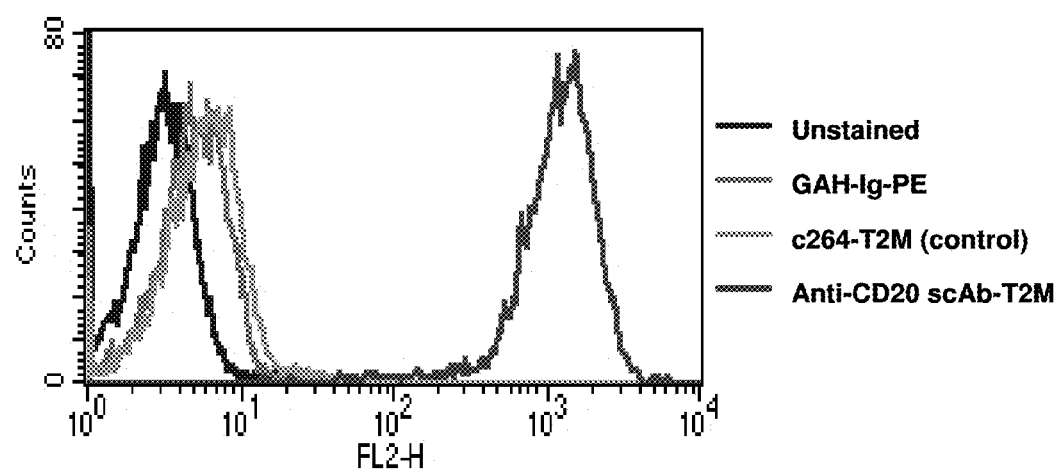
FIG. 57 shows results from flow cytometry assays to test the CD20 antigen specific binding of anti-CD20 scAb T2M molecules to Daudi cells.

Similar to analysis described above, the ELISA-based methods have confirmed formation of the anti-CD20 scAb/huIL-15N72D:anti-CD20 scAb/huIL-15RαSu/huIgG1 Fc complex. Additionally, IL-15 receptor binding and cell proliferation assays using 32Dβ cells as described above indicated that the complex exhibited IL-15 binding and biologic activity. The anti-CD20 scAb T2M complex was then tested for antigen specific binding activity against the human CD20+ Burkitt lymphoma Daudi cell line. Daudi cells were incubated with anti-CD20 scAb T2M, c264scTCR T2M or PBS. Following a wash step, cell bound fusion protein complexes were detected with PE-conjugated goat anti-human Ig antibody (GAH-Ig-PE) by flow cytometry (FIG. 57). The anti-CD20 scAb T2M complex showed significant binding to Daudi cells that was not observed with c264scTCR T2M or GAH-Ig-PE, indicating specific reactivity to these cells.

Figure 58:
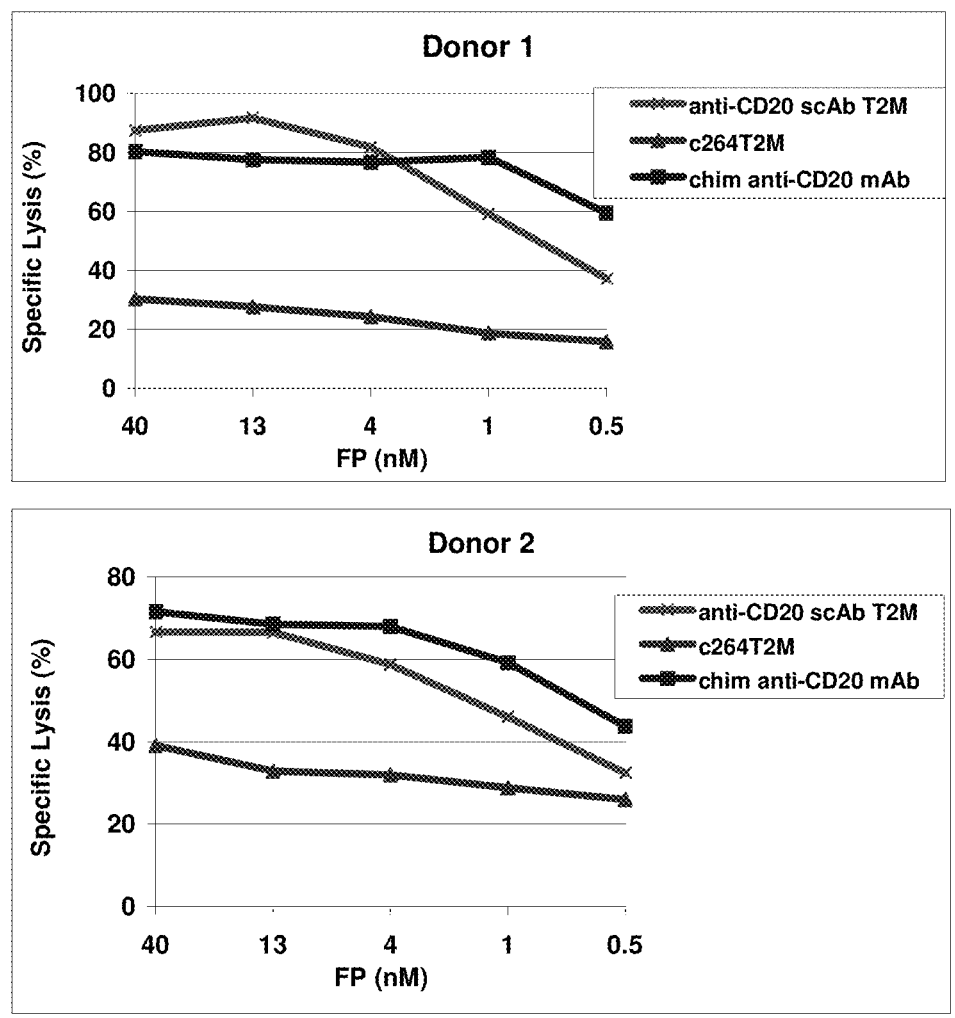
FIG. 58 shows results of an assay to determine the antibody dependent cellular cytotoxicity activity mediated by anti-CD20 scAb T2Ms against CD20+ human tumor cells. Various amounts of fusion protein (anti-CD20 scAb T2M, c264scTCR T2M (negative control) or chimeric anti-CD20 mAb (positive control)) were mixed with fresh human PBMCs (from 2 different donors) and Daudi cells (Calcein labeled) (E:T ratio, 100:1). After an incubation period, the culture medium was collected and analyzed quantitatively for Calcein released from lysed cells.
Figure 59:
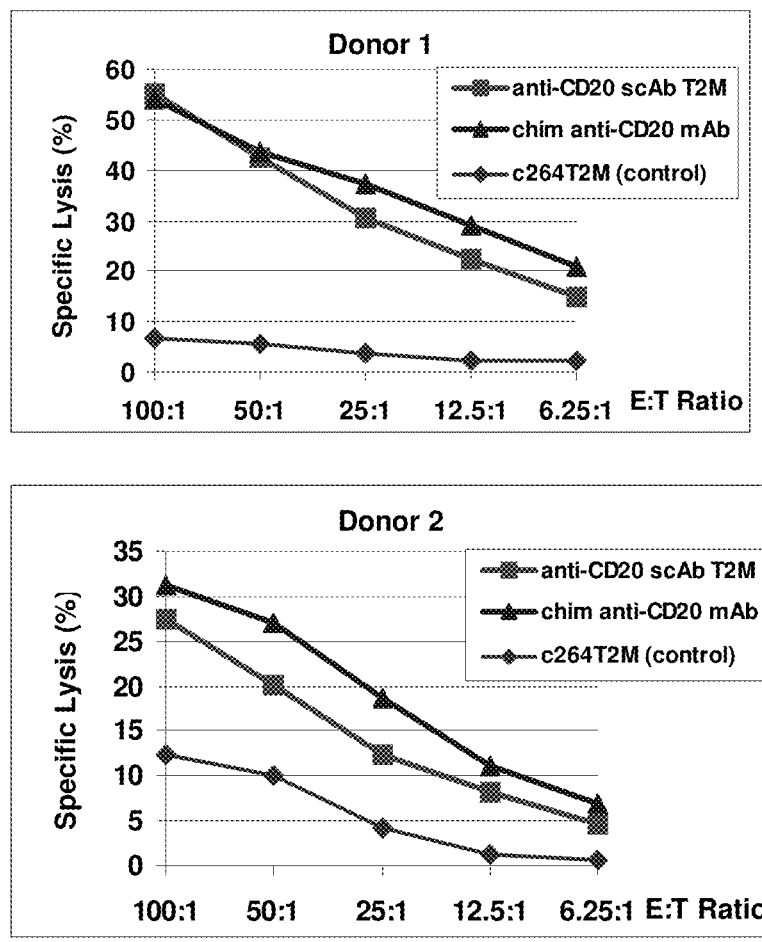
FIG. 59 shows results of an assay to determine the antibody dependent cellular cytotoxicity activity mediated by anti-CD20 scAb T2Ms against CD20+ human tumor cells. Fusion proteins (anti-CD20 scAb T2M, c264scTCR T2M (negative control) or chimeric anti-CD20 mAb (positive control)) were mixed with various rations of fresh human PBMCs (from 2 different donors) and Daudi cells (Calcein labeled). After an incubation period, the culture medium was collected and analyzed quantitatively for Calcein released from lysed cells.

Studies were also conducted to determine whether the anti-CD20 scAb T2M complexes were capable of killing CD20+ tumor cells via an ADCC-based mechanism. Calcein-AM labeled Daudi target cells were mixed with human PMBCs (E:T—100:1) and various concentrations of anti-CD20 scAb T2M, c264scTCR T2M (negative control) or chimeric anti-CD20 mAb (positive control). After an incubation period, target cell lysis was evaluated as described above. As shown in FIG. 58, the anti-CD20 scAb T2M complex was highly effective at mediating ADCC activity against CD20+ human lymphoma cells. This was verified by similar studies examining different effector to target cell ratios, where the anti-CD20 scAb T2M complex (at 2 nM) showed comparable activity as the chimeric anti-CD20 mAb (FIG. 59).

Based on these results, the anti-CD20 scAb T2M molecule is expected to exhibit antitumor activity against human lymphoma cells in standard xenograft tumor models (see for example, Rossi et al. Blood 2009; 114:3864; Gillis et al. Blood. 2005; 105:3972; and Xuan et al. Blood 2010; 115: 2864-2871).

Additionally T2M constructs comprising anti-CD20 light chains and heavy chain domains individually fused to the huIL-15N72D and huIL-15RαSu/huIgG1 CH2-CH3 (Fc) chains, respectively (or visa versa), could be generated and expressed as described herein. The nucleic acid and protein sequences of two such fusion constructs are shown in FIG. 60, FIG. 61, FIG. 62A and FIG. 62B, and FIG. 63. Purified complexes comprising these fusion proteins are expected to exhibit Fc domain and IL-15 biologic activity, and CD20-specific binding activity, as described above. These complexes are expected to mediate ADCC activity against CD20+ tumor cells and antitumor activity against CD20+ tumor cells in vivo.

Similar T2M constructs comprising scAb or antibody recognition domains could be readily generated with antibody sequences specific to other CD antigens, cytokines or chemokine receptors or ligands, growth factor receptors or ligands, cell adhesion molecules, MHC/MHC-like molecules, Fc receptors, Toll-like receptors, NK receptors, TCRs, BCRs, positive/negative co-stimulatory receptors or ligands, death receptors or ligands, tumor associated antigens, virus-encoded and bacterial-encoded antigens, and bacterial-specific. Of particular interest are T2M with antibody domains specific to epitopes of CD3, CD4, CD19, CD21, CD22, CD23, CD25, CD30, CD33, CD38, CD40, CD44, CD51, CD52, CD70, CD74, CD80, CD152, CD147, CD221, EGFR, HER-2/neu, HER-1, HER-3, HER-4, CEA, OX40 ligand, cMet, tissue factor, Nectin-4, PSA, PSMA, EGFL7, FGFR, IL-6 receptor, IGF-1 receptor, GD2, CA-125, EpCam, death receptor 5 MUC1, VEGFR1, VEGFR2, PDGFR, Trail R2, folate receptor, angiopoietin-2, alphavbeta3 integrin receptor and HLA-DR antigens. Antibody domains against viral antigens from HIV, HCV, HBC, CMV, HTLV, HPV, EBV, RSV and other virus are also of interest, particularly those recognizing the HIV envelope spike and/or gp120 and gp41 epitopes. Such antibody domains can be generated from sequences known in the art or isolated de novo from a variety of sources (i.e., vertebrate hosts or cells, combinatorial libraries, random synthetic libraries, computational modeling, etc.) know in the art.

Additionally, as indicated above, it is useful to increase or decrease the activity of the IL-15 domain and the IgG Fc domains to optimize the therapeutic index and minimize toxicity of the antibody-targeted T2 complexes. Methods of modifying the activity of Fc domains are described above and are well characterized in the art. In such a case, complexes containing a mutation in the IL-15 domain that reduces its activity are expected to provide better therapeutic activity and lower toxicity. Antibody-targeted T2 molecules containing N65D or D8N substitutions in the IL-15 domain described above or other substitutions including I6S, D8A, D61A, N65A, N72R, V104P or Q108A, which has been found to reduce IL-15 activity, are of particular interest.

EXAMPLE 19

Co-Expression of IL-15N72D and IL-15RαSu/Fc Fusion Gene in CHO Cells

Figure 64:
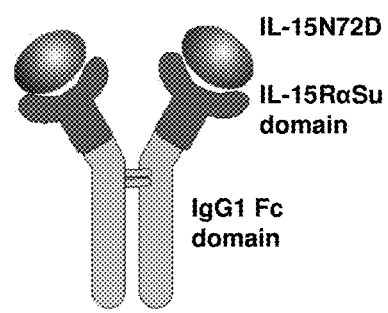
FIG. 64 is a schematic drawing of the IL-15N72D:IL-15RαSu/Fc complex consisting IL-15N72D noncovalently associated with the dimeric IL-15RαSu/Fc fusion protein.

Previous studies have shown that recombinant IL-15 is poorly expressed by mammalian cells (A. Ward et al., Protein Expr Purif 68 (2009) 42-48). However, it has been reported that intracellular complex formation with IL-15Rα prevents IL-15 degradation in the ER (C. Bergamaschi et al., J Biol Chem 283 (2008) 4189-4199). Hence, it was postulated that IL-15 could be produced at a higher level if it is co-expressed with IL-15Rα. It is known that soluble IL-15Rα fragment, containing the so-called "sushi" domain (Su) at the N terminus, bears most of the structural elements responsible for cytokine binding. Soluble IL-15RαSu (without its transmembrane domain) and IL-15 are able to form very stable heterodimeric complexes in solution ($K_d$ of complex=100 pM (G. Bouchaud et al., J Mol Biol 382 (2008) 1-12)) and these complexes are capable of modulating (i.e. either stimulating or blocking) immune responses via the IL-15Rβ$γ_c$ complex (E. Mortier et al., J Biol Chem 281 (2006) 1612-1619; M. P. Rubinstein et al., Proc Natl Acad Sci USA 103 (2006) 9166-9171; T. A. Stoklasek et al., J Immunol 177 (2006) 6072-6080; G. Bouchaud et al., J Mol Biol 382 (2008) 1-12). Thus, a complex consisting of IL-15N72D and an IL-15RαSu/Fc fusion protein was chosen for production (see FIG. 64). The IL-15RαSu domain was genetically fused to the human IgG1-Fc region to facilitate its purification and dimerization via interchain disulfide bonds. To co-express IL-15N72D and the IL-15RαSu/Fc, two individual retrovirus-based expression vectors, pMSGV-IL-15RαSu/Fc and pMSGV-IL-15N72D, were constructed and co-transfected into CHO cells. The recombinant CHO cells were selected based on the neomycin and puromycin resistance elements provided by the two expression vectors, and individual producing cell lines were then generated using limited dilution cloning. A clone that is capable of producing approximately 100 mg/L of IL-15N72D:IL-15RαSu/Fc complex, based on ELISA, in a serum-free, defined medium was identified. This result demonstrated that IL-15 could be expressed at high levels in mammalian cells if it is co-expressed with the IL-15RαSu domain.

EXAMPLE 20

Purification and Characterization of the IL-15N72D:IL-15RαSu/Fc Complex

When IL-15RαSu/Fc and IL-15N72D were co-expressed and assembled intracellularly in recombinant CHO cells, four different forms of proteins were expected in the cell culture supernatants: 1) dimeric IL-15RαSu/Fc molecule fully occupied with two IL-15N72D subunits, 2) dimeric IL-15RαSu/Fc molecule partially occupied with one IL-15N72D subunit, 3) a small amount of free homodimeric IL-15RαSu/Fc molecule with no IL-15 bound, and 4) free IL-15N72D. Since IL-15N72D lacks an Fc region, a rProtein A-based affinity purification step was used to separate the free IL-15N72D from all of the Fc-bearing fusion proteins in the culture supernatant.

Figure 65A:
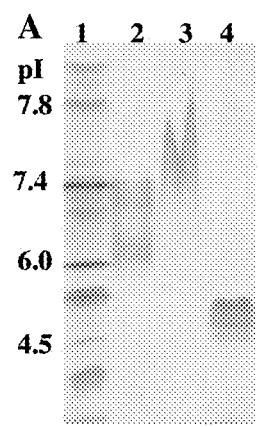
FIGS. 65A-65D are photographs of gel electrophoresis analysis profiles of IL-15N72D:IL-15RαSu/Fc preparations.
Figure 65B:
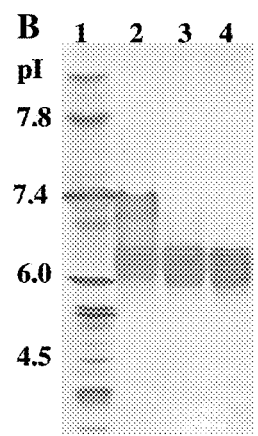

An ion exchange chromatography method was then developed to separate various forms of the IL-15RαSu/Fc complex. The calculated isoelectric point (pI) of the IL-15RαSu/Fc dimeric molecule is 8.5. As expected, this protein in 20 mM Tris-HCl, pH 8.0 solution was subsequently found to not bind to QSFF resin. Additionally, the calculated pI of IL-15N72D is 4.5. Therefore, it was predicted that the overall charge of the partially occupied IL-15N72D:IL-15RαSu/Fc (i.e. dimeric IL-15RαSu/Fc+one IL-15N72D molecule) and the fully occupied IL-15N72D:IL-15RαSu/Fc (dimeric IL-15RαSu/Fc+two IL-15N72D molecules) are different. This is consistent with IEF gel analysis of the Protein-A-purified preparations, which showed two major groups of complexes with pIs between 5.6-6.5 and 6.8-7.5 corresponding with the expected pIs of the fully occupied and partially occupied complexes, respectively (FIG. 65A). The heterogeneity among pI bands of each protein group is possibly due to the degree of glycosylation and C-terminal lysine variants in the IgG1 chain. Thus, buffers with different ionic strengths were employed to separately elute the partially occupied and fully occupied complexes from the QSFF. Using 130 mM NaCl, 20 mM Tris-HCl, pH 8.0, a single protein fraction (Q step 1) was eluted from QSSF and found to contain mainly the partially occupied complex based on ELISAs determining the fractional occupancy of the IL-15RαSu/Fc molecule. In the subsequent step using 300 mM NaCl, 20 mM Tris-HCl, pH 8.0, two protein fractions designated as Q1c and Q2c were further eluted from the QSFF. ELISA analyses performed on these preparations indicated that Q1c fraction contained a mixture of partially occupied (10% of total) and fully occupied (90%) complexes whereas Q2c fraction contained only the fully occupied complex (data not shown). These findings are consistent with IEF gel analysis of the purified protein preparations (FIG. 65B). Proteins eluted from Q step 1 have broad pIs ranging from 5.6 to 7.5; proteins of pIs 6.8 to 7.5 representing the partially occupied complex. Fraction Q1c of Q step 2 elution mainly contained protein with pIs ranging from 5.6 to 6.5 (i.e. fully occupied complex) but with small amounts of contaminant protein with pIs of 5.6 to 7.5. The Q2c fraction contained only proteins with pIs ranging from 5.6 to 6.5.

Figure 66:
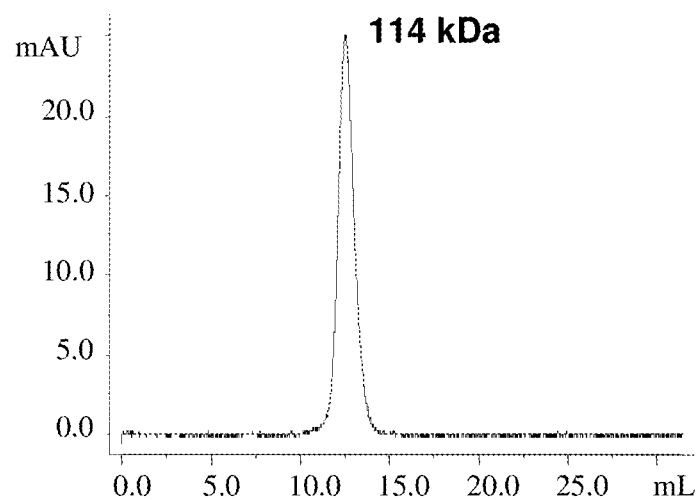
FIG. 66 is a graph of a SEC chromatogram using Superdex 200 HR 10/30 gel filtration column. The purified IL-15N72D:IL-15Rα/Fc complex was eluted as a single peak.

In SEC analysis, the purified IL-15N72D:IL-15RαSu/Fc Q2c preparation was found to elute as a single molecule with high purity (FIG. 66). The estimated molecular weight of the homodimer was approximately 114 kDa, which was larger than the 92 kDa molecular weight calculated based on the deduced amino acid sequence of IL-15N72D and IL-15RαSu/Fc fusion proteins. This is likely due to the glycosylation of the proteins produced by mammalian cells.

Figure 65C:
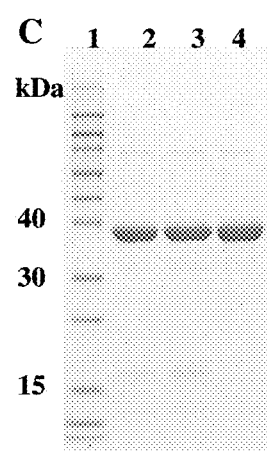
Figure 65D:
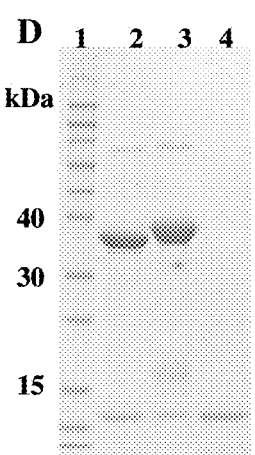

In reducing SDS-PAGE (FIG. 65C), the purified IL-15N72D:IL-15RαSu/Fc preparation was found to contain three proteins with molecular weights of 40 kDa, 16 kDa and 13 kDa. However, after a digestion with N-Glycosidase F, only two proteins, with molecular weights of ~37 kDa and 13 kDa, were detected (FIG. 65D). These molecular weights closely match the calculated molecular weights of IL-15RαSu/Fc and IL-15 or IL-15N72D. This suggests that these two proteins were glycosylated during mammalian cell production and the IL-15N72D was produced in two major glycosylation forms with molecular weights of 13 kDa and 16 kDa. The relative abundance of these IL-15N72D species in the different purification fractions shown in FIG. 65C is consistent with levels of complex occupancy determined by ELISA and IEF gel analysis.

The IL-15N72D and IL-15RαSu/Fc were separated in reducing SDS-PAGE and the N-terminus amino acid sequences of these proteins were determined using the Edman degradation method. Approximately 15 N-terminal amino acid sequences were obtained for IL-15RαSu/Fc and IL15N72D, respectively. The determined N-terminal amino acid sequences of these proteins matched their amino acid sequences deduced from the coding regions of the two genes. The amino acid sequences for the two major bands that appeared on reduced SDS-PAGE at 13 and 16 kDa were confirmed to be IL-15N72D. This sequence confirmation again provided the evidence of glycosylation of IL-15N72D in mammalian cells.

EXAMPLE 21

Pharmacokinetic Properties of the IL-15N72D:IL-15αSu/Fc Complex

It has previously been reported that IL-15 and in vitro assembled IL15:IL-15Rα/Fc complex had a 1 h and 20 h serum half-life, respectively, in mice when these proteins were injected intraperitoneally (T. A. Stoklasek et al., J Immunol 177 (2006) 6072-6080). To assess whether IL-15 and the co-expressed, purified IL-15:IL-15αSu/Fc complex behaved similarly when administered intravenously, their pharmacokinetic parameters were determined in CD-1 mice. Intravenous administration was chosen because this is likely the route of drug delivery to be used for the IL-15:IL-15αSu-Fc complex in humans. Female mice were injected intravenously with 1.0 mg/kg IL-15:IL-15αSu/Fc or 0.28 mg/kg IL-15 (a molar equivalent dose) and blood was collected at various time points from 15 min to 8 h for IL-15 and 30 min to 72 h for IL-15N72D:IL-15αSu/Fc post injection. Serum concentrations of IL-15N72D:IL-15αSu/Fc were evaluated using two ELISA formats, one (anti-IL-15 Ab detection) which detects the intact complex and the other (anti-human IgG Fc Ab detection) which detects only the IL-15αSu/Fc fusion protein. Concentrations of IL-15 were evaluated with a standard IL-15-specific ELISA.

Figure 67:
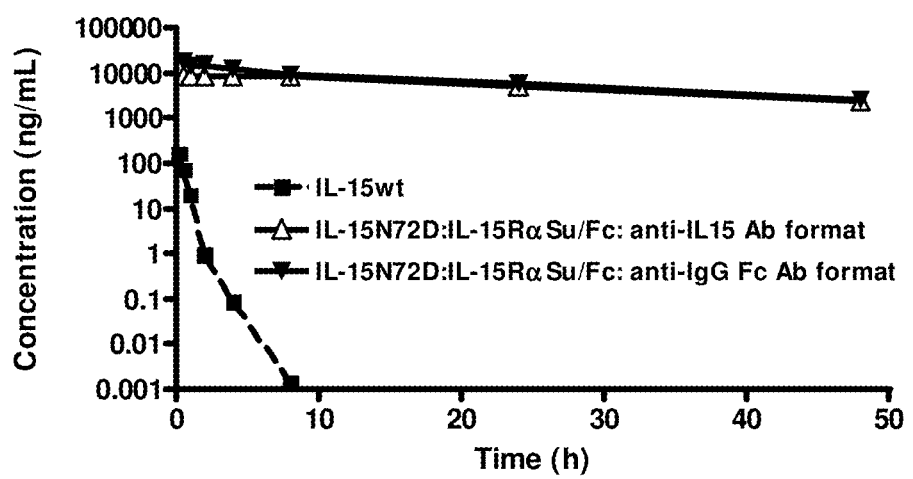
FIG. 67 is a graph showing a comparison of the pharmacokinetic profile of IL-15 wt and IL-15N72D:IL-15RαSu/Fc complex following intravenous administration in CD-1 mice. The anti-IL-15 Ab ELISA measures the concentration of IL-15 wt (■). The anti-IL-15 Ab ELISA measures the concentration of the intact IL-15N72D:IL-15RαSu/Fc molecule (Δ), whereas the anti-human IgG Fc Ab ELISA measures serum concentration of the IL-15RαSu/Fc fusion protein (▼). The observed concentrations are represented by symbols and the model-fitted curves are represented by lines.

The predicted fit and actual data for IL-15:IL-15αSu/Fc and IL-15 following the single intravenous bolus injections are shown in FIG. 67. The estimated half-life of IL-15:IL-15αSu/Fc using anti-IL-15 Ab-based or anti-human IgG Fc Ab-based ELISAs was about 25 or 18 h, respectively. These results indicate that the fusion protein was not cleaved and the IL-15 did not significantly disassociate from the IL-15RαSu/Fc molecule in vivo. The clearance (Cl) of IL-15:IL-15αSu/Fc ranged from 0.059 to 0.051 mL/h and the volume of distribution at steady state (Vss) ranged from 2.1 to 1.3 mL depending on the assay format. In comparison, IL-15 had an absorption half-life of 0.24 h and a terminal half-life of 0.64 h. The Cl of IL-15 was 49 mL/h, and the Vss was 18.4 mL. These results indicate that IL-15:IL-15αSu/Fc displays a >24 fold longer terminal half-life and is cleared >800 fold slower than IL-15.

EXAMPLE 22

In Vitro and In Vivo Biological Activities of the IL-15N72D:IL-15αSu/Fc Complex

Figure 68:
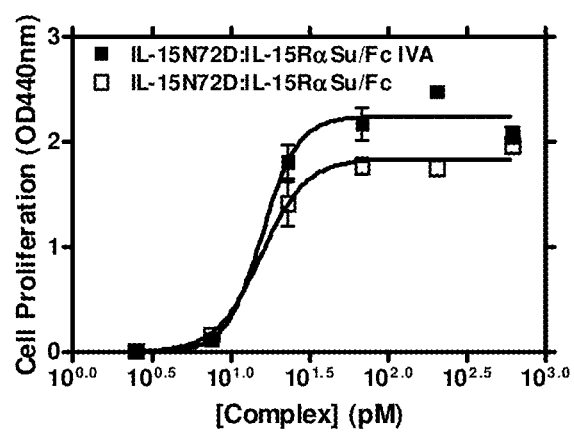
FIG. 68 is a graph showing a comparison of the biological activity of the in vitro assembled IL-15N72D:IL-15RαSu/Fc (IL-15N72D:IL-15RαSu/Fc IVA) with IL-15N72D:IL- 15RαSu/Fc. 32Dβ cells were incubated with increasing concentrations of the in vitro assembled IL-15N72D:IL-15RαSu/Fc (■) or IL-15N72D:IL-15RαSu/Fc (□) for 72 h prior to addition of WST-1 for 4 h. Cell proliferation was quantitated by absorbance reading at 440 nm to assess formazan levels. The data points shown are means (±standard error) of triplicate samples and the lines represent sigmoidal dose-response curve fit for $EC_{50}$ determination. The results are representative of at least three experiments.

The biological activity of the co-expressed and purified IL-15N72D:IL-15RαSu/Fc complex was evaluated using an IL-15 dependent 32Dβ cell proliferation assay. For this assay, an in vitro assembled (IVA) IL-15N72D:IL-15RαSu/Fc complex (IL-15N72D:IL-15RαSu/Fc IVA) was also generated by mixing IL-15N72D and IL-15RαSu/Fc at a 1:1 ratio for 30 min at 4° C. As shown in FIG. 68, the IL-15N72D:IL-15RαSu/Fc complex had equivalent biological activity as IL-15N72D:IL-15RαSu/Fc IVA to support growth of 32Dβ cells. The IL-15N72D:IL-15RαSu/Fc complex exhibited an $EC_{50}$ of 15.61 pM and the IL-15N72D:IL-15RαSu/Fc IVA displayed an $EC_{50}$ of 15.83 pM. This demonstrates that the co-expressed IL-15N72D:IL-15RαSu/Fc complex is appropriately processed intracellularly and retains full IL-15 activity after purification. Thus, the method presented herein represents a better approach for generating cGMP-grade clinical material than current strategies employing in vitro assembly individually produced and in some cases refolded proteins.

Figure 69:
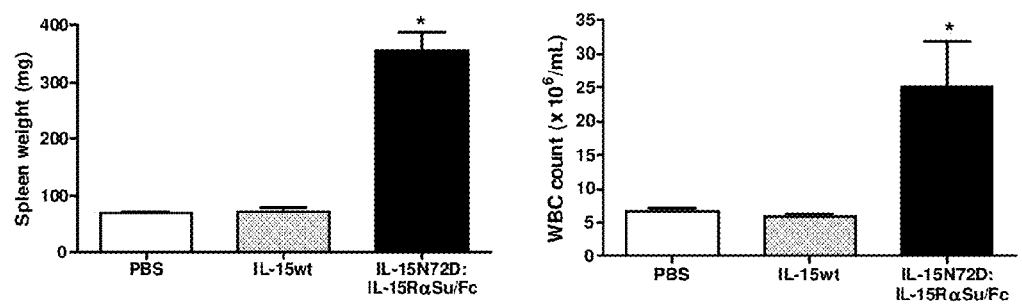
FIG. 69 is a set of graphs showing the effect of IL-15 wt and IL-15N72D:IL-15RαSu/Fc complex on spleen weight and white blood cell levels. C57BL/6 mice (5 mice per group) were injected intravenously with a single dose of IL-15N72D:IL-15RαSu/Fc fusion complex at 1 mg/kg IL-15 wt at 0.28 mg/kg (molar equivalent dose), or PBS as a negative control. Spleen weights (left panel) and white blood cell counts in blood (right panel) were determined 4 days after injection. The bars represent the mean±standard error (n=5). * $P>0.05$ compared to PBS and IL-15 wt. The results are representative of at least two experiments.
Figure 70:
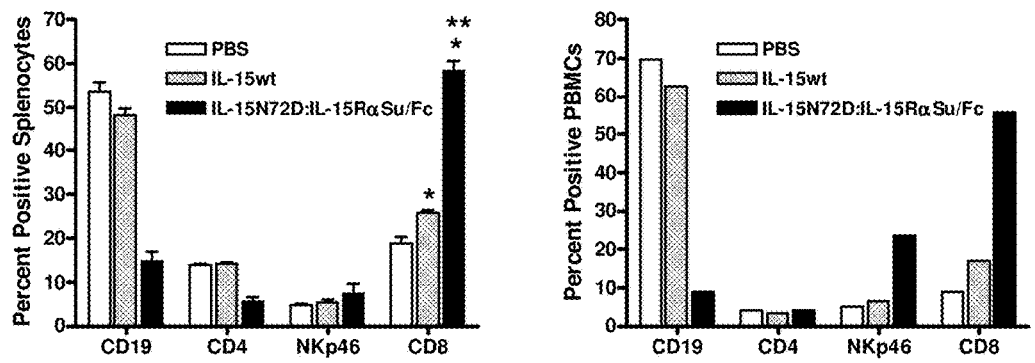
FIG. 70 is a set of graphs showing the effect of IL-15 wt and IL-15N72D:IL-15RαSu/Fc complex on mouse lymphocytes. C57BL/6 mice (5 mice per group) were injected intravenously with a single dose of IL-15N72D:IL-15RαSu/Fc fusion complex at 1 mg/kg, IL-15 wt at 0.28 mg/kg (molar equivalent dose), or PBS as a negative control. The percentage of B cells (CD19), CD4 T cells (CD4), NK cells (NKp46) and CD8 T cells (CD8) were determined in splenocytes (left panel: mean±standard error (n=5)) and PBMCs (right panel: levels in pooled blood (n=5)) 4 days after injection. * $P>0.05$ compared to PBS, ** $P>0.05$ compared to IL-15 wt. The results are representative of at least two experiments.

The IL-15N72D:IL-15RαSu/Fc complex and IL-15 wt were also compared for their ability to induce the expansion of NK cells and CD8+ T cells in C57BL/6 mice. As shown in FIG. 69, IL-15 wt has no significant effect on the expansion of NK and CD8+ cells four days after a single intravenous dose of 0.28 mg/kg. In contrast, the IL-15N72D:IL-15RαSu/Fc complex significantly promoted NK and CD8+ T cell proliferation in the blood and spleen, which led to lymphocytosis in blood and splenomegaly (FIG. 69 and FIG. 70). These findings are consistent with previous reports that IL-15:IL-15Rα complexes significantly increased the biological activities of IL-15 in vivo (M. P. Rubinstein et al., Proc Natl Acad Sci USA 103 (2006) 9166-9171; T. A. Stoklasek et al., J Immunol 177 (2006) 6072-6080; S. Dubois et al., J Immunol 180 (2008) 2099-2106; M. Epardaud et al., Cancer Res 68 (2008) 2972-2983; A. Bessard et al., Mol Cancer Ther 8 (2009) 2736-2745). This enhanced activity of the IL-15N72D:IL-15RαSu/Fc complex is likely the result of a combination of the increased binding activity of the N72D mutein to the IL-15Rβγ$_c$ complex (X. Zhu et al., J Immunol 183 (2009) 3598-3607), optimized cytokine trans-presentation by the IL-15Rα chain in vivo (through the FcR receptors on dendritic cells and macrophage), the dimeric nature of the cytokine domain (increased avidity of binding to IL-15Rβγ$_c$) and its increased in vivo half-life compared to IL-15 (25 h vs.<40 min).

In sum, the results described herein demonstrate that the IL-15N72D and IL-15RαSu/Fc genes can be co-expressed in recombinant CHO cells and a fully occupied IL-15N72D:IL-15RαSu/Fc complex can be highly purified from cell culture supernatants using a simple scalable purification method.

The above examples were carried out using the following materials and methods.
Construction of Vectors for Protein Complex Expression The IL-15RαSu/Fc fusion gene was constructed by overlap PCR amplification of DNA templates encoding the sushi domain of human IL-15Rα (aa1-66 of human IL-15Rα) and the human IgG1 Fc fragment. The signal peptide-IL-15RαSu coding region (R. L. Wong et al., Protein Eng Des Sel 24 (2011) 373-383) and human IgG1-Fc gene fragment (L. A. Mosquera et al., J Immunol 174 (2005) 4381-4388) were amplified using the primer pairs:

```
BA494:
                                   (SEQ ID NO: 16)
5'-GACTTCAAGCTTAATTAAGCCACCATGGACAGACTTACTTC
TTC-3';

BA550R:
                                   (SEQ ID NO: 22)
5'-GTGAGTTTTGTCACAAGATTTCGGCTCTCTAATGCATTTGA
GACTGGGGGTTG-3',
and BA550F:
                                   (SEQ ID NO: 23)
5' GAGCCGAAATCTTGTGACAAAACTCAC-3';

BA393R:
                                   (SEQ ID NO: 15)
5'-GTAATATTCTAGACGCGTTCATTATTTACCAGGAGACAGGG
AGAGGCTCTTC-3',
``` respectively. The resulting IL-15RαSu/Fc fusion gene was ligated into a puromycin-resistant expression vector pMSGV-1 (M. S. Hughes et al., Hum Gene Ther 16 (2005) 457-472) to construct the expression vector pMSGV-IL-15RαSu/Fc.

The coding sequence of IL-15N72D (X. Zhu et al., J Immunol 183 (2009) 3598-3607) was cloned into a modified retrovirus expression vector pMSGV-1 (M. S. Hughes et al., Hum Gene Ther 16 (2005) 457-472) that carries the neomycin resistance gene after an IRES region to construct the expression vector pMSGV-IL-15N72D.
Co-Expression of IL-15N72D:IL-15RαSu/Fc Fusion Complex in CHO Cells To co-express IL-15N72D and IL-15RαSu/Fc fusion proteins (see FIG. 64), pMSGV-IL-15RαSu/Fc and pMSGV-IL-15N72D were co-transfected into CHO cells followed by selection in medium containing 2 mg/mL G418 (Hyclone, Logan, Utah) and 10 □g/mL of puromycin (Hyclone, Logan, Utah). The IL-15RαSu/Fc fusion protein was also expressed individually in CHO cells for use in loading of recombinant human wild-type IL-15 (IL-15 wt) as a control. For production of the fusion proteins, the recombinant CHO cells were grown in serum free defined medium (SFM4CHO, Hyclone, Logan, Utah) at 37° C. When the viable cell density of the cultures reached a maximum, the incubation temperature was shifted down to 30° C. for accumulation of the soluble complex. Culture supernatants were then harvested when the viable cell density of the cultures reached approximately 10% viable cells.

Purification Procedure

The recombinant CHO cell culture medium was centrifuged and filtered to remove cells and debris before the supernatant was adjusted to pH 8.0 with 1 M Tris-HCl, pH 8.0. The soluble IL-15N72D:IL-15RαSu/Fc fusion protein complex was purified using a two-step affinity and ion exchange chromatography-based process.

Since the IL-15N72D:IL-15RαSu/Fc complex contains the IgG1-Fc domain, an rProtein A Sepharose Fast Flow (GE Healthcare) column was used as the first step in the purification process. Prior to sample loading, the column was washed with 5 column volumes (CV) of 20 mM Tris-HCl, pH 8.0, sanitized with 5 CV of 0.1 N NaOH for 1 h, and then equilibrated with 7 CV of 20 mM Tris-HCl, pH 8.0. The supernatant was loaded onto the 11 mL column at 2 mL/min, and the column was then washed with 8 CV of 20 mM Tris-HCl, pH8.0, followed by 7 CV of washing buffer (0.1 M Na-citrate, pH 5.0) to remove non-specifically bound proteins. The protein was then eluted with 0.2 M Na-citrate, pH 4.0 and the pH of collected peak fractions was immediately adjusted to pH 3.5 using 0.2 M citric acid; the eluted protein was held at this low pH for 30 minutes as a standard viral clearance step. After the low pH hold step, the pH of the eluted preparation was adjusted to pH 7.7 by using 2 M Tris-HCl, pH 8.0. The preparation was concentrated and buffer exchanged into 20 mM Tris-HCl, pH 8.0 by using an Amicon Ultra-15 centrifugal concentrator (30 kDa cut-off, Millipore, Billerica, Mass.) before sterile filtration using a 0.22 μm filter (Corning Life Sciences, Lowell, Mass.).

The protein preparation was then applied to a Q Sepharose Fast Flow (QSFF; GE Healthcare Bio-Sciences, Piscataway, N.J.) ion exchange column. A 5 mL column was washed with buffer A (20 mM Tris-HCl, pH 8.0), sanitized by 5 CV of 0.1 N NaOH for 1 h, and then equilibrated with buffer A. The protein concentration in the preparation was first adjusted to <1 mg/mL with 20 mM Tris-HCl, pH 8.0 and was then loaded onto the QSFF column at a rate of 1 mL/min. The protein was then eluted from the column using a three-step-gradient process as follows: 20 mM Tris-HCl, pH 8.0, 130 mM NaCl for four CV as the first step, 20 mM Tris-HCl, pH 8.0, 300 mM NaCl for four CV for the second step and 20 mM Tris-HCl, pH 8.0, 1 M NaCl for two CV as the last step. Protein peak fractions were collected, buffer exchanged into PBS (Hyclone, Logan, Utah), and filtered using a 0.22 μm filter. Protein concentration was determined by UV spectrophotometer at 280 nM using an extinction coefficient of 1 $A_{280nm}$=0.79 mg/mL. This extinction coefficient was calculated based on the deduced amino acid sequence of the IL-15N72D:IL-15RαSu/Fc complex.

Individually expressed IL-15RαSu/Fc was purified using rProtein A affinity chromatography as described above for assembling of complex in solution with IL-15N72D or IL-15 wt produced in E. coli and refolded (Zhu, 2009 #3315). These in vitro assembled complexes were used as standards for biological activity evaluation and estimation of degree of occupancy of the IL-15 binding sites in co-expressed complexes.

Gel Electrophoresis and Size Exclusion Chromatography (SEC) Analysis

Purified proteins were analyzed by different types of gel electrophoresis methods, which included NuPAGE 12% Bis-Tris gel (under reduced and non-reduced conditions), 4-20% Tris-glycine gel (native condition), and IEF pH3-10 gel (for pI determination). All supplies were from Invitrogen (Carlsbad, Calif.). Experimental methods were performed as described by the manufacturer. Superdex 200 HR 10/30 (GE Healthcare Bio-Sciences) chromatography with PBS (Hyclone, Logan, Utah) as the running buffer was used to examine purity and to estimate molecular mass of the proteins.

N-Terminal Amino Acid Sequence and Glycosylation Analysis

Protein bands of interest were separated on SDS-PAGE gels, blotted onto PVDF membrane and stained by Ponceau S solution. N-terminal amino acids sequencing was performed using the Edman degradation method (Molecular Structure Facility, UC Davis, Davis, Calif.).

To examine whether the fusion complex was glycosylated, 50 μg of the highly purified protein after the ion exchange chromatography was digested with 2 μL of N-Glycosidase F (Calbiochem, La Jolla, Calif.) in a total volume of 50 μL in PBS at room temperature for 48 h and then was subjected to electrophoresis in NuPAGE 12% Bis-Tris gel under a reduced condition.

Determination of IL-15N72D Occupancy of the Purified IL-15N72D:IL-15RαSu/Fc Complex Purified IL-15RαSu/Fc was loaded with IL-15 wt (produced in E. coli and refolded, provided by J. Yovandich, NCI, Fredrick, Md.) at various ratios for 15 h at 4° C. After incubation, the IL-15 wt:IL-15RαSu/Fc complex was purified using rProtein A affinity chromatography as described above. This purified complex was evaluated using two ELISA formats, one (anti-human IgG Fc capture and anti-IL-15 detection) which detects the intact complex and the other (anti-human IgG Fc capture and anti-human IgG Fc detection) which detects only the IL-15αSu/Fc fusion protein. The ratio between the intact IL-15 wt:IL-15αSu/Fc complex and IL-15RαSu/Fc protein levels reflects the occupancy rate of the IL-15 binding sites of the complex. [Occupancy rate (%)=the intact complex (ng/mL)/IL-15RαSu/Fc (ng/mL)×100%]. Fully occupied complex (pre-associated of IL-15RαSu/Fc and IL-15 wt at a 1:3 ratio) was then used as a standard to quantitate the occupancy rate of purified IL-15N72D:IL-15RαSu/Fc fusion protein complexes after purification.

Determination of IL-15 Biological Activity

An in vitro cell proliferation assay using the IL-15-depended 32Dβ cell line was employed to assess the IL-15 biological activities of the purified complex and IL-15 wt proteins as previously described (X. Zhu et al., J Immunol 183 (2009) 3598-3607).

Pharmacokinetic Evaluation

The pharmacokinetic profile of IL-15N72D:IL-15RαSu/Fc complex and IL-15 wt were evaluated in female CD-1 mice (4 mice/time point, Harlan, Indianapolis, Ind.) as previously described for IL-2 (H. J. Belmont et al., Clin Immunol 121 (2006) 29-39). Serum levels of the IL-15N72D:IL-15RαSu/Fc complex were assessed with the two ELISA formats described above. IL-15 wt levels were assessed by ELISA using anti-IL-15 capture (MAB647; R&D Systems, Minneapolis, Minn.) and anti-IL-15 detection (BAM247; R&D Systems, Minneapolis, Minn.). IL-15N72D:IL-15RαSu/Fc levels from each ELISA format were fit with a one-compartment model using PK Solution 2.0 (Summit Research Services, Montrose, Colo.). Data from mice treated with IL-15 wt were best modeled as a two-compartment model.

Lymphocyte Stimulation

C57BL/6 mice (male, 6 wks of age, Harlan, Indianapolis, Ind.) were injected intravenously with a single dose of IL-15N72D:IL-15RαSu/Fc fusion complex at 1 mg/kg or human IL-15 wt at 0.28 mg/kg (molar equivalent dose), respectively, or PBS as a negative control. Four days after treatment, pooled blood (5 mice per group) and splenocytes were collected. PBMCs were isolated from the blood using histopaque (Sigma, St. Louis, Mo.). The PBMC and splenocytes were then stained with PE-labeled anti-CD19, PE-labeled anti-CD335 (NKp46), FITC-labeled anti-CD4 and FITC-labeled anti-CD8 antibodies (BioLegend, San Diego, Calif.). The stained cells were analyzed on a FACScan flow cytometer (BD Bioscience, San Jose, Calif.). All animal studies were performed following Altor's IACUC approved protocols.

The following peptides were used in the studies presented in the above Examples.

| Protein | Amino acids | Sequence (SEQ ID NO) |
|---|---|---|
| p53 | 149-157 | STPPPGTRV (SEQ ID NO: 24) |
| p53 | 264-272 | LLGRNSFEV (SEQ ID NO: 25) |
| OVA | 257-264 | SIINFEKL (SEQ ID NO: 20) |
| VSV | 52-59 | RGYVYQGL (SEQ ID NO: 26) |

The following protein domain linker sequences of the fusion proteins used in the Examples presented.

| Linker | Linker Sequences | Fusion Protein |
|---|---|---|
| Single-chain TCR linker | TCR Vα-DTSGGGGSGGGGSGGGGSGGGGSSS TCR Vβ (linker sequence disclosed as SEQ ID NO: 27) | c264scTCR/hIL-15, c264scTCR/hIL-15RαSu/birA |
|  | TCR Vα-TSGGGGSGGGGSPGGGGSGGGGSSS TCR Vβ (linker sequence disclosed as SEQ ID NO: 28) | c149scTCR/hIL15N72D |
|  | TCR Vα-DTSGGGGSGGGASGGGGSGGGGSSS TCR Vβ (linker sequence disclosed as SEQ ID NO: 29) | OT1scTCR/birA |
|  | TCR Vα-SGGGGSGGGASGGGGSGGGGS TCR Vβ (linker sequence disclosed as SEQ ID NO: 30) | OT1scTCR/hIL-15D8N, OT1scTCR/hIL-15RαSu/birA |
| Mutated human IgG1 hinge | TCR domain-VNEPKSSDKTHTSPPSPTR-hIL-15RαSu (linker sequence disclosed as SEQ ID NO: 31) TCR domain-VNEPKSSDKTHTSPPSPTR-hIL-15 (linker sequence disclosed as SEQ ID NO: 31) | c264scTCR/hIL-15RαSu/birA, OT1scTCR/hIL-15RαSu/birA, OT1TCR□/hIL-15RαSu/birA, 264TCR□/hIL-15RαSu/birA 264TCRα/hIL-15D8N, OT1TCRα/hIL-15, OT1scTCR/hIL-15D8N |
| BirA linker | hIL-15RαSu-SGGGSGGGGSID-birA tag (linker sequence disclosed as SEQ ID NO: 32) | c264scTCR/hIL-15RαSu/birA, OT1TCR□/hIL-15RαSu/birA |
| Single-chain CD8 linker | CD8α-SGGGGSGGGGSGGGGSGGGGS-CD8α (linker sequence disclosed as SEQ ID NO: 33) | scCD8αβ/hIL-15RαSu/birA |

The references listed below as well as all of the references, patents, and GenBank numbers (in the version available as of the priority date of the application) cited in the application are each incorporated by reference as if they were incorporated individually.

1. Kouzarides, T., and Ziff, E. (1988) Nature 336, 646-651
2. Kouzarides, T., and Ziff, E. (1989) Nature 340, 568-571
3. Kouzarides, T., and Ziff, E. (1989) Cancer Cells 1, 71-76
4. Rieker, J. D., and Hu, J. C. (2000) Methods Enzymol 328, 282-296
5. Busch, R., Pashine, A., Garcia, K. C., and Mellins, E. D. (2002) J Immunol Methods 263, 111-121
6. Stern, L. J., and Wiley, D. C. (1992) Cell 68, 465-477
7. Sloan, V. S., Cameron, P., Porter, G., Gammon, M., Amaya, M., Mellins, E., and Zaller, D. M. (1995) Nature 375, 802-806
8. de Kruif, J., and Logtenberg, T. (1996) Journal of Biological Chemistry 271, 7630-7634
9. Kostelny, S., Cole, M., and Tso, J. (1992) J Immunol 148, 1547-1553
10. Holliger, P., and Hudson, P. J. (2005) Nat Biotechnol 23, 1126-1136
11. Hayden-Ledbetter, M. S., Cerveny, C. G., Espling, E., Brady, W. A., Grosmaire, L. S., Tan, P., Bader, R., Slater, S., Nilsson, C. A., Barone, D. S., Simon, A., Bradley, C., Thompson, P. A., Wahl, A. F., and Ledbetter, J. A. (2009) Clinical Cancer Research 15, 2739-2746
12. Kubetzko, S., Balic, E., Waibel, R., Zangemeister-Wittke, U., and Pluckthun, A. (2006) J Biol Chem 281, 35186-35201
13. Cuesta, A. M., Sanchez-Martin, D., Sanz, L., Bonet, J., Compte, M., Kremer, L., Blanco, F. J., Oliva, B., and Alvarez-Vallina, L. (2009) PLoS One 4, e5381
14. Mohler, K., Torrance, D., Smith, C., Goodwin, R., Stremler, K., Fung, V., Madani, H., and Widmer, M. (1993) J Immunol 151, 1548-1561
15. Feldmann, M. (2002) Nat Rev Immunol 2, 364-371
16. Weiner, L. M. (2007) Nat Rev Cancer 7, 701-706
17. Baeuerle, P. A., Kufer, P., and Bargou, R. (2009) Curr Opin Mol Ther 11, 22-30
18. Shen, J., Vil, M. D., Jimenez, X., Iacolina, M., Zhang, H., and Zhu, Z. (2006) J Biol Chem 281, 10706-10714
19. Lu, D., and Zhu, Z. (2009) Methods Mol Biol 525, 377-404, xiv
20. Jackman, J., Chen, Y., Huang, A., Moffat, B., Scheer, J. M., Leong, S. R., Lee, W. P., Zhang, J., Sharma, N., Lu, Y., Iyer, S., Shields, R. L., Chiang, N., Bauer, M. C., Wadley, D., Roose-Girma, M., Vandlen, R., Yansura, D. G., Wu, Y., and Wu, L. C. (2010) J Biol Chem (In Press)
21. Mortier, E., Quemener, A., Vusio, P., Lorenzen, I., Boublik, Y., Grotzinger, J., Plet, A., and Jacques, Y. (2006) J Biol Chem 281, 1612-1619
22. Waldmann, T. A. (2006) Nat Rev Immunol 6, 595-601
23. Bergamaschi, C., Rosati, M., Jalah, R., Valentin, A., Kulkarni, V., Alicea, C., Zhang, G. M., Patel, V., Felber, B. K., and Pavlakis, G. N. (2008) J Biol Chem 283, 4189-4199
24. Theobald, M., Biggs, J., Dittmer, D., Levine, A. J., and Sherman, L. A. (1995) Proc Natl Acad Sci USA 92, 11993-11997.
25. Zhu, X., Marcus, W. D., Xu, W., Lee, H. I., Han, K., Egan, J. O., Yovandich, J. L., Rhode, P. R., and Wong, H. C. (2009) J Immunol 183, 3598-3607
26. Deer, J. R., and Allison, D. S. (2004) Biotechnol Prog 20, 880-889
27. Zhao, Y., Bennett, A. D., Zheng, Z., Wang, Q. J., Robbins, P. F., Yu, L. Y. L., Li, Y., Molloy, P. E., Dunn, S. M., Jakobsen, B. K., Rosenberg, S. A., and Morgan, R. A. (2007) J Immunol 179, 5845-5854
28. Belmont, H. J., Price-Schiavi, S., Liu, B., Card, K. F., Lee, H. I., Han, K. P., Wen, J., Tang, S., Zhu, X., Merrill, J., Chavillaz, P. A., Wong, J. L., Rhode, P. R., and Wong, H. C. (2006) Clin Immunol 121, 29-39
29. Yang, S., Rosenberg, S. A., and Morgan, R. A. (2008) J Immunother 31, 830-839
30. Card, K. F., Price-Schiavi, S. A., Liu, B., Thomson, E., Nieves, E., Belmont, H., Builes, J., Jiao, J. A., Hernandez, J., Weidanz, J., Sherman, L., Francis, J. L., Amirkhosravi, A., and Wong, H. C. (2004) Cancer Immunol Immunother 53, 345-357
31. Garboczi, D. N., Hung, D. T., and Wiley, D. C. (1992) PNAS 89, 3429-3433
32. Zhu, X., Belmont, H. J., Price-Schiavi, S., Liu, B., Lee, H. I., Fernandez, M., Wong, R. L., Builes, J., Rhode, P. R., and Wong, H. C. (2006) J Immunol 176, 3223-3232
33. Chirifu, M., Hayashi, C., Nakamura, T., Toma, S., Shuto, T., Kai, H., Yamagata, Y., Davis, S. J., and Ikemizu, S. (2007) Nat Immunol 8, 1001-1007
34. Hogquist, K. A., Jameson, S. C., Heath, W. R., Howard, J. L., Bevan, M. J., and Carbone, F. R. (1994) Cell 76, 17-27
35. Daniels, M. A., and Jameson, S. C. (2000) J Exp Med 191, 335-346.
36. Nugent, C. T., Renteria, R. O., Kuus-Reichel, K., and Kumar, A. (2005) Immunol Lett 98, 208-215
37. Schott, E., and Ploegh, H. L. (2002) Eur J Immunol 32, 3425-3434
38. Neveu, B., Echasserieau, K., Hill, T., Kuus-Reichel, K., Houssaint, E., Bonneville, M., and Saulquin, X. (2006) Int. Immunol. 18, 1139-1145
39. Kern, P., Hussey, R. E., Spoerl, R., Reinherz, E. L., and Chang, H.-C. (1999) Journal of Biological Chemistry 274, 27237-27243
40. Arcaro, A., Gregoire, C., Bakker, T. R., Baldi, L., Jordan, M., Goffin, L., Boucheron, N., Wurm, F., van der Merwe, P. A., Malissen, B., and Luescher, I. F. (2001) J Exp Med 194, 1485-1495
41. Wang, R., Natarajan, K., and Margulies, D. H. (2009) J Immunol 183, 2554-2564
42. Garboczi, D. N., Ghosh, P., Utz, U., Fan, Q. R., Biddison, W. E., and Wiley, D. C. (1996) Nature 384, 134-141
43. Lin, A., Devaux, B., Green, A., Sagerstrom, C., Elliott, J., and Davis, M. (1990) Science 249, 677-679
44. Traunecker, A., Dolder, B., Oliveri, F., and Kari alainen, K. (1989) Immunol Today 10, 29-32
45. Laugel, B., van den Berg, H. A., Gostick, E., Cole, D. K., Wooldridge, L., Boulter, J., Milicic, A., Price, D. A., and Sewell, A. K. (2007) J Biol Chem 282, 23799-23810
46. Wooldridge, L., van den Berg, H. A., Glick, M., Gostick, E., Laugel, B., Hutchinson, S. L., Milicic, A., Brenchley, J. M., Douek, D. C., Price, D. A., and Sewell, A. K. (2005) J Biol Chem 280, 27491-27501
47. Gakamsky, D. M., Luescher, I. F., Pramanik, A., Kopito, R. B., Lemonnier, F., Vogel, H., Rigler, R., and Pecht, I. (2005) Biophys J 89, 2121-2133
48. Cole, D. K., Dunn, S. M., Sami, M., Boulter, J. M., Jakobsen, B. K., and Sewell, A. K. (2008) Mol Immunol 45, 2700-2709
49. Alam, S. M., Davies, G. M., Lin, C. M., Zal, T., Nasholds, W., Jameson, S. C., Hogquist, K. A., Gascoigne, N. R., and Travers, P. J. (1999) Immunity 10, 227-237

50. Cheever, M. A. (2008) Immunol Rev 222, 357-368
51. Ferrari-Lacraz, S., Zanelli, E., Neuberg, M., Donskoy, E., Kim, Y. S., Zheng, X. X., Hancock, W. W., Maslinski, W., Li, X. C., Strom, T. B., and Moll, T. (2004) J Immunol 173, 5818-5826
52. Zheng, X. X., Gao, W., Donskoy, E., Neuberg, M., Ruediger, M., Strom, T. B., and Moll, T. (2006) in Transplantation Vol. 81, pp. 109-116
53. Ferrari-Lacraz, S., Zheng, X. X., Fueyo, A. S., Maslinski, W., Moll, T., and Strom, T. B. (2006) Transplantation 82, 1510-1517

What is claimed is:

1. A method for treating a neoplasia or human immunodeficiency virus (HIV) in a subject in need thereof comprising administering to the subject an effective amount of a pharmaceutical composition comprising an isolated soluble fusion protein complex comprising at least two soluble fusion proteins, wherein
the first fusion protein comprises (a) a first antibody that comprises an anti-CD20 single chain antibody covalently linked to (b) interleukin-15 (IL-15) polypeptide; and
the second fusion protein comprises (c) a second antibody covalently linked to (d) soluble interleukin-15 receptor alpha (IL-15Rα) polypeptide,
wherein one or both of the first and second fusion proteins further comprise an immunoglobulin Fc domain or a functional fragment thereof,
wherein the IL-15 domain of the first fusion protein binds to the soluble IL-15Rα domain of the second fusion protein to form a soluble fusion protein complex,
thereby treating neoplasia or human immunodeficiency virus (HIV) in a subject.

2. The method of claim 1, wherein the second antibody is directed against a cell surface receptor or ligand.

3. The method of claim 1, wherein the second antibody is directed against a CD antigen, cytokine or chemokine receptor or ligand, growth factor receptor or ligand, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

4. The method of claim 1, wherein the second antibody is directed against CD3, CD4, CD19, CD20, CD21, CD22, CD23, CD25, CD30, CD33, CD38, CD40, CD44, CD51, CD52, CD70, CD74, CD80, CD152, CD147, CD221, EGFR, HER-2/neu, HER-1, HER-3, HER-4, CEA, OX40 ligand, cMet, tissue factor, Nectin-4, PSA, PSMA, EGFL7, FGFR, IL-6 receptor, IGF-1 receptor, GD2, CA-125, EpCam, death receptor 5, MUC1, VEGFR1, VEGFR2, PDGFR, Trail R2, folate receptor, angiopoietin-2, alphavbeta3 integrin receptor, or HLA-DR antigens.

5. The method of claim 1, wherein the second antibody is directed against HIV, HCV, HBV, CMV, HTLV, HPV, EBV, or RSV or HIV envelope spike, gp120 or gp41.

6. The method of claim 1, wherein the IL-15 polypeptide comprises an IL-15 polypeptide comprising an N72D mutation (IL-15N72D).

7. The method of claim 1, wherein
the first fusion protein comprises (a) a first anti-CD20 single chain antibody covalently linked to (b) an IL-15 polypeptide comprising an N72D mutation (IL-15N72D), and wherein
the second fusion protein comprises (c) a second anti-CD20 single chain antibody covalently linked to (d) soluble IL-15 receptor alpha (IL-15Rα) polypeptide.

8. The method of claim 7, wherein the second fusion protein comprises (c) an anti-CD20 single chain antibody covalently linked to (d) a soluble Il-15receptor alpha sushi-binding domain (IL-15RαSu) fused to an immunoglobulin Fc domain, and wherein the IL-15N72D domain of the first fusion protein binds to the soluble IL-15RαSu domain of the second fusion protein to form a soluble fusion protein complex.

9. The method of claim 8, wherein the first anti-CD20 single-chain antibody and the second anti-CD20 single-chain antibody each comprise an immunoglobulin light chain variable domain covalently linked to an immunoglobulin heavy chain variable domain by a polypeptide linker sequence.

10. The method of claim 7, wherein the first fusion protein is encoded by the nucleic acid sequence set forth in SEQ ID NO: 43.

11. The method of claim 7, wherein the first fusion protein comprises the amino acid sequence set forth in SEQ ID NO: 44.

12. The method of claim 7, wherein the second fusion protein is encoded by the nucleic acid sequence set forth in SEQ ID NO: 45.

13. The method of claim 7, wherein the second fusion protein comprises the amino acid sequence set forth in SEQ ID NO: 46.

14. The method of claim 7 wherein the subject is suffering from neoplasia.

15. The method of claim 7 wherein the subject is suffering from human immunodeficiency virus (HIV) in a subject.

16. The method of claim 1 wherein the subject is suffering from neoplasia.

17. The method of claim 1 wherein the subject is suffering from human immunodeficiency virus (HIV) in a subject.

18. The method of claim 1 wherein the second fusion protein comprises (c) a second anti-CD20 single chain antibody covalently linked to (d) soluble interleukin-15 receptor alpha (IL-15Rα) polypeptide.

* * * * *

SEQUENCE LISTING

```
<160> NUMBER OF SEQ ID NOS: 50

<210> SEQ ID NO 1
<211> LENGTH: 6
<212> TYPE: PRT
<213> ORGANISM: Homo sapiens

<400> SEQUENCE: 1

Pro Glu Leu Leu Gly Gly
1               5

<210> SEQ ID NO 2
<211> LENGTH: 6
<212> TYPE: PRT
<213> ORGANISM: Homo sapiens

<400> SEQUENCE: 2

Pro Glu Ala Ala Gly Gly
1               5

<210> SEQ ID NO 3
<211> LENGTH: 5
<212> TYPE: PRT
<213> ORGANISM: Homo sapiens

<400> SEQUENCE: 3

Lys Cys Lys Ser Leu
1               5

<210> SEQ ID NO 4
<211> LENGTH: 5
<212> TYPE: PRT
<213> ORGANISM: Homo sapiens

<400> SEQUENCE: 4

Lys Cys Ala Ser Leu
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ser Gly Gly Gly Gly Ser Gly Gly Gly
1               5                   10

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
```

```
tgttgggaat tcatcacgtg ccctc                                          25

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggtgtgaat tctctaatgc atttgagact gg                                  32

<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtacgactta attaactcga gccaccatgg agacagacac actcctgtta tgg           53

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cttcccgtta acccaccagc tcagctccac gtg                                 33

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctggtgggtt aacgggaagg aggtgcacag tggggtc                             37

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagggcacgt gatgtctgct ctaccccagg cctc                                34

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtagagcaga catcacgtgc cctccccca tg                                   32
```

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccttggtgct agctctaata catttgagac tgggggttgt cc                    42

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccagtctcaa atgtattaga gctagcacca agggcccatc ggtc                  44

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtaatattct agacgcgttc attatttacc aggagacagg gagaggctct tc         52

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gacttcaagc ttaattaagc caccatggac agacttactt cttc                  44

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cacccagttg tctgctctac cccaggcctc                                  30

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctggggtaga gcagacaact gggtgaatgt aataagtgat ttg                   43

<210> SEQ ID NO 19
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cctcatgcat tcgaatccgg atcattaaga agtgttgatg aacatttgg            49

<210> SEQ ID NO 20
<211> LENGTH: 8
<212> TYPE: PRT
<213> ORGANISM: Gallus gallus

<400> SEQUENCE: 20

Ser Ile Ile Asn Phe Glu Lys Leu
1               5

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Ser Gly Gly Gly Gly Ser Gly Gly Gly Gly Ser Gly
1               5                   10                  15

Gly Gly Gly Ser
            20

<210> SEQ ID NO 22
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtgagttttg tcacaagatt tcggctctct aatgcatttg agactggggg ttg        53

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gagccgaaat cttgtgacaa aactcac                                     27

<210> SEQ ID NO 24
<211> LENGTH: 9
<212> TYPE: PRT
<213> ORGANISM: Homo sapiens

<400> SEQUENCE: 24

Ser Thr Pro Pro Pro Gly Thr Arg Val
1               5

```
<210> SEQ ID NO 25
<211> LENGTH: 9
<212> TYPE: PRT
<213> ORGANISM: Homo sapiens

<400> SEQUENCE: 25

Leu Leu Gly Arg Asn Ser Phe Glu Val
1               5

<210> SEQ ID NO 26
<211> LENGTH: 8
<212> TYPE: PRT
<213> ORGANISM: Vesicular stomatitis virus

<400> SEQUENCE: 26

Arg Gly Tyr Val Tyr Gln Gly Leu
1               5

<210> SEQ ID NO 27
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Thr Ser Gly Gly Gly Gly Ser Gly Gly Gly Gly Ser Gly Gly Gly
1               5                   10                  15

Gly Ser Gly Gly Gly Gly Ser Ser Ser
            20                  25

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Ser Gly Gly Gly Gly Ser Gly Gly Gly Gly Ser Pro Gly Gly Gly
1               5                   10                  15

Gly Ser Gly Gly Gly Gly Ser Ser Ser
            20                  25

<210> SEQ ID NO 29
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Thr Ser Gly Gly Gly Gly Ser Gly Gly Gly Ala Ser Gly Gly Gly
1               5                   10                  15

Gly Ser Gly Gly Gly Gly Ser Ser Ser
            20                  25

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 30

Ser Gly Gly Gly Gly Ser Gly Gly Gly Ala Ser Gly Gly Gly Ser
1               5                   10                  15

Gly Gly Gly Gly Ser
            20

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Asn Glu Pro Lys Ser Ser Asp Lys Thr His Thr Ser Pro Pro Ser
1               5                   10                  15

Pro Thr Arg

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Gly Gly Gly Ser Gly Gly Gly Ser Ile Asp
1               5                   10

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Gly Gly Gly Gly Ser Gly Gly Gly Ser Gly Gly Gly Gly Ser
1               5                   10                  15

Gly Gly Gly Gly Ser
            20

<210> SEQ ID NO 34
<211> LENGTH: 2397
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggacagac ttacttcttc attcctgctc ctgattgtcc ctgcgtacgt cttgtcccag      60
tcagtgacgc agcccgatgc tcgcgtcact gtctctgaag agcctctctc gcagctgaga     120
tgcaagtatt cctactctgg acacccttat ctgttctggt atgtccagta cccgcggcag     180
gggctgcagc tgctcctcaa gtactattca ggagacccag tggttcaagg agtgaatggc     240
ttcgaggctg agttcagcaa gagtaactct tccttccacc tgcggaaagc ctctgtgcac     300
tggagcgact ctgctgtgta cttctgtgtt ttgagcgagg atagcaacta tcagttgatc     360

```
tggggctctg ggaccaagct aattataaag ccagacacta gtggtggcgg tggcagcggc    420
ggtggtggtt ccggtggcgg cggttctggc ggtggcggtt cctcgagcaa ttcaaaagtc    480
attcagactc caagatatct ggtgaaaggg caaggacaaa aagcaaagat gaggtgtatc    540
cctgaaaagg gacatccagt tgtattctgg tatcaacaaa ataagaacaa tgagtttaaa    600
tttttgatta actttcagaa tcaagaagtt cttcagcaaa tagacatgac tgaaaaacga    660
ttctctgctg agtgtccttc aaactcacct tgcagcctag aaattcagtc tctgaggca    720 ggagactcag cactgtacct ctgtgccagc agtctgtcag ggggcggcac agaagttttc    780
tttggtaaag gaaccaggct cacagttgta gaggacctga caaggtgtt cccacccgag    840 gtcgctgtgt ttgagccatc agaagcagag atctcccaca cccaaaaggc cacactggtg    900
tgcctggcca caggcttctt ccctgaccac gtggagctga gctggtgggt gaatgggaag    960
gaggtgcaca gtgggtcag cacggacccg cagcccctca aggagcagcc cgccctcaat   1020
gactccagat actgcctgag cagccgcctg agggtctcgg ccaccttctg gcagaacccc   1080
cgcaaccact tccgctgtca agtccagttc tacgggctct cggagaatga cgagtggacc   1140
caggataggg ccaaacccgt cacccagatc gtcagcgccg aggcctgggg tagagcagac   1200
gaattcatca cgtgccctcc ccccatgtcc gtggaacacg cagacatctg ggtcaagagc   1260
tacagcttgt actccaggga gcggtacatt tgtaactctg gtttcaagcg taaagccggc   1320
acgtccagcc tgacggagtg cgtgttgaac aaggccacga atgtcgccca ctggacaacc   1380
cccagtctca aatgcattag agaattcgcc tccaccaagg gcccatcggt cttcccctg   1440 gcaccctcct ccaagagcac ctctgggggc acagcggccc tgggctgcct ggtcaaggac   1500
tacttccccg aaccggtgac ggtgtcgtgg aactcaggcg ccctgaccag cggcgtgcac   1560
accttcccgg ctgtcctaca gtcctcagga ctctactccc tcagcagcgt ggtgaccgtg   1620
ccctccagca gcttgggcac ccagacctac atctgcaacg tgaatcacaa gcccagcaac   1680
accaaggtgg acaagaaagt tgagcccaaa tcttgtgaca aaactcacac atgcccaccg   1740
tgcccagcac ctgaactcct ggggggaccg tcagtcttcc tcttcccccc aaaacccaag   1800
gacaccctca tgatctcccg gacccctgag gtcacatgcg tggtggtgga cgtgagccac   1860
gaagaccctg aggtcaagtt caactggtac gtggacggcg tggaggtgca taatgccaag   1920
acaaagccgc gggaggagca gtacaacagc acgtaccgtg tggtcagcgt cctcaccgtc   1980
ctgcaccagg actggctgaa tggcaaggag tacaagtgca aggtctccaa caaagccctc   2040
ccagccccca tcgagaaaac catctccaaa gccaaaggc agccccgaga accacaggtg   2100
tacaccctgc ccccatcccg ggatgagctg accaagaacc aggtcagcct gacctgcctg   2160
gtcaaaggct tctatcccag cgacatcgcc gtggagtggg agagcaatgg gcagccggag   2220
aacaactaca agaccacgcc tcccgtgctg gactccgacg gctccttctt cctctacagc   2280
aagctcaccg tggacaagag caggtggcag caggggaacg tcttctcatg ctccgtgatg   2340
catgaggctc tgcacaacca ctacacgcag aagagcctct ccctgtctcc gggtaaa      2397
```

<210> SEQ ID NO 35
<211> LENGTH: 799
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

-continued

```
Met Asp Arg Leu Thr Ser Ser Phe Leu Leu Ile Val Pro Ala Tyr
 1               5                  10                  15

Val Leu Ser Gln Ser Val Thr Gln Pro Asp Ala Arg Val Thr Val Ser
             20                  25                  30

Glu Gly Ala Ser Leu Gln Leu Arg Cys Lys Tyr Ser Tyr Ser Gly Thr
             35                  40                  45

Pro Tyr Leu Phe Trp Tyr Val Gln Tyr Pro Arg Gln Gly Leu Gln Leu
 50                  55                  60

Leu Leu Lys Tyr Tyr Ser Gly Asp Pro Val Val Gln Gly Val Asn Gly
65                   70                  75                  80

Phe Glu Ala Glu Phe Ser Lys Ser Asn Ser Ser Phe His Leu Arg Lys
                 85                  90                  95

Ala Ser Val His Trp Ser Asp Ser Ala Val Tyr Phe Cys Val Leu Ser
                100                 105                 110

Glu Asp Ser Asn Tyr Gln Leu Ile Trp Gly Ser Gly Thr Lys Leu Ile
                115                 120                 125

Ile Lys Pro Asp Thr Ser Gly Gly Gly Ser Gly Gly Gly Gly Ser
130                 135                 140

Gly Gly Gly Gly Ser Gly Gly Gly Ser Ser Asn Ser Lys Val
145                 150                 155                 160

Ile Gln Thr Pro Arg Tyr Leu Val Lys Gly Gln Gly Gln Lys Ala Lys
                165                 170                 175

Met Arg Cys Ile Pro Glu Lys Gly His Pro Val Val Phe Trp Tyr Gln
                180                 185                 190

Gln Asn Lys Asn Asn Glu Phe Lys Phe Leu Ile Asn Phe Gln Asn Gln
                195                 200                 205

Glu Val Leu Gln Gln Ile Asp Met Thr Glu Lys Arg Phe Ser Ala Glu
                210                 215                 220

Cys Pro Ser Asn Ser Pro Cys Ser Leu Glu Ile Gln Ser Ser Glu Ala
225                 230                 235                 240

Gly Asp Ser Ala Leu Tyr Leu Cys Ala Ser Ser Leu Ser Gly Gly Gly
                245                 250                 255

Thr Glu Val Phe Phe Gly Lys Gly Thr Arg Leu Thr Val Glu Asp
                260                 265                 270

Leu Asn Lys Val Phe Pro Pro Glu Val Ala Val Phe Glu Pro Ser Glu
                275                 280                 285

Ala Glu Ile Ser His Thr Gln Lys Ala Thr Leu Val Cys Leu Ala Thr
                290                 295                 300

Gly Phe Phe Pro Asp His Val Glu Leu Ser Trp Trp Val Asn Gly Lys
305                 310                 315                 320

Glu Val His Ser Gly Val Ser Thr Asp Pro Gln Pro Leu Lys Glu Gln
                325                 330                 335

Pro Ala Leu Asn Asp Ser Arg Tyr Cys Leu Ser Ser Arg Leu Arg Val
                340                 345                 350

Ser Ala Thr Phe Trp Gln Asn Pro Arg Asn His Phe Arg Cys Gln Val
                355                 360                 365

Gln Phe Tyr Gly Leu Ser Glu Asn Asp Glu Trp Thr Gln Asp Arg Ala
                370                 375                 380

Lys Pro Val Thr Gln Ile Val Ser Ala Glu Ala Trp Gly Arg Ala Asp
385                 390                 395                 400

Glu Phe Ile Thr Cys Pro Pro Pro Met Ser Val Glu His Ala Asp Ile
                405                 410                 415
```

Trp Val Lys Ser Tyr Ser Leu Tyr Ser Arg Glu Arg Tyr Ile Cys Asn
            420                 425                 430

Ser Gly Phe Lys Arg Lys Ala Gly Thr Ser Ser Leu Thr Glu Cys Val
        435                 440                 445

Leu Asn Lys Ala Thr Asn Val Ala His Trp Thr Thr Pro Ser Leu Lys
    450                 455                 460

Cys Ile Arg Glu Phe Ala Ser Thr Lys Gly Pro Ser Val Phe Pro Leu
465                 470                 475                 480

Ala Pro Ser Ser Lys Ser Thr Ser Gly Gly Thr Ala Ala Leu Gly Cys
                485                 490                 495

Leu Val Lys Asp Tyr Phe Pro Glu Pro Val Thr Val Ser Trp Asn Ser
            500                 505                 510

Gly Ala Leu Thr Ser Gly Val His Thr Phe Pro Ala Val Leu Gln Ser
        515                 520                 525

Ser Gly Leu Tyr Ser Leu Ser Ser Val Val Thr Val Pro Ser Ser Ser
    530                 535                 540

Leu Gly Thr Gln Thr Tyr Ile Cys Asn Val Asn His Lys Pro Ser Asn
545                 550                 555                 560

Thr Lys Val Asp Lys Lys Val Glu Pro Lys Ser Cys Asp Lys Thr His
                565                 570                 575

Thr Cys Pro Pro Cys Pro Ala Pro Glu Leu Leu Gly Gly Pro Ser Val
            580                 585                 590

Phe Leu Phe Pro Pro Lys Pro Lys Asp Thr Leu Met Ile Ser Arg Thr
        595                 600                 605

Pro Glu Val Thr Cys Val Val Val Asp Val Ser His Glu Asp Pro Glu
    610                 615                 620

Val Lys Phe Asn Trp Tyr Val Asp Gly Val Glu Val His Asn Ala Lys
625                 630                 635                 640

Thr Lys Pro Arg Glu Glu Gln Tyr Asn Ser Thr Tyr Arg Val Val Ser
                645                 650                 655

Val Leu Thr Val Leu His Gln Asp Trp Leu Asn Gly Lys Glu Tyr Lys
            660                 665                 670

Cys Lys Val Ser Asn Lys Ala Leu Pro Ala Pro Ile Glu Lys Thr Ile
        675                 680                 685

Ser Lys Ala Lys Gly Gln Pro Arg Glu Pro Gln Val Tyr Thr Leu Pro
    690                 695                 700

Pro Ser Arg Asp Glu Leu Thr Lys Asn Gln Val Ser Leu Thr Cys Leu
705                 710                 715                 720

Val Lys Gly Phe Tyr Pro Ser Asp Ile Ala Val Glu Trp Glu Ser Asn
                725                 730                 735

Gly Gln Pro Glu Asn Asn Tyr Lys Thr Thr Pro Pro Val Leu Asp Ser
            740                 745                 750

Asp Gly Ser Phe Phe Leu Tyr Ser Lys Leu Thr Val Asp Lys Ser Arg
        755                 760                 765

Trp Gln Gln Gly Asn Val Phe Ser Cys Ser Val Met His Glu Ala Leu
    770                 775                 780

His Asn His Tyr Thr Gln Lys Ser Leu Ser Leu Ser Pro Gly Lys
785                 790                 795

<210> SEQ ID NO 36
<211> LENGTH: 2391
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
atggagacag acacactcct gttatgggta ctgctgctct gggttccagg ttccaccggt      60
cagtcagtga cgcagcccga tgctcgcgtc actgtctctg aaggagcctc tctgcagctg     120
agatgcaagt attcctactc tgggacacct tatctgttct ggtatgtcca gtacccgcgg     180
cagggggctgc agctgctcct caagtactat tcaggagacc cagtggttca aggagtgaat     240
ggcttcgagg ctgagttcag caagagtaac tcttccttcc acctgcggaa agcctctgtg     300
cactggagcg actctgctgt gtacttctgt gttttgagcg aggatagcaa ctatcagttg     360
atctggggct ctgggaccaa gctaattata aagccagaca ctagtggtgg cggtggcagc     420
ggcggtggtg gttccggtgg cggcggttct ggcggtggcg gttcctcgag caattcaaaa     480
gtcattcaga ctccaagata tctggtgaaa gggcaaggac aaaaagcaaa gatgaggtgt     540
atccctgaaa agggacatcc agttgtattc tggtatcaac aaaataagaa caatgagttt     600
aaattttga ttaactttca gaatcaagaa gttcttcagc aaatagacat gactgaaaaa     660
cgattctctg ctgagtgtcc ttcaaactca ccttgcagcc tagaaattca gtcctctgag     720
gcaggagact cagcactgta cctctgtgcc agcagtctgt caggggggcgg cacagaagtt     780
ttctttggta aaggaaccag gctcacagtt gtagaggacc tgaacaaggt gttcccaccc     840
gaggtcgctg tgtttgagcc atcagaagca gagatctccc acacccaaaa ggccacactg     900
gtgtgcctgg ccacaggctt cttccctgac cacgtggagc tgagctggtg ggttaacggg     960
aaggaggtgc acagtggggt cagcacggac ccgcagcccc tcaaggagca gcccgccctc    1020
aatgactcca gatactgcct gagcagccgc ctgagggtct cggccacctt ctggcagaac    1080
ccccgcaacc acttccgctg tcaagtccag ttctacgggc tctcggagaa tgacgagtgg    1140
acccaggata gggccaaacc cgtcacccag atcgtcagcg ccgaggcctg ggtagagca    1200
gacatcacgt gccctccccc catgtccgtg aacacgcag acatctgggt caagagctac    1260
agcttgtact ccagggagcg gtacatttgt aactctggtt tcaagcgtaa agccggcacg    1320
tccagcctga cggagtgcgt gttgaacaag gccacgaatg tcgcccactg gacaaccccc    1380
agtctcaaat gtattagagc tagcaccaag ggcccatcgg tcttcccct ggcaccctcc     1440
tccaagagca cctctggggg cacagcggcc ctgggctgcc tggtcaagga ctacttcccc    1500
gaaccggtga cggtgtcgtg gaactcaggc gccctgacca gcggcgtgca caccttcccg    1560
gctgtcctac agtcctcagg actctactcc ctcagcagcg tggtgaccgt gccctccagc    1620
agcttgggca cccagaccta catctgcaac gtgaatcaca agcccagcaa caccaaggtg    1680
gacaagaaag ttgagcccaa atcttgtgac aaaactcaca catgcccacc gtgcccagca    1740
cctgaactcc tggggggacc gtcagtcttc ctcttccccc caaaacccaa ggacaccctc    1800
atgatctccc ggacccctga ggtcacatgc gtggtggtgg acgtgagcca cgaagaccct    1860
gaggtcaagt tcaactggta cgtggacggc gtggaggtgc ataatgccaa gacaaagccg    1920
cgggaggagc agtacaacag cacgtaccgt gtggtcagcg tcctcaccgt cctgcaccag    1980
gactggctga atggcaagga gtacaagtgc aaggtctcca acaaagccct cccagccccc    2040
atcgagaaaa ccatctccaa agccaagggg cagccccgag aaccacaggt gtacaccctg    2100
cccccatccc gggatgagct gaccaagaac caggtcagcc tgacctgcct ggtcaaaggc    2160
ttctatccca gcgacatcgc cgtggagtgg gagagcaatg ggcagccgga gaacaactac    2220
aagaccacgc ctcccgtgct ggactccgac ggctccttct tcctctacag caagctcacc    2280
```

```
gtggacaaga gcaggtggca gcagggggaac gtcttctcat gctccgtgat gcatgaggct    2340
ctgcacaacc actacacgca gaagagcctc tccctgtctc cgggtaaata a               2391
```

<210> SEQ ID NO 37
<211> LENGTH: 796
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Met Glu Thr Asp Thr Leu Leu Leu Trp Val Leu Leu Leu Trp Val Pro
1               5                   10                  15

Gly Ser Thr Gly Gln Ser Val Thr Gln Pro Asp Ala Arg Val Thr Val
            20                  25                  30

Ser Glu Gly Ala Ser Leu Gln Leu Arg Cys Lys Tyr Ser Tyr Ser Gly
        35                  40                  45

Thr Pro Tyr Leu Phe Trp Tyr Val Gln Tyr Pro Arg Gln Gly Leu Gln
    50                  55                  60

Leu Leu Leu Lys Tyr Tyr Ser Gly Asp Pro Val Val Gln Gly Val Asn
65                  70                  75                  80

Gly Phe Glu Ala Glu Phe Ser Lys Ser Asn Ser Ser Phe His Leu Arg
                85                  90                  95

Lys Ala Ser Val His Trp Ser Asp Ser Ala Val Tyr Phe Cys Val Leu
            100                 105                 110

Ser Glu Asp Ser Asn Tyr Gln Leu Ile Trp Gly Ser Gly Thr Lys Leu
        115                 120                 125

Ile Ile Lys Pro Asp Thr Ser Gly Gly Gly Ser Gly Gly Gly Gly
    130                 135                 140

Ser Gly Gly Gly Gly Ser Gly Gly Gly Gly Ser Ser Asn Ser Lys
145                 150                 155                 160

Val Ile Gln Thr Pro Arg Tyr Leu Val Lys Gly Gln Gly Gln Lys Ala
                165                 170                 175

Lys Met Arg Cys Ile Pro Glu Lys Gly His Pro Val Val Phe Trp Tyr
            180                 185                 190

Gln Gln Asn Lys Asn Asn Glu Phe Lys Phe Leu Ile Asn Phe Gln Asn
        195                 200                 205

Gln Glu Val Leu Gln Gln Ile Asp Met Thr Glu Lys Arg Phe Ser Ala
    210                 215                 220

Glu Cys Pro Ser Asn Ser Pro Cys Ser Leu Glu Ile Gln Ser Ser Glu
225                 230                 235                 240

Ala Gly Asp Ser Ala Leu Tyr Leu Cys Ala Ser Ser Leu Ser Gly Gly
                245                 250                 255

Gly Thr Glu Val Phe Phe Gly Lys Gly Thr Arg Leu Thr Val Val Glu
            260                 265                 270

Asp Leu Asn Lys Val Phe Pro Pro Glu Val Ala Val Phe Glu Pro Ser
        275                 280                 285

Glu Ala Glu Ile Ser His Thr Gln Lys Ala Thr Leu Val Cys Leu Ala
    290                 295                 300

Thr Gly Phe Phe Pro Asp His Val Glu Leu Ser Trp Trp Val Asn Gly
305                 310                 315                 320

Lys Glu Val His Ser Gly Val Ser Thr Asp Pro Gln Pro Leu Lys Glu
                325                 330                 335
```

-continued

```
Gln Pro Ala Leu Asn Asp Ser Arg Tyr Cys Leu Ser Ser Arg Leu Arg
                340                 345                 350

Val Ser Ala Thr Phe Trp Gln Asn Pro Arg Asn His Phe Arg Cys Gln
            355                 360                 365

Val Gln Phe Tyr Gly Leu Ser Glu Asn Asp Glu Trp Thr Gln Asp Arg
        370                 375                 380

Ala Lys Pro Val Thr Gln Ile Val Ser Ala Glu Ala Trp Gly Arg Ala
385                 390                 395                 400

Asp Ile Thr Cys Pro Pro Met Ser Glu His Ala Asp Ile Trp
                405                 410                 415

Val Lys Ser Tyr Ser Leu Tyr Ser Arg Glu Arg Tyr Ile Cys Asn Ser
                420                 425                 430

Gly Phe Lys Arg Lys Ala Gly Thr Ser Ser Leu Thr Glu Cys Val Leu
            435                 440                 445

Asn Lys Ala Thr Asn Val Ala His Trp Thr Thr Pro Ser Leu Lys Cys
        450                 455                 460

Ile Arg Ala Ser Thr Lys Gly Pro Ser Val Phe Pro Leu Ala Pro Ser
465                 470                 475                 480

Ser Lys Ser Thr Ser Gly Gly Thr Ala Ala Leu Gly Cys Leu Val Lys
                485                 490                 495

Asp Tyr Phe Pro Glu Pro Val Thr Val Ser Trp Asn Ser Gly Ala Leu
            500                 505                 510

Thr Ser Gly Val His Thr Phe Pro Ala Val Leu Gln Ser Ser Gly Leu
        515                 520                 525

Tyr Ser Leu Ser Ser Val Val Thr Val Pro Ser Ser Ser Leu Gly Thr
530                 535                 540

Gln Thr Tyr Ile Cys Asn Val Asn His Lys Pro Ser Asn Thr Lys Val
545                 550                 555                 560

Asp Lys Lys Val Glu Pro Lys Ser Cys Asp Lys Thr His Thr Cys Pro
                565                 570                 575

Pro Cys Pro Ala Pro Glu Leu Leu Gly Gly Pro Ser Val Phe Leu Phe
            580                 585                 590

Pro Pro Lys Pro Lys Asp Thr Leu Met Ile Ser Arg Thr Pro Glu Val
        595                 600                 605

Thr Cys Val Val Val Asp Val Ser His Glu Asp Pro Glu Val Lys Phe
    610                 615                 620

Asn Trp Tyr Val Asp Gly Val Glu Val His Asn Ala Lys Thr Lys Pro
625                 630                 635                 640

Arg Glu Glu Gln Tyr Asn Ser Thr Tyr Arg Val Val Ser Val Leu Thr
                645                 650                 655

Val Leu His Gln Asp Trp Leu Asn Gly Lys Glu Tyr Lys Cys Lys Val
            660                 665                 670

Ser Asn Lys Ala Leu Pro Ala Pro Ile Glu Lys Thr Ile Ser Lys Ala
        675                 680                 685

Lys Gly Gln Pro Arg Glu Pro Gln Val Tyr Thr Leu Pro Pro Ser Arg
    690                 695                 700

Asp Glu Leu Thr Lys Asn Gln Val Ser Leu Thr Cys Leu Val Lys Gly
705                 710                 715                 720

Phe Tyr Pro Ser Asp Ile Ala Val Glu Trp Glu Ser Asn Gly Gln Pro
                725                 730                 735

Glu Asn Asn Tyr Lys Thr Thr Pro Pro Val Leu Asp Ser Asp Gly Ser
            740                 745                 750

Phe Phe Leu Tyr Ser Lys Leu Thr Val Asp Lys Ser Arg Trp Gln Gln
```

755                 760                 765
Gly Asn Val Phe Ser Cys Ser Val Met His Glu Ala Leu His Asn His
        770                 775                 780

Tyr Thr Gln Lys Ser Leu Ser Leu Ser Pro Gly Lys
785                 790                 795

<210> SEQ ID NO 38
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

| | | | | | |
|---|---|---|---|---|---|
| atggacagac | ttacttcttc | attcctgctc | ctgattgtcc | ctgcgtacgt | cttggcccag | 60 |
| aaggtaacac | agactcagac | ttcaatttct | gtgatggaga | gacaacggt | gacaatggac | 120 |
| tgtgtgtatg | aaacccggga | cagttcttac | ttcttattct | ggtacaagca | aacagcaagt | 180 |
| ggggaaatag | ttttccttat | tcgtcaggac | tcttacaaaa | aggaaaatgc | aacagaaggt | 240 |
| cattattctc | tgaactttca | gaagccaaaa | agttccatcg | gactcatcat | cactgccaca | 300 |
| cagattgagg | actcagcagt | atatttctgt | gctatgagag | acacaaatgc | ttacaaagtc | 360 |
| atctttggaa | aagggacaca | tcttcatgtt | ctgcctacta | gtggtggcgg | tggcagcggc | 420 |
| ggtggtggtt | cccctggtgg | cggcggttct | ggcggtggcg | gttcctcgag | cgaggctgca | 480 |
| gtcacccaaa | gtccaagaag | caaggtggca | gtaacaggag | aaaggtgac | attgagctgt | 540 |
| caccagacta | ataaccatga | ctatatgtac | tggtatcggc | aggacacggg | gcatgggctg | 600 |
| aggctgatcc | attactcata | tgtcgctgac | agcacggaga | aaggagatat | ccctgatggg | 660 |
| tacaaggcct | ccagaccaag | ccaagagaat | ttctctctca | ttctggagtt | ggcttccctt | 720 |
| tctcagacag | ctgtatattt | ctgtgccagc | agccccact | cctatgaaca | gtacttcggt | 780 |
| cccggcacca | ggctcacggt | tttagaggac | ctgaacaagg | tgttcccacc | cgaggtcgct | 840 |
| gtgtttgagc | catcagaagc | agagatctcc | cacacccaaa | aggccacact | ggtgtgcctg | 900 |
| gccacaggct | tcttccctga | ccacgtgag | ctgagctggt | gggttaacgg | aaggaggtg | 960 |
| cacagtgggg | tcagcacgga | cccgcagccc | ctcaaggagc | agcccgccct | caatgactcc | 1020 |
| agatactgcc | tgagcagccg | cctgagggtc | tcggccacct | tctggcagaa | ccccgcaac | 1080 |
| cacttccgct | gtcaagtcca | gttctacggg | ctctcggaga | tgacgagtg | acccaggat | 1140 |
| agggccaaac | ctgtcaccca | gatcgtcagc | gccgaggcct | ggggtagagc | agacaactgg | 1200 |
| gtgaatgtaa | taagtgattt | gaaaaaaatt | gaagatctta | ttcaatctat | gcatattgat | 1260 |
| gctactttat | atacggaaag | tgatgttcac | cccagttgca | aagtaacagc | aatgaagtgc | 1320 |
| tttctcttgg | agttacaagt | tatttcactt | gagtccggag | atgcaagtat | tcatgataca | 1380 |
| gtagaaaatc | tgatcatcct | agcaaacgac | agtttgtctt | ctaatgggaa | tgtaacagaa | 1440 |
| tctggatgca | aagaatgtga | ggaactggag | gaaaaaaata | ttaaagaatt | tttgcagagt | 1500 |
| tttgtacata | ttgtccaaat | gttcatcaac | acttcttaa | | | 1539 |

<210> SEQ ID NO 39
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Asp Arg Leu Thr Ser Ser Phe Leu Leu Ile Val Pro Ala Tyr
1               5                   10                  15

Val Leu Ala Gln Lys Val Thr Gln Thr Gln Thr Ser Ile Ser Val Met
            20                  25                  30

Glu Lys Thr Thr Val Thr Met Asp Cys Val Tyr Glu Thr Arg Asp Ser
        35                  40                  45

Ser Tyr Phe Leu Phe Trp Tyr Lys Gln Thr Ala Ser Gly Glu Ile Val
    50                  55                  60

Phe Leu Ile Arg Gln Asp Ser Tyr Lys Glu Asn Ala Thr Glu Gly
65              70                  75                  80

His Tyr Ser Leu Asn Phe Gln Lys Pro Lys Ser Ser Ile Gly Leu Ile
                85                  90                  95

Ile Thr Ala Thr Gln Ile Glu Asp Ser Ala Val Tyr Phe Cys Ala Met
            100                 105                 110

Arg Asp Thr Asn Ala Tyr Lys Val Ile Phe Gly Lys Gly Thr His Leu
        115                 120                 125

His Val Leu Pro Thr Ser Gly Gly Gly Ser Gly Gly Gly Ser
    130                 135                 140

Pro Gly Gly Gly Ser Gly Gly Gly Ser Ser Glu Ala Ala
145                 150                 155                 160

Val Thr Gln Ser Pro Arg Ser Lys Val Ala Val Thr Gly Gly Lys Val
                165                 170                 175

Thr Leu Ser Cys His Gln Thr Asn Asn His Asp Tyr Met Tyr Trp Tyr
            180                 185                 190

Arg Gln Asp Thr Gly His Gly Leu Arg Leu Ile His Tyr Ser Tyr Val
        195                 200                 205

Ala Asp Ser Thr Glu Lys Gly Asp Ile Pro Asp Gly Tyr Lys Ala Ser
210                 215                 220

Arg Pro Ser Gln Glu Asn Phe Ser Leu Ile Leu Glu Leu Ala Ser Leu
225                 230                 235                 240

Ser Gln Thr Ala Val Tyr Phe Cys Ala Ser Ser Pro His Ser Tyr Glu
                245                 250                 255

Gln Tyr Phe Gly Pro Gly Thr Arg Leu Thr Val Leu Glu Asp Leu Asn
            260                 265                 270

Lys Val Phe Pro Pro Glu Val Ala Val Phe Glu Pro Ser Glu Ala Glu
        275                 280                 285

Ile Ser His Thr Gln Lys Ala Thr Leu Val Cys Leu Ala Thr Gly Phe
    290                 295                 300

Phe Pro Asp His Val Glu Leu Ser Trp Trp Val Asn Gly Lys Glu Val
305                 310                 315                 320

His Ser Gly Val Ser Thr Asp Pro Gln Pro Leu Lys Glu Gln Pro Ala
                325                 330                 335

Leu Asn Asp Ser Arg Tyr Cys Leu Ser Ser Arg Leu Arg Val Ser Ala
            340                 345                 350

Thr Phe Trp Gln Asn Pro Arg Asn His Phe Arg Cys Gln Val Gln Phe
        355                 360                 365

Tyr Gly Leu Ser Glu Asn Asp Glu Trp Thr Gln Asp Arg Ala Lys Pro
    370                 375                 380

Val Thr Gln Ile Val Ser Ala Glu Ala Trp Gly Arg Ala Asp Asn Trp
385                 390                 395                 400

Val Asn Val Ile Ser Asp Leu Lys Lys Ile Glu Asp Leu Ile Gln Ser

```
                    405                 410                 415
Met His Ile Asp Ala Thr Leu Tyr Thr Glu Ser Asp Val His Pro Ser
            420                 425                 430

Cys Lys Val Thr Ala Met Lys Cys Phe Leu Leu Glu Leu Gln Val Ile
            435                 440                 445

Ser Leu Glu Ser Gly Asp Ala Ser Ile His Asp Thr Val Glu Asn Leu
            450                 455                 460

Ile Ile Leu Ala Asn Asp Ser Leu Ser Ser Asn Gly Asn Val Thr Glu
465                 470                 475                 480

Ser Gly Cys Lys Glu Cys Glu Glu Leu Glu Glu Lys Asn Ile Lys Glu
                485                 490                 495

Phe Leu Gln Ser Phe Val His Ile Val Gln Met Phe Ile Asn Thr Ser
            500                 505                 510

<210> SEQ ID NO 40
<211> LENGTH: 232
<212> TYPE: PRT
<213> ORGANISM: Homo sapiens

<400> SEQUENCE: 40

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 41
<211> LENGTH: 2097
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 41

```
atggagacag acacactcct gttatgggta ctgctgctct gggttccagg ttccaccggt      60
cagtcagtga cgcagcccga tgctcgcgtc actgtctctg aaggagcctc tctgcagctg     120
agatgcaagt attcctactc tgggacacct tatctgttct ggtatgtcca gtacccgcgg     180
caggggctgc agctgctcct caagtactat tcaggagacc cagtggttca aggagtgaat     240
ggcttcgagg ctgagttcag caagagtaac tcttccttcc acctgcggaa agcctctgtg     300
cactggagcg actctgctgt gtacttctgt gttttgagcg aggatagcaa ctatcagttg     360
atctggggct ctgggaccaa gctaattata aagccagaca ctagtggtgg cggtggcagc     420
ggcggtggtg gttccggtgg cggcggttct ggcggtggcg gttcctcgag caattcaaaa     480
gtcattcaga ctccaagata tctggtgaaa gggcaaggac aaaaagcaaa gatgaggtgt     540
atccctgaaa agggacatcc agttgtattc tggtatcaac aaaataagaa caatgagttt     600
aaattttga ttaactttca gaatcaagaa gttcttcagc aaatagacat gactgaaaaa     660
cgattctctg ctgagtgtcc ttcaaactca ccttgcagcc tagaaattca gtcctctgag     720
gcaggagact cagcactgta cctctgtgcc agcagtctgt caggggcgg cacagaagtc     780
ttctttggta aaggaaccag gctcacagtt gtagaggacc tgaacaaggt gttcccaccc     840
gaggtcgctg tgtttgagcc atcagaagca gagatctccc acacccaaaa ggccacactg     900
gtgtgcctgg ccacaggctt cttccctgac acgtggagc tgagctggtg ggttaacggg     960
aaggaggtgc acagtggggt cagcacggac ccgcagcccc tcaaggagca gcccgccctc    1020
aatgactcca gatactgcct gagcagccgc ctgagggtct cggccacctt ctggcagaac    1080
ccccgcaacc acttccgctg tcaagtccag ttctacgggc tctcggagaa tgacgagtgg    1140
acccaggata gggccaaacc cgtcacccag atcgtcagcg ccgaggcctg ggtagagca    1200
gacatcacgt gccctccccc catgtccgtg aacacgcag acatctgggt caagagctac    1260
agcttgtact ccagggagcg gtacatttgt aactctggtt tcaagcgtaa agccggcacg    1320
tccagcctga cggagtgcgt gttgaacaag gccacgaatg tcgcccactg gacaaccccc    1380
agtctcaaat gcattagaga gccgaaatct tgtgacaaaa ctcacacatg cccaccgtgc    1440
ccagcacctg aactcctggg gggaccgtca gtcttcctct ccccccaaa acccaaggac    1500
accctcatga tctcccggac ccctgaggtc acatgcgtgg tggtggacgt gagccacgaa    1560
gaccctgagg tcaagttcaa ctggtacgtg gacggcgtgg aggtgcataa tgccaagaca    1620
aagccgcggg aggagcagta caacagcacg taccgtgtgg tcagcgtcct caccgtcctg    1680
caccaggact ggctgaatgg caaggagtac aagtgcaagg tctccaacaa agccctccca    1740
gcccccatcg agaaaaccat ctccaaagcc aaagggcagc cccgagaacc acaggtgtac    1800
accctgcccc catcccggga tgagctgacc aagaaccagg tcagcctgac ctgcctggtc    1860
aaaggcttct atcccagcga catcgccgtg gagtgggaga gcaatgggca gccggagaac    1920
aactacaaga ccacgcctcc cgtgctggac tccgacggct ccttcttcct ctacagcaag    1980
ctcaccgtgg acaagagcag gtggcagcag gggaacgtct tctcatgctc cgtgatgcat    2040
gaggctctgc acaaccacta cacgcagaag agcctctccc tgtctcctgg taaataa      2097
```

<210> SEQ ID NO 42
<211> LENGTH: 678
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 42

```
Gln Ser Val Thr Gln Pro Asp Ala Arg Val Thr Val Ser Glu Gly Ala
1               5                   10                  15

Ser Leu Gln Leu Arg Cys Lys Tyr Ser Tyr Ser Gly Thr Pro Tyr Leu
            20                  25                  30

Phe Trp Tyr Val Gln Tyr Pro Arg Gln Gly Leu Gln Leu Leu Leu Lys
        35                  40                  45

Tyr Tyr Ser Gly Asp Pro Val Val Gln Gly Val Asn Gly Phe Glu Ala
    50                  55                  60

Glu Phe Ser Lys Ser Asn Ser Ser Phe His Leu Arg Lys Ala Ser Val
65                  70                  75                  80

His Trp Ser Asp Ser Ala Val Tyr Phe Cys Val Leu Ser Glu Asp Ser
                85                  90                  95

Asn Tyr Gln Leu Ile Trp Gly Ser Gly Thr Lys Leu Ile Ile Lys Pro
            100                 105                 110

Asp Thr Ser Gly Gly Gly Ser Gly Gly Gly Ser Gly Gly Gly Gly Gly
        115                 120                 125

Gly Ser Gly Gly Gly Ser Ser Ser Asn Ser Lys Val Ile Gln Thr
    130                 135                 140

Pro Arg Tyr Leu Val Lys Gly Gln Gly Gln Lys Ala Lys Met Arg Cys
145                 150                 155                 160

Ile Pro Glu Lys Gly His Pro Val Val Phe Trp Tyr Gln Gln Asn Lys
                165                 170                 175

Asn Asn Glu Phe Lys Phe Leu Ile Asn Phe Gln Asn Gln Glu Val Leu
            180                 185                 190

Gln Gln Ile Asp Met Thr Glu Lys Arg Phe Ser Ala Glu Cys Pro Ser
        195                 200                 205

Asn Ser Pro Cys Ser Leu Glu Ile Gln Ser Ser Glu Ala Gly Asp Ser
    210                 215                 220

Ala Leu Tyr Leu Cys Ala Ser Ser Leu Ser Gly Gly Thr Glu Val
225                 230                 235                 240

Phe Phe Gly Lys Gly Thr Arg Leu Thr Val Val Glu Asp Leu Asn Lys
                245                 250                 255

Val Phe Pro Pro Glu Val Ala Val Phe Glu Pro Ser Glu Ala Glu Ile
            260                 265                 270

Ser His Thr Gln Lys Ala Thr Leu Val Cys Leu Ala Thr Gly Phe Phe
        275                 280                 285

Pro Asp His Val Glu Leu Ser Trp Trp Val Asn Gly Lys Glu Val His
    290                 295                 300

Ser Gly Val Ser Thr Asp Pro Gln Pro Leu Lys Glu Gln Pro Ala Leu
305                 310                 315                 320

Asn Asp Ser Arg Tyr Cys Leu Ser Ser Arg Leu Arg Val Ser Ala Thr
                325                 330                 335

Phe Trp Gln Asn Pro Arg Asn His Phe Arg Cys Gln Val Gln Phe Tyr
            340                 345                 350

Gly Leu Ser Glu Asn Asp Glu Trp Thr Gln Asp Arg Ala Lys Pro Val
        355                 360                 365

Thr Gln Ile Val Ser Ala Glu Ala Trp Gly Arg Ala Asp Ile Thr Cys
    370                 375                 380
```

```
Pro Pro Pro Met Ser Val Glu His Ala Asp Ile Trp Val Lys Ser Tyr
385                 390                 395                 400

Ser Leu Tyr Ser Arg Glu Arg Tyr Ile Cys Asn Ser Gly Phe Lys Arg
            405                 410                 415

Lys Ala Gly Thr Ser Ser Leu Thr Glu Cys Val Leu Asn Lys Ala Thr
            420                 425                 430

Asn Val Ala His Trp Thr Thr Pro Ser Leu Lys Cys Ile Arg Glu Pro
            435                 440                 445

Lys Ser Cys Asp Lys Thr His Thr Cys Pro Pro Cys Pro Ala Pro Glu
        450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
            485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Asn
            515                 520                 525

Ser Thr Tyr Arg Val Val Ser Val Leu Thr Val Leu His Gln Asp Trp
530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
            565                 570                 575

Pro Gln Val Tyr Thr Leu Pro Pro Ser Arg Asp Glu Leu Thr Lys Asn
            580                 585                 590

Gln Val Ser Leu Thr Cys Leu Val Lys Gly Phe Tyr Pro Ser Asp Ile
            595                 600                 605

Ala Val Glu Trp Glu Ser Asn Gly Gln Pro Glu Asn Asn Tyr Lys Thr
            610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
            645                 650                 655

Ser Val Met His Glu Ala Leu His Asn His Tyr Thr Gln Lys Ser Leu
            660                 665                 670

Ser Leu Ser Pro Gly Lys
        675

<210> SEQ ID NO 43
<211> LENGTH: 1140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43 atggatttc aggtgcagat tatcagcttc ctgctaatca gtgcttcagt cataatgtcc      60
agaggacaaa ttgttctctc ccagtctcca gcaatcctgt ctgcatctcc aggggagaag    120
gtcacaatga cttgcagggc cagctcaagt gtaagttaca tccactggtt ccagcagaag    180
ccaggatcct cccccaaacc ctggatttat gccacatcca acctggcttc tggagtccct    240
gttcgcttca gtggcagtgg gtctgggact tcttactctc tcacaatcag cagagtggag    300
gctgaagatg ctgccactta ttactgccag cagtggacta gtaacccacc cacgttcgga    360
```

```
ggggggacca agctggaaat caaaagtgga ggtggcggat caggaggcgg aggttctggc    420
ggaggtggga gtcaggtaca actgcagcag cctggggctg agctggtgaa gcctggggcc    480
tcagtgaaga tgtcctgcaa ggcttctggc tacacattta ccagttacaa tatgcactgg    540
gtaaaacaga cacctggtcg gggcctggaa tggattggag ctatttatcc cggaaatggt    600
gatacttcct acaatcagaa gttcaaaggc aaggccacat tgactgcaga caaatcctcc    660
agcacagcct acatgcagct cagcagcctg acatctgagg actctgcggt ctattactgt    720
gcaagatcga cttactacgg cggtgactgg tacttcaatg tctggggcgc agggaccacg    780
gtcaccgtct ctgcaaactg ggtgaatgta ataagtgatt tgaaaaaaat tgaagatctt    840
attcaatcta tgcatattga tgctacttta tacggaaaa gtgatgttca ccccagttgc    900
aaagtaacag caatgaagtg ctttctcttg gagttacaag ttatttcact tgagtccgga    960
gatgcaagta ttcatgatac agtagaaaat ctgatcatcc tagcaaacga cagtttgtct   1020
tctaatggga atgtaacaga atctggatgc aaagaatgtg aggaactgga ggaaaaaaat   1080
attaaagaat ttttgcagag ttttgtacat attgtccaaa tgttcatcaa cacttcttaa   1140
```

<210> SEQ ID NO 44
<211> LENGTH: 357
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ser Gly Gly Gly Gly Ser
            100                 105                 110

Gly Gly Gly Gly Ser Gly Gly Gly Ser Gln Val Gln Leu Gln Gln
        115                 120                 125

Pro Gly Ala Glu Leu Val Lys Pro Gly Ala Ser Val Lys Met Ser Cys
    130                 135                 140

Lys Ala Ser Gly Tyr Thr Phe Thr Ser Tyr Asn Met His Trp Val Lys
145                 150                 155                 160

Gln Thr Pro Gly Arg Gly Leu Glu Trp Ile Gly Ala Ile Tyr Pro Gly
                165                 170                 175

Asn Gly Asp Thr Ser Tyr Asn Gln Lys Phe Lys Gly Lys Ala Thr Leu
            180                 185                 190

Thr Ala Asp Lys Ser Ser Thr Ala Tyr Met Gln Leu Ser Ser Leu
        195                 200                 205

Thr Ser Glu Asp Ser Ala Val Tyr Tyr Cys Ala Arg Ser Thr Tyr Tyr
    210                 215                 220
```

```
Gly Gly Asp Trp Tyr Phe Asp Val Trp Gly Ala Gly Thr Thr Val Thr
225                 230                 235                 240
Val Ser Ala Asn Trp Val Asn Val Ile Ser Asp Leu Lys Lys Ile Glu
                245                 250                 255
Asp Leu Ile Gln Ser Met His Ile Asp Ala Thr Leu Tyr Thr Glu Ser
            260                 265                 270
Asp Val His Pro Ser Cys Lys Val Thr Ala Met Lys Cys Phe Leu Leu
        275                 280                 285
Glu Leu Gln Val Ile Ser Leu Glu Ser Gly Asp Ala Ser Ile His Asp
    290                 295                 300
Thr Val Glu Asn Leu Ile Ile Leu Ala Asn Asp Ser Leu Ser Ser Asn
305                 310                 315                 320
Gly Asn Val Thr Glu Ser Gly Cys Lys Glu Cys Glu Glu Leu Glu Glu
                325                 330                 335
Lys Asn Ile Lys Glu Phe Leu Gln Ser Phe Val His Ile Val Gln Met
            340                 345                 350
Phe Ile Asn Thr Ser
        355

<210> SEQ ID NO 45
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atggattttc aggtgcagat tatcagcttc ctgctaatca gtgcttcagt cataatgtcc      60
agaggacaaa ttgttctctc ccagtctcca gcaatcctgt ctgcatctcc aggggagaag    120
gtcacaatga cttgcagggc cagctcaagt gtaagttaca tccactggtt ccagcagaag    180
ccaggatcct cccccaaacc ctggatttat gccacatcca acctggcttc tggagtccct    240
gttcgcttca gtggcagtgg gtctgggact tcttactctc tcacaatcag cagagtggag    300
gctgaagatg ctgccactta ttactgccag cagtggacta gtaacccacc cacgttcgga    360
ggggggacca agctggaaat caaaagtgga ggtggcggat ccggaggtgg aggttctggt    420
ggaggtggga gtcaggtaca actgcagcag cctggggctg agctggtgaa gcctggggcc    480
tcagtgaaga tgtcctgcaa ggcttctggc tacacattta ccagttacaa tatgcactgg    540
gtaaaacaga cacctggtcg gggcctggaa tggattggag ctatttatcc cggaaatggt    600
gatacttcct acaatcagaa gttcaaaggc aaggccacat tgactgcaga caaatcctcc    660
agcacagcct acatgcagct cagcagcctg acatctgagg actctgcggt ctattactgt    720
gcaagatcga cttactacgg cggtgactgg tacttcratg tctggggcgc agggaccacg    780
gtcacmgtct ctgcaatcac gtgccctccc cccatgtccg tggaacacgc agacatctgg    840
gtcaagagct acagcttgta ctccagggag cggtacattt gtaactctgg tttcaagcgt    900
aaagccggca cgtccagcct gacggagtgc gtgttgaaca aggccacgaa tgtcgcccac    960
tggacaaccc ccagtctcaa atgcattaga gagccgaaat cttgtgacaa aactcacaca   1020
tgcccaccgt gcccagcacc tgaactcctg ggggaccgtc agtcttcct cttccccccca   1080 aaacccaagg acaccctcat gatctcccgg acccctgagg tcacatgcgt ggtggtggac   1140
gtgagccacg aagaccctga ggtcaagttc aactggtacg tggacggcgt ggaggtgcat   1200
```

```
aatgccaaga caaagccgcg ggaggagcag tacaacagca cgtaccgtgt ggtcagcgtc   1260
ctcaccgtcc tgcaccagga ctggctgaat ggcaaggagt acaagtgcaa ggtctccaac   1320
aaagccctcc cagcccccat cgagaaaacc atctccaaag ccaaagggca gccccgagaa   1380
ccacaggtgt acaccctgcc cccatcccgg gatgagctga ccaagaacca ggtcagcctg   1440
acctgcctgg tcaaaggctt ctatcccagc gacatcgccg tggagtggga gagcaatggg   1500
cagccggaga acaactacaa gaccacgcct cccgtgctgg actccgacgg ctccttcttc   1560
ctctacagca agctcaccgt ggacaagagc aggtggcagc aggggaacgt cttctcatgc   1620
tccgtgatgc atgaggctct gcacaaccac tacacgcaga gagcctctc cctgtctcct   1680 ggtaaataa                                                              1689
```

<210> SEQ ID NO 46
<211> LENGTH: 540
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ser Gly Gly Gly Gly Ser
            100                 105                 110

Gly Gly Gly Gly Ser Gly Gly Gly Ser Gln Val Gln Leu Gln Gln
        115                 120                 125

Pro Gly Ala Glu Leu Val Lys Pro Gly Ala Ser Val Lys Met Ser Cys
    130                 135                 140

Lys Ala Ser Gly Tyr Thr Phe Thr Ser Tyr Asn Met His Trp Val Lys
145                 150                 155                 160

Gln Thr Pro Gly Arg Gly Leu Glu Trp Ile Gly Ala Ile Tyr Pro Gly
                165                 170                 175

Asn Gly Asp Thr Ser Tyr Asn Gln Lys Phe Lys Gly Lys Ala Thr Leu
            180                 185                 190

Thr Ala Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Ser Thr Tyr Tyr
    210                 215                 220

Gly Gly Asp Trp Tyr Phe Asn Val Trp Gly Ala Gly Thr Thr Val Thr
225                 230                 235                 240

Val Ser Ala Ile Thr Cys Pro Pro Met Ser Val Glu His Ala Asp
                245                 250                 255

Ile Trp Val Lys Ser Tyr Ser Leu Tyr Ser Arg Glu Arg Tyr Ile Cys
            260                 265                 270
```

```
Asn Ser Gly Phe Lys Arg Lys Ala Gly Thr Ser Ser Leu Thr Glu Cys
        275                 280                 285

Val Leu Asn Lys Ala Thr Asn Val Ala His Trp Thr Thr Pro Ser Leu
        290                 295                 300

Lys Cys Ile Arg Glu Pro Lys Ser Cys Asp Lys Thr His Thr Cys Pro
305                 310                 315                 320

Pro Cys Pro Ala Pro Glu Leu Leu Gly Gly Pro Ser Val Phe Leu Phe
                325                 330                 335

Pro Pro Lys Pro Lys Asp Thr Leu Met Ile Ser Arg Thr Pro Glu Val
        340                 345                 350

Thr Cys Val Val Val Asp Val Ser His Glu Asp Pro Glu Val Lys Phe
        355                 360                 365

Asn Trp Tyr Val Asp Gly Val Glu Val His Asn Ala Lys Thr Lys Pro
        370                 375                 380

Arg Glu Glu Gln Tyr Asn Ser Thr Tyr Arg Val Val Ser Val Leu Thr
385                 390                 395                 400

Val Leu His Gln Asp Trp Leu Asn Gly Lys Glu Tyr Lys Cys Lys Val
                405                 410                 415

Ser Asn Lys Ala Leu Pro Ala Pro Ile Glu Lys Thr Ile Ser Lys Ala
        420                 425                 430

Lys Gly Gln Pro Arg Glu Pro Gln Val Tyr Thr Leu Pro Pro Ser Arg
        435                 440                 445

Asp Glu Leu Thr Lys Asn Gln Val Ser Leu Thr Cys Leu Val Lys Gly
        450                 455                 460

Phe Tyr Pro Ser Asp Ile Ala Val Glu Trp Glu Ser Asn Gly Gln Pro
465                 470                 475                 480

Glu Asn Asn Tyr Lys Thr Thr Pro Pro Val Leu Asp Ser Asp Gly Ser
                485                 490                 495

Phe Phe Leu Tyr Ser Lys Leu Thr Val Asp Lys Ser Arg Trp Gln Gln
        500                 505                 510

Gly Asn Val Phe Ser Cys Ser Val Met His Glu Ala Leu His Asn His
        515                 520                 525

Tyr Thr Gln Lys Ser Leu Ser Leu Ser Pro Gly Lys
        530                 535                 540

<210> SEQ ID NO 47
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47 atggatttc aggtgcagat tatcagcttc ctgctaatca gtgcttcagt cataatgtcc      60
agaggacaaa ttgttctctc ccagtctcca gcaatcctgt ctgcatctcc aggggagaag    120
gtcacaatga cttgcagggc cagctcaagt gtaagttaca tccactggtt ccagcagaag    180
ccaggatcct cccccaaacc ctggatttat gccacatcca acctggcttc tggagtccct    240
gttcgcttca gtggcagtgg gtctgggact tcttactctc tcacaatcag cagagtggag    300
gctgaagatg ctgccactta ttactgccag cagtggacta gtaacccacc cacgttcgga    360
ggggggacca agctggaaat caaacgtacg gttgctgcac catctgtctt catcttcccg    420
ccatctgatg agcagttgaa atctggaact gcctctgttg tgtgcctgct gaataacttc    480
```

```
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgtaactg ggtgaatgta    720
ataagtgatt tgaaaaaaat tgaagatctt attcaatcta tgcatattga tgctacttta    780
tatacggaaa gtgatgttca ccccagttgc aaagtaacag caatgaagtg ctttctcttg    840
gagttacaag ttatttcact tgagtccgga gatgcaagta ttcatgatac agtagaaaat    900
ctgatcatcc tagcaaacga cagtttgtct tctaatggga atgtaacaga atctggatgc    960
aaagaatgtg aggaactgga ggaaaaaaat attaaagaat ttttgcagag ttttgtacat   1020
attgtccaaa tgttcatcaa cacttcttaa                                    1050
```

<210> SEQ ID NO 48
<211> LENGTH: 327
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Asn Trp Val Asn Val Ile Ser Asp Leu Lys Lys
    210                 215                 220

Ile Glu Asp Leu Ile Gln Ser Met His Ile Asp Ala Thr Leu Tyr Thr
225                 230                 235                 240

Glu Ser Asp Val His Pro Ser Cys Lys Val Thr Ala Met Lys Cys Phe
                245                 250                 255
```

```
Leu Leu Glu Leu Gln Val Ile Ser Leu Glu Ser Gly Asp Ala Ser Ile
            260                 265                 270

His Asp Thr Val Glu Asn Leu Ile Ile Leu Ala Asn Asp Ser Leu Ser
        275                 280                 285

Ser Asn Gly Asn Val Thr Glu Ser Gly Cys Lys Glu Cys Glu Glu Leu
    290                 295                 300

Glu Glu Lys Asn Ile Lys Glu Phe Leu Gln Ser Phe Val His Ile Val
305                 310                 315                 320

Gln Met Phe Ile Asn Thr Ser
                325

<210> SEQ ID NO 49
<211> LENGTH: 1608
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atgggttgga gtctcatctt gctcttcctt gtcgctgttg ctacacgtgt cctgtcccag      60
gtacaactgc agcagcctgg ggctgagctg gtgaagcctg ggcctcagt gaagatgtcc     120 tgcaaggctt ctggctacac atttaccagt tacaatatgc actgggtaaa cagacacct     180 ggtcggggcc tggaatggat tggagctatt tatcccggaa atggtgatac ttcctacaat     240
cagaagttca aggcaaggc cacattgact gcagacaaat cctccagcac agcctacatg     300
cagctcagca gcctgacatc tgaggactct gcggtctatt actgtgcaag atcgacttac     360
tacggcggtg actggtactt cgatgtctgg ggcgcaggga ccacggtcac cgtctctgca     420
gctagcacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag cgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagaa agttatcacg     720
tgccctcccc ccatgtccgt ggaacacgca gacatctggg tcaagagcta cagcttgtac     780
tccagggagc ggtacatttg taactctggt ttcaagcgta aagccggcac gtccagcctg     840
acggagtgcg tgttgaacaa ggccacgaat gtcgcccact ggacaacccc cagtctcaaa     900
tgcattagag agcccaaatc ttgtgacaaa actcacacat gcccaccgtg cccagcacct     960
gaactcctgg ggggaccgtc agtcttcctc ttccccccaa acccaaggga caccctcatg    1020
atctcccgga cccctgaggt cacatgcgtg gtggtggacg tgagccacga agaccctgag    1080
gtcaagttca actggtacgt ggacggcgtg gaggtgcata atgccaagac aaagccgcgg    1140
gaggagcagt acaacagcac gtaccgtgtg gtcagcgtcc tcaccgtcct gcaccaggac    1200
tggctgaatg gcaaggagta caagtgcaag gtctccaaca aagcccctcc agcccccatc    1260
gagaaaacca tctccaaagc caaagggcag ccccgagaac cacaggtgta caccctgccc    1320
ccatcccggg atgagctgac caagaaccag gtcagcctga cctgcctggt caaaggcttc    1380
tatcccagcg acatcgccgt ggagtgggag agcaatgggc agccggagaa caactacaag    1440
accacgcctc ccgtgctgga ctccgacggc tccttcttcc tctacagcaa gctcaccgtg    1500
gacaagagca ggtggcagca ggggaacgtc ttctcatgct ccgtgatgca tgaggctctg    1560
cacaaccact acacgcagaa gagcctctcc ctgtctcctg gtaaataa                 1608
```

-continued

<210> SEQ ID NO 50
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asp Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Ile Thr Cys Pro Pro
    210                 215                 220

Pro Met Ser Val Glu His Ala Asp Ile Trp Val Lys Ser Tyr Ser Leu
225                 230                 235                 240

Tyr Ser Arg Glu Arg Tyr Ile Cys Asn Ser Gly Phe Lys Arg Lys Ala
                245                 250                 255

Gly Thr Ser Ser Leu Thr Glu Cys Val Leu Asn Lys Ala Thr Asn Val
            260                 265                 270

Ala His Trp Thr Thr Pro Ser Leu Lys Cys Ile Arg Glu Pro Lys Ser
        275                 280                 285

Cys Asp Lys Thr His Thr Cys Pro Pro Cys Pro Ala Pro Glu Leu Leu
    290                 295                 300

Gly Gly Pro Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
                325                 330                 335

His Glu Asp Pro Glu Val Lys Phe Asn Trp Tyr Val Asp Gly Val Glu
            340                 345                 350

Val His Asn Ala Lys Thr Lys Pro Arg Glu Glu Gln Tyr Asn Ser Thr

-continued

```
             355                 360                 365
Tyr Arg Val Val Ser Val Leu Thr Val Leu His Gln Asp Trp Leu Asn
        370                 375             380

Gly Lys Glu Tyr Lys Cys Lys Val Ser Asn Lys Ala Leu Pro Ala Pro
385                     390                 395                 400

Ile Glu Lys Thr Ile Ser Lys Ala Lys Gly Gln Pro Arg Glu Pro Gln
                405                 410                 415

Val Tyr Thr Leu Pro Pro Ser Arg Asp Glu Leu Thr Lys Asn Gln Val
            420                 425                 430

Ser Leu Thr Cys Leu Val Lys Gly Phe Tyr Pro Ser Asp Ile Ala Val
            435                 440                 445

Glu Trp Glu Ser Asn Gly Gln Pro Glu Asn Asn Tyr Lys Thr Thr Pro
        450                 455                 460

Pro Val Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Met His Glu Ala Leu His Asn His Tyr Thr Gln Lys Ser Leu Ser Leu
            500                 505                 510

Ser Pro Gly Lys
            515
```